United States Patent
Drever et al.

(10) Patent No.: US 12,037,605 B2
(45) Date of Patent: Jul. 16, 2024

(54) PROSTATE CANCER CHIMERIC ANTIGEN RECEPTORS

(71) Applicant: Kite Pharma, Inc., Santa Monica, CA (US)

(72) Inventors: Matthew Drever, Concord, CA (US); Amy E. Gilbert, San Francisco, CA (US); Samuel T. Haile, San Pablo, CA (US); Catherine A. Hartzell, Berkeley, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 42 days.

(21) Appl. No.: 17/553,391

(22) Filed: Dec. 16, 2021

(65) Prior Publication Data

US 2022/0204930 A1 Jun. 30, 2022

Related U.S. Application Data

(60) Provisional application No. 63/130,529, filed on Dec. 24, 2020.

(51) Int. Cl.
| | |
|---|---|
| *C12N 5/0783* | (2010.01) |
| *A61K 35/17* | (2015.01) |
| *C07K 14/47* | (2006.01) |
| *C07K 14/725* | (2006.01) |

(52) U.S. Cl.
CPC ............ *C12N 5/0637* (2013.01); *A61K 35/17* (2013.01); *C07K 14/4702* (2013.01); *C07K 14/7051* (2013.01); *C07K 2317/51* (2013.01); *C07K 2317/515* (2013.01); *C07K 2317/53* (2013.01); *C07K 2317/565* (2013.01); *C07K 2317/622* (2013.01); *C07K 2319/03* (2013.01); *C07K 2319/715* (2013.01); *C12N 2510/00* (2013.01)

(58) Field of Classification Search
CPC .. C12N 5/0637; C12N 2510/00; A61K 35/17; C07K 14/4702; C07K 14/7051; C07K 2317/51; C07K 2317/515; C07K 2317/53; C07K 2317/565; C07K 2317/622; C07K 2319/03; C07K 2319/715

See application file for complete search history.

(56) References Cited

U.S. PATENT DOCUMENTS

| | | |
|---|---|---|
| 2016/0264665 A1 | 9/2016 | Lim et al. |
| 2019/0275083 A1 | 9/2019 | Zhao et al. |
| 2020/0308300 A1 | 10/2020 | Priceman et al. |
| 2021/0371491 A1 | 12/2021 | Cathomen et al. |

OTHER PUBLICATIONS

Nakanishi et al. Critical contribution of VH-VL interaction to reshaping of an antibody: The case of humanization of anti-lysozyme antibody, HyHEL-10. Protein Science. 2008, 17:261-270. (Year: 2008).*

Grunder et al. Gamma9 and Delta2CDR3 domains regulate functional avidity of T cells harboring Gamma9Delta2TCRs. Blood. 2012;120(26):5153-5162. (Year: 2012).*

Chung, H. et al. (2021) "Emerging Approaches for Solid Tumor Treatment Using CAR-T Cell Therapy" Int. J. Mol. Sci. 22(22):12126, 21 pages.

Intl. Search Report-Written Opinion dated May 16, 2022 for Intl. Appl. No. PCT/US2021/063855.

Office Action dated Dec. 13, 2022 for Taiwanese Appl. No. 110148380.

Roybal, K.T. et al. (2016) "Precision Tumor Recognition by T Cells With Combinatorial Antigen-Sensing Circuits" Cell 164(4):770-779.

Schepisi, G. et al. (2019) "CAR-T cell therapy: a potential new strategy against prostate cancer" J Immunother Cancer 7(1):258, 11 pages.

\* cited by examiner

*Primary Examiner* — Arthur S Leonard
*Assistant Examiner* — Jianjian Zhu

(57) ABSTRACT

Provided are antibodies, fragments thereof, chimeric antigen receptors (CARs) and T cell receptors (TCRs) comprising one or more of the anti-PMCA antigen binding domains disclosed herein. SynNotch receptors that comprise an anti-PSCA binding domain Provided are polynucleotides encoding antibodies, fragments thereof, CARs, T cell receptors (TCR) and SynNotch receptors. Provided are compositions, cells and cell therapies comprising the same. Further provided are methods of treatment.

21 Claims, 6 Drawing Sheets

Specification includes a Sequence Listing.

SEQUENCE LISTING

<160> NUMBER OF SEQ ID NOS: 260

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Ile
        35                  40                  45

Ala Asn Ile Asn Tyr Asp Gly Ser Asn Thr Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Asp Gly Tyr Tyr Gly Tyr Phe Asp Val Trp Gly Gln
            100                 105                 110

Gly Thr Thr Val Thr Val Ser Ser
        115                 120

<210> SEQ ID NO 2
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gaggtgcaac ttgtggagag cggaggaggt ttagtgcaac ccggaggcag catgagactg        60
agctgcgccg ccagcggctt cacattctcc gactactaca tggcttgggt ccgacaagct       120
cccgaaaaag gactggagtg gatcgccaac atcaactacg acggctccaa cacctactac       180
gccgactctt taaagggtcg tttcacaatc tctcgtgaca acagcaagaa cactttatat       240
ttacaaatga actctttaag ggccgaggat accgccgtgt actactgcgc tcgtaactgg       300
gacggctact acggctactt cgacgtgtgg ggccaaggaa ccaccgtgac cgtgagcagc       360
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Thr Phe Ser Asp Tyr Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Tyr Met Ala
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Thr Phe Ser Asp
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Asn Tyr Asp Gly Ser Asn Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Asn Ile Asn Tyr Asp Gly Ser Asn Thr Tyr Tyr Ala Asp Ser Leu Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ile Asn Tyr Asp Gly Ser Asn Thr Tyr Tyr Ala Asp Ser Leu Lys
1               5                   10                  15

Gly

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Asn Trp Asp Gly Tyr Tyr Gly Tyr Phe Asp Val
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Trp Asp Gly Tyr Tyr Gly Tyr Phe Asp Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Trp Asp Gly Tyr Tyr Gly Tyr Phe Asp Val
1               5                   10

<210> SEQ ID NO 12
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Leu Thr Gln Ser Pro Ser Ser Leu Ser Ala Ser Val Gly
1               5                   10                  15
```

Asp Arg Val Thr Ile Thr Cys Arg Ala Ser Ser Val Ser His Ile
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr His Thr Tyr Pro Pro Thr
                85                  90                  95

Phe Gly Gln Gly Thr Lys Leu Glu Ile Lys
            100                 105

<210> SEQ ID NO 13
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gatatccagc tgacccagtc cccttcctct ctgtctgcgt ctgttggcga tcgtgtcacc        60
atcacttgtc gtgccagcag cagcgtgagc cacatttatt ggtaccaaca aaagcccggc       120
aaagccccta agccttggat ctacagaacc tccaatctgg ccagcggcgt gcccagcaga       180
ttcagcggaa gcggatccgg caccgactac actttaacca tcagctcttt acagcccgag       240
gacttcgcca catactactg ccagcagtac cacacctatc cccccacatt cggccaagga       300
acaaagctgg agattaag                                                    318

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ser Val Ser His
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Ser Ser Val Ser His Ile Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Arg Ala Ser Ser Ser Val Ser His Ile Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Thr Ser
1

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Thr Ser Asn Leu Ala Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Thr Ser Asn Leu Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Tyr His Thr Tyr Pro Pro Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Tyr His Thr Tyr Pro Pro Thr
1               5

<210> SEQ ID NO 22
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 22

Gln Gln Tyr His Thr Tyr Pro Pro Thr
1               5

<210> SEQ ID NO 23
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser His Ile
            20                  25                  30

Tyr Trp Tyr Gln Gln Lys Pro Gly Lys Ala Pro Lys Pro Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr His Thr Tyr Pro Pro Thr
                85                  90                  95

Phe Gly Gln Gly Thr Lys Leu Glu Ile Lys Gly Ser Thr Ser Gly Ser
            100                 105                 110

Gly Lys Pro Gly Ser Gly Glu Gly Ser Thr Lys Gly Glu Val Gln Leu
        115                 120                 125

Val Glu Ser Gly Gly Gly Leu Val Gln Pro Gly Gly Ser Met Arg Leu
130                 135                 140

Ser Cys Ala Ala Ser Gly Phe Thr Phe Ser Asp Tyr Tyr Met Ala Trp
145                 150                 155                 160

Val Arg Gln Ala Pro Gly Lys Gly Leu Glu Trp Ile Ala Asn Ile Asn
                165                 170                 175

Tyr Asp Gly Ser Asn Thr Tyr Tyr Ala Asp Ser Leu Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Arg Asn Trp
210                 215                 220

Asp Gly Tyr Tyr Gly Tyr Phe Asp Val Trp Gly Gln Gly Thr Thr Val
225                 230                 235                 240

Thr Val Ser Ser

<210> SEQ ID NO 24
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
```

```
gatatccagc tgacccagtc cccttcctct ctgtctgcgt ctgttggcga tcgtgtcacc     60
atcacttgtc gtgccagcag cagcgtgagc cacatttatt ggtaccaaca aaagcccggc    120
aaagccccta agccttggat ctacagaacc tccaatctgg ccagcggcgt gcccagcaga    180
ttcagcggaa gcggatccgg caccgactac actttaacca tcagctcttt acagcccgag    240
gacttcgcca catactactg ccagcagtac cacacctatc cccccacatt cggccaagga    300
acaaagctgg agattaaggg ctccacctcc ggaagcggca aacccggtag cggcgagggc    360
tccacaaagg gcgaggtgca acttgtggag agcggaggag gtttagtgca acccggaggc    420
agcatgagac tgagctgcgc cgccagcggc ttcacattct ccgactacta catggcttgg    480
gtccgacaag ctcccggaaa aggactggag tggatcgcca acatcaacta cgacggctcc    540
aacacctact acgccgactc tttaaagggt cgtttcacaa tctctcgtga caacagcaag    600
aacactttat atttacaaat gaactcttta agggccgagg ataccgccgt gtactactgc    660
gctcgtaact gggacggcta ctacggctac ttcgacgtgt ggggccaagg aaccaccgtg    720
accgtgagca gc                                                        732
```

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Met Ile His Pro Asn Ser Gly Ser Thr Asn Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Tyr Asp Tyr Gly Glu Asp Phe Asp Val Trp Gly Gln
            100                 105                 110

Gly Thr Thr Val Thr Val Ser Ser
        115                 120
```

<210> SEQ ID NO 26
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
caagtgcagc tggtgcagtc cggcgccgag gtgaagaagc ccggtgcttc cgtgaagctg     60
tcttgcaaag ccagcggcta caccttcacc acctattgga tgcactgggt ccgacaagct    120
cccggtcaag gtctggagtg gattggcatg atccacccca actccggctc caccaactac    180
gcccagaagt tccaaggtcg tgccacttta acagtggata ccagcaccag caccgcctac    240
```

```
atggagctga gtagtttgag gagcgaggac accgccgtgt actattgcgc tcgtgacccc    300
tacgactacg gcgaggactt cgacgtgtgg ggccaaggaa caacagtgac cgtgagcagc    360
```

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Tyr Thr Phe Thr Thr Tyr Trp
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Tyr Trp Met His
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Tyr Thr Phe Thr Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile His Pro Asn Ser Gly Ser Thr
1               5

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Ile His Pro Asn Ser Gly Ser Thr Asn Tyr Ala Gln Lys Phe Gln
1               5                   10                  15

Gly

<210> SEQ ID NO 32

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Ile His Pro Asn Ser Gly Ser Thr Asn Tyr Ala Gln Lys Phe Gln
1               5                   10                  15

Gly

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asp Pro Tyr Asp Tyr Gly Glu Asp Phe Asp Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Pro Tyr Asp Tyr Gly Glu Asp Phe Asp Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Pro Tyr Asp Tyr Gly Glu Asp Phe Asp Val
1               5                   10

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Asn Val Asn Thr Asn
            20                  25                  30

Val Ala Trp Tyr Gln Gln Lys Pro Gly Lys Ala Pro Lys Val Leu Ile
        35                  40                  45

Tyr Ser Ala Ser Tyr Arg Asn Ser Gly Val Pro Ser Arg Phe Ser Gly
    50                  55                  60
```

```
Ser Gly Ser Gly Thr Asp Phe Thr Leu Thr Ile Ser Ser Val Gln Pro
 65                  70                  75                  80

Glu Asp Phe Ala Thr Tyr Tyr Cys Gln Gln Tyr Asn Ser Tyr Pro Phe
                 85                  90                  95

Thr Phe Gly Gln Gly Thr Lys Leu Glu Ile Lys
            100                 105

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacatccaga tgacccagag ccccagctct ttaagtgcca gcgtgggcga cagagtgaca      60
gtgacttgtc gtgccagcca gaacgtgaat accaacgtgg cttggtacca gcagaagccc    120
ggcaaagccc ctaaggtgct gatctattcc gcgtcttatc gtaactccgg cgtgccttcg    180 cgttttctg ggtctggtag cggcaccgac ttcactttaa caatcagcag cgttcagccc     240
gaagacttcg ccacctacta ctgccagcag tacaacagct atccctttac tttcggtcaa    300
gggaccaagc tcgagatcaa a                                              321

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Asn Val Asn Thr Asn
 1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ala Ser Gln Asn Val Asn Thr Asn Val Ala
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ala Ser Gln Asn Val Asn Thr Asn Val Ala
 1               5                  10

<210> SEQ ID NO 41
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 41

Met Ile His Pro Asn Ser Gly Ser Thr Asn Tyr Ala Gln Lys Phe Gln
1               5                   10                  15

Gly

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ala Ser Tyr Arg Asn Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ala Ser Tyr Arg Asn Ser
1               5

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Pro Tyr Asp Tyr Gly Glu Asp Phe Asp Val
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Tyr Asn Ser Tyr Pro Phe Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Tyr Asn Ser Tyr Pro Phe Thr
```

<210> SEQ ID NO 47
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Asn Val Asn Thr Asn
            20                  25                  30

Val Ala Trp Tyr Gln Gln Lys Pro Gly Lys Ala Pro Lys Val Leu Ile
        35                  40                  45

Tyr Ser Ala Ser Tyr Arg Asn Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Gln Gly Thr Lys Leu Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ala Ser Val Lys
    130                 135                 140

Leu Ser Cys Lys Ala Ser Gly Tyr Thr Phe Thr Thr Tyr Trp Met His
145                 150                 155                 160

Trp Val Arg Gln Ala Pro Gly Gln Gly Leu Glu Trp Ile Gly Met Ile
                165                 170                 175

His Pro Asn Ser Gly Ser Thr Asn Tyr Ala Gln Lys Phe Gln Gly Arg
            180                 185                 190

Ala Thr Leu Thr Val Asp Thr Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Pro Tyr Asp Tyr Gly Glu Asp Phe Asp Val Trp Gly Gln Gly Thr Thr
225                 230                 235                 240

Val Thr Val Ser Ser
                245

<210> SEQ ID NO 48
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gacatccaga tgacccagag ccccagctct ttaagtgcca gcgtgggcga cagagtgaca      60
gtgacttgtc gtgccagcca gaacgtgaat accaacgtgg cttggtacca gcagaagccc    120
ggcaaagccc ctaaggtgct gatctattcc gcgtcttatc gtaactccgg cgtgccttcg    180 cgttttctg ggtctggtag cggcaccgac ttcactttaa caatcagcag cgttcagccc     240

```
gaagacttcg ccacctacta ctgccagcag tacaacagct atcccttac tttcggtcaa      300 gggaccaagc tcgagatcaa aggctccacc agcggtagcg gcaaacccgg ttccggcgag      360
ggctctacca agggccaagt gcagctggtg cagtccggcg ccgaggtgaa gaagcccggt      420
gcttccgtga agctgtcttg caaagccagc ggctacacct tcaccaccta ttggatgcac      480
tgggtccgac aagctcccgg tcaaggtctg gagtggattg gcatgatcca ccccaactcc      540
ggctccacca actacgccca gaagttccaa ggtcgtgcca ctttaacagt ggataccagc      600
accagcaccg cctacatgga gctgagtagt ttgaggagcg aggacaccgc cgtgtactat      660
tgcgctcgtg accccctacga ctacggcgag gacttcgacg tgtggggcca aggaacaaca      720
gtgaccgtga gcagc                                                      735

<210> SEQ ID NO 49
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Thr Ser Thr Tyr Tyr Ala Asp Ser Leu
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Gly Tyr Tyr Gly Tyr Leu Asp Val Trp Gly Gln
            100                 105                 110

Gly Thr Thr Val Thr Val Ser Ser
        115                 120

<210> SEQ ID NO 50
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gaggtgcagc tggtggagtc cggaggaggt ttagtccaac ccggtggcag catgaggctg       60
tcttgtgctg cctccggctt cactttttct gattactaca tggcttgggt ccgacaagct      120
cccggaaaag gtttagagtg ggtggctaac atcaactacg acggcaccag cacctactat      180
gccgacagcc tcaagggcag attcaccatc tctcgtgatt cgtctaaaaa cactttatat      240
ttacaaatga actcttttaag agccgaagat accgccgtgt actattgcgc tcgtgccctc      300
gacggctact acggatattt agacgtgtgg ggtcaaggaa caaccgtgac cgtgtccagc      360

<210> SEQ ID NO 51
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Thr Phe Ser Asp Tyr Tyr
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Tyr Tyr Met Ala
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Thr Phe Ser Asp
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Asn Tyr Asp Gly Thr Ser Thr
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Ile Asn Tyr Asp Gly Thr Ser Thr Tyr Tyr Ala Asp Ser Leu Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Asn Ile Asn Tyr Asp Gly Thr Ser Thr Tyr Tyr Ala Asp Ser Leu Lys
1               5                   10                  15

Gly

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Arg Ala Leu Asp Gly Tyr Tyr Gly Tyr Leu Asp Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Leu Asp Gly Tyr Tyr Gly Tyr Leu Asp Val
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Leu Asp Gly Tyr Tyr Gly Tyr Leu Asp Val
1               5                   10

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Leu Thr Gln Ser Pro Ser Leu Ser Ala Ser Val Gly
1               5                   10                  15

Asp Arg Val Thr Leu Thr Cys Arg Ala Ser Gln Ser Ile Ser Asn Asn
                20                  25                  30

Leu His Trp Tyr Gln Gln Lys Pro Gly Lys Ala Pro Lys Leu Leu Ile
            35                  40                  45

Lys Tyr Val Ser Gln Ser Ile Ser Gly Ile Pro Ser Arg Phe Ser Gly
        50                  55                  60

Ser Gly Leu Gly Thr Asp Phe Thr Leu Thr Ile Ser Ser Val Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
```

<210> SEQ ID NO 61
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gacatccagc tgacccagag ccctagctct ttaagcgcta gcgtgggcga tagggtgact      60
ctgacttgtc gtgcgtccca aagcattagc aacaatttac actggtacca gcagaagccc     120
ggaaaagccc ccaagctgct gatcaaatat gtgagccaga gcatctccgg catcccctct     180 cgttttctg gtagcggact gggcaccgac tttactttaa ccatcagcag cgtccagccc      240
gaggacttcg ccacatacta ctgccagcag agcaacagct ggccctatac tttcggccaa     300
ggaacaaagc tggagatcaa g                                                321

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Ile Ser Asn Asn
1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ala Ser Gln Ser Ile Ser Asn Asn Leu His
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ala Ser Gln Ser Ile Ser Asn Asn Leu His
1               5                   10

<210> SEQ ID NO 65
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Val Ser

```
-continued

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Val Ser Gln Ser Ile Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Val Ser Gln Ser Ile Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Ser Asn Ser Trp Pro Tyr Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Ser Asn Ser Trp Pro Tyr Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Ser Asn Ser Trp Pro Tyr Thr
1               5

<210> SEQ ID NO 71
<211> LENGTH: 245
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 71

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Thr Ser Thr Tyr Tyr Ala Asp Ser Leu
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Gly Tyr Tyr Gly Tyr Leu Asp Val Trp Gly Gln
            100                 105                 110

Gly Thr Thr Val Thr Val Ser Ser Gly Ser Thr Ser Gly Ser Gly Lys
        115                 120                 125

Pro Gly Ser Gly Glu Gly Ser Thr Lys Gly Asp Ile Gln Leu Thr Gln
    130                 135                 140

Ser Pro Ser Ser Leu Ser Ala Ser Val Gly Asp Arg Val Thr Leu Thr
145                 150                 155                 160

Cys Arg Ala Ser Gln Ser Ile Ser Asn Asn Leu His Trp Tyr Gln Gln
                165                 170                 175

Lys Pro Gly Lys Ala Pro Lys Leu Leu Ile Lys Tyr Val Ser Gln Ser
            180                 185                 190

Ile Ser Gly Ile Pro Ser Arg Phe Ser Gly Ser Gly Leu Gly Thr Asp
        195                 200                 205

Phe Thr Leu Thr Ile Ser Ser Val Gln Pro Glu Asp Phe Ala Thr Tyr
    210                 215                 220

Tyr Cys Gln Gln Ser Asn Ser Trp Pro Tyr Thr Phe Gly Gln Gly Thr
225                 230                 235                 240

Lys Leu Glu Ile Lys
                245

<210> SEQ ID NO 72
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gaggtgcagc tggtggagtc cggaggaggt ttagtccaac ccggtggcag catgaggctg    60
tcttgtgctg cctccggctt cacttttttct gattactaca tggcttgggt ccgacaagct   120
cccggaaaag gtttagagtg gtggctaac atcaactacg acggcaccag cacctactat    180
gccgacagcc tcaagggcag attcaccatc tctcgtgatt cgtctaaaaa cactttatat    240
ttacaaatga actcttttaag agccgaagat accgccgtgt actattgcgc tcgtgccctc    300
gacggctact acggatattt agacgtgtgg ggtcaaggaa caaccgtgac cgtgtccagc    360
ggatccacct ccgaagcgg caaacccggt agcggcgaag cagcaccaa aggagacatc     420 cagctgaccc agagccctag ctctttaagc gctagcgtgg gcgatagggt gactctgact    480

```
tgtcgtgcgt cccaaagcat tagcaacaat ttacactggt accagcagaa gcccggaaaa    540
gcccccaagc tgctgatcaa atatgtgagc cagagcatct ccggcatccc ctctcgtttt    600
tctggtagcg gactgggcac cgactttact ttaaccatca gcagcgtcca gcccgaggac    660
ttcgccacat actactgcca gcagagcaac agctggccct atactttcgg ccaaggaaca    720
aagctggaga tcaag                                                    735
```

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Ser Ser Thr Phe Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Gln Val Gly Tyr Tyr Asp Pro Met Asp Tyr Trp Gly Gln Gly
            100                 105                 110

Thr Thr Val Thr Val Ser Ser
        115
```

<210> SEQ ID NO 74
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gaggtgcagt tggtggagag cggaggagga ctggtgcagc ccggtggctc tttaagactc     60
agctgtgccg ccagcggatt tacattctcc gactactaca tggcttgggt ccgacaagcc    120
cccggaaaag gtttagagtg ggtggccaac atcaactacg acggctcctc cacattctac    180
gccgactctt taagggtcg tttcaccatc tctcgtgaca acagcaaaaa tactttatat    240
ttacaaatga actctttaag ggccgaggac accgccgtgt actactgcgg tcgtcaagtt    300
ggctattacg accccatgga ctactggggc caaggaacta ccgtgaccgt gagcagc       357
```

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Gly Phe Thr Phe Ser Asp Tyr Tyr
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Tyr Tyr Met Ala
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Thr Phe Ser Asp
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Asn Tyr Asp Gly Ser Ser Thr
1               5

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asn Ile Asn Tyr Asp Gly Ser Ser Thr Phe Tyr Ala Asp Ser Leu Lys
1               5                   10                  15
Gly

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Ile Asn Tyr Asp Gly Ser Ser Thr Phe Tyr Ala Asp Ser Leu Lys
1               5                   10                  15
Gly

<210> SEQ ID NO 81
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Arg Gln Val Gly Tyr Tyr Asp Pro Met Asp Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Val Gly Tyr Tyr Asp Pro Met Asp Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Val Gly Tyr Tyr Asp Pro Met Asp Tyr
1               5                   10

<210> SEQ ID NO 84
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser His Met
                20                  25                  30

Tyr Trp Tyr Gln Gln Lys Pro Gly Lys Ala Pro Lys Pro Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Met Gln Pro Glu
65                  70                  75                  80

Asp Phe Ala Thr Tyr Tyr Cys Gln Gln Tyr His Ser Tyr Pro Leu Thr
                85                  90                  95

Phe Gly Gln Gly Thr Lys Leu Glu Ile Lys
            100                 105

<210> SEQ ID NO 85
<211> LENGTH: 318
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 85

```
gacatccagc tgacccagtc ccccagctct ttatccgcta gcgtgggcga tagggtgacc    60
atcacttgtc gtgcgtcttc gtctgtgtct catatgtact ggtaccagca gaagcccggc   120
aaggccccca agccttggat ctatcgtaca tccaatcttg caagcggcgt cccttctcgt   180
ttttctggtt ccgggtctgg taccgactac actttaacca tcagcagcat gcagcccgag   240
gacttcgcca cctactactg ccagcagtat cactcctatc ctttaacttt tggccaagga   300
acaaagttgg agatcaag                                                 318
```

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Ser Val Ser His
1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ala Ser Ser Ser Val Ser His Met Tyr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ala Ser Ser Ser Val Ser His Met Tyr
1               5                   10

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Thr Ser
1

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Arg Thr Ser Asn Leu Ala Ser
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Thr Ser Asn Leu Ala Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Tyr His Ser Tyr Pro Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Tyr His Ser Tyr Pro Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Tyr His Ser Tyr Pro Leu Thr
1               5

<210> SEQ ID NO 95
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser His Met
            20                  25                  30

```
Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
 50                  55                  60

Gly Ser Gly Thr Asp Tyr Thr Leu Thr Ile Ser Ser Met Gln Pro Glu
65                  70                  75                  80

Asp Phe Ala Thr Tyr Tyr Cys Gln Gln Tyr His Ser Tyr Pro Leu Thr
                85                  90                  95

Phe Gly Gln Gly Thr Lys Leu Glu Ile Lys Gly Ser Thr Ser Gly Ser
            100                 105                 110

Gly Lys Pro Gly Ser Gly Glu Gly Ser Thr Lys Gly Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Thr Phe Ser Asp Tyr Tyr Met Ala Trp
145                 150                 155                 160

Val Arg Gln Ala Pro Gly Lys Gly Leu Glu Trp Val Ala Asn Ile Asn
                165                 170                 175

Tyr Asp Gly Ser Ser Thr Phe Tyr Ala Asp Ser Leu Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Gly Arg Gln Val
210                 215                 220

Gly Tyr Tyr Asp Pro Met Asp Tyr Trp Gly Gln Gly Thr Thr Val Thr
225                 230                 235                 240

Val Ser Ser

<210> SEQ ID NO 96
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gacatccagc tgacccagtc ccccagctct ttatccgcta gcgtgggcga tagggtgacc      60
atcacttgtc gtgcgtcttc gtctgtgtct catatgtact ggtaccagca gaagcccggc    120
aaggccccca agccttggat ctatcgtaca tccaatcttg caagcggcgt cccttctcgt    180
ttttctggtt ccgggtctgg taccgactac actttaacca tcagcagcat gcagcccgag    240
gacttcgcca cctactactg ccagcagtat cactcctatc ctttaacttt tggccaagga    300
acaaagttgg agatcaaggg cagcacctcc ggtagcggaa agcccggtag cggcgagggc    360
agcaccaagg gagaggtgca gttggtggag agcggaggag gactggtgca gcccggtggc    420
tctttaagac tcagctgtgc cgccagcgga tttacattct ccgactacta catggcttgg    480
gtccgacaag cccccggaaa aggtttagag tgggtggcca acatcaacta cgacggctcc    540
tccacattct acgccgactc tttaaagggt cgtttcacca tctctcgtga caacagcaaa    600
aatactttat atttacaaat gaactcttta agggccgagg acaccgccgt gtactactgc    660
ggtcgtcaag ttggctatta cgaccccatg gactactggg gccaaggaac taccgtgacc    720
gtgagcagc                                                             729
```

<210> SEQ ID NO 97
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
        35                  40                  45

Gly Asn Ile Asn Pro Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 98
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gaagttcaac ttgtgcaaag cggggcagaa gtgaaaaaac ccggggcgag cgttaaaata      60
tcttgtaaaa caagtggcta caccttcacg gagtacacca tccactgggt taaacaagct    120
tctggaaagg gacttgaatg gatcgggaac ataaacccca acaatggggg cactacttat    180
aatcaaaagt ttgaggatcg ggctacccct acagtggata gtccacctc cacagcttat     240 atggaattga gtagccttag gagcgaggat acagccgttt attattgtgc ggcgggctgg    300
aactttgact attgggggca agggacgacg gtgacggtgt cctcc                    345

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Tyr Thr Phe Thr Glu Tyr Thr
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Glu Tyr Thr Ile His
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Tyr Thr Phe Thr Glu
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Asn Pro Asn Asn Gly Gly Thr
1               5

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Ile Asn Pro Asn Asn Gly Gly Thr Thr Tyr Asn Gln Lys Phe Glu
1               5                   10                  15

Asp

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Ile Asn Pro Asn Asn Gly Gly Thr Thr Tyr Asn Gln Lys Phe Glu
1               5                   10                  15

Asp

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Ala Gly Trp Asn Phe Asp Tyr

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Trp Asn Phe Asp Tyr
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Trp Asn Phe Asp Tyr
1               5

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 109
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gacattgtga tgactcagtc tccttcttct ctttccgctt ccgttgggga ccgcgtcact    60
ataacttgta aagcgtccca agatgtcggc accgccgttg actggtacca gcaaaaaccc   120
gggaaagcgc cgaaactgct catctactgg gcttcaaccc gccacacggg tgtcccggac   180

```
cggtttacgg ggagcggtag tggaaccgat tcactctga ccatttcctc ccttcaaccg    240
gaagatttcg ctgactactt tgtcaacaa tataattcat atcccctcac tttcggaggg    300
ggcacgaagt tggaaataaa g                                              321
```

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Asp Val Gly Thr Ala
1               5

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Ala Ser Gln Asp Val Gly Thr Ala Val Asp
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Ala Ser Gln Asp Val Gly Thr Ala Val Asp
1               5                   10

<210> SEQ ID NO 113
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Ala Ser
1

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Trp Ala Ser Thr Arg His Thr
1               5

<210> SEQ ID NO 115
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Trp Ala Ser Thr Arg His Thr
1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Tyr Asn Ser Tyr Pro Leu Thr Phe
1               5                   10

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Tyr Asn Ser Tyr Pro Leu Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Gln Tyr Asn Ser Tyr Pro Leu Thr
1               5

<210> SEQ ID NO 119
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Val Met Thr Gln Ser Pro Ser Leu Ser Ala Ser Val Gly
1               5                   10                  15

Asp Arg Val Thr Ile Thr Cys Lys Ala Ser Gln Asp Val Gly Thr Ala
                20                  25                  30

Val Asp Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Ser Leu Gln Pro
65                  70                  75                  80
```

Glu Asp Phe Ala Asp Tyr Phe Cys Gln Gln Tyr Asn Ser Tyr Pro Leu
            85                  90                  95

Thr Phe Gly Gly Gly Thr Lys Leu Glu Ile Lys Gly Ser Thr Ser Gly
        100                 105                 110

Ser Gly Lys Pro Gly Ser Gly Glu Ser Thr Lys Gly Glu Val Gln
        115                 120                 125

Leu Val Gln Ser Gly Ala Glu Val Lys Lys Pro Gly Ala Ser Val Lys
        130                 135                 140

Ile Ser Cys Lys Thr Ser Gly Tyr Thr Phe Thr Glu Tyr Thr Ile His
145                 150                 155                 160

Trp Val Lys Gln Ala Ser Gly Lys Gly Leu Glu Trp Ile Gly Asn Ile
                165                 170                 175

Asn Pro Asn Asn Gly Gly Thr Thr Tyr Asn Gln Lys Phe Glu Asp Arg
                180                 185                 190

Ala Thr Leu Thr Val Asp Lys Ser Thr Ser Thr Ala Tyr Met Glu Leu
        195                 200                 205

Ser Ser Leu Arg Ser Glu Asp Thr Ala Val Tyr Tyr Cys Ala Ala Gly
        210                 215                 220

Trp Asn Phe Asp Tyr Trp Gly Gln Gly Thr Thr Val Thr Val Ser Ser
225                 230                 235                 240

<210> SEQ ID NO 120
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gacattgtga tgactcagtc tccttcttct ctttccgctt ccgttgggga ccgcgtcact      60
ataacttgta aagcgtccca agatgtcggc accgccgttg actggtacca gcaaaaaccc    120
gggaaagcgc cgaaactgct catctactgg gcttcaaccc gccacacggg tgtcccggac    180
cggtttacgg ggagcggtag tggaaccgat ttcactctga ccatttcctc ccttcaaccg    240
gaagatttcg ctgactactt tgtcaacaa tataattcat atcccctcac tttcggaggg    300
ggcacgaagt tggaaataaa gggtagcacc tctggtagcg gcaagcctgg ctctggcgag    360
ggtagtacca aggagaagt tcaacttgtg caaagcgggg cagaagtgaa aaaacccggg    420
gcgagcgtta aatatcttg taaaacaagt ggctacacct tcacggagta ccatccac      480 tgggttaaac aagcttctgg aaagggactt gaatggatcg gaaacataaa ccccaacaat    540
gggggcacta cttataatca aaagtttgag gatcgggcta ccctcacagt ggataagtcc    600
acctccacag cttatatgga attgagtagc cttaggagcg aggatacagc cgtttattat    660
tgtgcggcgg gctggaactt tgactattgg gggcaaggga cgacggtgac ggtgtcctcc    720

<210> SEQ ID NO 121
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Ser
1

```
<210> SEQ ID NO 122
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122 ggatcc                                                                    6

<210> SEQ ID NO 123
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123 gggtcc                                                                    6

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Gly Ser Gly Gly Gly Ser
1               5

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggcggtggaa gcggaggagg ttcc                                               24

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ser Thr Ser Gly Ser Gly Lys Pro Gly Ser Gly Glu Gly Ser Thr
1               5                   10                  15

Lys Gly

<210> SEQ ID NO 127
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
```

```
ggctccacct ccggaagcgg caaacccggt agcggcgagg gctccacaaa gggc       54
```

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Ile Glu Ala Val Lys Ser Glu
1               5

<210> SEQ ID NO 129
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 130
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
accacgacgc cagcgccgcg accaccaaca ccggcgccca ccatcgcgtc gcaaccsctg     60
tccctgcgcc ccgaggcgtg ccggccagcg gcggggggcg cagtgcacac gaggggggctg   120 gacttcgcct gtgat                                                    135
```

<210> SEQ ID NO 131
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 132
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

```
atctacatct gggcgcccct ggccgggact tgtggggtcc ttctcctgtc actggttatc    60 acccttat gc                                                          72
```

<210> SEQ ID NO 133
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 134
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
ttgagagtga agttcagcag gagcgcagac gcccccgcct atcagcaagg ccagaaccag    60
ctctataacg agctcaattt agggcgaaga gaggagtacg atgttttgga caagaggcgt   120
ggccgggacc ccgaaatggg gggaaagccg agaaggaaga accctcagga aggcttgtac   180
aatgaattgc agaaggataa gatggcggag gcatacagtg agattgggat gaaaggcgag   240
cgccggaggg gcaaggggca cgatggcctt tatcagggtc tcagtacagc caccaaggac   300
acctacgacg cccttcacat gcaagccctg ccccctcgc                           339
```

<210> SEQ ID NO 135
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
```

```
                    20                  25                  30

Pro Glu Glu Glu Glu Gly Gly Cys Glu
            35                  40

<210> SEQ ID NO 136
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
aaacggggca gaaagaaact cctgtatata ttcaaacaac catttatgag accagtacaa    60
actactcaag aggaagatgg ctgtagctgc cgatttccag aagaagaaga aggaggatgt   120
gaa                                                                 123

<210> SEQ ID NO 137
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Met Glu Trp Thr Trp Val Phe Leu Phe Leu Leu Ser Val Thr Ala Gly
1               5                   10                  15

Val His Ser

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Met Ala Leu Pro Val Thr Ala Leu Leu Leu Pro Leu Ala Leu Leu Leu
1               5                   10                  15

His Ala Ala Arg Pro
            20

<210> SEQ ID NO 140
<211> LENGTH: 469
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 140

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser His Ile
            20                  25                  30

Tyr Trp Tyr Gln Gln Lys Pro Gly Lys Ala Pro Lys Pro Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr His Thr Tyr Pro Pro Thr
                85                  90                  95

Phe Gly Gln Gly Thr Lys Leu Glu Ile Lys Gly Ser Thr Ser Gly Ser
            100                 105                 110

Gly Lys Pro Gly Ser Gly Glu Gly Ser Thr Lys Gly Glu Val Gln Leu
        115                 120                 125

Val Glu Ser Gly Gly Gly Leu Val Gln Pro Gly Gly Ser Met Arg Leu
130                 135                 140

Ser Cys Ala Ala Ser Gly Phe Thr Phe Ser Asp Tyr Tyr Met Ala Trp
145                 150                 155                 160

Val Arg Gln Ala Pro Gly Lys Gly Leu Glu Trp Ile Ala Asn Ile Asn
                165                 170                 175

Tyr Asp Gly Ser Asn Thr Tyr Tyr Ala Asp Ser Leu Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Arg Asn Trp
210                 215                 220

Asp Gly Tyr Tyr Gly Tyr Phe Asp Val Trp Gly Gln Gly Thr Thr Val
225                 230                 235                 240

Thr Val Ser Ser Gly Ser Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
            340                 345                 350

Gly Gly Cys Glu Leu Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
370                 375                 380

Arg Arg Glu Glu Tyr Asp Val Leu Asp Lys Arg Arg Gly Arg Asp Pro
385                 390                 395                 400
```

```
Glu Met Gly Gly Lys Pro Arg Arg Lys Asn Pro Gln Glu Gly Leu Tyr
            405                 410                 415

Asn Glu Leu Gln Lys Asp Lys Met Ala Glu Ala Tyr Ser Glu Ile Gly
        420                 425                 430

Met Lys Gly Glu Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 141
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gatatccagc tgacccagtc cccttcctct ctgtctgcgt ctgttggcga tcgtgtcacc      60
atcacttgtc gtgccagcag cagcgtgagc cacatttatt ggtaccaaca aaagcccggc     120
aaagccccta agccttggat ctacagaacc tccaatctgg ccagcggcgt gcccagcaga     180
ttcagcggaa gcggatccgg caccgactac acttttaacca tcagctcttt acagcccgag     240
gacttcgcca catactactg ccagcagtac cacacctatc cccccacatt cggccaagga     300
acaaagctgg agattaaggg ctccacctcc ggaagcggca aacccggtag cggcgagggc     360
tccacaaagg gcgaggtgca acttgtggag agcggaggag gtttagtgca acccggaggc     420
agcatgagac tgagctgcgc cgccagcggc ttcacattct ccgactacta catggcttgg     480
gtccgacaag ctcccggaaa aggactggag tggatcgcca acatcaacta cgacggctcc     540
aacacctact acgccgactc tttaaagggt cgtttcacaa tctctcgtga caacagcaag     600
aacactttat atttacaaat gaactcttta agggccgagg ataccgccgt gtactactgc     660
gctcgtaact gggacggcta ctacggctac ttcgacgtgt ggggccaagg aaccaccgtg     720
accgtgagca gcgggtccac cacgacgcca gcgccgcgac caccaacacc ggcgcccacc     780
atcgcgtcgc aaccctgtc cctgcgcccc gaggcgtgcc ggccagcggc gggggcgca     840
gtgcacacga gggggctgga cttcgcctgt gatatctaca tctgggcgcc cttggccggg     900
acttgtgggg tccttctcct gtcactggtt atcacccttt attgcaaacg ggcagaaaag     960
aaactcctgt atatattcaa acaaccattt atgagaccag tacaaactac tcaagaggaa    1020
gatggctgta gctgccgatt tccagaagaa gaagaaggag gatgtgaatt gagagtgaag    1080
ttcagcagga gcgcagacgc ccccgcctat cagcaaggcc agaaccagct ctataacgag    1140
ctcaatttag gcgaagaga ggagtacgat gttttggaca gaggcgtgg ccgggacccc    1200
gaaatggggg gaaagccgag aaggaagaac cctcaggaag gcttgtacaa tgaattgcag    1260
aaggataaga tggcggaggc atacagtgag attgggatga aggcgagcg ccggagggc    1320
aaggggcacg atggcctta tcagggtctc agtacagcca ccaaggacac ctacgacgcc    1380
cttcacatgc aagccctgcc ccctcgc                                       1407

<210> SEQ ID NO 142
<211> LENGTH: 470
<212> TYPE: PRT
<213> ORGANISM: Artificial Sequence
```

-continued

<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Asn Val Asn Thr Asn
            20                  25                  30

Val Ala Trp Tyr Gln Gln Lys Pro Gly Lys Ala Pro Lys Val Leu Ile
        35                  40                  45

Tyr Ser Ala Ser Tyr Arg Asn Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Gln Gly Thr Lys Leu Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ala Ser Val Lys
130                 135                 140

Leu Ser Cys Lys Ala Ser Gly Tyr Thr Phe Thr Thr Tyr Trp Met His
145                 150                 155                 160

Trp Val Arg Gln Ala Pro Gly Gln Gly Leu Glu Trp Ile Gly Met Ile
                165                 170                 175

His Pro Asn Ser Gly Ser Thr Asn Tyr Ala Gln Lys Phe Gln Gly Arg
            180                 185                 190

Ala Thr Leu Thr Val Asp Thr Ser Thr Ser Thr Ala Tyr Met Glu Leu
        195                 200                 205

Ser Ser Leu Arg Ser Glu Asp Thr Ala Val Tyr Tyr Cys Ala Arg Asp
    210                 215                 220

Pro Tyr Asp Tyr Gly Glu Asp Phe Asp Val Trp Gly Gln Gly Thr Thr
225                 230                 235                 240

Val Thr Val Ser Ser Gly Ser Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp

```
385                 390                 395                 400
Pro Glu Met Gly Gly Lys Pro Arg Arg Lys Asn Pro Gln Glu Gly Leu
                405                 410                 415
Tyr Asn Glu Leu Gln Lys Asp Lys Met Ala Glu Ala Tyr Ser Glu Ile
            420                 425                 430
Gly Met Lys Gly Glu Arg Arg Arg Gly Lys Gly His Asp Gly Leu Tyr
        435                 440                 445
Gln Gly Leu Ser Thr Ala Thr Lys Asp Thr Tyr Asp Ala Leu His Met
    450                 455                 460
Gln Ala Leu Pro Pro Arg
465                 470

<210> SEQ ID NO 143
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gacatccaga tgacccagag ccccagctct ttaagtgcca gcgtgggcga cagagtgaca        60
gtgacttgtc gtgccagcca gaacgtgaat accaacgtgg cttggtacca gcagaagccc       120
ggcaaagccc ctaaggtgct gatctattcc gcgtcttatc gtaactccgg cgtgccttcg       180 cgttttttctg ggtctggtag cggcaccgac ttcacttaa caatcagcag cgttcagccc       240
gaagacttcg ccacctacta ctgccagcag tacaacagct atccctttac tttcggtcaa       300
gggaccaagc tcgagatcaa aggctccacc agcggtagcg gcaaacccgg ttccggcgag       360
ggctctacca agggccaagt gcagctggtg cagtccggcg ccgaggtgaa gaagcccggt       420
gcttccgtga agctgtcttg caaagccagc ggctacacct tcaccaccta ttggatgcac       480
tgggtccgac aagctcccgg tcaaggtctg gagtggattg gcatgatcca ccccaactcc       540
ggctccacca actacgccca agttccaa gtcgtgcca ctttaacagt ggataccagc       600
accagcaccg cctacatgga gctgagtagt ttgaggagcg aggacaccgc cgtgtactat       660
tgcgctcgtg accctacga ctacggcgag gacttcgacg tgtgggcca aggaacaaca       720 gtgaccgtga gcagcgggtc caccacgacg ccagcgccgc gaccaccaac accggcgccc       780
accatcgcgt cgcaacccct gtccctgcgc ccgaggcgt gccggccagc ggcgggggggc       840 gcagtgcaca cgagggggct ggacttcgcc tgtgatatct acatctgggc gcccttggcc       900
gggacttgtg gggtccttct cctgtcactg gttatcaccc tttattgcaa acggggcaga       960
aagaaactcc tgtatatatt caaacaacca tttatgagac cagtacaaac tactcaagag      1020
gaagatggct gtagctgccg atttccagaa gaagaagaag gaggatgtga attgagagtg      1080
aagttcagca ggagcgcaga cgccccgcc tatcagcaag ccagaaccag ctctataac      1140 gagctcaatt tagggcgaag agaggagtac gatgttttgg acaagaggcg tggccggac      1200 cccgaaatgg ggggaaagcc gagaaggaag aaccctcagg aaggcttgta caatgaattg      1260
cagaaggata gatggcggga ggcatacagt gagattggga tgaaaggcga gcgcggaggg      1320
ggcaaggggc acgatggcct ttatcagggt ctcagtacag ccaccaagga cacctacgac      1380
gcccttcaca tgcaagccct gccccctcgc                                       1410

<210> SEQ ID NO 144
<211> LENGTH: 470
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144
```

| | | | | | | | | | | | | | | | |
|---|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly|
|1| | | |5| | | | |10| | | | |15| |

| | | | | | | | | | | | | | | | |
|---|---|---|---|---|---|---|---|---|---|---|---|---|---|---|---|
|Ser|Met|Arg|Leu|Ser|Cys|Ala|Ala|Ser|Gly|Phe|Thr|Phe|Ser|Asp|Tyr|
| | | |20| | | | |25| | | | |30| | |

| | | | | | | | | | | | | | | | |
|---|---|---|---|---|---|---|---|---|---|---|---|---|---|---|---|
|Tyr|Met|Ala|Trp|Val|Arg|Gln|Ala|Pro|Gly|Lys|Gly|Leu|Glu|Trp|Val|
| | |35| | | | |40| | | | |45| | | |

| | | | | | | | | | | | | | | | |
|---|---|---|---|---|---|---|---|---|---|---|---|---|---|---|---|
|Ala|Asn|Ile|Asn|Tyr|Asp|Gly|Thr|Ser|Thr|Tyr|Ala|Asp|Ser|Leu|
| |50| | | | |55| | | | |60| | | | |

| | | | | | | | | | | | | | | | |
|---|---|---|---|---|---|---|---|---|---|---|---|---|---|---|---|
|Lys|Gly|Arg|Phe|Thr|Ile|Ser|Arg|Asp|Ser|Lys|Asn|Thr|Leu|Tyr|
|65| | | | |70| | | | |75| | | | |80|

| | | | | | | | | | | | | | | | |
|---|---|---|---|---|---|---|---|---|---|---|---|---|---|---|---|
|Leu|Gln|Met|Asn|Ser|Leu|Arg|Ala|Glu|Asp|Thr|Ala|Val|Tyr|Tyr|Cys|
| | | | |85| | | | |90| | | | |95| |

| | | | | | | | | | | | | | | | |
|---|---|---|---|---|---|---|---|---|---|---|---|---|---|---|---|
|Ala|Arg|Ala|Leu|Asp|Gly|Tyr|Tyr|Gly|Tyr|Leu|Asp|Val|Trp|Gly|Gln|
| | | |100| | | | |105| | | | |110| | |

| | | | | | | | | | | | | | | | |
|---|---|---|---|---|---|---|---|---|---|---|---|---|---|---|---|
|Gly|Thr|Thr|Val|Thr|Val|Ser|Ser|Gly|Ser|Thr|Ser|Gly|Ser|Gly|Lys|
| | |115| | | | |120| | | | |125| | | |

| | | | | | | | | | | | | | | | |
|---|---|---|---|---|---|---|---|---|---|---|---|---|---|---|---|
|Pro|Gly|Ser|Gly|Glu|Gly|Ser|Thr|Lys|Gly|Asp|Ile|Gln|Leu|Thr|Gln|
| |130| | | | |135| | | | |140| | | | |

| | | | | | | | | | | | | | | | |
|---|---|---|---|---|---|---|---|---|---|---|---|---|---|---|---|
|Ser|Pro|Ser|Ser|Leu|Ser|Ala|Ser|Val|Gly|Asp|Arg|Val|Thr|Leu|Thr|
|145| | | | |150| | | | |155| | | | |160|

| | | | | | | | | | | | | | | | |
|---|---|---|---|---|---|---|---|---|---|---|---|---|---|---|---|
|Cys|Arg|Ala|Ser|Gln|Ser|Ile|Ser|Asn|Asn|Leu|His|Trp|Tyr|Gln|Gln|
| | | | |165| | | | |170| | | | |175| |

| | | | | | | | | | | | | | | | |
|---|---|---|---|---|---|---|---|---|---|---|---|---|---|---|---|
|Lys|Pro|Gly|Lys|Ala|Pro|Lys|Leu|Leu|Ile|Lys|Tyr|Val|Ser|Gln|Ser|
| | | |180| | | | |185| | | | |190| | |

| | | | | | | | | | | | | | | | |
|---|---|---|---|---|---|---|---|---|---|---|---|---|---|---|---|
|Ile|Ser|Gly|Ile|Pro|Ser|Arg|Phe|Ser|Gly|Ser|Gly|Leu|Gly|Thr|Asp|
| | |195| | | | |200| | | | |205| | | |

| | | | | | | | | | | | | | | | |
|---|---|---|---|---|---|---|---|---|---|---|---|---|---|---|---|
|Phe|Thr|Leu|Thr|Ile|Ser|Ser|Val|Gln|Pro|Glu|Asp|Phe|Ala|Thr|Tyr|
| |210| | | | |215| | | | |220| | | | |

| | | | | | | | | | | | | | | | |
|---|---|---|---|---|---|---|---|---|---|---|---|---|---|---|---|
|Tyr|Cys|Gln|Gln|Ser|Asn|Ser|Trp|Pro|Tyr|Thr|Phe|Gly|Gln|Gly|Thr|
|225| | | | |230| | | | |235| | | | |240|

| | | | | | | | | | | | | | | | |
|---|---|---|---|---|---|---|---|---|---|---|---|---|---|---|---|
|Lys|Leu|Glu|Ile|Lys|Gly|Ser|Thr|Thr|Thr|Pro|Ala|Pro|Arg|Pro|Pro|
| | | | |245| | | | |250| | | | |255| |

| | | | | | | | | | | | | | | | |
|---|---|---|---|---|---|---|---|---|---|---|---|---|---|---|---|
|Thr|Pro|Ala|Pro|Thr|Ile|Ala|Ser|Gln|Pro|Leu|Ser|Leu|Arg|Pro|Glu|
| | | |260| | | | |265| | | | |270| | |

| | | | | | | | | | | | | | | | |
|---|---|---|---|---|---|---|---|---|---|---|---|---|---|---|---|
|Ala|Cys|Arg|Pro|Ala|Ala|Gly|Gly|Ala|Val|His|Thr|Arg|Gly|Leu|Asp|
| | |275| | | | |280| | | | |285| | | |

| | | | | | | | | | | | | | | | |
|---|---|---|---|---|---|---|---|---|---|---|---|---|---|---|---|
|Phe|Ala|Cys|Asp|Ile|Tyr|Ile|Trp|Ala|Pro|Leu|Ala|Gly|Thr|Cys|Gly|
| |290| | | | |295| | | | |300| | | | |

| | | | | | | | | | | | | | | | |
|---|---|---|---|---|---|---|---|---|---|---|---|---|---|---|---|
|Val|Leu|Leu|Leu|Ser|Leu|Val|Ile|Thr|Leu|Tyr|Cys|Lys|Arg|Gly|Arg|
|305| | | | |310| | | | |315| | | | |320|

| | | | | | | | | | | | | | | | |
|---|---|---|---|---|---|---|---|---|---|---|---|---|---|---|---|
|Lys|Lys|Leu|Leu|Tyr|Ile|Phe|Lys|Gln|Pro|Phe|Met|Arg|Pro|Val|Gln|
| | | | |325| | | | |330| | | | |335| |

| | | | | | | | | | | | | | | | |
|---|---|---|---|---|---|---|---|---|---|---|---|---|---|---|---|
|Thr|Thr|Gln|Glu|Glu|Asp|Gly|Cys|Ser|Cys|Arg|Phe|Pro|Glu|Glu|Glu|
| | | |340| | | | |345| | | | |350| | |

| | | | | | | | | | | | | | | | |
|---|---|---|---|---|---|---|---|---|---|---|---|---|---|---|---|
|Glu|Gly|Gly|Cys|Glu|Leu|Arg|Val|Lys|Phe|Ser|Arg|Ser|Ala|Asp|Ala|
| | |355| | | | |360| | | | |365| | | |

| | | | | | | | | | | | | | | | |
|---|---|---|---|---|---|---|---|---|---|---|---|---|---|---|---|
|Pro|Ala|Tyr|Gln|Gln|Gly|Gln|Asn|Gln|Leu|Tyr|Asn|Glu|Leu|Asn|Leu|
| |370| | | | |375| | | | |380| | | | |

```
Gly Arg Arg Glu Glu Tyr Asp Val Leu Asp Lys Arg Gly Arg Asp
385                 390                 395                 400

Pro Glu Met Gly Gly Lys Pro Arg Arg Lys Asn Pro Gln Glu Gly Leu
            405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465             470

<210> SEQ ID NO 145
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
```

| | | | | | |
|---|---|---|---|---|---|
| gaggtgcagc | tggtggagtc | cggaggaggt | ttagtccaac | ccggtggcag | catgaggctg | 60 |
| tcttgtgctg | cctccggctt | cacttttct | gattactaca | tggcttgggt | ccgacaagct | 120 |
| cccggaaaag | gtttagagtg | ggtggctaac | atcaactacg | acggcaccag | cacctactat | 180 |
| gccgacagcc | tcaagggcag | attcaccatc | tctcgtgatt | cgtctaaaaa | cactttatat | 240 |
| ttacaaatga | actctttaag | agccgaagat | accgccgtgt | actattgcgc | tcgtgccctc | 300 |
| gacggctact | acgatatttt | agacgtgtgg | ggtcaaggaa | caaccgtgac | cgtgtccagc | 360 |
| ggatccacct | ccggaagcgg | caaacccggt | agcggcgaag | gcagcaccaa | aggagacatc | 420 |
| cagctgaccc | agagccctag | ctcttttaagc | gctagcgtgg | gcgataggt | gactctgact | 480 |
| tgtcgtgcgt | cccaaagcat | tagcaacaat | ttacactggt | accagcagaa | gcccggaaaa | 540 |
| gcccccaagc | tgctgatcaa | atatgtgagc | cagagcatct | ccggcatccc | ctctcgtttt | 600 |
| tctggtagcg | gactgggcac | cgactttact | ttaaccatca | gcagcgtcca | gcccgaggac | 660 |
| ttcgccacat | actactgcca | gcagagcaac | agctggccct | atactttcgg | ccaaggaaca | 720 |
| aagctggaga | tcaaggggtc | caccacgacg | ccagcgccgc | gaccaccaac | accggcgccc | 780 |
| accatcgcgt | cgcaacccct | gtccctgcgc | ccgaggcgt | gccggccagc | ggcgggggc | 840 |
| gcagtgcaca | cgagggggct | ggacttcgcc | tgtgatatct | acatctgggc | gcccttggcc | 900 |
| gggacttgtg | gggtccttct | cctgtcactg | gttatcaccc | tttattgcaa | acggggcaga | 960 |
| aagaaactcc | tgtatatatt | caaacaacca | tttatgagac | cagtacaaac | tactcaagag | 1020 |
| gaagatggct | gtagctgccg | atttccagaa | gaagaagaag | gaggatgtga | attgagagtg | 1080 |
| aagttcagca | ggagcgcaga | cgcccccgcc | tatcagcaag | ccagaaccca | gctctataac | 1140 |
| gagctcaatt | tagggcgaag | agaggagtac | gatgttttgg | acaagaggcg | tggccgggac | 1200 |
| cccgaaatgg | ggggaaagcc | gagaaggaag | aaccctcagg | aaggcttgta | caatgaattg | 1260 |
| cagaaggata | agatggcgga | ggcatacagt | gagattggga | tgaaaggcga | gcgccggagg | 1320 |
| ggcaaggggc | acgatggcct | ttatcagggt | ctcagtacag | ccaccaagga | cacctacgac | 1380 |
| gcccttcaca | tgcaagccct | gccccctcgc | | | | 1410 |

```
<210> SEQ ID NO 146
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Gln Ser Gly Ala Glu Val Lys Lys Pro Gly Ala Ser Val Lys
130                 135                 140

Ile Ser Cys Lys Thr Ser Gly Tyr Thr Phe Thr Glu Tyr Thr Ile His
145                 150                 155                 160

Trp Val Lys Gln Ala Ser Gly Lys Gly Leu Glu Trp Ile Gly Asn Ile
                165                 170                 175

Asn Pro Asn Asn Gly Gly Thr Thr Tyr Asn Gln Lys Phe Glu Asp Arg
            180                 185                 190

Ala Thr Leu Thr Val Asp Lys Ser Thr Ser Thr Ala Tyr Met Glu Leu
        195                 200                 205

Ser Ser Leu Arg Ser Glu Asp Thr Ala Val Tyr Tyr Cys Ala Ala Gly
    210                 215                 220

Trp Asn Phe Asp Tyr Trp Gly Gln Gly Thr Thr Val Thr Val Ser Ser
225                 230                 235                 240

Gly Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Gln Gln
        355                 360                 365
```

```
Gly Gln Asn Gln Leu Tyr Asn Glu Leu Asn Leu Gly Arg Arg Glu Glu
    370                 375                 380
Tyr Asp Val Leu Asp Lys Arg Arg Gly Arg Asp Pro Glu Met Gly Gly
385                 390                 395                 400
Lys Pro Arg Arg Lys Asn Pro Gln Glu Gly Leu Tyr Asn Glu Leu Gln
                    405                 410                 415
Lys Asp Lys Met Ala Glu Ala Tyr Ser Glu Ile Gly Met Lys Gly Glu
                420                 425                 430
Arg Arg Arg Gly Lys Gly His Asp Gly Leu Tyr Gln Gly Leu Ser Thr
                435                 440                 445
Ala Thr Lys Asp Thr Tyr Asp Ala Leu His Met Gln Ala Leu Pro Pro
    450                 455                 460
Arg
465

<210> SEQ ID NO 147
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
```

| | | | | | |
|---|---|---|---|---|---|
| gacattgtga | tgactcagtc | tccttcttct | ctttccgctt | ccgttgggga | ccgcgtcact | 60 |
| ataacttgta | aagcgtccca | agatgtcggc | accgccgttg | actggtacca | gcaaaaaccc | 120 |
| gggaaagcgc | cgaaactgct | catctactgg | gcttcaaccc | gccacacggg | tgtcccggac | 180 |
| cggtttacgg | ggagcggtag | tggaaccgat | ttcactctga | ccatttcctc | ccttcaaccg | 240 |
| gaagatttcg | ctgactactt | tgtcaacaa | tataattcat | atcccctcac | tttcggaggg | 300 |
| ggcacgaagt | tggaaataaa | gggtagcacc | tctggtagcg | gcaagcctgg | ctctggcgag | 360 |
| ggtagtacca | aggagaagt | tcaacttgtg | caaagcgggg | cagaagtgaa | aaaacccggg | 420 |
| gcgagcgtta | aaatatcttg | taaaacaagt | ggctacacct | tcacggagta | caccatccac | 480 |
| tgggttaaac | aagcttctgg | aaagggactt | gaatggatcg | gaacataaa | ccccaacaat | 540 |
| gggggcacta | cttataatca | aaagtttgag | gatcgggcta | ccctcacagt | ggataagtcc | 600 |
| acctccacag | cttatatgga | attgagtagc | cttaggagcg | aggatacagc | cgtttattat | 660 |
| tgtgcggcgg | gctggaactt | tgactattgg | gggcaaggga | cgacggtgac | ggtgtcctcc | 720 |
| gggtccacca | cgacgccagc | gccgcgacca | ccaacaccgg | cgcccaccat | cgcgtcgcaa | 780 |
| ccccctgtccc | tgcgccccga | ggcgtgccgg | ccagcggcgg | ggggcgcagt | gcacacgagg | 840 |
| gggctggact | tcgcctgtga | tatctacatc | tgggcgccct | tggccgggac | ttgtggggtc | 900 |
| cttctcctgt | cactggttat | caccctttat | tgcaaacggg | gcagaaagaa | actcctgtat | 960 |
| atattcaaac | aaccatttat | gagaccagta | caaactactc | aagaggaaga | tggctgtagc | 1020 |
| tgccgatttc | cagaagaaga | agaaggagga | tgtgaattga | gagtgaagtt | cagcaggagc | 1080 |
| gcagacgccc | ccgcctatca | gcaaggccag | aaccagctct | ataacgagct | caatttaggg | 1140 |
| cgaagagagg | agtacgatgt | tttggacaag | aggcgtggcc | gggaccccga | aatgggggga | 1200 |
| aagccgagaa | ggaagaaccc | tcaggaaggc | ttgtacaatg | aattgcagaa | ggataagatg | 1260 |
| gcggaggcat | acagtgagat | tgggatgaaa | ggcgagcgcc | ggagggggcaa | ggggcacgat | 1320 |
| ggcctttatc | agggtctcag | tacagccacc | aaggacacct | acgacgccct | tcacatgcaa | 1380 |
| gccctgcccc | ctcgc | | | | | 1395 |

<210> SEQ ID NO 148
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser His Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Met Gln Pro Glu
65                  70                  75                  80

Asp Phe Ala Thr Tyr Tyr Cys Gln Gln Tyr His Ser Tyr Pro Leu Thr
                85                  90                  95

Phe Gly Gln Gly Thr Lys Leu Glu Ile Lys Gly Ser Thr Ser Gly Ser
            100                 105                 110

Gly Lys Pro Gly Ser Gly Glu Gly Ser Thr Lys Gly Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Thr Phe Ser Asp Tyr Tyr Met Ala Trp
145                 150                 155                 160

Val Arg Gln Ala Pro Gly Lys Gly Leu Glu Trp Val Ala Asn Ile Asn
                165                 170                 175

Tyr Asp Gly Ser Ser Thr Phe Tyr Ala Asp Ser Leu Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Gly Arg Gln Val
    210                 215                 220

Gly Tyr Tyr Asp Pro Met Asp Tyr Trp Gly Gln Gly Thr Thr Val Thr
225                 230                 235                 240

Val Ser Ser Gly Ser Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
```

```
          355                 360                 365
Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
                420                 425                 430

Lys Gly Glu Arg Arg Arg Gly Lys Gly His Asp Gly Leu Tyr Gln Gly
                435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 149
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
```

| | | |
|---|---|---|
| gacatccagc tgacccagtc ccccagctct ttatccgcta gcgtgggcga tagggtgacc | 60 |
| atcacttgtc gtgcgtcttc gtctgtgtct catatgtact ggtaccagca gaagcccggc | 120 |
| aaggccccca agccttggat ctatcgtaca tccaatcttg caagcggcgt cccttctcgt | 180 |
| ttttctggtt ccgggtctgg taccgactac actttaacca tcagcagcat gcagcccgag | 240 |
| gacttcgcca cctactactg ccagcagtat cactcctatc ctttaacttt tggccaagga | 300 |
| acaaagttgg agatcaaggg cagcacctcc ggtagcggaa agcccggtag cggcgagggc | 360 |
| agcaccaagg agaggtgcag ttggtggag agcggaggag gactggtgca gcccggtggc | 420 |
| tctttaagac tcagctgtgc cgccagcgga tttacattct ccgactacta catggcttgg | 480 |
| gtccgacaag cccccggaaa aggtttagag tgggtggcca acatcaacta cgacggctcc | 540 |
| tccacattct acgccgactc tttaaagggt cgtttcacca tctctcgtga caacagcaaa | 600 |
| aatactttat atttacaaat gaactcttta agggccgagg acaccgccgt gtactactgc | 660 |
| ggtcgtcaag ttggctatta cgaccccatg gactactggg gccaaggaac taccgtgacc | 720 |
| gtgagcagcg ggtccaccac gacgccagcg ccgcgaccac caacaccggc gcccaccatc | 780 |
| gcgtcgcaac ccctgtccct gcgccccgag gcgtgccggc cagcggcggg gggcgcagtg | 840 |
| cacacgaggg ggctggactt cgcctgtgat atctacatct gggcgccctt ggccgggact | 900 |
| tgtgggggtcc ttctcctgtc actggttatc acccttatt gcaaacgggg cagaaagaaa | 960 |
| ctcctgtata tattcaaaca accatttatg agaccagtac aaactactca agaggaagat | 1020 |
| ggctgtagct gccgatttcc agaagaagaa gaaggaggat gtgaattgag agtgaagttc | 1080 |
| agcaggagcg cagacgcccc cgcctatcag caaggccaga accagctcta taacgagctc | 1140 |
| aatttagggc gaagagagga gtacgatgtt ttggacaaga gcgtggccg ggaccccgaa | 1200 |
| atgggggga agccgagaag gaagaaccct caggaaggct tgtacaatga attgcagaag | 1260 |
| gataagatgg cggaggcata cagtgagatt gggatgaaag cgagcgccg gagggggcaag | 1320 |
| gggcacgatg gcctttatca gggtctcagt acagccacca aggacaccta cgacgccctt | 1380 | cacatgcaag ccctgccccc tcgc                                          1404

<210> SEQ ID NO 150
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Asn
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Tyr Asn Tyr Phe Asp Tyr Trp Gly Gln Gly Thr Leu
            100                 105                 110

Val Thr Val Ser Ser
        115

<210> SEQ ID NO 151
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
caagttcagc tgcagcagtg gggagctggt ttactgaagc ctagcgagac actgtcttta      60
acatgcgccg tgtacggcgg aagcttcagc ggcaactatt ggagctggat cagacagcct     120 cccgtaagg gtttagagtg gatcggcgag atcaaccact ccggctccac caactataac     180
ccctctttaa agtctcgtgt gaccatctcc gtggacacca gcaagaacca gttctcttta     240
aagctgagct ccgtgacagc cgccgacacc gctgtgtatt actgtgctcg tggcggcagc     300
tacaactact tcgactactg gggccaaggt accctcgtga ccgtgtccag c              351

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Gly Ser Phe Ser Gly Asn Tyr
1               5

<210> SEQ ID NO 153
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 153

Gly Asn Tyr Trp Ser
1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Gly Ser Phe Ser Gly
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ile Asn His Ser Gly Ser Thr
1               5

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Ile Asn His Ser Gly Ser Thr Asn Tyr Asn Pro Ser Leu Lys Ser
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Ile Asn His Ser Gly Ser Thr Asn Tyr Asn Pro Ser Leu Lys Ser
1               5                   10                  15

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Arg Gly Gly Ser Tyr Asn Tyr Phe Asp Tyr
1               5                   10
```

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Gly Gly Ser Tyr Asn Tyr Phe Asp Tyr
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Gly Gly Ser Tyr Asn Tyr Phe Asp Tyr
1               5

<210> SEQ ID NO 161
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Val Trp Tyr Leu Gln Lys Pro Gly Gln Ser
        35                  40                  45

Pro Gln Leu Leu Ile Tyr Leu Gly Ser Ile Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95

Leu Gln Thr Pro Ile Thr Phe Gly Gln Gly Thr Arg Leu Glu Ile Lys
            100                 105                 110

<210> SEQ ID NO 162
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162
gacatcgtga tgacacagag ccctctgtct ttacccgtta cccccggtga acccgctagc      60
atcagctgca gaagctccca gtctttactc cacagcaacg gctacaacta tttagtgtgg     120
tatttacaga aacccggcca gagccccag ctgctgattt atctgggctc cattcgtgct     180
agcggcgtgc ccgatagatt ttccggcagc ggaagcggca ccgacttcac tttaaagatc     240

```
tctcgtgtgg aggccgagga cgtgggcgtc tactactgta tgcagcctct gcagaccccc    300
attaccttcg gccaaggtac tcgtctggaa atcaag                              336
```

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Ser Leu Leu His Ser Asn Gly Tyr Asn Tyr
1               5                   10

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Arg Ser Ser Gln Ser Leu Leu His Ser Asn Gly Tyr Asn Tyr Leu Val
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Ser Ser Gln Ser Leu Leu His Ser Asn Gly Tyr Asn Tyr Leu Val
1               5                   10                  15

<210> SEQ ID NO 166
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Gly Ser
1

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Gly Ser Ile Arg Ala Ser
1               5

<210> SEQ ID NO 168
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 168

Leu Gly Ser Ile Arg Ala Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Met Gln Pro Leu Gln Thr Pro Ile Thr Phe
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Met Gln Pro Leu Gln Thr Pro Ile Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Met Gln Pro Leu Gln Thr Pro Ile Thr
1               5

<210> SEQ ID NO 172
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Val Trp Tyr Leu Gln Lys Pro Gly Gln Ser
        35                  40                  45

Pro Gln Leu Leu Ile Tyr Leu Gly Ser Ile Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
```

```
                    85                   90                  95
Leu Gln Thr Pro Ile Thr Phe Gly Gln Gly Thr Arg Leu Glu Ile Lys
                100                 105                 110
Gly Ser Thr Ser Gly Ser Gly Lys Pro Gly Ser Gly Glu Gly Ser Thr
            115                 120                 125
Lys Gly Gln Val Gln Leu Gln Gln Trp Gly Ala Gly Leu Leu Lys Pro
        130                 135                 140
Ser Glu Thr Leu Ser Leu Thr Cys Ala Val Tyr Gly Gly Ser Phe Ser
145                 150                 155                 160
Gly Asn Tyr Trp Ser Trp Ile Arg Gln Pro Pro Gly Lys Gly Leu Glu
                165                 170                 175
Trp Ile Gly Glu Ile Asn His Ser Gly Ser Thr Asn Tyr Asn Pro Ser
                180                 185                 190
Leu Lys Ser Arg Val Thr Ile Ser Val Asp Thr Ser Lys Asn Gln Phe
            195                 200                 205
Ser Leu Lys Leu Ser Ser Val Thr Ala Ala Asp Thr Ala Val Tyr Tyr
        210                 215                 220
Cys Ala Arg Gly Gly Ser Tyr Asn Tyr Phe Asp Tyr Trp Gly Gln Gly
225                 230                 235                 240
Thr Leu Val Thr Val Ser Ser
                245
```

<210> SEQ ID NO 173
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173

```
gacatcgtga tgacacagag ccctctgtct ttacccgtta cccccggtga acccgctagc    60
atcagctgca gaagctccca gtctttactc cacagcaacg gctacaacta tttagtgtgg   120
tatttacaga aacccggcca gagccccag ctgctgattt atctgggctc cattcgtgct    180
agcggcgtgc ccgatagatt ttccggcagc ggaagcggca ccgacttcac tttaaagatc   240
tctcgtgtgg aggccgagga cgtgggcgtc tactactgta tgcagcctct gcagaccccc   300
attaccttcg gccaaggtac tcgtctggaa atcaagggca gcaccagcgg cagcggaaaa   360
cccggaagcg gcgagggaag caccaaaggc caagttcagc tgcagcagtg gggagctggt   420
ttactgaagc ctagcgagac actgtcttta acatgcgccg tgtacggcgg aagcttcagc   480
ggcaactatt ggagctggat cagacagcct cccggtaagg gtttagagtg gatcggcgag   540
atcaaccact ccggctccac caactataac ccctctttaa agtctcgtgt gaccatctcc   600
gtggacacca gcaagaacca gttctcttta aagctgagct ccgtgacagc cgccgacacc   660
gctgtgtatt actgtgctcg tggcggcagc tacaactact tcgactactg gggccaaggt   720
accctcgtga ccgtgtccag c                                             741
```

<210> SEQ ID NO 174
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Ile Pro Tyr Lys Ile Glu Ala Val Lys Ser Glu Pro Val Glu Pro Pro
1               5                   10                  15

Leu Pro Ser Gln Leu His Leu Met Tyr Val Ala Ala Ala Phe Val
            20                  25                  30

Leu Leu Phe Phe Val Gly Cys Gly Val Leu Ser Arg Lys Arg Arg
        35                  40                  45

Arg Gln His Gly Gln Leu
    50

<210> SEQ ID NO 175
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Ile Pro Tyr Lys Ile Glu Ala Val Lys Ser Glu Pro Val Glu Pro Pro
1               5                   10                  15

Leu Pro Ser Gln Leu His Leu Met Tyr Val Ala Ala Ala Phe Val
            20                  25                  30

Leu Leu Phe Phe Val Gly Cys Gly Val Leu Ser Arg Lys Arg Arg
        35                  40                  45

Arg Gln Leu Cys Ile Gln Lys Leu
    50                  55

<210> SEQ ID NO 176
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30

Trp Asp Gly Gly Asp Cys Ser Leu Asn Phe Asn Asp Pro Trp Lys Asn
        35                  40                  45

Cys Thr Gln Ser Leu Gln Cys Trp Lys Tyr Phe Ser Asp Gly His Cys
    50                  55                  60

Asp Ser Gln Cys Asn Ser Ala Gly Cys Leu Phe Asp Gly Phe Asp Cys
65                  70                  75                  80

Gln Leu Thr Glu Gly Gln Cys Asn Pro Leu Tyr Asp Gln Tyr Cys Lys
                85                  90                  95

Asp His Phe Ser Asp Gly His Cys Asp Gln Gly Cys Asn Ser Ala Glu
            100                 105                 110

Cys Glu Trp Asp Gly Leu Asp Cys
        115                 120

<210> SEQ ID NO 177
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Ala Ala Gly Thr Leu Val Leu Val Val Leu Leu Pro Pro Asp Gln Leu
1               5                   10                  15

Arg Asn Asn Ser Phe His Phe Leu Arg Glu Leu Ser His Val Leu His
            20                  25                  30

Thr Asn Val Val Phe Lys Arg Asp Ala Gln Gly Gln Gln Met Ile Phe
        35                  40                  45

Pro Tyr Tyr Gly His Glu Glu Leu Arg Lys His Pro Ile Lys Arg
    50                  55                  60

Ser Thr Val Gly Trp Ala Thr Ser Ser Leu Leu Pro Gly Thr Ser Gly
65                  70                  75                  80

Gly Arg Gln Arg Arg Glu Leu Asp Pro Met Asp Ile Arg Gly Ser Ile
                85                  90                  95

Val Tyr Leu Glu Ile Asp Asn Arg Gln Cys Val Gln Ser Ser Ser Gln
            100                 105                 110

Cys Phe Gln Ser Ala Thr Asp Val Ala Ala Phe Leu Gly Ala Leu Ala
        115                 120                 125

Ser Leu Gly Ser Leu Asn Ile Pro Tyr Lys Ile Glu Ala Val Lys Ser
130                 135                 140

Glu Pro Val Glu Pro Pro Leu Pro
145                 150

<210> SEQ ID NO 178
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

His Leu Met Tyr Val Ala Ala Ala Ala Phe Val Leu Leu Phe Phe Val
1               5                   10                  15

Gly Cys Gly Val Leu Leu Ser
            20

<210> SEQ ID NO 179
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30

Trp Asp Gly Gly Asp Cys Ser Leu Asn Phe Asn Asp Pro Trp Lys Asn
        35                  40                  45

Cys Thr Gln Ser Leu Gln Cys Trp Lys Tyr Phe Ser Asp Gly His Cys
    50                  55                  60

Asp Ser Gln Cys Asn Ser Ala Gly Cys Leu Phe Asp Gly Phe Asp Cys
65                  70                  75                  80

Gln Leu Thr Glu Gly Gln Cys Asn Pro Leu Tyr Asp Gln Tyr Cys Lys
                85                  90                  95

Asp His Phe Ser Asp Gly His Cys Asp Gln Gly Cys Asn Ser Ala Glu
            100                 105                 110

Cys Glu Trp Asp Gly Leu Asp Cys Ala Glu His Val Pro Glu Arg Leu
        115                 120                 125

Ala Ala Gly Thr Leu Val Leu Val Leu Leu Pro Pro Asp Gln Leu
    130                 135                 140

Arg Asn Asn Ser Phe His Phe Leu Arg Glu Leu Ser His Val Leu His
145                 150                 155                 160

Thr Asn Val Val Phe Lys Arg Asp Ala Gln Gly Gln Gln Met Ile Phe
                165                 170                 175

Pro Tyr Tyr Gly His Glu Glu Leu Arg Lys His Pro Ile Lys Arg
            180                 185                 190

Ser Thr Val Gly Trp Ala Thr Ser Leu Leu Pro Gly Thr Ser Gly
        195                 200                 205

Gly Arg Gln Arg Glu Leu Asp Pro Met Asp Ile Arg Gly Ser Ile
    210                 215                 220

Val Tyr Leu Glu Ile Asp Asn Arg Gln Cys Val Gln Ser Ser Gln
225                 230                 235                 240

Cys Phe Gln Ser Ala Thr Asp Val Ala Ala Phe Leu Gly Ala Leu Ala
                245                 250                 255

Ser Leu Gly Ser Leu Asn Ile Pro Tyr Lys Ile Glu Ala Val Lys Ser
            260                 265                 270

Glu Pro Val Glu Pro Pro Leu Pro Ser Gln Leu His Leu Met Tyr Val
        275                 280                 285

Ala Ala Ala Ala Phe Val Leu Leu Phe Phe Val Gly Cys Gly Val Leu
    290                 295                 300

Leu Ser
305

<210> SEQ ID NO 180
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His Ile Leu Asp Tyr Ser Phe Thr Gly Gly Ala Gly
        35                  40                  45

Arg Asp Ile Pro Pro Gln Ile Glu Glu Ala Cys Glu Leu Pro Glu
    50                  55                  60

Cys Gln Val Asp Ala Gly Asn Lys Val Cys Asn Leu Gln Cys Asn Asn
65                  70                  75                  80

His Ala Cys Gly Trp Asp Gly Gly Asp Cys Ser Leu Asn Phe Asn Asp
                85                  90                  95

Pro Trp Lys Asn Cys Thr Gln Ser Leu Gln Cys Trp Lys Tyr Phe Ser
            100                 105                 110

Asp Gly His Cys Asp Ser Gln Cys Asn Ser Ala Gly Cys Leu Phe Asp
        115                 120                 125

Gly Phe Asp Cys Gln Leu Thr Glu Gly Gln Cys Asn Pro Leu Tyr Asp
    130                 135                 140

```
Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
            165                 170                 175

Pro Glu Arg Leu Ala Ala Gly Thr Leu Val Leu Val Val Leu Leu Pro
        180                 185                 190

Pro Asp Gln Leu Arg Asn Asn Ser Phe His Phe Leu Arg Glu Leu Ser
            195                 200                 205

His Val Leu His Thr Asn Val Val Phe Lys Arg Asp Ala Gln Gly Gln
210                 215                 220

Gln Met Ile Phe Pro Tyr Tyr Gly His Glu Glu Leu Arg Lys His
225                 230                 235                 240

Pro Ile Lys Arg Ser Thr Val Gly Trp Ala Thr Ser Ser Leu Leu Pro
                245                 250                 255

Gly Thr Ser Gly Gly Arg Gln Arg Glu Leu Asp Pro Met Asp Ile
            260                 265                 270

Arg Gly Ser Ile Val Tyr Leu Glu Ile Asp Asn Arg Gln Cys Val Gln
                275                 280                 285

Ser Ser Ser Gln Cys Phe Gln Ser Ala Thr Asp Val Ala Ala Phe Leu
    290                 295                 300

Gly Ala Leu Ala Ser Leu Gly Ser Leu Asn Ile Pro Tyr Lys Ile Glu
305                 310                 315                 320

Ala Val Lys Ser Glu Pro Val Glu Pro Pro Leu Pro Ser Gln Leu His
                325                 330                 335

Leu Met Tyr Val Ala Ala Ala Phe Val Leu Phe Phe Val Gly
            340                 345                 350

Cys Gly Val Leu Leu Ser
        355

<210> SEQ ID NO 181
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His
        35

<210> SEQ ID NO 182
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30
```

```
Trp Asp Gly Gly Asp Cys Ser Leu Asn Phe Asn Asp Pro Trp Lys Asn
            35                  40                  45

Cys Thr Gln Ser Leu Gln Cys Trp Lys Tyr Phe Ser Asp Gly His Cys
 50                  55                  60

Asp Ser Gln Cys Asn Ser Ala Gly Cys Leu Phe Asp Gly Phe Asp Cys
 65                  70                  75                  80

Gln Leu Thr Glu Gly Gln Cys Asn Pro Leu Tyr Asp Gln Tyr Cys Lys
                85                  90                  95

Asp His Phe Ser Asp Gly His Cys Asp Gln Gly Cys Asn Ser Ala Glu
               100                 105                 110

Cys Glu Trp Asp Gly Leu Asp Cys
               115                 120
```

<210> SEQ ID NO 183
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Ala Ala Gly Thr Leu Val Leu Val Val Leu Pro Pro Asp Gln Leu
1               5                   10                  15

Arg Asn Asn Ser Phe His Phe Leu Arg Glu Leu Ser His Val Leu His
                20                  25                  30

Thr Asn Val Val Phe Lys Arg Asp Ala Gln Gly Gln Gln Met Ile Phe
            35                  40                  45

Pro Tyr Tyr Gly His Glu Glu Glu Leu Arg Lys His Pro Ile Lys Arg
 50                  55                  60

Ser Thr Val Gly Trp Ala Thr Ser Ser Leu Leu Pro Gly Thr Ser Gly
 65                  70                  75                  80

Gly Arg Gln Arg Arg Glu Leu Asp Pro Met Asp Ile Arg Gly Ser Ile
                85                  90                  95

Val Tyr Leu Glu Ile Asp Asn Arg Gln Cys Val Gln Ser Ser Ser Gln
               100                 105                 110

Cys Phe Gln Ser Ala Thr Asp Val Ala Ala Phe Leu Gly Ala Leu Ala
               115                 120                 125

Ser Leu Gly Ser Leu Asn Ile Pro Tyr Lys Ile Glu Ala Val Lys Ser
               130                 135                 140

Glu Pro Val Glu Pro Pro Leu Pro
145                 150
```

<210> SEQ ID NO 184
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
His Leu Met Tyr Val Ala Ala Ala Ala Phe Val Leu Leu Phe Phe Val
1               5                   10                  15

Gly Cys Gly Val Leu Leu Ser
                20
```

<210> SEQ ID NO 185

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Asn Glu Cys Val Leu Ser Pro Cys Arg His Gly Ala Ser Cys
1               5                   10                  15

Gln Asn Thr His Gly Gly Tyr Arg Cys His Cys Gln Ala Gly Tyr Ser
            20                  25                  30

Gly Arg Asn Cys Glu
        35

<210> SEQ ID NO 186
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Asp Asp Cys Arg Pro Asn Pro Cys His Asn Gly Gly Ser Cys
1               5                   10                  15

Thr Asp Gly Ile Asn Thr Ala Phe Cys Asp Cys Leu Pro Gly Phe Arg
            20                  25                  30

Gly Thr Phe Cys
        35

<210> SEQ ID NO 187
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Asn Glu Cys Ala Ser Asp Pro Cys Arg Asn Gly Ala Asn Cys
1               5                   10                  15

Thr Asp Cys Val Asp Ser Tyr Thr Cys Thr Cys Pro Ala Gly Phe Ser
            20                  25                  30

Gly Ile His Cys Glu
        35

<210> SEQ ID NO 188
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Thr Glu Ser Ser Cys Phe Asn Gly Gly Thr Cys Val Asp Gly Ile Asn
1               5                   10                  15

Ser Phe Thr Cys Leu Cys Pro Pro Gly Phe Thr Gly Ser Tyr Cys Gln
            20                  25                  30

<210> SEQ ID NO 189
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 189

Asp Val Asn Glu Cys Asp Ser Gln Pro Cys Leu His Gly Gly Thr Cys
1               5                   10                  15

Gln Asp Gly Cys Gly Ser Tyr Arg Cys Thr Cys Pro Gln Gly Tyr Thr
                20                  25                  30

Gly Pro Asn Cys Gln
            35

<210> SEQ ID NO 190
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Ser Ser Pro Cys Lys Asn Gly Gly Lys Cys Trp Gln Thr His Thr
1               5                   10                  15

Gln Tyr Arg Cys Glu Cys Pro Ser Gly Trp Thr
                20                  25

<210> SEQ ID NO 191
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Leu Val Asp Glu Cys Ser Pro Ser Pro Cys Gln Asn Gly Ala Thr Cys
1               5                   10                  15

Thr Asp Tyr Leu Gly Gly Tyr Ser Cys Lys Cys Val Ala Gly Tyr His
                20                  25                  30

Gly Val Asn Cys
            35

<210> SEQ ID NO 192
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ile Asp Glu Cys Leu Ser His Pro Cys Gln Asn Gly Gly Thr Cys Leu
1               5                   10                  15

Asp Leu Pro Asn Thr Tyr Lys Cys Ser Cys Pro Arg Gly Thr Gln Gly
                20                  25                  30

Val His Cys Glu
            35

<210> SEQ ID NO 193
<211> LENGTH: 28
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 193

Cys Phe Asn Asn Gly Thr Cys Val Asp Gln Val Gly Gly Tyr Ser Cys
1               5                   10                  15

Thr Cys Pro Pro Gly Phe Val Gly Glu Arg Cys Glu
            20                  25

<210> SEQ ID NO 194
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Val Asn Glu Cys Leu Ser Asn Pro Cys Asp Ala Arg Gly Thr Gln
1               5                   10                  15

Asn Cys Val Gln Arg Val Asn Asp Phe His Cys Glu Cys Arg Ala Gly
            20                  25                  30

His Thr Gly Arg Arg Cys Glu
        35

<210> SEQ ID NO 195
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His
        35

<210> SEQ ID NO 196
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30

Trp Asp Gly Gly Asp Cys Ser Leu Asn Phe Asn Asp Pro Trp Lys Asn
        35                  40                  45

Cys Thr Gln Ser Leu Gln Cys Trp Lys Tyr Phe Ser Asp Gly His Cys
    50                  55                  60

Asp Ser Gln Cys Asn Ser Ala Gly Cys Leu Phe Asp Gly Phe Asp Cys
65                  70                  75                  80

Gln Leu Thr Glu Gly Gln Cys Asn Pro Leu Tyr Asp Gln Tyr Cys Lys
                85                  90                  95
```

Asp His Phe Ser Asp Gly His Cys Asp Gln Gly Cys Asn Ser Ala Glu
            100                 105                 110

Cys Glu Trp Asp Gly Leu Asp Cys
        115                 120

<210> SEQ ID NO 197
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ala Ala Gly Thr Leu Val Leu Val Val Leu Pro Pro Asp Gln Leu
1               5                   10                  15

Arg Asn Asn Ser Phe His Phe Leu Arg Glu Leu Ser His Val Leu His
                20                  25                  30

Thr Asn Val Val Phe Lys Arg Asp Ala Gln Gly Gln Gln Met Ile Phe
            35                  40                  45

Pro Tyr Tyr Gly His Glu Glu Glu Leu Arg Lys His Pro Ile Lys Arg
50                  55                  60

Ser Thr Val Gly Trp Ala Thr Ser Ser Leu Leu Pro Gly Thr Ser Gly
65                  70                  75                  80

Gly Arg Gln Arg Arg Glu Leu Asp Pro Met Asp Ile Arg Gly Ser Ile
                85                  90                  95

Val Tyr Leu Glu Ile Asp Asn Arg Gln Cys Val Gln Ser Ser Ser Gln
            100                 105                 110

Cys Phe Gln Ser Ala Thr Asp Val Ala Ala Phe Leu Gly Ala Leu Ala
        115                 120                 125

Ser Leu Gly Ser Leu Asn Ile Pro Tyr Lys Ile Glu Ala Val Lys Ser
    130                 135                 140

Glu Pro Val Glu Pro Pro Leu Pro
145                 150

<210> SEQ ID NO 198
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

His Leu Met Tyr Val Ala Ala Ala Ala Phe Val Leu Leu Phe Phe Val
1               5                   10                  15

Gly Cys Gly Val Leu Leu Ser
            20

<210> SEQ ID NO 199
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

His Leu Met Tyr Val Ala Ala Ala Ala Phe Val Leu Leu Phe Phe Val
1               5                   10                  15

```
Gly Cys Gly Val Leu Leu Ser
            20

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Arg Arg Arg Arg Glu Leu Asp Pro Met
1               5                   10

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Gln Arg Arg Glu Leu Asp Pro Met
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Lys Ile Glu Ala Val Gln Ser Glu
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Val Gly Cys Gly Val Leu Leu Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Cys Gly Val Leu Leu Ser
1               5

<210> SEQ ID NO 205
<211> LENGTH: 394
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 205

Ile Leu Asp Tyr Ser Phe Thr Gly Gly Ala Gly Arg Asp Ile Pro Pro
1               5                   10                  15

Pro Gln Ile Glu Glu Ala Cys Glu Leu Pro Glu Cys Gln Val Asp Ala
            20                  25                  30

Gly Asn Lys Val Cys Asn Leu Gln Cys Asn Asn His Ala Cys Gly Trp
        35                  40                  45

Asp Gly Gly Asp Cys Ser Leu Asn Phe Asn Asp Pro Trp Lys Asn Cys
    50                  55                  60

Thr Gln Ser Leu Gln Cys Trp Lys Tyr Phe Ser Asp Gly His Cys Asp
65                  70                  75                  80

Ser Gln Cys Asn Ser Ala Gly Cys Leu Phe Asp Gly Phe Asp Cys Gln
                85                  90                  95

Leu Thr Glu Gly Gln Cys Asn Pro Leu Tyr Asp Gln Tyr Cys Lys Asp
            100                 105                 110

His Phe Ser Asp Gly His Cys Asp Gln Gly Cys Asn Ser Ala Glu Cys
        115                 120                 125

Glu Trp Asp Gly Leu Asp Cys Ala Glu His Val Pro Glu Arg Leu Ala
    130                 135                 140

Ala Gly Thr Leu Val Leu Val Val Leu Pro Pro Asp Gln Leu Arg
145                 150                 155                 160

Asn Asn Ser Phe His Phe Leu Arg Glu Leu Ser His Val Leu His Thr
                165                 170                 175

Asn Val Val Phe Lys Arg Asp Ala Gln Gly Gln Gln Met Ile Phe Pro
            180                 185                 190

Tyr Tyr Gly His Glu Glu Glu Leu Arg Lys His Pro Ile Lys Arg Ser
        195                 200                 205

Thr Val Gly Trp Ala Thr Ser Ser Leu Leu Pro Gly Thr Ser Gly Gly
    210                 215                 220

Arg Gln Arg Arg Glu Leu Asp Pro Met Asp Ile Arg Gly Ser Ile Val
225                 230                 235                 240

Tyr Leu Glu Ile Asp Asn Arg Gln Cys Val Gln Ser Ser Ser Gln Cys
                245                 250                 255

Phe Gln Ser Ala Thr Asp Val Ala Ala Phe Leu Gly Ala Leu Ala Ser
            260                 265                 270

Leu Gly Ser Leu Asn Ile Pro Tyr Lys Ile Glu Ala Val Lys Ser Glu
        275                 280                 285

Pro Val Glu Pro Pro Leu Pro Ser Gln Leu His Leu Met Tyr Val Ala
    290                 295                 300

Ala Ala Ala Phe Val Leu Leu Phe Phe Val Gly Cys Gly Val Leu Leu
305                 310                 315                 320

Ser Arg Lys Arg Arg Arg Gln His Gly Gln Leu Trp Phe Pro Glu Gly
                325                 330                 335

Phe Lys Val Ser Glu Ala Ser Lys Lys Arg Arg Glu Pro Leu Gly
            340                 345                 350

Glu Asp Ser Val Gly Leu Lys Pro Leu Lys Asn Ala Ser Asp Gly Ala
        355                 360                 365

Leu Met Asp Asp Asn Gln Asn Glu Trp Gly Asp Glu Asp Leu Glu Thr
    370                 375                 380

Lys Lys Phe Arg Phe Glu Glu Pro Val Val
385                 390

<210> SEQ ID NO 206
<211> LENGTH: 978
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206

```
atcctggact acagcttcac aggtggcgct gggcgcgaca ttcccccacc gcagattgag      60
gaggcctgtg agctgcctga gtgccaggtg gatgcaggca ataaggtctg caacctgcag     120
tgtaataatc acgcatgtgg ctgggatggt ggcgactgct ccctcaactt caatgacccc     180
tggaagaact gcacgcagtc tctacagtgc tggaagtatt ttagcgacgg ccactgtgac     240
agccagtgca actcggccgg ctgcctcttt gatggcttcg actgccagct caccgaggga     300
cagtgcaacc ccctgtatga ccagtactgc aaggaccact tcagtgatgg ccactgcgac     360
cagggctgta acagtgccga atgtgagtgg gatggcctag actgtgctga gcatgtaccc     420
gagcggctgg cagccggcac cctggtgctg gtggtgctgc ttccacccga ccagctacgg     480
aacaactcct tccactttct gcgggagctc agccacgtgc tgcacaccaa cgtggtcttc     540
aagcgtgatg cgcaaggcca gcagatgatc ttcccgtact atggccacga ggaagagctg     600
cgcaagcacc caatcaagcg ctctacagtg ggttgggcca cctcttcact gcttcctggt     660
acaagtggtg ggcgccagcg cagggagctg acccccatgg acatccgtgg ctccattgtc     720
tacctggaga tcgacaaccg gcaatgtgtg cagtcatcct cgcagtgctt ccagagtgcc     780
accgatgtgg ctgccttcct aggtgctctt gcgtcacttg gcagcctcaa tattccttac     840
aagattgagg ccgtgaagag tgagccggtg gagcctccgc tgccctcgca gctgcacctc     900
atgtacgtgg cagcagccgc cttcgtgctc ctgttctttg tgggctgtgg ggtgctgctg     960
tcccgcaagc gccggcgg                                                  978
```

<210> SEQ ID NO 207
<211> LENGTH: 147
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

```
Met Lys Leu Leu Ser Ser Ile Glu Gln Ala Cys Asp Ile Cys Arg Leu
1               5                   10                  15
Lys Lys Leu Lys Cys Ser Lys Glu Lys Pro Lys Cys Ala Lys Cys Leu
            20                  25                  30
Lys Asn Asn Trp Glu Cys Arg Tyr Ser Pro Lys Thr Lys Arg Ser Pro
        35                  40                  45
Leu Thr Arg Ala His Leu Thr Glu Val Glu Ser Arg Leu Glu Arg Leu
    50                  55                  60
Glu Gln Leu Phe Leu Leu Ile Phe Pro Arg Glu Asp Leu Asp Met Ile
65                  70                  75                  80
Leu Lys Met Asp Ser Leu Gln Asp Ile Lys Ala Leu Leu Thr Gly Leu
                85                  90                  95
Phe Val Gln Asp Asn Val Asn Lys Asp Ala Val Thr Asp Arg Leu Ala
            100                 105                 110
Ser Val Glu Thr Asp Met Pro Leu Thr Leu Arg Gln His Arg Ile Ser
```

```
            115                 120                 125

Ala Thr Ser Ser Ser Glu Glu Ser Ser Asn Lys Gly Gln Arg Gln Leu
        130                 135                 140

Thr Val Ser
145

<210> SEQ ID NO 208
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
            180                 185                 190

Leu Asp Met Leu Gly Ser Asp Ala Leu Asp Asp Phe Asp Leu Asp Met
        195                 200                 205

Leu Gly Ser
    210

<210> SEQ ID NO 209
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
```

```
                35                  40                  45
Leu Thr Arg Ala His Leu Thr Glu Val Glu Ser Arg Leu Glu Arg Leu
 50                  55                  60
Glu Gln Leu Phe Leu Leu Ile Phe Pro Arg Glu Asp Leu Asp Met Ile
 65                  70                  75                  80
Leu Lys Met Asp Ser Leu Gln Asp Ile Lys Ala Leu Leu Thr Gly Leu
                 85                  90                  95
Phe Val Gln Asp Asn Val Asn Lys Asp Ala Val Thr Asp Arg Leu Ala
                100                 105                 110
Ser Val Glu Thr Asp Met Pro Leu Thr Leu Arg Gln His Arg Ile Ser
            115                 120                 125
Ala Thr Ser Ser Glu Glu Ser Ser Asn Lys Gly Gln Arg Gln Leu
        130                 135                 140
Thr Val Ser Gly Gly Gly Ser Gly Gly Gly Ser Asp Ala Leu Asp Asp
145                 150                 155                 160
Phe Asp Leu Asp Met Leu Gly Ser Asp Ala Leu Asp Asp Phe Asp Leu
                165                 170                 175
Asp Met Leu Gly Ser Asp Ala Leu Asp Asp Phe Asp Leu Asp Met Leu
            180                 185                 190
Gly Ser Asp Ala Leu Asp Asp Phe Asp Leu Asp Met Leu
        195                 200                 205

<210> SEQ ID NO 210
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Asp Ile Val Met Thr Gln Ser Pro Leu Ser Leu Pro Val Thr Pro Gly
 1                   5                  10                  15
Glu Pro Ala Ser Ile Ser Cys Arg Ser Ser Gln Ser Leu Leu His Ser
                 20                  25                  30
Asn Gly Tyr Asn Tyr Leu Val Trp Tyr Leu Gln Lys Pro Gly Gln Ser
             35                  40                  45
Pro Gln Leu Leu Ile Tyr Leu Gly Ser Ile Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Pro
                 85                  90                  95
Leu Gln Thr Pro Ile Thr Phe Gly Gln Gly Thr Arg Leu Glu Ile Lys
                100                 105                 110
Gly Ser Thr Ser Gly Ser Gly Lys Pro Gly Ser Gly Glu Gly Ser Thr
            115                 120                 125
Lys Gly Gln Val Gln Leu Gln Gln Trp Gly Ala Gly Leu Leu Lys Pro
        130                 135                 140
Ser Glu Thr Leu Ser Leu Thr Cys Ala Val Tyr Gly Gly Ser Phe Ser
145                 150                 155                 160
Gly Asn Tyr Trp Ser Trp Ile Arg Gln Pro Pro Gly Lys Gly Leu Glu
                165                 170                 175
Trp Ile Gly Glu Ile Asn His Ser Gly Ser Thr Asn Tyr Asn Pro Ser
            180                 185                 190
```

```
Leu Lys Ser Arg Val Thr Ile Ser Val Asp Thr Ser Lys Asn Gln Phe
            195                 200                 205

Ser Leu Lys Leu Ser Ser Val Thr Ala Ala Asp Thr Ala Val Tyr Tyr
    210                 215                 220

Cys Ala Arg Gly Gly Ser Tyr Asn Tyr Phe Asp Tyr Trp Gly Gln Gly
225                 230                 235                 240

Thr Leu Val Thr Val Ser Ser Ile Leu Asp Tyr Ser Phe Thr Gly Gly
                245                 250                 255

Ala Gly Arg Asp Ile Pro Pro Gln Ile Glu Glu Ala Cys Glu Leu
                260                 265                 270

Pro Glu Cys Gln Val Asp Ala Gly Asn Lys Val Cys Asn Leu Gln Cys
            275                 280                 285

Asn Asn His Ala Cys Gly Trp Asp Gly Gly Asp Cys Ser Leu Asn Phe
    290                 295                 300

Asn Asp Pro Trp Lys Asn Cys Thr Gln Ser Leu Gln Cys Trp Lys Tyr
305                 310                 315                 320

Phe Ser Asp Gly His Cys Asp Ser Gln Cys Asn Ser Ala Gly Cys Leu
                325                 330                 335

Phe Asp Gly Phe Asp Cys Gln Leu Thr Glu Gly Gln Cys Asn Pro Leu
                340                 345                 350

Tyr Asp Gln Tyr Cys Lys Asp His Phe Ser Asp Gly His Cys Asp Gln
            355                 360                 365

Gly Cys Asn Ser Ala Glu Cys Glu Trp Asp Gly Leu Asp Cys Ala Glu
    370                 375                 380

His Val Pro Glu Arg Leu Ala Ala Gly Thr Leu Val Leu Val Val Leu
385                 390                 395                 400

Leu Pro Pro Asp Gln Leu Arg Asn Asn Ser Phe His Phe Leu Arg Glu
                405                 410                 415

Leu Ser His Val Leu His Thr Asn Val Val Phe Lys Arg Asp Ala Gln
                420                 425                 430

Gly Gln Gln Met Ile Phe Pro Tyr Tyr Gly His Glu Glu Leu Arg
            435                 440                 445

Lys His Pro Ile Lys Arg Ser Thr Val Gly Trp Ala Thr Ser Ser Leu
    450                 455                 460

Leu Pro Gly Thr Ser Gly Gly Arg Gln Arg Arg Glu Leu Asp Pro Met
465                 470                 475                 480

Asp Ile Arg Gly Ser Ile Val Tyr Leu Glu Ile Asp Asn Arg Gln Cys
                485                 490                 495

Val Gln Ser Ser Ser Gln Cys Phe Gln Ser Ala Thr Asp Val Ala Ala
            500                 505                 510

Phe Leu Gly Ala Leu Ala Ser Leu Gly Ser Leu Asn Ile Pro Tyr Lys
    515                 520                 525

Ile Glu Ala Val Lys Ser Glu Pro Val Glu Pro Leu Pro Ser Gln
530                 535                 540

Leu His Leu Met Tyr Val Ala Ala Ala Phe Val Leu Leu Phe Phe
545                 550                 555                 560

Val Gly Cys Gly Val Leu Leu Ser Arg Lys Arg Arg Arg Gln His Gly
                565                 570                 575

Gln Leu Trp Phe Pro Glu Gly Phe Lys Val Ser Glu Ala Ser Lys Lys
            580                 585                 590

Lys Arg Arg Glu Pro Leu Gly Glu Asp Ser Val Gly Leu Lys Pro Leu
            595                 600                 605

Lys Asn Ala Ser Asp Gly Ala Leu Met Asp Asp Asn Gln Asn Glu Trp
```

610                 615                 620
Gly Asp Glu Asp Leu Glu Thr Lys Lys Phe Arg Phe Glu Glu Pro Val
625                 630                 635                 640

Val Gly Ser Met Lys Leu Leu Ser Ser Ile Glu Gln Ala Cys Asp Ile
                645                 650                 655

Cys Arg Leu Lys Lys Leu Lys Cys Ser Lys Glu Lys Pro Lys Cys Ala
                660                 665                 670

Lys Cys Leu Lys Asn Asn Trp Glu Cys Arg Tyr Ser Pro Lys Thr Lys
                675                 680                 685

Arg Ser Pro Leu Thr Arg Ala His Leu Thr Glu Val Glu Ser Arg Leu
                690                 695                 700

Glu Arg Leu Glu Gln Leu Phe Leu Leu Ile Phe Pro Arg Glu Asp Leu
705                 710                 715                 720

Asp Met Ile Leu Lys Met Asp Ser Leu Gln Asp Ile Lys Ala Leu Leu
                725                 730                 735

Thr Gly Leu Phe Val Gln Asp Asn Val Asn Lys Asp Ala Val Thr Asp
                740                 745                 750

Arg Leu Ala Ser Val Glu Thr Asp Met Pro Leu Thr Leu Arg Gln His
                755                 760                 765

Arg Ile Ser Ala Thr Ser Ser Ser Glu Glu Ser Ser Asn Lys Gly Gln
                770                 775                 780

Arg Gln Leu Thr Val Ser Gly Gly Ser Gly Gly Ser Asp Ala
785                 790                 795                 800

Leu Asp Asp Phe Asp Leu Asp Met Leu Gly Ser Asp Ala Leu Asp Asp
                805                 810                 815

Phe Asp Leu Asp Met Leu Gly Ser Asp Ala Leu Asp Asp Phe Asp Leu
                820                 825                 830

Asp Met Leu Gly Ser Asp Ala Leu Asp Asp Phe Asp Leu Asp Met Leu
                835                 840                 845

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221
<211> LENGTH: 2544
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221

```
gacatcgtga tgacacagag ccctctgtct ttacccgtta ccccggtga accgctagc      60
atcagctgca gaagctccca gtctttactc cacagcaacg gctacaacta tttagtgtgg    120
tatttacaga aacccggcca gagccccag ctgctgattt atctgggctc cattcgtgct    180
agcggcgtgc ccgatagatt ttccggcagc ggaagcggca ccgacttcac tttaaagatc    240
tctcgtgtgg aggccgagga cgtgggcgtc tactactgta tgcagcctct gcagaccccc    300
attaccttcg gccaaggtac tcgtctggaa atcaagggca gcaccagcgg cagcggaaaa    360
cccggaagcg gcgagggaag caccaaaggc caagttcagc tgcagcagtg gggagctggt    420
ttactgaagc ctagcgagac actgtcttta acatgcgccg tgtacggcgg aagcttcagc    480
ggcaactatt ggagctggat cagacagcct cccggtaagg gtttagagtg gatcggcgag    540
atcaaccact ccggctccac caactataac ccctctttaa agtctcgtgt gaccatctcc    600
gtggacacca gcaagaacca gttctcttta aagctgagct ccgtgacagc cgccgacacc    660
gctgtgtatt actgtgctcg tggcggcagc tacaactact tcgactactg gggccaaggt    720
accctcgtga ccgtgtccag catcctggac tacagcttca caggtggcgc tgggcgcgac    780
attcccccac cgcagattga ggaggcctgt gagctgcctg agtgccaggt ggatgcaggc    840
aataaggtct gcaacctgca gtgtaataat cacgcatgtg gctgggatgg tggcgactgc    900
tccctcaact tcaatgaccc ctggaagaac tgcacgcagt ctctacagtg ctggaagtat    960
tttagcgacg gccactgtga cagccagtgc aactcggccg gctgcctctt tgatggcttc   1020
```

```
gactgccagc tcaccgaggg acagtgcaac ccctgtatg accagtactg caaggaccac   1080
ttcagtgatg gccactgcga ccagggctgt aacagtgccg aatgtgagtg ggatggccta   1140
gactgtgctg agcatgtacc cgagcggctg gcagccggca ccctggtgct ggtggtgctg   1200
cttccacccg accagctacg gaacaactcc ttccactttc tgcgggagct cagccacgtg   1260
ctgcacacca acgtggtctt caagcgtgat gcgcaaggcc agcagatgat cttcccgtac   1320
tatggccacg aggaagagct gcgcaagcac ccaatcaagc gctctacagt ggggttgggcc   1380 acctcttcac tgcttcctgg tacaagtggt gggcgccagc gcagggagct ggaccccatg   1440
gacatccgtg ctccattgt ctacctggag atcgacaacc ggcaatgtgt gcagtcatcc   1500
tcgcagtgct ccagagtgc caccgatgtg gctgccttcc taggtgctct tgcgtcactt   1560
ggcagcctca atattcctta caagattgag gccgtgaaga gtgagccggt ggagcctccg   1620
ctgccctcgc agctgcacct catgtacgtg gcagcagccg ccttcgtgct cctgttctt    1680 gtgggctgtg ggtgctgct gtcccgcaag cgccggcgg cagcacggtca actttggttc   1740 ccagaaggct tcaaggtctc cgaagcctcc aagaaaaagc gaagggaacc actcggggaa   1800
gacagtgtag ggttgaaacc tttgaagaac gccagcgatg gagccttgat ggatgataac   1860
caaaatgaat ggggtgatga agacctggaa accaaaagt ttcgctttga ggaacctgtg   1920
gtaggatcca tgaaactcct tagcagcatc gaacaggctt gcgacatctg caggttgaaa   1980
aaactcaagt gctcaaaaga aaagcctaag tgcgcaaagt gccttaaaaa caattgggaa   2040
tgtcgctata gccccaagac aaagcggagc cctctcacga gcacacct gactgaggta   2100 gaatctcgct tggagaggct ggaacagctt ttcctgctta tctttccacg cgaggatctc   2160
gatatgatcc tcaaaatgga ctccctccag gacatcaaag ctctgctgac tggactgttt   2220
gtacaggata atgtgaacaa ggacgctgtg acagacagat tggcaagcgt ggagaccgat   2280 atgccccctga cccttagaca gcaccggatc agtgccacct cttctagcga ggaaagttca   2340
aataaaggac agcgccagct gacggtgagt ggcggtggaa gcggaggagg ttccgacgct   2400
cttgatgatt tcgatctcga catgctggga tcagacgctc tcgacgactt cgatttggac   2460
atgcttggat ccgacgctct cgatgattc gacctcgaca tgctcggatc cgatgctctg   2520
gatgactttg atcttgatat gctg                                        2544
```

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Glu Gln Lys Leu Ile Ser Glu Glu Asp Leu
1               5                   10

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
gagcagaagc tgattagcga ggaggattta                                    30

<210> SEQ ID NO 224
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala

<210> SEQ ID NO 225
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu
        115                 120                 125

<210> SEQ ID NO 226
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 227

Met Leu Leu Leu Val Thr Ser Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

<210> SEQ ID NO 228
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Arg Val Asn Arg Gln
145                 150

<210> SEQ ID NO 229
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95
```

```
Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys
        115                 120                 125

Pro Gly Glu Thr Phe Phe Met Cys Ser Cys Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Pro Pro Leu
                165                 170                 175

Gly Val Ala Ile Ser Val Ile Ile Ile Phe Tyr Cys Tyr Arg Val Asn
            180                 185                 190

Arg Gln

<210> SEQ ID NO 230
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 231
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45
```

```
Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
 65                  70                  75                  80

Asp Pro Lys Leu Pro Tyr His Asp Phe Ile Leu Glu Asp Ala Ala Ser
                 85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Leu Leu Leu Val Ile Phe Gln
130                 135                 140

Val Thr Gly Ile Ser Leu Leu Pro Pro Leu Gly Val Ala Ile Ser Val
145                 150                 155                 160

Ile Ile Ile Phe Tyr Cys Tyr
                165

<210> SEQ ID NO 232
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Thr Ile Pro Pro His Val Gln Lys Ser Val Asn Asn Asp Met Ile Val
 1               5                  10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
 65                  70                  75                  80

Asp Pro Lys Leu Pro Tyr His Asp Phe Ile Leu Glu Asp Ala Ala Ser
                 85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Ser Gly Pro Ile Leu Leu Thr
130                 135                 140

Ile Ser Ile Leu Ser Phe Phe Ser Val Ala Leu Leu Val Ile Leu
145                 150                 155

<210> SEQ ID NO 233
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Thr Ile Pro Pro His Val Gln Lys Ser Val Asn Asn Asp Met Ile Val
 1               5                  10                  15
```

```
Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
50                      55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Ser Gly Pro Ile Leu Leu Thr
            130                 135                 140

Cys Pro Thr Ile Ser Ile Leu Ser Phe Phe Ser Val Ala Leu Leu Val
145                 150                 155                 160

Ile Leu

<210> SEQ ID NO 234
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Ala Cys Val Leu Trp Lys Lys Arg Ile Lys Pro Ile Val Trp Pro Ser
1               5                   10                  15

Leu Pro Asp His Lys Lys Thr Leu Glu His Leu Cys Lys Lys Pro Arg
            20                  25                  30

Lys Asn Leu Asn Val Ser Phe Asn Pro Glu Ser Phe Leu Asp Cys Gln
            35                  40                  45

Ile His Arg Val Asp Asp Ile Gln Ala Arg Asp Glu Val Glu Gly Phe
        50                  55                  60

Leu Gln Asp Thr Phe Pro Gln Gln Leu Glu Glu Ser Glu Lys Gln Arg
65                  70                  75                  80

Leu Gly Gly Asp Val Gln Ser Pro Asn Cys Pro Ser Glu Asp Val Val
                85                  90                  95

Ile Thr Pro Glu Ser Phe Gly Arg Asp Ser Ser Leu Thr Cys Leu Ala
            100                 105                 110

Gly Asn Val Ser Ala Cys Asp Ala Pro Ile Leu Ser Ser Ser Arg Ser
            115                 120                 125

Leu Asp Cys Arg Glu Ser Gly Lys Asn Gly Pro His Val Tyr Gln Asp
130                 135                 140

Leu Leu Leu Ser Leu Gly Thr Thr Asn Ser Thr Leu Pro Pro Pro Phe
145                 150                 155                 160

Ser Leu Gln Ser Gly Ile Leu Thr Leu Asn Pro Val Ala Gln Gly Gln
                165                 170                 175

Pro Ile Leu Thr Ser Leu Gly Ser Asn Gln Glu Glu Ala Tyr Val Thr
            180                 185                 190

Met Ser Ser Phe Tyr Gln Asn Gln
            195                 200
```

```
<210> SEQ ID NO 235
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
                100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Ser Gly Pro Ile Leu Leu Thr
        130                 135                 140

Ile Ser Ile Leu Ser Phe Phe Ser Val Ala Leu Leu Val Ile Leu Ala
145                 150                 155                 160

Cys Val Leu Trp Lys Lys Arg Ile Lys Pro Ile Val Trp Pro Ser Leu
                165                 170                 175

Pro Asp His Lys Lys Thr Leu Glu His Leu Cys Lys Lys Pro Arg Lys
                180                 185                 190

Asn Leu Asn Val Ser Phe Asn Pro Glu Ser Phe Leu Asp Cys Gln Ile
            195                 200                 205

His Arg Val Asp Asp Ile Gln Ala Arg Asp Glu Val Glu Gly Phe Leu
        210                 215                 220

Gln Asp Thr Phe Pro Gln Gln Leu Glu Glu Ser Glu Lys Gln Arg Leu
225                 230                 235                 240

Gly Gly Asp Val Gln Ser Pro Asn Cys Pro Ser Glu Asp Val Val Ile
                245                 250                 255

Thr Pro Glu Ser Phe Gly Arg Asp Ser Ser Leu Thr Cys Leu Ala Gly
                260                 265                 270

Asn Val Ser Ala Cys Asp Ala Pro Ile Leu Ser Ser Ser Arg Ser Leu
            275                 280                 285

Asp Cys Arg Glu Ser Gly Lys Asn Gly Pro His Val Tyr Gln Asp Leu
        290                 295                 300

Leu Leu Ser Leu Gly Thr Thr Asn Ser Thr Leu Pro Pro Pro Phe Ser
305                 310                 315                 320

Leu Gln Ser Gly Ile Leu Thr Leu Asn Pro Val Ala Gln Gly Gln Pro
                325                 330                 335

Ile Leu Thr Ser Leu Gly Ser Asn Gln Glu Glu Ala Tyr Val Thr Met
            340                 345                 350

Ser Ser Phe Tyr Gln Asn Gln
        355
```

<210> SEQ ID NO 236
<211> LENGTH: 362
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 236

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Ser Gly Pro Ile Leu Leu Thr
    130                 135                 140

Cys Pro Thr Ile Ser Ile Leu Ser Phe Phe Ser Val Ala Leu Leu Val
145                 150                 155                 160

Ile Leu Ala Cys Val Leu Trp Lys Lys Arg Ile Lys Pro Ile Val Trp
                165                 170                 175

Pro Ser Leu Pro Asp His Lys Lys Thr Leu Glu His Leu Cys Lys Lys
            180                 185                 190

Pro Arg Lys Asn Leu Asn Val Ser Phe Asn Pro Glu Ser Phe Leu Asp
        195                 200                 205

Cys Gln Ile His Arg Val Asp Asp Ile Gln Ala Arg Asp Glu Val Glu
    210                 215                 220

Gly Phe Leu Gln Asp Thr Phe Pro Gln Gln Leu Glu Glu Ser Glu Lys
225                 230                 235                 240

Gln Arg Leu Gly Gly Asp Val Gln Ser Pro Asn Cys Pro Ser Glu Asp
                245                 250                 255

Val Val Ile Thr Pro Glu Ser Phe Gly Arg Asp Ser Ser Leu Thr Cys
            260                 265                 270

Leu Ala Gly Asn Val Ser Ala Cys Asp Ala Pro Ile Leu Ser Ser Ser
        275                 280                 285

Arg Ser Leu Asp Cys Arg Glu Ser Gly Lys Asn Gly Pro His Val Tyr
    290                 295                 300

Gln Asp Leu Leu Leu Ser Leu Gly Thr Thr Asn Ser Thr Leu Pro Pro
305                 310                 315                 320

Pro Phe Ser Leu Gln Ser Gly Ile Leu Thr Leu Asn Pro Val Ala Gln
                325                 330                 335

Gly Gln Pro Ile Leu Thr Ser Leu Gly Ser Asn Gln Glu Glu Ala Tyr
            340                 345                 350

Val Thr Met Ser Ser Phe Tyr Gln Asn Gln

```
                    355                 360

<210> SEQ ID NO 237
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp
145                 150                 155

<210> SEQ ID NO 238
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
        35                  40                  45

Thr Asp Asn Asn Gly Ala Val Lys Phe Pro Gln Leu Cys Lys Phe Cys
    50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
            100                 105                 110

Asp Pro Lys Leu Pro Tyr His Asp Phe Ile Leu Glu Asp Ala Ala Ser
        115                 120                 125

Pro Lys Cys Ile Met Lys Glu Lys Lys Lys Pro Gly Glu Thr Phe Phe
```

```
                130             135             140
Met Cys Ser Cys Ser Asp Glu Cys Asn Asp Asn Ile Ile Phe Ser
145             150             155             160

Glu Glu Tyr Asn Thr Ser Asn Pro Asp
                165

<210> SEQ ID NO 239
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Ser
145                 150                 155                 160

Gly Pro Ile Leu Leu Thr Ile Ser Ile Leu Ser Phe Phe Ser Val Ala
                165                 170                 175

Leu Leu Val Ile Leu Ala Cys Val Leu Trp Lys Lys Arg Ile Lys Pro
                180                 185                 190

Ile Val Trp Pro Ser Leu Pro Asp His Lys Lys Thr Leu Glu His Leu
            195                 200                 205

Cys Lys Lys Pro Arg Lys Asn Leu Asn Val Ser Phe Asn Pro Glu Ser
    210                 215                 220

Phe Leu Asp Cys Gln Ile His Arg Val Asp Asp Ile Gln Ala Arg Asp
225                 230                 235                 240

Glu Val Glu Gly Phe Leu Gln Asp Thr Phe Pro Gln Gln Leu Glu Glu
                245                 250                 255

Ser Glu Lys Gln Arg Leu Gly Gly Asp Val Gln Ser Pro Asn Cys Pro
                260                 265                 270

Ser Glu Asp Val Val Ile Thr Pro Glu Ser Phe Gly Arg Asp Ser Ser
            275                 280                 285

Leu Thr Cys Leu Ala Gly Asn Val Ser Ala Cys Asp Ala Pro Ile Leu
        290                 295                 300

Ser Ser Ser Arg Ser Leu Asp Cys Arg Glu Ser Gly Lys Asn Gly Pro
305                 310                 315                 320
```

```
His Val Tyr Gln Asp Leu Leu Leu Ser Leu Gly Thr Thr Asn Ser Thr
            325                 330                 335

Leu Pro Pro Phe Ser Leu Gln Ser Gly Ile Leu Thr Leu Asn Pro
        340                 345                 350

Val Ala Gln Gly Gln Pro Ile Leu Thr Ser Leu Gly Ser Asn Gln Glu
            355                 360                 365

Glu Ala Tyr Val Thr Met Ser Ser Phe Tyr Gln Asn Gln
        370                 375                 380

<210> SEQ ID NO 240
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
        35                  40                  45

Thr Asp Asn Asn Gly Ala Val Lys Phe Pro Gln Leu Cys Lys Phe Cys
    50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
            100                 105                 110

Asp Pro Lys Leu Pro Tyr His Asp Phe Ile Leu Glu Asp Ala Ala Ser
        115                 120                 125

Pro Lys Cys Ile Met Lys Glu Lys Lys Pro Gly Glu Thr Phe Phe
    130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp Ser Gly Pro Ile Leu Leu Thr
                165                 170                 175

Ile Ser Ile Leu Ser Phe Phe Ser Val Ala Leu Leu Val Ile Leu Ala
            180                 185                 190

Cys Val Leu Trp Lys Lys Arg Ile Lys Pro Ile Val Trp Pro Ser Leu
        195                 200                 205

Pro Asp His Lys Lys Thr Leu Glu His Leu Cys Lys Lys Pro Arg Lys
    210                 215                 220

Asn Leu Asn Val Ser Phe Asn Pro Glu Ser Phe Leu Asp Cys Gln Ile
225                 230                 235                 240

His Arg Val Asp Asp Ile Gln Ala Arg Asp Glu Val Glu Gly Phe Leu
                245                 250                 255

Gln Asp Thr Phe Pro Gln Gln Leu Glu Glu Ser Glu Lys Gln Arg Leu
            260                 265                 270

Gly Gly Asp Val Gln Ser Pro Asn Cys Pro Ser Glu Asp Val Val Ile
        275                 280                 285

Thr Pro Glu Ser Phe Gly Arg Asp Ser Ser Leu Thr Cys Leu Ala Gly
    290                 295                 300
```

```
Asn Val Ser Ala Cys Asp Ala Pro Ile Leu Ser Ser Ser Arg Ser Leu
305                 310                 315                 320

Asp Cys Arg Glu Ser Gly Lys Asn Gly Pro His Val Tyr Gln Asp Leu
            325                 330                 335

Leu Leu Ser Leu Gly Thr Thr Asn Ser Thr Leu Pro Pro Phe Ser
        340                 345                 350

Leu Gln Ser Gly Ile Leu Thr Leu Asn Pro Val Ala Gln Gly Gln Pro
        355                 360                 365

Ile Leu Thr Ser Leu Gly Ser Asn Gln Glu Glu Ala Tyr Val Thr Met
370                 375                 380

Ser Ser Phe Tyr Gln Asn Gln
385                 390

<210> SEQ ID NO 241
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Ser
145                 150                 155                 160

Gly Pro Ile Leu Leu Thr Ile Ser Ile Leu Ser Phe Phe Ser Val Ala
                165                 170                 175

Leu Leu Val Ile Leu Ala Cys Val Leu Trp Lys Lys Arg Ile Lys Pro
            180                 185                 190

Ile Val Trp Pro Ser Leu Pro Asp His Lys Lys Thr Leu Glu His Leu
        195                 200                 205

Cys Lys Lys Pro Arg Lys Asn Leu Asn Val Ser Phe Asn Pro Glu Ser
    210                 215                 220

Phe Leu Asp Cys Gln Ile His Arg Val Asp Asp Ile Gln Ala Arg Asp
225                 230                 235                 240

Glu Val Glu Gly Phe Leu Gln Asp Thr Phe Pro Gln Gln Leu Glu Glu
                245                 250                 255

Ser Glu Lys Gln Arg Leu Gly Gly Asp Val Gln Ser Pro Asn Cys Pro
```

```
                260                 265                 270
Ser Glu Asp Val Val Ile Thr Pro Glu Ser Phe Gly Arg Asp Ser Ser
            275                 280                 285

Leu Thr Cys Leu Ala Gly Asn Val Ser Ala Cys Asp Ala Pro Ile Leu
        290                 295                 300

Ser Ser Ser Arg Ser Leu Asp Cys Arg Glu Ser Gly Lys Asn Gly Pro
305                 310                 315                 320

His Val Tyr Gln Asp Leu Leu Leu Ser Leu Gly Thr Thr Asn Ser Thr
                325                 330                 335

Leu Pro Pro Pro Phe Ser Leu Gln Ser Gly Ile Leu Thr Leu Asn Pro
            340                 345                 350

Val Ala Gln Gly Gln Pro Ile Leu Thr Ser Leu Gly Ser Asn Gln Glu
        355                 360                 365

Glu Ala Tyr Val Thr Met Ser Ser Phe Tyr Gln Asn Gln
                370                 375                 380

<210> SEQ ID NO 242
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Thr Ile Pro Pro His Val Gln Lys Ser Val Asn Asn Asp Met Ile Val
        35                  40                  45

Thr Asp Asn Asn Gly Ala Val Lys Phe Pro Gln Leu Cys Lys Phe Cys
    50                  55                  60

Asp Val Arg Phe Ser Thr Cys Asp Asn Gln Lys Ser Cys Met Ser Asn
65                  70                  75                  80

Cys Ser Ile Thr Ser Ile Cys Glu Lys Pro Gln Glu Val Cys Val Ala
                85                  90                  95

Val Trp Arg Lys Asn Asp Glu Asn Ile Thr Leu Glu Thr Val Cys His
            100                 105                 110

Asp Pro Lys Leu Pro Tyr His Asp Phe Ile Leu Glu Asp Ala Ala Ser
        115                 120                 125

Pro Lys Cys Ile Met Lys Glu Lys Lys Lys Pro Gly Glu Thr Phe Phe
    130                 135                 140

Met Cys Ser Cys Ser Ser Asp Glu Cys Asn Asp Asn Ile Ile Phe Ser
145                 150                 155                 160

Glu Glu Tyr Asn Thr Ser Asn Pro Asp Ser Gly Pro Ile Leu Leu Thr
                165                 170                 175

Cys Pro Thr Ile Ser Ile Leu Ser Phe Phe Ser Val Ala Leu Leu Val
            180                 185                 190

Ile Leu Ala Cys Val Leu Trp Lys Lys Arg Ile Lys Pro Ile Val Trp
        195                 200                 205

Pro Ser Leu Pro Asp His Lys Lys Thr Leu Glu His Leu Cys Lys Lys
    210                 215                 220

Pro Arg Lys Asn Leu Asn Val Ser Phe Asn Pro Glu Ser Phe Leu Asp
225                 230                 235                 240
```

```
Cys Gln Ile His Arg Val Asp Asp Ile Gln Ala Arg Asp Glu Val Glu
            245                 250                 255

Gly Phe Leu Gln Asp Thr Phe Pro Gln Gln Leu Glu Glu Ser Glu Lys
            260                 265                 270

Gln Arg Leu Gly Gly Asp Val Gln Ser Pro Asn Cys Pro Ser Glu Asp
            275                 280                 285

Val Val Ile Thr Pro Glu Ser Phe Gly Arg Asp Ser Ser Leu Thr Cys
            290                 295                 300

Leu Ala Gly Asn Val Ser Ala Cys Asp Ala Pro Ile Leu Ser Ser Ser
305                 310                 315                 320

Arg Ser Leu Asp Cys Arg Glu Ser Gly Lys Asn Gly Pro His Val Tyr
            325                 330                 335

Gln Asp Leu Leu Leu Ser Leu Gly Thr Thr Asn Ser Thr Leu Pro Pro
            340                 345                 350

Pro Phe Ser Leu Gln Ser Gly Ile Leu Thr Leu Asn Pro Val Ala Gln
            355                 360                 365

Gly Gln Pro Ile Leu Thr Ser Leu Gly Ser Asn Gln Glu Glu Ala Tyr
            370                 375                 380

Val Thr Met Ser Ser Phe Tyr Gln Asn Gln
385                 390

<210> SEQ ID NO 243
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Leu Leu Leu Val Thr Ser Leu Leu Leu Cys Glu Leu Pro His Pro
1               5                   10                  15

Ala Phe Leu Leu Ile Pro Thr Ile Pro Pro His Val Gln Lys Ser Val
            20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
            85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Ser
145                 150                 155                 160

Gly Pro Ile Leu Leu Thr Cys Pro Thr Ile Ser Ile Leu Ser Phe Phe
            165                 170                 175

Ser Val Ala Leu Leu Val Ile Leu Ala Cys Val Leu Trp Lys Lys Arg
            180                 185                 190

Ile Lys Pro Ile Val Trp Pro Ser Leu Pro Asp His Lys Lys Thr Leu
            195                 200                 205
```

```
Glu His Leu Cys Lys Lys Pro Arg Lys Asn Leu Asn Val Ser Phe Asn
    210                 215                 220

Pro Glu Ser Phe Leu Asp Cys Gln Ile His Arg Val Asp Asp Ile Gln
225                 230                 235                 240

Ala Arg Asp Glu Val Glu Gly Phe Leu Gln Asp Thr Phe Pro Gln Gln
                245                 250                 255

Leu Glu Glu Ser Glu Lys Gln Arg Leu Gly Gly Asp Val Gln Ser Pro
                260                 265                 270

Asn Cys Pro Ser Glu Asp Val Val Ile Thr Pro Glu Ser Phe Gly Arg
            275                 280                 285

Asp Ser Ser Leu Thr Cys Leu Ala Gly Asn Val Ser Ala Cys Asp Ala
            290                 295                 300

Pro Ile Leu Ser Ser Ser Arg Ser Leu Asp Cys Arg Glu Ser Gly Lys
305                 310                 315                 320

Asn Gly Pro His Val Tyr Gln Asp Leu Leu Leu Ser Leu Gly Thr Thr
                325                 330                 335

Asn Ser Thr Leu Pro Pro Pro Phe Ser Leu Gln Ser Gly Ile Leu Thr
                340                 345                 350

Leu Asn Pro Val Ala Gln Gly Gln Pro Ile Leu Thr Ser Leu Gly Ser
            355                 360                 365

Asn Gln Glu Glu Ala Tyr Val Thr Met Ser Ser Phe Tyr Gln Asn Gln
            370                 375                 380

<210> SEQ ID NO 244
<211> LENGTH: 2555
<212> TYPE: PRT
<213> ORGANISM: Homo sapiens

<400> SEQUENCE: 244

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
                100                 105                 110

Asn Gly Gly Thr Cys Asp Leu Leu Thr Leu Thr Glu Tyr Lys Cys Arg
            115                 120                 125

Cys Pro Pro Gly Trp Ser Gly Lys Ser Cys Gln Gln Ala Asp Pro Cys
            130                 135                 140

Ala Ser Asn Pro Cys Ala Asn Gly Gly Gln Cys Leu Pro Phe Glu Ala
145                 150                 155                 160

Ser Tyr Thr Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
                180                 185                 190

Gly Thr Cys His Asn Glu Val Gly Ser Tyr Arg Cys Val Cys Arg Ala
```

-continued

```
            195                 200                 205
Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
                260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
                340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
        370                 375                 380

Ser Asn Cys Asp Thr Asn Pro Val Asn Gly Lys Ala Thr Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Thr Gly Glu Phe Gln Cys Thr Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620
```

-continued

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
            645                 650                 655

Asp Lys Ile Asp Gly Tyr Glu Cys Ala Cys Glu Pro Cys Tyr Thr Gly
            660                 665                 670

Ser Met Cys Asn Ile Asn Ile Asp Glu Cys Ala Gly Asn Pro Cys His
            675                 680                 685

Asn Gly Gly Thr Cys Glu Asp Gly Ile Asn Gly Phe Thr Cys Arg Cys
            690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
            725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
                835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
                915                 920                 925

Ala Phe Cys Asp Cys Leu Pro Gly Phe Arg Gly Thr Phe Cys Glu Glu
                930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
                980                 985                 990

Phe Asn Gly Gly Thr Cys Val Asp Gly Ile Asn Ser Phe Thr Cys Leu
                995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

-continued

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
    1235                1240                1245

Gly Gly Tyr Ser Cys Thr Cys Pro Pro Gly Phe Val Gly Glu Arg
    1250                1255                1260

Cys Glu Gly Asp Val Asn Glu Cys Leu Ser Asn Pro Cys Asp Ala
    1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Thr Cys Lys Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro

-continued

```
            1430                1435                1440

Leu Ile Glu Glu Ala Cys Glu Leu Pro Glu Cys Gln Glu Asp Ala
        1445                1450                1455

Gly Asn Lys Val Cys Ser Leu Gln Cys Asn Asn His Ala Cys Gly
        1460                1465                1470

Trp Asp Gly Gly Asp Cys Ser Leu Asn Phe Asn Asp Pro Trp Lys
        1475                1480                1485

Asn Cys Thr Gln Ser Leu Gln Cys Trp Lys Tyr Phe Ser Asp Gly
        1490                1495                1500

His Cys Asp Ser Gln Cys Asn Ser Ala Gly Cys Leu Phe Asp Gly
        1505                1510                1515

Phe Asp Cys Gln Arg Ala Glu Gly Gln Cys Asn Pro Leu Tyr Asp
        1520                1525                1530

Gln Tyr Cys Lys Asp His Phe Ser Asp Gly His Cys Asp Gln Gly
        1535                1540                1545

Cys Asn Ser Ala Glu Cys Glu Trp Asp Gly Leu Asp Cys Ala Glu
        1550                1555                1560

His Val Pro Glu Arg Leu Ala Ala Gly Thr Leu Val Val Val Val
        1565                1570                1575

Leu Met Pro Pro Glu Gln Leu Arg Asn Ser Ser Phe His Phe Leu
        1580                1585                1590

Arg Glu Leu Ser Arg Val Leu His Thr Asn Val Val Phe Lys Arg
        1595                1600                1605

Asp Ala His Gly Gln Gln Met Ile Phe Pro Tyr Tyr Gly Arg Glu
        1610                1615                1620

Glu Glu Leu Arg Lys His Pro Ile Lys Arg Ala Ala Glu Gly Trp
        1625                1630                1635

Ala Ala Pro Asp Ala Leu Leu Gly Gln Val Lys Ala Ser Leu Leu
        1640                1645                1650

Pro Gly Gly Ser Glu Gly Gly Arg Arg Arg Arg Glu Leu Asp Pro
        1655                1660                1665

Met Asp Val Arg Gly Ser Ile Val Tyr Leu Glu Ile Asp Asn Arg
        1670                1675                1680

Gln Cys Val Gln Ala Ser Ser Gln Cys Phe Gln Ser Ala Thr Asp
        1685                1690                1695

Val Ala Ala Phe Leu Gly Ala Leu Ala Ser Leu Gly Ser Leu Asn
        1700                1705                1710

Ile Pro Tyr Lys Ile Glu Ala Val Gln Ser Glu Thr Val Glu Pro
        1715                1720                1725

Pro Pro Pro Ala Gln Leu His Phe Met Tyr Val Ala Ala Ala Ala
        1730                1735                1740

Phe Val Leu Leu Phe Phe Val Gly Cys Gly Val Leu Leu Ser Arg
        1745                1750                1755

Lys Arg Arg Arg Gln His Gly Gln Leu Trp Phe Pro Glu Gly Phe
        1760                1765                1770

Lys Val Ser Glu Ala Ser Lys Lys Arg Arg Glu Pro Leu Gly
        1775                1780                1785

Glu Asp Ser Val Gly Leu Lys Pro Leu Lys Asn Ala Ser Asp Gly
        1790                1795                1800

Ala Leu Met Asp Asp Asn Gln Asn Glu Trp Gly Asp Glu Asp Leu
        1805                1810                1815

Glu Thr Lys Lys Phe Arg Phe Glu Glu Pro Val Val Leu Pro Asp
        1820                1825                1830
```

-continued

```
Leu Asp Asp Gln Thr Asp His Arg Gln Trp Thr Gln Gln His Leu
1835                    1840                1845

Asp Ala Ala Asp Leu Arg Met Ser Ala Met Ala Pro Thr Pro Pro
1850                    1855                1860

Gln Gly Glu Val Asp Ala Asp Cys Met Asp Val Asn Val Arg Gly
1865                    1870                1875

Pro Asp Gly Phe Thr Pro Leu Met Ile Ala Ser Cys Ser Gly Gly
1880                    1885                1890

Gly Leu Glu Thr Gly Asn Ser Glu Glu Glu Asp Ala Pro Ala
1895                    1900                1905

Val Ile Ser Asp Phe Ile Tyr Gln Gly Ala Ser Leu His Asn Gln
1910                    1915                1920

Thr Asp Arg Thr Gly Glu Thr Ala Leu His Leu Ala Ala Arg Tyr
1925                    1930                1935

Ser Arg Ser Asp Ala Ala Lys Arg Leu Leu Glu Ala Ser Ala Asp
1940                    1945                1950

Ala Asn Ile Gln Asp Asn Met Gly Arg Thr Pro Leu His Ala Ala
1955                    1960                1965

Val Ser Ala Asp Ala Gln Gly Val Phe Gln Ile Leu Ile Arg Asn
1970                    1975                1980

Arg Ala Thr Asp Leu Asp Ala Arg Met His Asp Gly Thr Thr Pro
1985                    1990                1995

Leu Ile Leu Ala Ala Arg Leu Ala Val Glu Gly Met Leu Glu Asp
2000                    2005                2010

Leu Ile Asn Ser His Ala Asp Val Asn Ala Val Asp Asp Leu Gly
2015                    2020                2025

Lys Ser Ala Leu His Trp Ala Ala Ala Val Asn Asn Val Asp Ala
2030                    2035                2040

Ala Val Val Leu Leu Lys Asn Gly Ala Asn Lys Asp Met Gln Asn
2045                    2050                2055

Asn Arg Glu Glu Thr Pro Leu Phe Leu Ala Ala Arg Glu Gly Ser
2060                    2065                2070

Tyr Glu Thr Ala Lys Val Leu Leu Asp His Phe Ala Asn Arg Asp
2075                    2080                2085

Ile Thr Asp His Met Asp Arg Leu Pro Arg Asp Ile Ala Gln Glu
2090                    2095                2100

Arg Met His His Asp Ile Val Arg Leu Leu Asp Glu Tyr Asn Leu
2105                    2110                2115

Val Arg Ser Pro Gln Leu His Gly Ala Pro Leu Gly Gly Thr Pro
2120                    2125                2130

Thr Leu Ser Pro Pro Leu Cys Ser Pro Asn Gly Tyr Leu Gly Ser
2135                    2140                2145

Leu Lys Pro Gly Val Gln Gly Lys Lys Val Arg Lys Pro Ser Ser
2150                    2155                2160

Lys Gly Leu Ala Cys Gly Ser Lys Glu Ala Lys Asp Leu Lys Ala
2165                    2170                2175

Arg Arg Lys Lys Ser Gln Asp Gly Lys Gly Cys Leu Leu Asp Ser
2180                    2185                2190

Ser Gly Met Leu Ser Pro Val Asp Ser Leu Glu Ser Pro His Gly
2195                    2200                2205

Tyr Leu Ser Asp Val Ala Ser Pro Pro Leu Leu Pro Ser Pro Phe
2210                    2215                2220
```

-continued

```
Gln Gln Ser Pro Ser Val Pro Leu Asn His Leu Pro Gly Met Pro
    2225                2230                2235

Asp Thr His Leu Gly Thr Gly His Leu Asn Val Ala Ala Lys Pro
    2240                2245                2250

Glu Met Ala Ala Leu Gly Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555
```

<210> SEQ ID NO 245
<211> LENGTH: 2472
<212> TYPE: PRT
<213> ORGANISM: Homo sapiens

<400> SEQUENCE: 245

```
Ser Met Pro Ala Leu Arg Pro Ala Leu Leu Trp Ala Leu Leu Ala Leu
1               5                   10                  15
```

```
Trp Leu Cys Cys Ala Ala Pro Ala His Ala Leu Gln Cys Arg Asp Gly
            20                  25                  30

Tyr Glu Pro Cys Val Asn Glu Gly Met Cys Val Thr Tyr His Asn Gly
            35                  40                  45

Thr Gly Tyr Cys Lys Cys Pro Glu Gly Phe Leu Gly Glu Tyr Cys Gln
 50                  55                  60

His Arg Asp Pro Cys Glu Lys Asn Arg Cys Gln Asn Gly Gly Thr Cys
 65                  70                  75                  80

Val Ala Gln Ala Met Leu Gly Lys Ala Thr Cys Arg Cys Ala Ser Gly
                85                  90                  95

Phe Thr Gly Glu Asp Cys Gln Tyr Ser Thr Ser His Pro Cys Phe Val
                100                 105                 110

Ser Arg Pro Cys Leu Asn Gly Gly Thr Cys His Met Leu Ser Arg Asp
            115                 120                 125

Thr Tyr Glu Cys Thr Cys Gln Val Gly Phe Thr Gly Lys Glu Cys Gln
    130                 135                 140

Trp Thr Asp Ala Cys Leu Ser His Pro Cys Ala Asn Gly Ser Thr Cys
145                 150                 155                 160

Thr Thr Val Ala Asn Gln Phe Ser Cys Lys Cys Leu Thr Gly Phe Thr
                165                 170                 175

Gly Gln Lys Cys Glu Thr Asp Val Asn Glu Cys Asp Ile Pro Gly His
            180                 185                 190

Cys Gln His Gly Gly Thr Cys Leu Asn Leu Pro Gly Ser Tyr Gln Cys
            195                 200                 205

Gln Cys Pro Gln Gly Phe Thr Gly Gln Tyr Cys Asp Ser Leu Tyr Val
            210                 215                 220

Pro Cys Ala Pro Ser Pro Cys Val Asn Gly Gly Thr Cys Arg Gln Thr
225                 230                 235                 240

Gly Asp Phe Thr Phe Glu Cys Asn Cys Leu Pro Gly Phe Glu Gly Ser
                245                 250                 255

Thr Cys Glu Arg Asn Ile Asp Asp Cys Pro Asn His Arg Cys Gln Asn
            260                 265                 270

Gly Gly Val Cys Val Asp Gly Val Asn Thr Tyr Asn Cys Arg Cys Pro
            275                 280                 285

Pro Gln Trp Thr Gly Gln Phe Cys Thr Glu Asp Val Asp Glu Cys Leu
290                 295                 300

Leu Gln Pro Asn Ala Cys Gln Asn Gly Gly Thr Cys Ala Asn Arg Asn
305                 310                 315                 320

Gly Gly Tyr Gly Cys Val Cys Val Asn Gly Trp Ser Gly Asp Asp Cys
                325                 330                 335

Ser Glu Asn Ile Asp Asp Cys Ala Phe Ala Ser Cys Thr Pro Gly Ser
            340                 345                 350

Thr Cys Ile Asp Arg Val Ala Ser Phe Ser Cys Met Cys Pro Glu Gly
            355                 360                 365

Lys Ala Gly Leu Leu Cys His Leu Asp Asp Ala Cys Ile Ser Asn Pro
            370                 375                 380

Cys His Lys Gly Ala Leu Cys Asp Thr Asn Pro Leu Asn Gly Gln Tyr
385                 390                 395                 400

Thr Cys Thr Cys Pro Gln Gly Tyr Lys Gly Ala Asp Cys Thr Glu Asp
                405                 410                 415

Val Asp Glu Cys Ala Met Ala Asn Ser Asn Pro Cys Glu His Ala Gly
            420                 425                 430
```

```
Lys Cys Val Asn Thr Asp Gly Ala Phe His Cys Glu Cys Leu Lys Gly
            435                 440                 445

Tyr Ala Gly Pro Arg Cys Glu Met Asp Ile Asn Glu Cys His Ser Asp
450                 455                 460

Pro Cys Gln Asn Asp Ala Thr Cys Leu Asp Lys Thr Gly Gly Phe Thr
465                 470                 475                 480

Cys Leu Cys Met Pro Gly Phe Lys Gly Val His Cys Glu Leu Glu Ile
                485                 490                 495

Asn Glu Cys Gln Ser Asn Pro Cys Val Asn Gly Gln Cys Val Asp
                500                 505                 510

Lys Val Asn Arg Phe Gln Cys Leu Cys Pro Pro Gly Phe Thr Gly Pro
            515                 520                 525

Val Cys Gln Ile Asp Ile Asp Asp Cys Ser Ser Thr Pro Cys Leu Asn
        530                 535                 540

Gly Ala Lys Cys Ile Asp His Pro Asn Gly Tyr Glu Cys Gln Cys Ala
545                 550                 555                 560

Thr Gly Phe Thr Gly Val Leu Cys Glu Glu Asn Ile Asp Asn Cys Asp
                565                 570                 575

Pro Asp Pro Cys His His Gly Gln Cys Gln Asp Gly Ile Asp Ser Tyr
                580                 585                 590

Thr Cys Ile Cys Asn Pro Gly Tyr Met Gly Ala Thr Cys Ser Asp Gln
            595                 600                 605

Ile Asp Glu Cys Tyr Ser Ser Pro Cys Leu Asn Asp Gly Arg Cys Ile
        610                 615                 620

Asp Leu Val Asn Gly Tyr Gln Cys Asn Cys Gln Pro Gly Thr Ser Gly
625                 630                 635                 640

Val Asn Cys Glu Ile Asn Phe Asp Asp Cys Ala Ser Asn Pro Cys Ile
                645                 650                 655

His Gly Thr Cys Met Asp Gly Ile Asn Arg Tyr Ser Cys Val Cys Ser
                660                 665                 670

Pro Gly Phe Thr Gly Gln Arg Cys Asn Ile Asp Ile Asp Glu Cys Ala
            675                 680                 685

Ser Asn Pro Cys Arg Lys Gly Ala Thr Cys Ile Asn Gly Val Asn Gly
        690                 695                 700

Phe Arg Cys Thr Cys Pro Glu Gly Pro His His Pro Ser Cys Tyr Ser
705                 710                 715                 720

Gln Val Asn Glu Cys Leu Ser Asn Pro Cys Ile His Gly Asn Cys Thr
                725                 730                 735

Gly Gly Leu Ser Gly Tyr Lys Cys Leu Cys Asp Ala Gly Trp Val Gly
                740                 745                 750

Ile Asn Cys Glu Val Asp Lys Asn Glu Cys Leu Ser Asn Pro Cys Gln
            755                 760                 765

Asn Gly Gly Thr Cys Asp Asn Leu Val Asn Gly Tyr Arg Cys Thr Cys
        770                 775                 780

Lys Lys Gly Phe Lys Gly Tyr Asn Cys Gln Val Asn Ile Asp Glu Cys
785                 790                 795                 800

Ala Ser Asn Pro Cys Leu Asn Gln Gly Thr Cys Phe Asp Asp Ile Ser
                805                 810                 815

Gly Tyr Thr Cys His Cys Val Leu Pro Tyr Thr Gly Lys Asn Cys Gln
                820                 825                 830

Thr Val Leu Ala Pro Cys Ser Pro Asn Pro Cys Glu Asn Ala Ala Val
            835                 840                 845

Cys Lys Glu Ser Pro Asn Phe Glu Ser Tyr Thr Cys Leu Cys Ala Pro
```

-continued

```
            850                 855                 860
Gly Trp Gln Gly Gln Arg Cys Thr Ile Asp Ile Asp Glu Cys Ile Ser
865                 870                 875                 880

Lys Pro Cys Met Asn His Gly Leu Cys His Asn Thr Gln Gly Ser Tyr
                885                 890                 895

Met Cys Glu Cys Pro Pro Gly Phe Ser Gly Met Asp Cys Glu Glu Asp
                900                 905                 910

Ile Asp Asp Cys Leu Ala Asn Pro Cys Gln Asn Gly Gly Ser Cys Met
            915                 920                 925

Asp Gly Val Asn Thr Phe Ser Cys Leu Cys Leu Pro Gly Phe Thr Gly
        930                 935                 940

Asp Lys Cys Gln Thr Asp Met Asn Glu Cys Leu Ser Glu Pro Cys Lys
945                 950                 955                 960

Asn Gly Gly Thr Cys Ser Asp Tyr Val Asn Ser Tyr Thr Cys Lys Cys
                965                 970                 975

Gln Ala Gly Phe Asp Gly Val His Cys Glu Asn Asn Ile Asn Glu Cys
                980                 985                 990

Thr Glu Ser Ser Cys Phe Asn Gly  Gly Thr Cys Val Asp  Gly Ile Asn
        995                 1000                1005

Ser Phe  Ser Cys Leu Cys Pro  Val Gly Phe Thr Gly  Ser Phe Cys
    1010                 1015                1020

Leu His  Glu Ile Asn Glu Cys  Ser Ser His Pro Cys  Leu Asn Glu
    1025                 1030                1035

Gly Thr  Cys Val Asp Gly Leu  Gly Thr Tyr Arg Cys  Ser Cys Pro
    1040                 1045                1050

Leu Gly  Tyr Thr Gly Lys Asn  Cys Gln Thr Leu Val  Asn Leu Cys
    1055                 1060                1065

Ser Arg  Ser Pro Cys Lys Asn  Lys Gly Thr Cys Val  Gln Lys Lys
    1070                 1075                1080

Ala Glu  Ser Gln Cys Leu Cys  Pro Ser Gly Trp Ala  Gly Ala Tyr
    1085                 1090                1095

Cys Asp  Val Pro Asn Val Ser  Cys Asp Ile Ala Ala  Ser Arg Arg
    1100                 1105                1110

Gly Val  Leu Val Glu His Leu  Cys Gln His Ser Gly  Val Cys Ile
    1115                 1120                1125

Asn Ala  Gly Asn Thr His Tyr  Cys Gln Cys Pro Leu  Gly Tyr Thr
    1130                 1135                1140

Gly Ser  Tyr Cys Glu Glu Gln  Leu Asp Glu Cys Ala  Ser Asn Pro
    1145                 1150                1155

Cys Gln  His Gly Ala Thr Cys  Ser Asp Phe Thr Gly  Gly Tyr Arg
    1160                 1165                1170

Cys Glu  Cys Val Pro Gly Tyr  Gln Gly Val Asn Cys  Glu Tyr Glu
    1175                 1180                1185

Val Asp  Glu Cys Gln Asn Gln  Pro Cys Gln Asn Gly  Gly Thr Cys
    1190                 1195                1200

Ile Asp  Leu Val Asn His Phe  Lys Cys Ser Cys Pro  Pro Gly Thr
    1205                 1210                1215

Arg Gly  Leu Leu Cys Glu Glu  Asn Ile Asp Asp Cys  Ala Arg Gly
    1220                 1225                1230

Pro His  Cys Leu Asn Gly Gly  Gln Cys Met Asp Arg  Thr Gly Gly
    1235                 1240                1245

Tyr Ser  Cys Arg Cys Leu Pro  Gly Phe Ala Gly Glu  Arg Cys Glu
    1250                 1255                1260
```

```
Gly Asp Ile Asn Glu Cys Leu Ser Asn Pro Cys Ser  Ser Glu Gly
1265                 1270                 1275

Ser Leu Asp Cys Ile Gln Leu Thr Asn Asp Tyr Leu  Cys Val Cys
1280                 1285                 1290

Arg Ser Ala Phe Thr Gly Arg His Cys Glu Thr Phe  Val Asp Val
1295                 1300                 1305

Cys Pro Gln Met Pro Cys Leu Asn Gly Gly Thr Cys  Ala Val Ala
1310                 1315                 1320

Ser Asn Met Pro Asp Gly Phe Thr Cys Arg Cys Pro  Pro Gly Phe
1325                 1330                 1335

Ser Gly Ala Arg Cys Gln Ser Ser Cys Gly Gln Val  Lys Cys Arg
1340                 1345                 1350

Lys Gly Glu Gln Cys Val His Thr Ala Ser Gly Pro  Arg Cys Phe
1355                 1360                 1365

Cys Pro Ser Pro Arg Asp Cys Glu Ser Gly Cys Ala  Ser Ser Pro
1370                 1375                 1380

Cys Gln His Gly Gly Ser Cys His Pro Gln Arg Gln  Pro Pro Tyr
1385                 1390                 1395

Tyr Ser Cys Gln Cys Ala Pro Pro Phe Ser Gly Ser  Arg Cys Glu
1400                 1405                 1410

Leu Tyr Thr Ala Pro Pro Ser Thr Pro Pro Ala Thr  Cys Leu Ser
1415                 1420                 1425

Gln Tyr Cys Ala Asp Lys Ala Arg Asp Gly Val Cys  Asp Glu Ala
1430                 1435                 1440

Cys Asn Ser His Ala Cys Gln Trp Asp Gly Gly Asp  Cys Ser Leu
1445                 1450                 1455

Ile Met Glu Asn Pro Trp Ala Asn Cys Ser Ser Pro  Leu Pro Cys
1460                 1465                 1470

Trp Asp Tyr Ile Asn Asn Gln Cys Asp Glu Leu Cys  Asn Thr Val
1475                 1480                 1485

Glu Cys Leu Phe Asp Asn Phe Glu Cys Gln Gly Asn  Ser Lys Thr
1490                 1495                 1500

Cys Lys Tyr Asp Lys Tyr Cys Ala Asp His Phe Lys  Asp Asn His
1505                 1510                 1515

Cys Asp Gln Gly Cys Asn Ser Glu Glu Cys Gly Trp  Asp Gly Leu
1520                 1525                 1530

Asp Cys Ala Ala Asp Gln Pro Glu Asn Leu Ala Glu  Gly Thr Leu
1535                 1540                 1545

Val Ile Val Val Leu Met Pro Pro Glu Gln Leu Leu  Gln Asp Ala
1550                 1555                 1560

Arg Ser Phe Leu Arg Ala Leu Gly Thr Leu Leu His  Thr Asn Leu
1565                 1570                 1575

Arg Ile Lys Arg Asp Ser Gln Gly Glu Leu Met Val  Tyr Pro Tyr
1580                 1585                 1590

Tyr Gly Glu Lys Ser Ala Ala Met Lys Lys Gln Arg  Met Thr Arg
1595                 1600                 1605

Arg Ser Leu Pro Gly Glu Gln Glu Gln Glu Val Ala  Gly Ser Lys
1610                 1615                 1620

Val Phe Leu Glu Ile Asp Asn Arg Gln Cys Val Gln  Asp Ser Asp
1625                 1630                 1635

His Cys Phe Lys Asn Thr Asp Ala Ala Ala Ala Leu  Leu Ala Ser
1640                 1645                 1650
```

His Ala Ile Gln Gly Thr Leu Ser Tyr Pro Leu Val Ser Val Val
1655                1660                1665

Ser Glu Ser Leu Thr Pro Glu Arg Thr Gln Leu Leu Tyr Leu Leu
1670                1675                1680

Ala Val Ala Val Val Ile Ile Leu Phe Ile Ile Leu Leu Gly Val
1685                1690                1695

Ile Met Ala Lys Arg Lys Arg Lys His Gly Ser Leu Trp Leu Pro
1700                1705                1710

Glu Gly Phe Thr Leu Arg Arg Asp Ala Ser Asn His Lys Arg Arg
1715                1720                1725

Glu Pro Val Gly Gln Asp Ala Val Gly Leu Lys Asn Leu Ser Val
1730                1735                1740

Gln Val Ser Glu Ala Asn Leu Thr Gly Thr Gly Thr Ser Glu His
1745                1750                1755

Trp Val Asp Asp Glu Gly Pro Gln Pro Lys Lys Val Lys Ala Glu
1760                1765                1770

Asp Glu Ala Leu Leu Ser Glu Glu Asp Asp Pro Ile Asp Arg Arg
1775                1780                1785

Pro Trp Thr Gln Gln His Leu Glu Ala Ala Asp Ile Arg Arg Thr
1790                1795                1800

Pro Ser Leu Ala Leu Thr Pro Pro Gln Ala Glu Gln Glu Val Asp
1805                1810                1815

Val Leu Asp Val Asn Val Arg Gly Pro Asp Gly Cys Thr Pro Leu
1820                1825                1830

Met Leu Ala Ser Leu Arg Gly Gly Ser Ser Asp Leu Ser Asp Glu
1835                1840                1845

Asp Glu Asp Ala Glu Asp Ser Ser Ala Asn Ile Ile Thr Asp Leu
1850                1855                1860

Val Tyr Gln Gly Ala Ser Leu Gln Ala Gln Thr Asp Arg Thr Gly
1865                1870                1875

Glu Met Ala Leu His Leu Ala Ala Arg Tyr Ser Arg Ala Asp Ala
1880                1885                1890

Ala Lys Arg Leu Leu Asp Ala Gly Ala Asp Ala Asn Ala Gln Asp
1895                1900                1905

Asn Met Gly Arg Cys Pro Leu His Ala Ala Val Ala Ala Asp Ala
1910                1915                1920

Gln Gly Val Phe Gln Ile Leu Ile Arg Asn Arg Val Thr Asp Leu
1925                1930                1935

Asp Ala Arg Met Asn Asp Gly Thr Thr Pro Leu Ile Leu Ala Ala
1940                1945                1950

Arg Leu Ala Val Glu Gly Met Val Ala Glu Leu Ile Asn Cys Gln
1955                1960                1965

Ala Asp Val Asn Ala Val Asp Asp His Gly Lys Ser Ala Leu His
1970                1975                1980

Trp Ala Ala Ala Val Asn Asn Val Glu Ala Thr Leu Leu Leu Leu
1985                1990                1995

Lys Asn Gly Ala Asn Arg Asp Met Gln Asp Asn Lys Glu Glu Thr
2000                2005                2010

Pro Leu Phe Leu Ala Ala Arg Glu Gly Ser Tyr Glu Ala Ala Lys
2015                2020                2025

Ile Leu Leu Asp His Phe Ala Asn Arg Asp Ile Thr Asp His Met
2030                2035                2040

Asp Arg Leu Pro Arg Asp Val Ala Arg Asp Arg Met His His Asp

```
            2045                2050                2055
Ile Val Arg Leu Leu Asp Glu Tyr Asn Val Thr Pro Ser Pro Pro
    2060                2065                2070

Gly Thr Val Leu Thr Ser Ala Leu Ser Pro Val Thr Cys Gly Pro
    2075                2080                2085

Asn Arg Ser Phe Leu Ser Leu Lys His Thr Pro Met Gly Lys Lys
    2090                2095                2100

Ser Arg Arg Pro Ser Ala Lys Ser Thr Met Pro Thr Ser Leu Pro
    2105                2110                2115

Asn Leu Ala Lys Glu Ala Lys Asp Ala Lys Gly Ser Arg Arg Lys
    2120                2125                2130

Lys Ser Leu Ser Glu Lys Val Gln Leu Ser Glu Ser Ser Val Thr
    2135                2140                2145

Leu Ser Pro Val Asp Ser Leu Glu Ser Pro His Thr Tyr Val Ser
    2150                2155                2160

Asp Thr Thr Ser Ser Pro Met Ile Thr Ser Pro Gly Ile Leu Gln
    2165                2170                2175

Ala Ser Pro Asn Pro Met Leu Ala Thr Ala Pro Pro Ala Pro
    2180                2185                2190

Val His Ala Gln His Ala Leu Ser Phe Ser Asn Leu His Glu Met
    2195                2200                2205

Gln Pro Leu Ala His Gly Ala Ser Thr Val Leu Pro Ser Val Ser
    2210                2215                2220

Gln Leu Leu Ser His His His Ile Val Ser Pro Gly Ser Gly Ser
    2225                2230                2235

Ala Gly Ser Leu Ser Arg Leu His Pro Val Pro Val Pro Ala Asp
    2240                2245                2250

Trp Met Asn Arg Met Glu Val Asn Glu Thr Gln Tyr Asn Glu Met
    2255                2260                2265

Phe Gly Met Val Leu Ala Pro Ala Glu Gly Thr His Pro Gly Ile
    2270                2275                2280

Ala Pro Gln Ser Arg Pro Pro Glu Gly Lys His Ile Thr Thr Pro
    2285                2290                2295

Arg Glu Pro Leu Pro Pro Ile Val Thr Phe Gln Leu Ile Pro Lys
    2300                2305                2310

Gly Ser Ile Ala Gln Pro Ala Gly Ala Pro Gln Pro Gln Ser Thr
    2315                2320                2325

Cys Pro Pro Ala Val Ala Gly Pro Leu Pro Thr Met Tyr Gln Ile
    2330                2335                2340

Pro Glu Met Ala Arg Leu Pro Ser Val Ala Phe Pro Thr Ala Met
    2345                2350                2355

Met Pro Gln Gln Asp Gly Gln Val Ala Gln Thr Ile Leu Pro Ala
    2360                2365                2370

Tyr His Pro Phe Pro Ala Ser Val Gly Lys Tyr Pro Thr Pro Pro
    2375                2380                2385

Ser Gln His Ser Tyr Ala Ser Ser Asn Ala Ala Glu Arg Thr Pro
    2390                2395                2400

Ser His Ser Gly His Leu Gln Gly Glu His Pro Tyr Leu Thr Pro
    2405                2410                2415

Ser Pro Glu Ser Pro Asp Gln Trp Ser Ser Ser Pro His Ser
    2420                2425                2430

Ala Ser Asp Trp Ser Asp Val Thr Thr Ser Pro Thr Pro Gly Gly
    2435                2440                2445
```

```
Ala Gly Gly Gly Gln Arg Gly Pro Gly Thr His Met Ser Glu Pro
    2450                2455                2460

Pro His Asn Asn Met Gln Val Tyr Ala
    2465                2470

<210> SEQ ID NO 246
<211> LENGTH: 1235
<212> TYPE: PRT
<213> ORGANISM: Homo sapiens

<400> SEQUENCE: 246

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Ile Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
```

```
            340                 345                 350
Cys Ile Asp Arg Val Ala Ser Phe Ser Cys Met Cys Pro Glu Gly Lys
            355                 360                 365
Ala Gly Leu Leu Cys His Leu Asp Asp Ala Cys Ile Ser Asn Pro Cys
            370                 375                 380
His Lys Gly Ala Leu Cys Asp Thr Asn Pro Leu Asn Gly Gln Tyr Thr
385                 390                 395                 400
Cys Thr Cys Pro Gln Gly Tyr Lys Gly Ala Asp Cys Thr Glu Asp Val
                    405                 410                 415
Asp Glu Cys Ala Met Ala Asn Ser Asn Pro Cys Glu His Ala Gly Lys
                420                 425                 430
Cys Val Asn Thr Asp Gly Ala Phe His Cys Glu Cys Leu Lys Gly Tyr
            435                 440                 445
Ala Gly Pro Arg Cys Glu Met Asp Ile Asn Glu Cys His Ser Asp Pro
        450                 455                 460
Cys Gln Asn Asp Ala Thr Cys Leu Asp Lys Thr Gly Gly Phe Thr Cys
465                 470                 475                 480
Leu Cys Met Pro Gly Phe Lys Gly Val His Cys Glu Leu Glu Ile Asn
                    485                 490                 495
Glu Cys Gln Ser Asn Pro Cys Val Asn Asn Gly Gln Cys Val Asp Lys
                500                 505                 510
Val Asn Arg Phe Gln Cys Leu Cys Pro Pro Gly Phe Thr Gly Pro Val
            515                 520                 525
Cys Gln Ile Asp Ile Asp Asp Cys Ser Ser Thr Pro Cys Leu Asn Gly
        530                 535                 540
Ala Lys Cys Ile Asp His Pro Asn Gly Tyr Glu Cys Gln Cys Ala Thr
545                 550                 555                 560
Gly Phe Thr Gly Val Leu Cys Glu Glu Asn Ile Asp Asn Cys Asp Pro
                    565                 570                 575
Asp Pro Cys His His Gly Gln Cys Gln Asp Gly Ile Asp Ser Tyr Thr
                580                 585                 590
Cys Ile Cys Asn Pro Gly Tyr Met Gly Ala Thr Cys Ser Asp Gln Ile
            595                 600                 605
Asp Glu Cys Tyr Ser Ser Pro Cys Leu Asn Asp Gly Arg Cys Ile Asp
        610                 615                 620
Leu Val Asn Gly Tyr Gln Cys Asn Cys Gln Pro Gly Thr Ser Gly Val
625                 630                 635                 640
Asn Cys Glu Ile Asn Phe Asp Asp Cys Ala Ser Asn Pro Cys Ile His
                    645                 650                 655
Gly Thr Cys Met Asp Gly Ile Asn Arg Tyr Ser Cys Val Cys Ser Pro
                660                 665                 670
Gly Phe Thr Gly Gln Arg Cys Asn Ile Asp Ile Asp Glu Cys Ala Ser
            675                 680                 685
Asn Pro Cys Arg Lys Gly Ala Thr Cys Ile Asn Gly Val Asn Gly Phe
        690                 695                 700
Arg Cys Thr Cys Pro Glu Gly Pro His His Pro Ser Cys Tyr Ser Gln
705                 710                 715                 720
Val Asn Glu Cys Leu Ser Asn Pro Cys Ile His Gly Asn Cys Thr Gly
                    725                 730                 735
Gly Leu Ser Gly Tyr Lys Cys Leu Cys Asp Ala Gly Trp Val Gly Ile
                740                 745                 750
Asn Cys Glu Val Asp Lys Asn Glu Cys Leu Ser Asn Pro Cys Gln Asn
            755                 760                 765
```

```
Gly Gly Thr Cys Asp Asn Leu Val Asn Gly Tyr Arg Cys Thr Cys Lys
        770             775             780

Lys Gly Phe Lys Gly Tyr Asn Cys Gln Val Asn Ile Asp Glu Cys Ala
785             790             795             800

Ser Asn Pro Cys Leu Asn Gln Gly Thr Cys Phe Asp Asp Ile Ser Gly
            805             810             815

Tyr Thr Cys His Cys Val Leu Pro Tyr Thr Gly Lys Asn Cys Gln Thr
            820             825             830

Val Leu Ala Pro Cys Ser Pro Asn Pro Cys Glu Asn Ala Ala Val Cys
        835             840             845

Lys Glu Ser Pro Asn Phe Glu Ser Tyr Thr Cys Leu Cys Ala Pro Gly
850             855             860

Trp Gln Gly Gln Arg Cys Thr Ile Asp Ile Asp Glu Cys Ile Ser Lys
865             870             875             880

Pro Cys Met Asn His Gly Leu Cys His Asn Thr Gln Gly Ser Tyr Met
            885             890             895

Cys Glu Cys Pro Pro Gly Phe Ser Gly Met Asp Cys Glu Glu Asp Ile
            900             905             910

Asp Asp Cys Leu Ala Asn Pro Cys Gln Asn Gly Gly Ser Cys Met Asp
        915             920             925

Gly Val Asn Thr Phe Ser Cys Leu Cys Leu Pro Gly Phe Thr Gly Asp
        930             935             940

Lys Cys Gln Thr Asp Met Asn Glu Cys Leu Ser Glu Pro Cys Lys Asn
945             950             955             960

Gly Gly Thr Cys Ser Asp Tyr Val Asn Ser Tyr Thr Cys Lys Cys Gln
            965             970             975

Ala Gly Phe Asp Gly Val His Cys Glu Asn Asn Ile Asn Glu Cys Thr
            980             985             990

Glu Ser Ser Cys Phe Asn Gly Gly Thr Cys Val Asp Gly Ile Asn Ser
        995             1000            1005

Phe Ser Cys Leu Cys Pro Val Gly Phe Thr Gly Ser Phe Cys Leu
        1010            1015            1020

His Glu Ile Asn Glu Cys Ser Ser His Pro Cys Leu Asn Glu Gly
        1025            1030            1035

Thr Cys Val Asp Gly Leu Gly Thr Tyr Arg Cys Ser Cys Pro Leu
        1040            1045            1050

Gly Tyr Thr Gly Lys Asn Cys Gln Thr Leu Val Asn Leu Cys Ser
        1055            1060            1065

Arg Ser Pro Cys Lys Asn Lys Gly Thr Cys Val Gln Lys Lys Ala
        1070            1075            1080

Glu Ser Gln Cys Leu Cys Pro Ser Gly Trp Ala Gly Ala Tyr Cys
        1085            1090            1095

Asp Val Pro Asn Val Ser Cys Asp Ile Ala Ala Ser Arg Arg Gly
        1100            1105            1110

Val Leu Val Glu His Leu Cys Gln His Ser Gly Val Cys Ile Asn
        1115            1120            1125

Ala Gly Asn Thr His Tyr Cys Gln Cys Pro Leu Gly Tyr Thr Gly
        1130            1135            1140

Ser Tyr Cys Glu Glu Gln Leu Asp Glu Cys Ala Ser Asn Pro Cys
        1145            1150            1155

Gln His Gly Ala Thr Cys Ser Asp Phe Thr Gly Gly Tyr Arg Cys
        1160            1165            1170
```

```
Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215

Gly Met Lys Ser Ser Leu Ser Ile Phe His Pro Gly His Cys Leu
    1220                1225                1230

Lys Leu
    1235

<210> SEQ ID NO 247
<211> LENGTH: 2321
<212> TYPE: PRT
<213> ORGANISM: Homo sapiens

<400> SEQUENCE: 247

Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
                115                 120                 125

Ala His Gly Ala Arg Cys Ser Val Gly Pro Asp Gly Arg Phe Leu Cys
                130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
                180                 185                 190

Leu Cys Glu Asn Pro Ala Val Pro Cys Ala Pro Ser Pro Cys Arg Asn
                195                 200                 205

Gly Gly Thr Cys Arg Gln Ser Gly Asp Leu Thr Tyr Asp Cys Ala Cys
                210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
                260                 265                 270

Glu Asp Val Asp Glu Cys Gln Leu Gln Pro Asn Ala Cys His Asn Gly
                275                 280                 285

Gly Thr Cys Phe Asn Thr Leu Gly Gly His Ser Cys Val Cys Val Asn
                290                 295                 300
```

```
Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
            325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Thr Cys Asp Thr
            355                 360                 365

Asn Pro Val Asn Gly Arg Ala Thr Cys Thr Cys Pro Pro Gly Phe Thr
370                 375                 380

Gly Gly Ala Cys Asp Gln Asp Val Asp Glu Cys Ser Thr Gly Ala Asn
385                 390                 395                 400

Pro Cys Glu His Leu Gly Arg Cys Val Asn Thr Gln Gly Ser Phe Leu
            405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Thr Gly Gln Phe Thr Cys Thr Cys Met Ala Gly Phe Thr Gly Thr
450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
            485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
            565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
            645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Ser His Pro Cys Ala His Glu Pro Cys
            690                 695                 700

Ser His Gly Thr Cys Tyr Asp Ala Pro Gly Gly Phe Arg Cys Val Cys
705                 710                 715                 720
```

-continued

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Ile Pro Asn Pro Cys Glu His Gly Gly
            770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Thr Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
            850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
            930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
            995                 1000                1005

Cys Gln Asn Gly Gly Arg Cys Val Gln Thr Gly Ala Tyr Cys Leu
        1010                1015                1020

Cys Pro Pro Gly Trp Ser Gly Arg Leu Cys Asp Ile Arg Ser Leu
        1025                1030                1035

Pro Cys Arg Glu Ala Ala Ala Gln Thr Gly Val Arg Leu Glu Gln
        1040                1045                1050

Leu Cys Gln Ala Gly Gly Gln Cys Val Asp Glu Asp Ser Ser His
        1055                1060                1065

Tyr Cys Val Cys Pro Glu Gly Arg Thr Gly Ser His Cys Glu Gln
        1070                1075                1080

Glu Val Asp Pro Cys Leu Ala Gln Pro Cys Gln His Gly Gly Thr
        1085                1090                1095

Cys Arg Gly Tyr Met Gly Gly Tyr Met Cys Glu Cys Leu Pro Gly
        1100                1105                1110

Tyr Asn Gly Asp Asn Cys Glu Asp Asp Val Asp Glu Cys Ala Ser
        1115                1120                1125

Gln Pro Cys Gln His Gly Gly Ser Cys Ile Asp Leu Val Ala Arg

-continued

```
            1130                1135                1140

Tyr Leu Cys Ser Cys Pro Pro Gly Thr Leu Gly Val Leu Cys Glu
        1145                1150                1155

Ile Asn Glu Asp Asp Cys Gly Pro Gly Pro Pro Leu Asp Ser Gly
        1160                1165                1170

Pro Arg Cys Leu His Asn Gly Thr Cys Val Asp Leu Val Gly Gly
        1175                1180                1185

Phe Arg Cys Thr Cys Pro Pro Gly Tyr Thr Gly Leu Arg Cys Glu
        1190                1195                1200

Ala Asp Ile Asn Glu Cys Arg Ser Gly Ala Cys His Ala Ala His
        1205                1210                1215

Thr Arg Asp Cys Leu Gln Asp Pro Gly Gly Phe Arg Cys Leu
        1220                1225                1230

Cys His Ala Gly Phe Ser Gly Pro Arg Cys Gln Thr Val Leu Ser
        1235                1240                1245

Pro Cys Glu Ser Gln Pro Cys Gln His Gly Gly Gln Cys Arg Pro
        1250                1255                1260

Ser Pro Gly Pro Gly Gly Gly Leu Thr Phe Thr Cys His Cys Ala
        1265                1270                1275

Gln Pro Phe Trp Gly Pro Arg Cys Glu Arg Val Ala Arg Ser Cys
        1280                1285                1290

Arg Glu Leu Gln Cys Pro Val Gly Val Pro Cys Gln Gln Thr Pro
        1295                1300                1305

Arg Gly Pro Arg Cys Ala Cys Pro Pro Gly Leu Ser Gly Pro Ser
        1310                1315                1320

Cys Arg Ser Phe Pro Gly Ser Pro Pro Gly Ala Ser Asn Ala Ser
        1325                1330                1335

Cys Ala Ala Ala Pro Cys Leu His Gly Gly Ser Cys Arg Pro Ala
        1340                1345                1350

Pro Leu Ala Pro Phe Phe Arg Cys Ala Cys Ala Gln Gly Trp Thr
        1355                1360                1365

Gly Pro Arg Cys Glu Ala Pro Ala Ala Ala Pro Glu Val Ser Glu
        1370                1375                1380

Glu Pro Arg Cys Pro Arg Ala Ala Cys Gln Ala Lys Arg Gly Asp
        1385                1390                1395

Gln Arg Cys Asp Arg Glu Cys Asn Ser Pro Gly Cys Gly Trp Asp
        1400                1405                1410

Gly Gly Asp Cys Ser Leu Ser Val Gly Asp Pro Trp Arg Gln Cys
        1415                1420                1425

Glu Ala Leu Gln Cys Trp Arg Leu Phe Asn Asn Ser Arg Cys Asp
        1430                1435                1440

Pro Ala Cys Ser Ser Pro Ala Cys Leu Tyr Asp Asn Phe Asp Cys
        1445                1450                1455

His Ala Gly Gly Arg Glu Arg Thr Cys Asn Pro Val Tyr Glu Lys
        1460                1465                1470

Tyr Cys Ala Asp His Phe Ala Asp Gly Arg Cys Asp Gln Gly Cys
        1475                1480                1485

Asn Thr Glu Glu Cys Gly Trp Asp Gly Leu Asp Cys Ala Ser Glu
        1490                1495                1500

Val Pro Ala Leu Leu Ala Arg Gly Val Leu Val Leu Thr Val Leu
        1505                1510                1515

Leu Pro Pro Glu Glu Leu Leu Arg Ser Ser Ala Asp Phe Leu Gln
        1520                1525                1530
```

-continued

```
Arg Leu Ser Ala Ile Leu Arg Thr Ser Leu Arg Phe Arg Leu Asp
    1535                1540                1545

Ala His Gly Gln Ala Met Val Phe Pro Tyr His Arg Pro Ser Pro
    1550                1555                1560

Gly Ser Glu Pro Arg Ala Arg Arg Glu Leu Ala Pro Glu Val Thr
    1565                1570                1575

Gly Ser Val Val Met Leu Glu Ile Asp Asn Arg Leu Cys Leu Gln
    1580                1585                1590

Ser Pro Glu Asn Asp His Cys Phe Pro Asp Ala Gln Ser Ala Ala
    1595                1600                1605

Asp Tyr Leu Gly Ala Leu Ser Ala Val Glu Arg Leu Asp Phe Pro
    1610                1615                1620

Tyr Pro Leu Arg Asp Val Arg Gly Glu Pro Leu Glu Pro Pro Glu
    1625                1630                1635

Pro Ser Val Pro Leu Leu Pro Leu Leu Val Ala Gly Ala Val Leu
    1640                1645                1650

Leu Leu Val Ile Leu Val Leu Gly Val Met Val Ala Arg Arg Lys
    1655                1660                1665

Arg Glu His Ser Thr Leu Trp Phe Pro Glu Gly Phe Ser Leu His
    1670                1675                1680

Lys Asp Val Ala Ser Gly His Lys Gly Arg Arg Glu Pro Val Gly
    1685                1690                1695

Gln Asp Ala Leu Gly Met Lys Asn Met Ala Lys Gly Glu Ser Leu
    1700                1705                1710

Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu
    1730                1735                1740

Ala Val Asp Cys Arg Gln Trp Thr Gln His His Leu Val Ala Ala
    1745                1750                1755

Asp Ile Arg Val Ala Pro Ala Met Ala Leu Thr Pro Pro Gln Gly
    1760                1765                1770

Asp Ala Asp Ala Asp Gly Met Asp Val Asn Val Arg Gly Pro Asp
    1775                1780                1785

Gly Phe Thr Pro Leu Met Leu Ala Ser Phe Cys Gly Gly Ala Leu
    1790                1795                1800

Glu Pro Met Pro Thr Glu Glu Asp Glu Ala Asp Asp Thr Ser Ala
    1805                1810                1815

Ser Ile Ile Ser Asp Leu Thr Cys Gln Gly Ala Gln Leu Gly Ala
    1820                1825                1830

Arg Thr Asp Arg Thr Gly Glu Thr Ala Leu His Leu Ala Ala Arg
    1835                1840                1845

Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920
```

-continued

Glu Leu Ile Ala Ser His Ala Asp Val Asn Ala Val Asp Glu Leu
1925                1930                1935

Gly Lys Ser Ala Leu His Trp Ala Ala Ala Val Asn Asn Val Glu
1940                1945                1950

Ala Thr Leu Ala Leu Leu Lys Asn Gly Ala Asn Lys Asp Met Gln
1955                1960                1965

Asp Ser Lys Glu Glu Thr Pro Leu Phe Leu Ala Ala Arg Glu Gly
1970                1975                1980

Ser Tyr Glu Ala Ala Lys Leu Leu Leu Asp His Phe Ala Asn Arg
1985                1990                1995

Glu Ile Thr Asp His Leu Asp Arg Leu Pro Arg Asp Val Ala Gln
2000                2005                2010

Glu Arg Leu His Gln Asp Ile Val Arg Leu Leu Asp Gln Pro Ser
2015                2020                2025

Gly Pro Arg Ser Pro Pro Gly Pro His Gly Leu Gly Pro Leu Leu
2030                2035                2040

Cys Pro Pro Gly Ala Phe Leu Pro Gly Leu Lys Ala Ala Gln Ser
2045                2050                2055

Gly Ser Lys Lys Ser Arg Arg Pro Pro Gly Lys Ala Gly Leu Gly
2060                2065                2070

Pro Gln Gly Pro Arg Gly Arg Gly Lys Lys Leu Thr Leu Ala Cys
2075                2080                2085

Pro Gly Pro Leu Ala Asp Ser Ser Val Thr Leu Ser Pro Val Asp
2090                2095                2100

Ser Leu Asp Ser Pro Arg Pro Phe Gly Gly Pro Pro Ala Ser Pro
2105                2110                2115

Gly Gly Phe Pro Leu Glu Gly Pro Tyr Ala Ala Ala Thr Ala Thr
2120                2125                2130

Ala Val Ser Leu Ala Gln Leu Gly Gly Pro Gly Arg Ala Gly Leu
2135                2140                2145

Gly Arg Gln Pro Pro Gly Gly Cys Val Leu Ser Leu Gly Leu Leu
2150                2155                2160

Asn Pro Val Ala Val Pro Leu Asp Trp Ala Arg Leu Pro Pro Pro
2165                2170                2175

Ala Pro Pro Gly Pro Ser Phe Leu Leu Pro Leu Ala Pro Gly Pro
2180                2185                2190

Gln Leu Leu Asn Pro Gly Thr Pro Val Ser Pro Gln Glu Arg Pro
2195                2200                2205

Pro Pro Tyr Leu Ala Val Pro Gly His Gly Glu Glu Tyr Pro Ala
2210                2215                2220

Ala Gly Ala His Ser Ser Pro Pro Lys Ala Arg Phe Leu Arg Val
2225                2230                2235

Pro Ser Glu His Pro Tyr Leu Thr Pro Ser Pro Glu Ser Pro Glu
2240                2245                2250

His Trp Ala Ser Pro Ser Pro Pro Ser Leu Ser Asp Trp Ser Glu
2255                2260                2265

Ser Thr Pro Ser Pro Ala Thr Ala Thr Gly Ala Met Ala Thr Thr
2270                2275                2280

Thr Gly Ala Leu Pro Ala Gln Pro Leu Pro Leu Ser Val Pro Ser
2285                2290                2295

Ser Leu Ala Gln Ala Gln Thr Gln Leu Gly Pro Gln Pro Glu Val
2300                2305                2310

Thr Pro Lys Arg Gln Val Leu Ala

<210> SEQ ID NO 248
<211> LENGTH: 2003
<212> TYPE: PRT
<213> ORGANISM: Homo sapiens

<400> SEQUENCE: 248

```
Met Gln Pro Pro Ser Leu Leu Leu Leu Leu Leu Leu Leu Leu
1               5                   10                  15

Cys Val Ser Val Val Arg Pro Arg Gly Leu Leu Cys Gly Ser Phe Pro
                20                  25                  30

Glu Pro Cys Ala Asn Gly Gly Thr Cys Leu Ser Leu Ser Leu Gly Gln
            35                  40                  45

Gly Thr Cys Gln Cys Ala Pro Gly Phe Leu Gly Glu Thr Cys Gln Phe
        50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Thr Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365
```

-continued

```
Thr Cys Ile Asp Arg Val Gly Ser Phe Ser Cys Leu Cys Pro Pro Gly
    370             375             380
Arg Thr Gly Leu Leu Cys His Leu Glu Asp Met Cys Leu Ser Gln Pro
385             390             395             400
Cys His Gly Asp Ala Gln Cys Ser Thr Asn Pro Leu Thr Gly Ser Thr
            405             410             415
Leu Cys Leu Cys Gln Pro Gly Tyr Ser Gly Pro Thr Cys His Gln Asp
        420             425             430
Leu Asp Glu Cys Leu Met Ala Gln Gln Gly Pro Ser Pro Cys Glu His
        435             440             445
Gly Gly Ser Cys Leu Asn Thr Pro Gly Ser Phe Asn Cys Leu Cys Pro
450             455             460
Pro Gly Tyr Thr Gly Ser Arg Cys Glu Ala Asp His Asn Glu Cys Leu
465             470             475             480
Ser Gln Pro Cys His Pro Gly Ser Thr Cys Leu Asp Leu Leu Ala Thr
            485             490             495
Phe His Cys Leu Cys Pro Pro Gly Leu Glu Gly Gln Leu Cys Glu Val
        500             505             510
Glu Thr Asn Glu Cys Ala Ser Ala Pro Cys Leu Asn His Ala Asp Cys
        515             520             525
His Asp Leu Leu Asn Gly Phe Gln Cys Thr Cys Leu Pro Gly Phe Ser
530             535             540
Gly Thr Arg Cys Glu Glu Asp Ile Asp Glu Cys Arg Ser Ser Pro Cys
545             550             555             560
Ala Asn Gly Gly Gln Cys Gln Asp Gln Pro Gly Ala Phe His Cys Lys
            565             570             575
Cys Leu Pro Gly Phe Glu Gly Pro Arg Cys Gln Thr Glu Val Asp Glu
        580             585             590
Cys Leu Ser Asp Pro Cys Pro Val Gly Ala Ser Cys Leu Asp Leu Pro
        595             600             605
Gly Ala Phe Phe Cys Leu Cys Pro Ser Gly Phe Thr Gly Gln Leu Cys
610             615             620
Glu Val Pro Leu Cys Ala Pro Asn Leu Cys Gln Pro Lys Gln Thr Cys
625             630             635             640
Lys Asp Gln Lys Asp Lys Ala Asn Cys Leu Cys Pro Asp Gly Ser Pro
            645             650             655
Gly Cys Ala Pro Pro Glu Asp Asn Cys Thr Cys His His Gly His Cys
        660             665             670
Gln Arg Ser Ser Cys Val Cys Asp Val Gly Trp Thr Gly Pro Glu Cys
        675             680             685
Glu Ala Glu Leu Gly Gly Cys Ile Ser Ala Pro Cys Ala His Gly Gly
690             695             700
Thr Cys Tyr Pro Gln Pro Ser Gly Tyr Asn Cys Thr Cys Pro Thr Gly
705             710             715             720
Tyr Thr Gly Pro Thr Cys Ser Glu Glu Met Thr Ala Cys His Ser Gly
            725             730             735
Pro Cys Leu Asn Gly Gly Ser Cys Asn Pro Ser Pro Gly Gly Tyr Tyr
        740             745             750
Cys Thr Cys Pro Pro Ser His Thr Gly Pro Gln Cys Gln Thr Ser Thr
        755             760             765
Asp Tyr Cys Val Ser Ala Pro Cys Phe Asn Gly Gly Thr Cys Val Asn
770             775             780
Arg Pro Gly Thr Phe Ser Cys Leu Cys Ala Met Gly Phe Gln Gly Pro
```

```
                785                 790                 795                 800
Arg Cys Glu Gly Lys Leu Arg Pro Ser Cys Ala Asp Ser Pro Cys Arg
                    805                 810                 815
Asn Arg Ala Thr Cys Gln Asp Ser Pro Gln Gly Pro Arg Cys Leu Cys
                    820                 825                 830
Pro Thr Gly Tyr Thr Gly Gly Ser Cys Gln Thr Leu Met Asp Leu Cys
                    835                 840                 845
Ala Gln Lys Pro Cys Pro Arg Asn Ser His Cys Leu Gln Thr Gly Pro
            850                 855                 860
Ser Phe His Cys Leu Cys Leu Gln Gly Trp Thr Gly Pro Leu Cys Asn
865                 870                 875                 880
Leu Pro Leu Ser Ser Cys Gln Lys Ala Ala Leu Ser Gln Gly Ile Asp
                    885                 890                 895
Val Ser Ser Leu Cys His Asn Gly Gly Leu Cys Val Asp Ser Gly Pro
                900                 905                 910
Ser Tyr Phe Cys His Cys Pro Pro Gly Phe Gln Gly Ser Leu Cys Gln
                915                 920                 925
Asp His Val Asn Pro Cys Glu Ser Arg Pro Cys Gln Asn Gly Ala Thr
            930                 935                 940
Cys Met Ala Gln Pro Ser Gly Tyr Leu Cys Gln Cys Ala Pro Gly Tyr
945                 950                 955                 960
Asp Gly Gln Asn Cys Ser Lys Glu Leu Asp Ala Cys Gln Ser Gln Pro
                    965                 970                 975
Cys His Asn His Gly Thr Cys Thr Pro Lys Pro Gly Gly Phe His Cys
                    980                 985                 990
Ala Cys Pro Pro Gly Phe Val Gly Leu Arg Cys Glu Gly Asp Val Asp
                995                 1000                1005
Glu Cys Leu Asp Gln Pro Cys His Pro Thr Gly Thr Ala Ala Cys
            1010                1015                1020
His Ser Leu Ala Asn Ala Phe Tyr Cys Gln Cys Leu Pro Gly His
            1025                1030                1035
Thr Gly Gln Trp Cys Glu Val Glu Ile Asp Pro Cys His Ser Gln
            1040                1045                1050
Pro Cys Phe His Gly Gly Thr Cys Glu Ala Thr Ala Gly Ser Pro
            1055                1060                1065
Leu Gly Phe Thr Cys His Cys Pro Lys Gly Phe Glu Gly Pro Thr
            1070                1075                1080
Cys Ser His Arg Ala Pro Ser Cys Gly Phe His His Cys His His
            1085                1090                1095
Gly Gly Leu Cys Leu Pro Ser Pro Lys Pro Gly Phe Pro Pro Arg
            1100                1105                1110
Cys Ala Cys Leu Ser Gly Tyr Gly Gly Pro Asp Cys Leu Thr Pro
            1115                1120                1125
Pro Ala Pro Lys Gly Cys Gly Pro Pro Ser Pro Cys Leu Tyr Asn
            1130                1135                1140
Gly Ser Cys Ser Glu Thr Thr Gly Leu Gly Gly Pro Gly Phe Arg
            1145                1150                1155
Cys Ser Cys Pro His Ser Ser Pro Gly Pro Arg Cys Gln Lys Pro
            1160                1165                1170
Gly Ala Lys Gly Cys Glu Gly Arg Ser Gly Asp Gly Ala Cys Asp
            1175                1180                1185
Ala Gly Cys Ser Gly Pro Gly Gly Asn Trp Asp Gly Gly Asp Cys
            1190                1195                1200
```

```
Ser Leu Gly Val Pro Asp Pro Trp Lys Gly Cys Pro Ser His Ser
1205                1210                1215

Arg Cys Trp Leu Leu Phe Arg Asp Gly Gln Cys His Pro Gln Cys
1220                1225                1230

Asp Ser Glu Glu Cys Leu Phe Asp Gly Tyr Asp Cys Glu Thr Pro
1235                1240                1245

Pro Ala Cys Thr Pro Ala Tyr Asp Gln Tyr Cys His Asp His Phe
1250                1255                1260

His Asn Gly His Cys Glu Lys Gly Cys Asn Thr Ala Glu Cys Gly
1265                1270                1275

Trp Asp Gly Gly Asp Cys Arg Pro Glu Asp Gly Asp Pro Glu Trp
1280                1285                1290

Gly Pro Ser Leu Ala Leu Leu Val Val Leu Ser Pro Pro Ala Leu
1295                1300                1305

Asp Gln Gln Leu Phe Ala Leu Ala Arg Val Leu Ser Leu Thr Leu
1310                1315                1320

Arg Val Gly Leu Trp Val Arg Lys Asp Arg Asp Gly Arg Asp Met
1325                1330                1335

Val Tyr Pro Tyr Pro Gly Ala Arg Ala Glu Glu Lys Leu Gly Gly
1340                1345                1350

Ile Arg Asp Pro Thr Tyr Gln Glu Arg Ala Ala Pro Gln Thr Gln
1355                1360                1365

Pro Leu Gly Lys Glu Thr Asp Ser Leu Ser Ala Gly Phe Val Val
1370                1375                1380

Val Met Gly Val Asp Leu Ser Arg Cys Gly Pro Asp His Pro Ala
1385                1390                1395

Ser Arg Cys Pro Trp Asp Pro Gly Leu Leu Leu Arg Phe Leu Ala
1400                1405                1410

Ala Met Ala Ala Val Gly Ala Leu Glu Pro Leu Leu Pro Gly Pro
1415                1420                1425

Leu Leu Ala Val His Pro His Ala Gly Thr Ala Pro Pro Ala Asn
1430                1435                1440

Gln Leu Pro Trp Pro Val Leu Cys Ser Pro Val Ala Gly Val Ile
1445                1450                1455

Leu Leu Ala Leu Gly Ala Leu Leu Val Leu Gln Leu Ile Arg Arg
1460                1465                1470

Arg Arg Arg Glu His Gly Ala Leu Trp Leu Pro Pro Gly Phe Thr
1475                1480                1485

Arg Arg Pro Arg Thr Gln Ser Ala Pro His Arg Arg Arg Pro Pro
1490                1495                1500

Leu Gly Glu Asp Ser Thr Gly Leu Lys Ala Leu Lys Pro Lys Ala
1505                1510                1515

Glu Val Asp Glu Asp Gly Val Val Met Cys Ser Gly Pro Glu Glu
1520                1525                1530

Gly Glu Glu Val Gly Gln Ala Glu Glu Thr Gly Pro Pro Ser Thr
1535                1540                1545

Cys Gln Leu Trp Ser Leu Ser Gly Gly Cys Gly Ala Leu Pro Gln
1550                1555                1560

Ala Ala Met Leu Ile Pro Pro Gln Glu Ser Glu Met Glu Ala Pro
1565                1570                1575

Asp Leu Asp Thr Arg Gly Pro Asp Gly Val Thr Pro Leu Met Ser
1580                1585                1590
```

-continued

Ala Val Cys Cys Gly Glu Val Gln Ser Gly Thr Phe Gln Gly Ala
1595                1600                1605

Trp Leu Gly Cys Pro Glu Pro Trp Glu Pro Leu Leu Asp Gly Gly
1610                1615                1620

Ala Cys Pro Gln Ala His Thr Val Gly Thr Gly Glu Thr Pro Leu
1625                1630                1635

His Leu Ala Ala Arg Phe Ser Arg Pro Thr Ala Ala Arg Arg Leu
1640                1645                1650

Leu Glu Ala Gly Ala Asn Pro Asn Gln Pro Asp Arg Ala Gly Arg
1655                1660                1665

Thr Pro Leu His Ala Ala Val Ala Ala Asp Ala Arg Glu Val Cys
1670                1675                1680

Gln Leu Leu Leu Arg Ser Arg Gln Thr Ala Val Asp Ala Arg Thr
1685                1690                1695

Glu Asp Gly Thr Thr Pro Leu Met Leu Ala Ala Arg Leu Ala Val
1700                1705                1710

Glu Asp Leu Val Glu Glu Leu Ile Ala Ala Gln Ala Asp Val Gly
1715                1720                1725

Ala Arg Asp Lys Trp Gly Lys Thr Ala Leu His Trp Ala Ala Ala
1730                1735                1740

Val Asn Asn Ala Arg Ala Ala Arg Ser Leu Leu Gln Ala Gly Ala
1745                1750                1755

Asp Lys Asp Ala Gln Asp Asn Arg Glu Gln Thr Pro Leu Phe Leu
1760                1765                1770

Ala Ala Arg Glu Gly Ala Val Glu Val Ala Gln Leu Leu Leu Gly
1775                1780                1785

Leu Gly Ala Ala Arg Glu Leu Arg Asp Gln Ala Gly Leu Ala Pro
1790                1795                1800

Ala Asp Val Ala His Gln Arg Asn His Trp Asp Leu Leu Thr Leu
1805                1810                1815

Leu Glu Gly Ala Gly Pro Pro Glu Ala Arg His Lys Ala Thr Pro
1820                1825                1830

Gly Arg Glu Ala Gly Pro Phe Pro Arg Ala Arg Thr Val Ser Val
1835                1840                1845

Ser Val Pro Pro His Gly Gly Ala Leu Pro Arg Cys Arg Thr
1850                1855                1860

Leu Ser Ala Gly Ala Gly Pro Arg Gly Gly Ala Cys Leu Gln
1865                1870                1875

Ala Arg Thr Trp Ser Val Asp Leu Ala Ala Arg Gly Gly Gly Ala
1880                1885                1890

Tyr Ser His Cys Arg Ser Leu Ser Gly Val Gly Ala Gly Gly Gly
1895                1900                1905

Pro Thr Pro Arg Gly Arg Arg Phe Ser Ala Gly Met Arg Gly Pro
1910                1915                1920

Arg Pro Asn Pro Ala Ile Met Arg Gly Arg Tyr Gly Val Ala Ala
1925                1930                1935

Gly Arg Gly Gly Arg Val Ser Thr Asp Asp Trp Pro Cys Asp Trp
1940                1945                1950

Val Ala Leu Gly Ala Cys Gly Ser Ala Ser Asn Ile Pro Ile Pro
1955                1960                1965

Pro Pro Cys Leu Thr Pro Ser Pro Glu Arg Gly Ser Pro Gln Leu
1970                1975                1980

Asp Cys Gly Pro Pro Ala Leu Gln Glu Met Pro Ile Asn Gln Gly

Gly Glu  Gly Lys Lys
    2000

<210> SEQ ID NO 249
<211> LENGTH: 5
<212> TYPE: PRT
<213> ORGANISM: Homo sapiens

<400> SEQUENCE: 249

Arg Lys Arg Arg Arg
1               5

<210> SEQ ID NO 250
<211> LENGTH: 339
<212> TYPE: PRT
<213> ORGANISM: Homo sapiens

<400> SEQUENCE: 250

Ile Leu Asp Tyr Ser Phe Gly Gly Ala Gly Arg Asp Ile Pro Pro
1               5                   10                  15

Pro Leu Ile Glu Glu Ala Cys Glu Leu Pro Glu Cys Gln Glu Asp Ala
            20                  25                  30

Gly Asn Lys Val Cys Ser Leu Gln Cys Asn Asn His Ala Cys Gly Trp
        35                  40                  45

Asp Gly Gly Asp Cys Ser Leu Asn Phe Asn Asp Pro Trp Lys Asn Cys
    50                  55                  60

Thr Gln Ser Leu Gln Cys Trp Lys Tyr Phe Ser Asp Gly His Cys Asp
65                  70                  75                  80

Ser Gln Cys Asn Ser Ala Gly Cys Leu Phe Asp Gly Phe Asp Cys Gln
                85                  90                  95

Arg Ala Glu Gly Gln Cys Asn Pro Leu Tyr Asp Gln Tyr Cys Lys Asp
            100                 105                 110

His Phe Ser Asp Gly His Cys Asp Gln Gly Cys Asn Ser Ala Glu Cys
        115                 120                 125

Glu Trp Asp Gly Leu Asp Cys Ala Glu His Val Pro Glu Arg Leu Ala
    130                 135                 140

Ala Gly Thr Leu Val Val Val Leu Met Pro Pro Glu Gln Leu Arg
145                 150                 155                 160

Asn Ser Ser Phe His Phe Leu Arg Glu Leu Ser Arg Val Leu His Thr
                165                 170                 175

Asn Val Val Phe Lys Arg Asp Ala His Gly Gln Gln Met Ile Phe Pro
            180                 185                 190

Tyr Tyr Gly Arg Glu Glu Glu Leu Arg Lys His Pro Ile Lys Arg Ala
        195                 200                 205

Ala Glu Gly Trp Ala Ala Pro Asp Ala Leu Leu Gly Gln Val Lys Ala
    210                 215                 220

Ser Leu Leu Pro Gly Gly Ser Glu Gly Gly Arg Arg Arg Glu Leu
225                 230                 235                 240

Asp Pro Met Asp Val Arg Gly Ser Ile Val Tyr Leu Glu Ile Asp Asn
                245                 250                 255

Arg Gln Cys Val Gln Ala Ser Ser Gln Cys Phe Gln Ser Ala Thr Asp
            260                 265                 270

Val Ala Ala Phe Leu Gly Ala Leu Ala Ser Leu Gly Ser Leu Asn Ile
        275                 280                 285

Pro Tyr Lys Ile Glu Ala Val Gln Ser Glu Thr Val Glu Pro Pro Pro

```
            290                 295                 300
Pro Ala Gln Leu His Phe Met Tyr Val Ala Ala Ala Phe Val Leu
305                 310                 315                 320

Leu Phe Phe Val Gly Cys Gly Val Leu Leu Ser Arg Lys Arg Arg
                325                 330                 335

Asn Arg Arg

<210> SEQ ID NO 251
<211> LENGTH: 292
<212> TYPE: PRT
<213> ORGANISM: Homo sapiens

<400> SEQUENCE: 251

Leu Tyr Thr Ala Pro Ser Thr Pro Ala Thr Cys Leu Ser Gln
1               5                   10                  15

Tyr Cys Ala Asp Lys Ala Arg Asp Gly Val Cys Asp Glu Ala Cys Asn
                20                  25                  30

Ser His Ala Cys Gln Trp Asp Gly Gly Asp Cys Ser Leu Thr Met Glu
            35                  40                  45

Asn Pro Trp Ala Asn Cys Ser Ser Pro Leu Pro Cys Trp Asp Tyr Ile
        50                  55                  60

Asn Asn Gln Cys Asp Glu Leu Cys Asn Thr Val Glu Cys Leu Phe Asp
65                  70                  75                  80

Asn Phe Glu Cys Gln Gly Asn Ser Lys Thr Cys Lys Tyr Asp Lys Tyr
                85                  90                  95

Cys Ala Asp His Phe Lys Asp Asn His Cys Asp Gln Gly Cys Asn Ser
            100                 105                 110

Glu Glu Cys Gly Trp Asp Gly Leu Asp Cys Ala Ala Asp Gln Pro Glu
        115                 120                 125

Asn Leu Ala Glu Gly Thr Leu Val Ile Val Leu Met Pro Pro Glu
130                 135                 140

Gln Leu Leu Gln Asp Ala Arg Ser Phe Leu Arg Ala Leu Gly Thr Leu
145                 150                 155                 160

Leu His Thr Asn Leu Arg Ile Lys Arg Asp Ser Gln Gly Glu Leu Met
                165                 170                 175

Val Tyr Pro Tyr Tyr Gly Glu Lys Ser Ala Ala Met Lys Lys Gln Arg
            180                 185                 190

Met Thr Arg Arg Ser Leu Pro Gly Glu Gln Glu Gln Glu Val Ala Gly
        195                 200                 205

Ser Lys Val Phe Leu Glu Ile Asp Asn Arg Gln Cys Val Gln Asp Ser
    210                 215                 220

Asp His Cys Phe Lys Asn Thr Asp Ala Ala Ala Leu Leu Ala Ser
225                 230                 235                 240

His Ala Ile Gln Gly Thr Leu Ser Tyr Pro Leu Val Ser Val Val Ser
                245                 250                 255

Glu Ser Leu Thr Pro Glu Arg Thr Gln Leu Leu Tyr Leu Leu Ala Val
            260                 265                 270

Ala Val Val Ile Ile Leu Phe Ile Ile Leu Leu Gly Val Ile Met Ala
        275                 280                 285

Lys Arg Lys Arg
    290

<210> SEQ ID NO 252
<211> LENGTH: 295
<212> TYPE: PRT
```

<213> ORGANISM: Homo sapiens

<400> SEQUENCE: 252

```
Pro Ala Ala Ala Pro Glu Val Ser Glu Glu Pro Arg Cys Pro Arg Ala
1               5                   10                  15

Ala Cys Gln Ala Lys Arg Gly Asp Gln Arg Cys Asp Arg Glu Cys Asn
            20                  25                  30

Ser Pro Gly Cys Gly Trp Asp Gly Gly Asp Cys Ser Leu Ser Val Gly
        35                  40                  45

Asp Pro Trp Arg Gln Cys Glu Ala Leu Gln Cys Trp Arg Leu Phe Asn
    50                  55                  60

Asn Ser Arg Cys Asp Pro Ala Cys Ser Ser Pro Ala Cys Leu Tyr Asp
65                  70                  75                  80

Asn Phe Asp Cys His Ala Gly Arg Glu Arg Thr Cys Asn Pro Val
                85                  90                  95

Tyr Glu Lys Tyr Cys Ala Asp His Phe Ala Asp Gly Arg Cys Asp Gln
            100                 105                 110

Gly Cys Asn Thr Glu Glu Cys Gly Trp Asp Gly Leu Asp Cys Ala Ser
            115                 120                 125

Glu Val Pro Ala Leu Leu Ala Arg Gly Val Leu Val Leu Thr Val Leu
130                 135                 140

Leu Pro Pro Glu Glu Leu Leu Arg Ser Ser Ala Asp Phe Leu Gln Arg
145                 150                 155                 160

Leu Ser Ala Ile Leu Arg Thr Ser Leu Arg Phe Arg Leu Asp Ala His
                165                 170                 175

Gly Gln Ala Met Val Phe Pro Tyr His Arg Pro Ser Pro Gly Ser Glu
            180                 185                 190

Pro Arg Ala Arg Arg Glu Leu Ala Pro Glu Val Ile Gly Ser Val Val
        195                 200                 205

Met Leu Glu Ile Asp Asn Arg Leu Cys Leu Gln Ser Pro Glu Asn Asp
210                 215                 220

His Cys Phe Pro Asp Ala Gln Ser Ala Ala Asp Tyr Leu Gly Ala Leu
225                 230                 235                 240

Ser Ala Val Glu Arg Leu Asp Phe Pro Tyr Pro Leu Arg Asp Val Arg
                245                 250                 255

Gly Glu Pro Leu Glu Pro Pro Glu Pro Ser Val Pro Leu Leu Pro Leu
            260                 265                 270

Leu Val Ala Gly Ala Val Leu Leu Leu Val Ile Leu Val Leu Gly Val
        275                 280                 285

Met Val Ala Arg Arg Lys Arg
290                 295
```

<210> SEQ ID NO 253
<211> LENGTH: 7
<212> TYPE: PRT
<213> ORGANISM: Homo sapiens

<400> SEQUENCE: 253

```
Arg Arg Arg Arg Arg Arg Arg
1               5
```

<210> SEQ ID NO 254
<211> LENGTH: 315
<212> TYPE: PRT
<213> ORGANISM: Homo sapiens

<400> SEQUENCE: 254

```
Pro His Ser Ser Pro Gly Pro Arg Cys Gln Lys Pro Gly Ala Lys Gly
1               5                   10                  15

Cys Glu Gly Arg Ser Gly Asp Gly Ala Cys Asp Ala Gly Cys Ser Gly
                20                  25                  30

Pro Gly Gly Asn Trp Asp Gly Asp Cys Ser Leu Gly Val Pro Asp
            35                  40                  45

Pro Trp Lys Gly Cys Pro Ser His Ser Arg Cys Trp Leu Leu Phe Arg
50                  55                  60

Asp Gly Gln Cys His Pro Gln Cys Asp Ser Glu Glu Cys Leu Phe Asp
65                  70                  75                  80

Gly Tyr Asp Cys Glu Thr Pro Pro Ala Cys Thr Pro Ala Tyr Asp Gln
                85                  90                  95

Tyr Cys His Asp His Phe His Asn Gly His Cys Glu Lys Gly Cys Asn
                100                 105                 110

Thr Ala Glu Cys Gly Trp Asp Gly Gly Asp Cys Arg Pro Glu Asp Gly
            115                 120                 125

Asp Pro Glu Trp Gly Pro Ser Leu Ala Leu Leu Val Val Leu Ser Pro
130                 135                 140

Pro Ala Leu Asp Gln Gln Leu Phe Ala Leu Ala Arg Val Leu Ser Leu
145                 150                 155                 160

Thr Leu Arg Val Gly Leu Trp Val Arg Lys Asp Arg Asp Gly Arg Asp
                165                 170                 175

Met Val Tyr Pro Tyr Pro Gly Ala Arg Ala Glu Glu Lys Leu Gly Gly
            180                 185                 190

Thr Arg Asp Pro Thr Tyr Gln Glu Arg Ala Ala Pro Gln Thr Gln Pro
                195                 200                 205

Leu Gly Lys Glu Thr Asp Ser Leu Ser Ala Gly Phe Val Val Met
            210                 215                 220

Gly Val Asp Leu Ser Arg Cys Gly Pro Asp His Pro Ala Ser Arg Cys
225                 230                 235                 240

Pro Trp Asp Pro Gly Leu Leu Leu Arg Phe Leu Ala Ala Met Ala Ala
                245                 250                 255

Val Gly Ala Leu Glu Pro Leu Pro Gly Pro Leu Leu Ala Val His
            260                 265                 270

Pro His Ala Gly Thr Ala Pro Pro Ala Asn Gln Leu Pro Trp Pro Val
            275                 280                 285

Leu Cys Ser Pro Val Ala Gly Val Ile Leu Leu Ala Leu Gly Ala Leu
            290                 295                 300

Leu Val Leu Gln Leu Ile Arg Arg Arg Arg
305                 310                 315

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 255
```

```
Asp Xaa Glu Xaa Asn Pro Gly Pro
1               5
```

<210> SEQ ID NO 256
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256

```
atgcttctcc tggtgacaag ccttctgctc tgtgaattgc cacacccagc attcctcctg    60
attcct                                                               66
```

<210> SEQ ID NO 257
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (1)..(50)
<223> OTHER INFORMATION: This sequence may encompass 1-5
      "(Gly)1-5(Ser)1-5" repeating units
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues

<400> SEQUENCE: 257

```
Gly Gly Gly Gly Gly Ser Ser Ser Ser Ser Gly Gly Gly Gly Ser
1               5                   10                  15

Ser Ser Ser Ser Gly Gly Gly Gly Gly Ser Ser Ser Ser Gly Gly
```

-continued

```
                20              25              30
Gly Gly Gly Ser Ser Ser Ser Ser Gly Gly Gly Gly Gly Ser Ser Ser
            35              40              45
Ser Ser
    50

<210> SEQ ID NO 258
<211> LENGTH: 4
<212> TYPE: PRT
<213> ORGANISM: Homo sapiens

<400> SEQUENCE: 258

Lys Arg Lys Arg
1

<210> SEQ ID NO 259
<211> LENGTH: 4
<212> TYPE: PRT
<213> ORGANISM: Homo sapiens

<400> SEQUENCE: 259

Arg Arg Lys Arg
1

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 260

His His His His His His
1               5
```

PROSTATE CANCER CHIMERIC ANTIGEN RECEPTORS

CROSS-REFERENCE TO RELATED APPLICATIONS

This application claims priority to U.S. Provisional Application No. 63/130,529, filed Dec. 24, 2020 which is hereby incorporated herein by reference in its entirety for all purposes.

TECHNICAL FIELD

The present disclosure relates to the field of cell therapy, and more specifically, to CARs and/or TCRs that target antigens present on prostate cancer cells.

REFERENCE TO SEQUENCE LISTING

This application incorporates by reference the Sequence Listing submitted in Computer Readable Form as file K-1096-US-NP_SL.txt, created on Dec. 14, 2021 and containing 296,034 bytes.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current therapies T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen. A need exists for CARs and TCRs for targeting and killing cancer cells and, in particular, solid tumor cells, such as prostate cancer cells.

SUMMARY

Disclosed is an antibody, or antigen binding fragment thereof comprising an anti-PSMA binding domain, wherein the anti-PSMA binding domain comprises sequences of three heavy chain complementarity determining regions (HCDRs) of any one of the heavy chain variable region (HCVR) selected from the group consisting of SEQ ID NOs: 1, 25, 49, and 73, and sequences of three light chain CDRs (LCDRs) of the light chain variable region (LCVR) selected from the group consisting of SEQ ID NOs: 12, 36, 60, and 84.

In certain embodiments, the anti-PSMA binding domain comprises a first domain comprising three heavy chain complementarity determining regions (HCDR1, HCDR2 and HCDR3) and a second domain comprising three light chain complementarity determining regions (LCDR1, LCDR2 and LCDR3), wherein (i) the HCDR1 has a sequence according to any one of SEQ ID NOs: 3-5, 27-29, 51-53, and 75-77; (ii) the HCDR2 has a sequence according to any one of SEQ ID NOs: 6-8, 30-32, 54-56, and 78-80; (iii) the HCDR3 has a sequence according to any one of SEQ ID NOs: 9-11, 33-35, 57-59, and 81-83; (iv) the LCDR1 has a sequence according to any one of SEQ ID NOs: 14-16, 38-40, 62-64, and 86-88; (v) the LCDR2 has a sequence according to any one of SEQ ID NOs: 17-19, 41-43, 65-67, and 89-91; and (vi) the LCDR3 has a sequence according to any one of SEQ ID NOs: 20-22, 44-46, 68-70, and 92-94.

In certain embodiments, the HCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; (ii) an HCDR1 according to any of SEQ ID NOs: 27-29; an HCDR2 according to any of SEQ ID NOs: 30-32; an HCDR3 according to any one of SEQ ID NOs: 33-35; (iii) an HCDR1 according to any of SEQ ID NOs: 51-53; an HCDR2 according to any of SEQ ID NOs: 54-56; an HCDR3 according to any one of SEQ ID NOs: 57-59; or (iv) an HCDR1 according to any of SEQ ID NOs: 75-77; an HCDR2 according to any of SEQ ID NOs: 78-80; an HCDR3 according to any one of SEQ ID NOs: 81-83; and the LCDRs comprise: (i) an LCDR1 according to any of SEQ ID NOs: 14-16; an LCDR2 according to any of SEQ ID NOs: 17-19; an LCDR3 according to any one of SEQ ID NOs: 20-22; (ii) an LCDR1 according to any of SEQ ID NOs: 38-40; an LCDR2 according to any of SEQ ID NOs: 41-43; an LCDR3 according to any one of SEQ ID NOs: 44-46; (iii) an LCDR1 according to any of SEQ ID NOs: 62-64; an LCDR2 according to any of SEQ ID NOs: 65-67; an LCDR3 according to any one of SEQ ID NOs: 68-70; or (iv) an LCDR1 according to any of SEQ ID NOs: 86-88; an LCDR2 according to any of SEQ ID NOs: 89-91; an LCDR3 according to any one of SEQ ID NOs: 92-94.

In certain embodiments, the antigen binding system, antibody, or antigen binding fragment thereof comprises a first domain comprising three heavy chain complementarity determining regions (HCDRs) and a second domain comprising three light chain complementarity determining regions (LCDRs), wherein: the HCDRs and LCDRs comprise: (i) an HCDR1 according to any of SEQ ID NOs: 3-5; an HCDR2 according to any of SEQ ID NOs: 6-8; an HCDR3 according to any one of SEQ ID NOs: 9-11; an LCDR1 according to any of SEQ ID NOs: 14-16; an LCDR2 according to any of SEQ ID NOs: 17-19; an LCDR3 according to any one of SEQ ID NOs: 20-22; (ii) an HCDR1 according to any of SEQ ID NOs: 27-29; an HCDR2 according to any of SEQ ID NOs: 30-32; an HCDR3 according to any one of SEQ ID NOs: 33-35; an LCDR1 according to any of SEQ ID NOs: 38-40; an LCDR2 according to any of SEQ ID NOs: 41-43; an LCDR3 according to any one of SEQ ID NOs: 44-46; (iii) an HCDR1 according to any of SEQ ID NOs: 51-53; an HCDR2 according to any of SEQ ID NOs: 54-56; an HCDR3 according to any one of SEQ ID NOs: 57-59; an LCDR1 according to any of SEQ ID NOs: 62-64; an LCDR2 according to any of SEQ ID NOs: 65-67; an LCDR3 according to any one of SEQ ID NOs: 68-70; or (iv) an HCDR1 according to any of SEQ ID NOs: 75-77; an HCDR2 according to any of SEQ ID NOs: 78-80; an HCDR3 according to any one of SEQ ID NOs: 81-83; an LCDR1 according to any of SEQ ID NOs: 86-88; an LCDR2 according to any of SEQ ID NOs: 89-91; an LCDR3 according to any one of SEQ ID NOs: 92-94.

In certain embodiments, the antibody, or antigen binding fragment thereof comprises a first heavy chain variable domain comprising three HCDRs and a light chain variable domain comprising three LCDRs, wherein: (i) the heavy chain variable domain is at least 80% identical to SEQ ID NO: 1 SEQ ID NO: 25, SEQ ID NO: 49, and SEQ ID NO: 73; and (ii) the light chain variable domain is at least 80% identical to SEQ ID NO: 12, SEQ ID NO: 36, SEQ ID NO: 60, and SEQ ID NO: 84.

In certain embodiments, the antibody, or antigen binding fragment thereof comprises a first heavy chain variable domain comprising three HCDRs and a light chain variable domain comprising three LCDRs, wherein: (i) the heavy chain variable domain is at least 80% identical to SEQ ID NO: 1 and the light chain variable domain is at least 80% identical to SEQ ID NO: 12; (ii) the heavy chain variable domain is at least 80% identical to SEQ ID NO: 25 and the light chain variable domain is at least 80% identical to SEQ ID NO: 36; (iii) the heavy chain variable domain is at least 80% identical to SEQ ID NO: 49 and the light chain variable domain is at least 80% identical to SEQ ID NO: 60; or (iv) the heavy chain variable domain is at least 80% identical to SEQ ID NO: 73 and the light chain variable domain is at least 80% identical to SEQ ID NO: 84.

In certain embodiments, the three HCDRs and the three LCDRs are comprised by a single polypeptide. In certain embodiments, the antigen binding fragment thereof comprises an scFv.

Disclosed is a nucleic acid encoding a disclosed antibody, or antigen binding fragment thereof.

Disclosed is chimeric antigen receptor, comprising the antibody, or antigen binding fragment thereof disclosed herein.

In embodiments the chimeric antigen receptor comprises an antibody, or antigen binding fragment thereof comprising comprises a heavy chain variable domain that is at least 80% identical to SEQ ID NO: 1 and the light chain variable domain that is at least 80% identical to SEQ ID NO: 12; (ii) a heavy chain variable domain that is at least 80% identical to SEQ ID NO: 25 and a light chain variable domain that is at least 80% identical to SEQ ID NO: 36; (iii) a heavy chain variable domain that is at least 80% identical to SEQ ID NO: 49 and a light chain variable domain that is at least 80% identical to SEQ ID NO: 60; (iv) a heavy chain variable domain that is at least 80% identical to SEQ ID NO: 73 and a light chain variable domain that is at least 80% identical to SEQ ID NO: 84; or (v) or a heavy chain variable domain that is at least 80% identical to SEQ ID NO: 97 and a light chain variable domain that is at least 80% identical to SEQ ID NO: 103.

In embodiments the chimeric antigen receptor comprises a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof.

Disclosed is a nucleic acid comprising a chimeric antigen receptor disclosed herein. Disclosed is recombinant vector comprising a nucleic acid disclosed herein. In embodiments the nucleic acid encoding the antibody, antigen binding fragment thereof or chimeric antigen receptor is operatively connected to a constitutively active promotor or a conditionally activated promoter. In embodiments the conditionally activated promoter comprises at least one transcriptional activator binding site. In embodiments the transcriptional activator binding site comprises one or more GAL4 binding sites.

In embodiments a disclosed recombinant vector or nucleic acid further comprises a nucleic acid encoding a dominant negative TGFβ receptor (DN TGFβR), comprising: an extracellular domain (ECD) from a TGF-β receptor and a transmembrane domain (TMD), wherein the recombinant polypeptide lacks amino acid residues responsible for signaling and phosphorylation present in a wild-type TGF-β receptor. In embodiments the ECD is selected from TGF-βRI or TGF-βRII. In embodiments the TMD is selected from TGF-βRI, TGF-βRII, PDGFR, CD4, CD8, CD28, CD127, CD132, CD3ζ, 4-IBB, OX40, ICOS, CTLA-4, PD-1, LAG-3, 2B4, IL-5, IL-7, IL-7Rα, BTLA or mutants of any of the foregoing. In embodiments the DN TGFβR further comprises a heterologous intracellular domain (ICD) which lacks amino acid residues responsible for signaling and phosphorylation present in wild-type TGF-β receptor. In embodiments the DN TGFβR binds TGF-β1.

Disclosed is a s synthetic notch (synNotch) receptor polypeptide comprising from N to C terminus: an extracellular anti-PSCA binding domain, a Notch core domain comprising one or more proteolytic cleavage sites, and an intracellular domain comprising a transcriptional activator comprising a DNA binding domain and a transactivation domain, wherein binding of the binding extracellular anti-PSCA binding domain to PSCA induces cleavage of the Notch core domain at the one or more proteolytic cleavage sites, thereby releasing the intracellular domain and the transcriptional regulator.

In embodiments the anti-PSCA binding domain comprising a first domain comprising three heavy chain complementarity determining regions (HCDR1, HCDR2 and HCDR3) and a second domain comprising three light chain complementarity determining regions (LCDR1, LCDR2 and LCDR3), wherein (i) the HCDR1 has a sequence according to any one of SEQ ID NOs: 152-154, (ii) the HCDR2 has a sequence according to any one of SEQ ID NOs: 155-157; (iii) the HCDR3 has a sequence according to any one of SEQ ID NOs: 158-160; (iv) the LCDR1 has a sequence according to any one of SEQ ID NOs: 163-165; (v) the LCDR2 has a sequence according to any one of SEQ ID NOs: 166-168; and (vi) the LCDR3 has a sequence according to any one of SEQ ID NOs: 169-171. In embodiments the synNotch receptor polypeptide comprises a first heavy chain variable domain comprising the three HCDRs and a light chain variable domain comprising the three LCDRs, wherein: (i) the heavy chain variable domain is at least 80% identical to SEQ ID NO: 150; and (ii) the light chain variable domain is at least 80% identical to SEQ ID NO: 161.

In embodiments the transcriptional regulator is a transcriptional activator. In embodiments the transcriptional activator comprises GAL4, HNF1 alpha or HNF1 beta. In embodiments the transcriptional activator comprises a transactivation domain selected from the group consisting of VP64, RelA (p65), YAP, WWTR1(TAZ), CREB3(LZIP), and MyoD.

Disclosed is a nucleic encoding a disclosed synNotch receptor polypeptide.

Disclosed is a recombinant vector comprising a disclosed synNotch receptor polypeptide.

Disclosed is a host cell transformed with a disclosed nucleic acid or disclosed recombinant vector. In embodiments the host cell comprises a T cell or an NK cell.

Disclosed is a pharmaceutical composition comprising a T cell and/or an NK cell transformed with a disclosed nucleic acid or disclosed recombinant vector.

Disclosed is a method of treating disease in a patient in need of thereof, comprising administering a T cell and/or an NK cell transformed with a disclosed nucleic acid or disclosed recombinant vector or the pharmaceutical composition comprising the same to the patient. In embodiments the disease is prostate cancer.

Disclosed is a method of inducing an immune response in a subject or immunizing a subject against a prostate cancer, the method comprising administering to the subject a T cell and/or an NK cell transformed with a disclosed nucleic acid or disclosed recombinant vector or the pharmaceutical composition comprising the same to the patient. In embodiments the T cell and/or the NK cell is allogeneic to the patient. In embodiments the T cell and/or the NK cell is allogeneic to the patient.

DETAILED DESCRIPTION OF THE INVENTION

Terms

Figure 1:
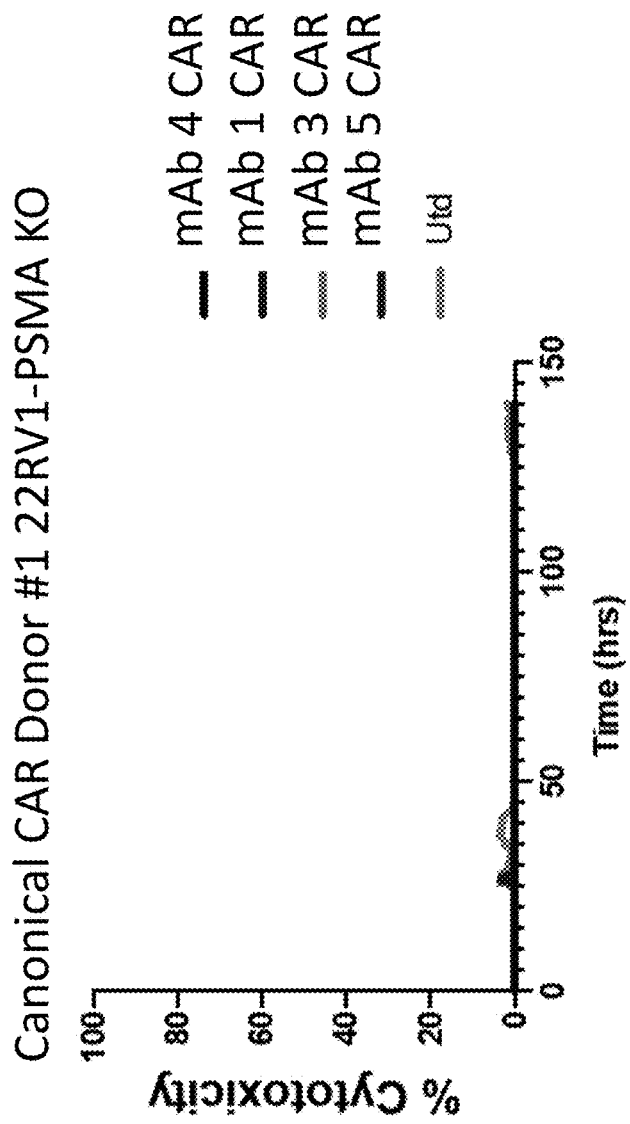
FIG. 1 is a graph of cytotoxicity vs time for the indicated canonical CARs.

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "e.g.," as used herein, is used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Systéme International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", $2^{nd}$ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"Administering" refers to the physical introduction of an agent to a subject, such as a modified T cell disclosed herein, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms, "activated" and "activation" refer to the state of a T cell that has been sufficiently stimulated to induce detectable cellular proliferation. In one embodiment, activation may also be associated with induced cytokine production, and detectable effector functions. The term "activated T cells" refers to, among other things, T cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

The term "agent" may refer to a molecule or entity of any class comprising, or a plurality of molecules or entities, any of which may be, for example, a polypeptide, nucleic acid, saccharide, lipid, small molecule, metal, cell (such as a T cell or NK cell or progenitor of such cells), or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

The term "allogeneic" refers to any material derived from one individual which is then introduced to another individual of the same species, e.g., allogeneic T cell transplantation.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Transbodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," "antigen binding fragment," or "antibody fragment" or "antigen binding domain" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments an antigen binding molecule is a chimeric antigen receptor (CAR) or an engineered T cell receptor (TCR). In certain embodiments, the antigen binding molecule or domain binds to prostate stem cell antigen (PSCA) or prostate-specific membrane antigen (PSMA). In certain embodiments, the antigen binding molecule or domain is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule or domain comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR (e.g., a CDR provided in the present disclosure) in that it is either identical in sequence or contains between 1, 2, 3, 4, or 5 (e.g., 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g., 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody. In various embodiments, an antigen binding fragment cross-competes with the reference antibody, for example, binding to substantially the same or identical epitope as the reference antibody An antigen binding fragment may be produced by any means. For example, in some embodiments, an antigen binding fragment may be enzymatically or chemically produced by fragmentation of an intact antibody. In some embodiments, an antigen binding fragment may be recombinantly produced (such as by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|---|---|---|---|---|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B (Kabat Numbering) | H26-H35B | H26-H32 ... 34 | H30-H35B |
| H1 | H31-H35 (Chothia Numbering) | H26-H35 | H26-H32 | H30-H35 |
| H2 | H50-H65 | H50-H58 | H52-H56 | H47-H58 |
| H3 | H95-H102 | H95-H102 | H95-H102 | H93-H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

An "antigen" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a TCR or CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of prostate stem cell antigen (PSCA) or prostate-specific membrane antigen (PSMA). A "target" is any molecule bound by a binding motif, antigen binding system, CAR or antigen binding agent, e.g., an antibody.

"Antigen-specific targeting region" (ASTR) refers to the region of the CAR which targets specific antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of this disclosure. In fact, almost any molecule that binds a given antigen with high affinity can be used as an antigen-specific targeting region, as will be appreciated by those of skill in the art.

"Antigen presenting cell" or "APC" refers to cells that process and present antigens to T cells. Exemplary APCs comprise dendritic cells, macrophages, B cells, certain activated epithelial cells, and other cell types capable of TCR stimulation and appropriate T cell costimulation.

An "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

"Binding affinity" generally refers to the strength of the sum total of non-covalent interactions between a single binding site of a molecule (e.g., an antibody) and its binding partner (e.g., an antigen). Unless indicated otherwise "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

The term "KD" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody binding fragment. The association equilibrium constant is obtained by dividing the $k_a$ by the $k_d$.

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding motif, antibody, or antigen binding system with a target of the binding motif, antibody, or antigen binding system as compared to association of the binding motif, antibody, or antigen binding system with an entity that is not the target (i.e. non-target). In some embodiments, a binding motif, antibody, or antigen binding system selectively binds a target if binding between the binding motif, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding motif, antibody, or antigen binding system and a non-target. In some embodiments, a binding motif, antibody, or antigen binding system selectively binds a target if the binding affinity is less than about $10^{-3}$ M, less than about $10^{-6}$ M, less than about $10^{-7}$ M, less than about $10^{-8}$ M, or less than about $10^{-9}$ M.

In another embodiment, molecules that specifically bind to an antigen bind with a dissociation constant ($K_d$) of about $1 \times 10^{-7}$ M. In some embodiments, the antigen binding molecule specifically binds an antigen with "high affinity" when the $K_d$ is about $1 \times 10^{-9}$ M to about $5 \times 10^{-9}$ M. In some embodiments, the antigen binding molecule specifically binds an antigen with "very high affinity" when the $K_d$ is $1 \times 10^{-10}$ M to about $5 \times 10^{-10}$ M. In one embodiment, the antigen binding molecule has a $K_d$ of $10^{-9}$ M. In one embodiment, the off-rate is less than about $1 \times 10^{-5}$. In embodiments, the antigen binding molecule binds prostate stem cell antigen (PSCA) or prostate-specific membrane antigen (PSMA) with a $K_d$ of about $1 \times 10^{-10}$ M to about $5 \times 10^{-10}$ M.

In certain embodiments, provided herein is an antibody or an antigen binding molecule thereof that binds to the target human antigen, e.g., In certain embodiments, the antigen binding molecule binds to prostate stem cell antigen (PSCA) or prostate-specific membrane antigen (PSMA) with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. In some embodiments, the methods of the present disclosure can be used to reduce the tumor size of a tumor derived from, for example, prostate cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL)(including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In one particular embodiment, the cancer is prostate cancer. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

"Chimeric antigen receptor" or "CAR" refers to a molecule engineered to comprise a binding motif and a means of activating immune cells (for example T cells such as naive T cells, central memory T cells, effector memory T cells, NK cells or combination thereof) upon antigen binding. CARs are also known as artificial T cell receptors, chimeric T cell receptors or chimeric immunoreceptors. In some embodiments, a CAR comprises a binding motif, an extracellular domain, a transmembrane domain, one or more co-stimulatory domains, and an intracellular signaling domain. A T cell that has been genetically engineered to express a chimeric antigen receptor may be referred to as a CAR T cell. Similarly an NK cell that has been genetically engineered to express a chimeric antigen receptor may be referred to as a CAR NK cell.

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include a decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition.

"Extracellular domain" (or "ECD") refers to a portion of a polypeptide that, when the polypeptide is present in a cell membrane, is understood to reside outside of the cell membrane, in the extracellular space.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular use in the disclosure include those derived from DAP10, DAP12, TCRzeta, FcRgamma, FcRbeta, CD3gamma, CD3delta, CD3epsilon, CD5, CD22, CD79a, CD79b and CD66d.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1 BB (CD137), 0X40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from 4-1 BB, other costimulatory domains are contemplated for use with the CARs described herein. The inclusion of one or more co stimulatory signaling domains may enhance the efficacy and expansion of T cells expressing CAR receptors. The intracellular signaling and costimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from 4-1BB, CD28, CD137, CD134 and CD278) may more effectively direct antitumor activity as well as increased cytokine secretion, lytic activity, survival and proliferation in CAR expressing T cells in vitro, and in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

A "costimulatory signal" refers to a signal, which in combination with a primary signal, such as TCR/CD3 ligation, leads to a T cell response, such as, but not limited to, proliferation and/or upregulation or down regulation of key molecules.

A "costimulatory ligand" includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSFi4), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Lyl08), SLAMF7, SLP-76, TNF, TNFr, TNFR2, Toll ligand receptor, TRANCE/RANKL, VLA1, or VLA-6, or fragments, truncations, or combinations thereof.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

An antigen binding molecule, such as an antibody, an antigen binding fragment thereof, CAR or TCR, "cross-competes" with a reference binding molecule, such as an antibody or an antigen binding fragment thereof, if the interaction between an antigen and the first antigen binding molecule blocks, limits, inhibits, or otherwise reduces the ability of the reference binding molecule to interact with the antigen. Cross competition can be complete, e.g., binding of the antigen binding molecule to the antigen completely blocks the ability of the reference binding molecule to bind the antigen, or it can be partial, e.g., binding of the antigen binding molecule to the antigen reduces the ability of the reference antigen binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137: 3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

A "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence motif, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, PSMA, which is a transmembrane protein expressed prostate tissue, including carcinoma.

In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, which are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

An "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

"Endogenous" with reference to a gene, protein, and/or nucleic acid refers to the natural presence of that gene, protein, and/or nucleic acid in a cell, such as an immune cell.

"Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g. without introduction of the exogenous nucleic acid.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man. In embodiments, a CAR is a fusion protein. In embodiments, a synthetic Notch receptor (synNotch receptor) is a fusion protein.

The term "gene product" or "expression product" generally refers to an RNA transcribed from the gene (pre- and/or post-processing) or a polypeptide (pre- and/or post-modification) encoded by an RNA transcribed from the gene.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or NK cell, which can either be obtained from a patient or a donor. The cell can be modified to express an exogenous construct, such as, e.g., a chimeric antigen receptor (CAR) or a T cell receptor (TCR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell or NK cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents.

A "T cell receptor" or "TCR" refers to antigen-recognition molecules present on the surface of T cells. During normal T cell development, each of the four TCR genes, α, β, γ, and δ, may rearrange leading to highly diverse TCR proteins.

The term "heterologous" means from any source other than naturally occurring sequences. For example, a heterologous sequence included as a part of a costimulatory protein is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-1000/a).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, NK cells and T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells or NK cells of the immunotherapy can come from any source known in the art. For example, T cells and NK cells can be differentiated in vitro from a hematopoietic stem cell population or can be obtained from a subject. T cells and NK cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell or an NK cell. The term "in vivo" refers to events that occur within a multi-cellular organism, such as a human or a non-human animal.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Linker" (L) or "linker domain" or "linker region" refers to an oligo- or polypeptide region from about 1 to 100 amino acids in length, for example linking together any of the domains/regions of a CAR, a synNotch receptor, a DN TFGbeta receptor and/or scFv, or ever one or more of those polypeptides together. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ motif (SEQ ID NO: 255), which results in cleavage between the 2A glycine and the 2B proline. Other linkers will be apparent to those of skill in the art and may be used in connection with this disclosure. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a CAR or a synNotch receptor. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide. In another example it may be used to connect to or more polypeptides to be expressed, such as a CAR, a synNotch receptor and/or a TGFβ-DNR as disclosed herein. In some examples, the CAR, the synNotch receptor and/or the DN TGFβ-R are connected by a cleavable linker.

Other linkers include non-cleavable linkers. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs.

The term "lymphocyte" includes natural killer (NK) cells, T cells, or B cells. NK cells are a type of cytotoxic (cell toxic) lymphocyte that represent a component of the inherent immune system. NK cells reject tumors and cells infected by viruses. It works through the process of apoptosis or programmed cell death. They were termed "natural killers" because they do not require activation in order to kill cells. T cells play a role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element. In embodiments, a promotor is operably linked to nucleic a A "patient" includes any human who is afflicted with a cancer (e.g., prostate cancer). The terms "subject" and "patient" are used interchangeably herein.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "proliferation" refers to an increase in cell division, either symmetric or asymmetric division of cells.

In some embodiments, "proliferation" refers to the symmetric or asymmetric division of T cells. "Increased proliferation" occurs when there is an increase in the number of cells in a treated sample compared to cells in a non-treated sample.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+ T lymphocytes. However, Treg cells within a tumor microenvironment (i.e. tumor-infiltrating Treg cells), Treg cells may make up as much as 20-30% of the total CD4+ T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., broncheoalveolar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

"Single chain variable fragment", "single-chain antibody variable fragments" or "scFv" antibodies refer to forms of antibodies comprising the variable regions of only the heavy and light chains, connected by a linker peptide.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

"Stimulation," refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

A "therapeutically effective amount," "effective dose," "effective amount," or "therapeutically effective dosage" of a therapeutic agent, e.g., engineered CAR T cells or NK cell, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Chimeric Notch receptor" also referred to as "Chimeric Notch receptor," or "chimeric Notch receptor" or "synthetic Notch receptor" (synNotch receptor) as described in international patent publications WO16138034 and WO18236825, comprises, from N-terminal to C-terminal and in covalent linkage: a) an extracellular ligand binding domain, for example an antigen binding domain, that specifically binds an antigen present on the surface of a cells, such prostate specific membrane antigen (PSMA); b) wherein the synNotch receptor polypeptide has a length of from 50 amino acids to 1000 amino acids, and comprises one or more ligand-binding inducible proteolytic cleavage sites; and c) an intracellular domain, wherein the ligand binding domain is heterologous to the synNotch receptor polypeptide, and wherein binding of ligand to ligand binding domain induces cleavage of the synNotch receptor polypeptide at the one or more ligand binding-inducible proteolytic cleavage sites, thereby releasing the intracellular domain. In some cases, the synNotch receptor polypeptide has a length of from 300 amino acids to 400 amino acids.

In embodiments a synNotch receptor polypeptide comprises a linker interposed between the extracellular ligand binding domain and the Notch receptor polypeptide. In embodiments the intracellular domain is a transcriptional activator, such as a transcription factor. In embodiments, the extracellular ligand binding domain comprises an antibody or antigen binding fragment thereof, that specifically binds to prostate stem cell antigen (PSCA). In some cases, where the first member of the specific binding pair is an antibody, the antibody is a single-chain Fv (scFv), such as an scFv that specifically binds to a prostate stem cell antigen (PSCA). In embodiments, the extracellular ligand binding domain is a nanobody, a single-domain antibody, a diabody, a triabody, or a minibody.

A "transmembrane domain" is a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. A transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

The disclosure may employ, unless indicated specifically to the contrary, methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual*(3rd Edition, 2001); Maniatis et al., *Molecular Cloning. A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning. A Practical Approach*, vol. I & II (IRL Press, Oxford, 1985); Anand, *Techniques for the Analysis of Complex Genomes,* (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology; as well as monographs in journals such as Advances in Immunology.*

The present disclosure provides antigen binding agents, such as antibodies, chimeric antigen receptors (CARs) and T cell receptors (TCRs) comprising at least an anti-PSMA binding domain. Among other things, the present disclosure provides methods and compositions useful for treatment of cancer and/or for initiating or modulating immune responses. In various embodiments, one or more anti-PSMA binding domain is an scFv. Exemplary anti-PSMA binding domain amino acid sequences, and nucleic acid sequences encoding the same, are provided herein, for example in Tables 4-8. In some embodiments, an antigen binding agent of the present disclosure is a chimeric antigen receptor (CAR). In some embodiments, an antigen binding agent of the present disclosure is an engineered T cell receptor (TCR). In some embodiments, the CARs and/or TCRs are expressed with a dominant negative TFGβ Receptor (DN TFGβ R).

The present disclosure further provides for synthetic Notch receptors (synNotch receptors) comprising at least an anti-PSCA binding domain. In various embodiments, one or more anti-PSCA binding domain is an scFv. An exemplary anti-PSCA binding domain amino acid sequences, and nucleic acid sequence encoding the same, is provided herein, for example in Table 9. In some embodiments, the synNotch receptors CARs and/or TCRs are expressed with a dominant negative TFGβ Receptor.

Various embodiments of the present disclosure provide a vector encoding an anti-PSMA binding domain or antigen anti-PSMA binding agent provided herein, e.g., a vector encoding an anti-PSMA CAR. Various embodiments of the present disclosure provide a vector encoding a DN TFGβ R, e.g., a vector encoding an anti-PSMA CAR and a DN TFGβ R. In some embodiments the DN TFGβ R is encoded in a separate vector from the vector encoding the anti-PSMA CAR. In some embodiments the DN TFGβ R is encoded in the same vector encoding the anti-PSMA CAR. Various embodiments of the present disclosure provide a vector encoding an anti-PSCA synNotch receptor. In some embodiments the DN TFGβ R is encoded in a separate vector from the vector encoding the anti-PSCA synNotch receptor. In some embodiments the DN TFGβ R is encoded in the same vector encoding the anti-PSCA synNotch receptor.

Various embodiments of the present disclosure provide an anti-PSMA antigen binding agent that is a cell encoding or expressing an anti-PSMA antigen binding agent, e.g., a T cell or NK cell engineered to encode or express an anti-PSMA chimeric antigen receptor or TCR. The present disclosure provides immune cells genetically modified with an integrated gene, e.g., a nucleotide sequence of interest (e.g., a constitutive expression construct and/or an inducible expression construct that comprises such nucleotide sequence, for example a synthetic notch (synNotch) receptor inducible expression construct, such as an anti-PSCA synNotch receptor described herein. In embodiments the immune cells are further engineered to express an anti-PSCA synNotch receptor. In embodiments, the immune cells are further engineered to express a DN TFGβ R. In some embodiments, the present disclosure provides methods of treating a subject having a tumor, such as a prostate tumor, comprising administering to the subject an anti-PSMA binding agent therapy described herein and/or a protein therapeutic described herein. In some embodiments, methods further comprise administration of one or more additional therapies (e.g., a second binding agent (e.g., CAR-T cell, CAR-NK cell, TCR-T cell, TIL cell, allogeneic NK cell, and autologous NK cell), an antibody-drug conjugate, an antibody, a bispecific antibody, a T cell-engaging bispecific antibody, an engineered antibody, and/or a polypeptide described herein).

Other features, objects, and advantages of the present disclosure are apparent in the detailed description that follows. It should be understood, however, that the detailed description, while indicating embodiments of the present disclosure, is given by way of illustration only, not limitation.

An anti-PSMA binding domain of the present disclosure may comprise antigen-binding sequences as found in an antibody described herein. In some instances, an anti-PSMA binding domain of the present disclosure comprises an anti-PSMA binding domain described herein, such as an scFv. Unless otherwise indicated, it is to be appreciated the references to PSMA in the present disclosure relate to human PSMA. In various embodiments, an anti-PSMA binding domain of the present disclosure comprises at least one heavy chain CDR (HCDR) provided herein, e.g., at least one HCDR disclosed in any one of Tables 4-8. In various embodiments, an anti-PSMA binding domain of the present disclosure comprises two HCDRs provided herein, e.g., at least two HCDRs disclosed in any one of Tables 4-8. In various embodiments, an anti-PSMA binding domain of the present disclosure comprises three HCDRs provided herein, e.g., three HCDRs disclosed in any one of Tables 4-8. In various embodiments, an anti-PSMA binding domain of the present disclosure comprises at least one light chain CDR (LCDR) provided herein, e.g., at least one LCDR disclosed in any one of Tables 4-8. In various embodiments, an anti-PSMA binding domain of the present disclosure comprises two LCDRs provided herein, e.g., at least two LCDRs disclosed in any one of Tables 4-8. In various embodiments, an anti-PSMA binding domain of the present disclosure comprises three LCDRs provided herein, e.g., three LCDRs disclosed in any one of Tables 4-8.

In various embodiments, an anti-PSMA binding domain of the present disclosure comprises at least one HCDR provided herein, e.g., at least one HCDR disclosed in any one of Tables 4-8, and at least one LCDR provided herein, e.g., at least one LCDR disclosed in any one of Tables 4-8. In various embodiments, an anti-PSMA binding domain of the present disclosure comprises one HCDR provided herein, e.g., at least one HCDR disclosed in any one of Tables 4-8, and one LCDR provided herein, e.g., derived from the same Table of Tables 4-8 as the HCDR(s). In various embodiments, an anti-PSMA binding domain of the present disclosure comprises two HCDRs provided herein, e.g., at least two HCDRs disclosed in any one of Tables 4-8, and two LCDRs provided herein, e.g., at least two LCDRs disclosed in any one of Tables 4-8. In various embodiments, an anti-PSMA binding domain of the present disclosure comprises two HCDRs provided herein, e.g., at least two HCDRs disclosed in any one of Tables 4-8, and two LCDRs provided herein, e.g., derived from the same Table of Tables 4-8 as the HCDR(s). In various embodiments, an anti-PSMA binding domain of the present disclosure comprises three HCDRs provided herein, e.g., three HCDRs disclosed in any one of Tables 4-8, and three LCDRs provided herein, e.g., three LCDRs disclosed in any one of Tables 4-8. In various embodiments, an anti-PSMA binding domain of the present disclosure comprises three HCDRs provided herein, e.g., three HCDRs disclosed in any one of Tables 4-8, and three LCDRs derived from the same Table of Tables 4-8 as the HCDR(s).

In various embodiments, an anti-PSMA binding domain of the present disclosure comprises at least one heavy chain framework region (heavy chain FR) of a heavy chain variable domain disclosed herein, e.g., at least one heavy chain FR of a heavy chain variable domain disclosed in any one of Tables 4-8. In various embodiments, an anti-PSMA binding domain of the present disclosure comprises two heavy chain FRs of a heavy chain variable domain disclosed herein, e.g., at least two heavy chain FRs of a heavy chain variable domain disclosed in any one of Tables 4-8. In various embodiments, an anti-PSMA binding domain of the present disclosure comprises three heavy chain FRs of a heavy chain variable domain disclosed herein, e.g., three heavy chain FRs of a heavy chain variable domain disclosed in any one of Tables 4-8.

In various embodiments, an anti-PSMA binding domain of the present disclosure comprises at least one light chain FR of a light chain variable domain disclosed herein, e.g., at least one light chain FR of a light chain variable domain disclosed in any one of Tables 4-8. In various embodiments, an anti-PSMA binding domain of the present disclosure comprises two light chain FRs of a light chain variable domain disclosed herein, e.g., at least two light chain FRs of a light chain variable domain disclosed in any one of Tables 4-8. In various embodiments, an anti-PSMA binding domain of the present disclosure comprises three light chain FRs of a light chain variable domain disclosed herein, e.g., three light chain FRs of a light chain variable domain disclosed in any one of Tables 4-8.

In various embodiments, an anti-PSMA binding domain of the present disclosure comprises at least one heavy chain FR of a heavy chain variable domain disclosed herein, e.g., at least one heavy chain FR of a heavy chain variable domain disclosed in any one of Tables 4-8, and at least one light chain FR of a light chain variable domain disclosed herein, e.g., at least one light chain FR of a light chain variable domain disclosed in any one of Tables 4-8. In various embodiments, an anti-PSMA binding domain of the present disclosure comprises one heavy chain FR of a heavy chain variable domain disclosed herein, e.g., at least one heavy chain FR of a heavy chain variable domain disclosed in any one of Tables 4-8, and one light chain FR of a light chain variable domain disclosed herein, e.g., derived from the same Table of Tables 4-8 as the heavy chain FR(s). In various embodiments, an anti-PSMA binding domain of the present disclosure comprises two heavy chain FRs of a heavy chain variable domain disclosed herein, e.g., at least two heavy chain FRs of a heavy chain variable domain disclosed in any one of Tables 4-8, and two light chain FRs of a light chain variable domain disclosed herein, e.g., at least two light chain FRs of a light chain variable domain disclosed in any one of Tables 4-8. In various embodiments, an anti-PSMA binding domain of the present disclosure comprises two heavy chain FRs of a heavy chain variable domain disclosed herein, e.g., at least two heavy chain FRs of a heavy chain variable domain disclosed in any one of Tables 4-8, and two light chain FRs of a light chain variable domain disclosed herein, e.g., derived from the same Table of Tables 4-8 as the heavy chain FR(s). In various embodiments, an anti-PSMA binding domain of the present disclosure comprises three heavy chain FRs of a heavy chain variable domain disclosed herein, e.g., three heavy chain FRs of a heavy chain variable domain disclosed in any one of Tables 4-8, and three light chain FRs of a light chain variable domain disclosed herein, e.g., three light chain FRs of a light chain variable domain disclosed in any one of Tables 4-8. In various embodiments, an anti-PSMA binding domain of the present disclosure comprises three heavy chain FRs of a heavy chain variable domain disclosed herein, e.g., three light chain FRs of a light chain variable domain disclosed in any one of Tables 4-8, and three light chain FRs derived from the same Table of Tables 4-8 as the heavy chain FR(s).

Exemplary antibody sequences provided in Tables 4-8 are suitable for use in any antibody format, comprising, e.g., a tetrameric antibody, a monospecific antibody, a bispecific antibody, an antigen binding fragment, or a binding motif. Heavy chain variable domains and light chain variable domains and portions thereof provided in Tables 4-8 may be comprised in anti-PSMA binding domain.

In various embodiments, an anti-PSMA binding domain of the present disclosure comprises one, two, or three FRs that together or each individually have at least 75% identity (e.g., at least 75%, at least 80%, at least 90%, at least 95%, or 100%, e.g., 85-90%, 85-95%, 85-100%, 90-95%, 90-100%, or 95-100%) to corresponding FR(s) of a heavy chain variable domain of a heavy chain variable domain disclosed in in any one of Tables 4-8. In various embodiments, an anti-PSMA binding domain of the present disclosure comprises one, two, or three FRs that together or each individually have at least 75% identity (e.g., at least 75%, at least 80%, at least 90%, at least 95%, or 100%) to corresponding FR(s) of a light chain variable domain of a light chain variable domain disclosed in any one of Tables 4-8.

In various embodiments, an anti-PSMA binding domain of the present disclosure comprises at least one heavy chain variable domain having at least 75% sequence identity to a heavy chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%). In various embodiments, an anti-PSMA binding domain of the present disclosure comprises two heavy chain variable domains each having at least 75% sequence identity to a heavy chain variable domain disclosed in Tables 4-8 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, an anti-PSMA binding domain of the present disclosure comprises at least one light chain variable domain having at least 75% sequence identity to a light chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%). In various embodiments, an anti-PSMA binding domain of the present disclosure comprises two light chain variable domains each having at least 75% sequence identity to a light chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, an anti-PSMA binding domain of the present disclosure comprises at least one heavy chain variable domain having at least 75% sequence identity to a heavy chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-PSMA binding domain of the present disclosure comprises one heavy chain variable domain having at least 75% sequence identity to a heavy chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%) and one light chain variable domain having at least 75% sequence identity to a light chain variable domain disclosed in any one of Tables 4-8 (e.g., at least 75%, at least 80%, at least 90%, at least 95%, or 100% identity; e.g., 85-90%, 85-95%, 85-100%, 90-95%, 90-100%, or 95-100%), where the heavy chain variable domain and light chain variable domain are optionally derived from the same Table of Tables 4-8.

In various embodiments, an anti-PSMA binding domain of the present disclosure comprises two heavy chain variable domains each having at least 75% sequence identity to a heavy chain variable domain disclosed in Tables 4-8 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Tables 4-8 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; (ii) each of the light chain variable domains may be same or different; (iii) at least one heavy chain variable domain and at least one light chain variable domain may be derived from the same Table of Tables 4-8; or (iv) the two heavy chain variable domains and the two light chain variable domains are all derived from the same Table of Tables 4-8. Each of Tables 4-8 represents the heavy chain variable domain and light chain variable domain sequences of an exemplary antibody, comprising (i) the heavy chain variable domain of the exemplary antibody; (ii) a DNA sequence encoding the heavy chain variable domain (iii) three heavy chain variable domain CDRs of the heavy chain variable domain, according to IMGT, Kabat, and Chothia numbering; (iv) the light chain variable domain of the exemplary antibody; (v) a DNA sequence encoding the light chain variable domain; and (vi) three light chain variable domain CDRs of the light chain variable domain, according to IMGT, Kabat, and Chothia numbering. Information provided in each table provides framework amino acid sequences, as well as nucleotide sequences encoding each CDR amino acid sequence and nucleotide sequences encoding corresponding FR amino acid sequence.

In various embodiments an anti-PSMA binding domain may comprise a heavy chain variable domain of the present disclosure (e.g., having at least 75% sequence identity to a heavy chain variable domain of any one of Tables 4-8, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-8, e.g., at least 80%, 85%, 90%, 95%, or 100% identity; e.g., 85-90%, 85-95%, 85-100%, 90-95%, 90-100%, or 95-100%), and a linker (e.g., a linker according to SEQ ID NO: 126. In various embodiments an anti-PSMA binding domain may comprise a leader sequence, a heavy chain variable domain of the present disclosure (e.g., having at least 75% sequence identity to a heavy chain variable domain of any one of Tables 4-8, e.g., at least 80%, 85%, 90%, 95%, or 100% identity; e.g., 85-90%, 85-95%, 85-100%, 90-95%, 90-100%, or 95-100%), a light chain variable domain of the present disclosure (e.g., having at least 75% sequence identity to a light chain variable domain of any one of Tables 4-8, e.g., at least 80%, 85%, 90%, 95%, or 100% identity; e.g., 85-90%, 85-95%, 85-100%, 90-95%, 90-100%, or 95-100%), and a linker. If provided with an amino acid or nucleotide sequence of an anti-PSMA binding domain comprising a heavy chain variable domain of the present disclosure and a light chain variable domain of the present disclosure, the linker joining the two variable domains will be apparent from the sequence in view of the present disclosure. If provided with an amino acid or nucleotide sequence of an anti-PSMA biding domain comprising a heavy chain variable domain of the present disclosure and a light chain variable domain of the present disclosure, the leader sequence will be apparent in view of the present disclosure. For the avoidance of doubt, a heavy chain variable domain and a light chain variable domain of the present disclosure may be present in any orientation, e.g., an orientation in which the heavy chain variable domain is C terminal of the light chain variable domain or in which the heavy chain variable domain is N terminal of the light chain variable domain. In various embodiments an anti-PSMA biding domain may comprise a linker according to SEQ ID NO: 126.

In certain embodiments, an anti-PSMA binding domain of the present disclosure comprises an anti-PSMA biding domain that comprises a heavy chain variable domain of the present disclosure, a light chain variable domain of the present disclosure, and a linker having at least 75% sequence identity to SEQ ID NO: 8 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-PSMA binding domain of the present disclosure comprises an anti-PSMA biding domain that comprises a linker according to SEQ ID NO: 126. In certain embodiments, an anti-PSMA binding domain of the present disclosure comprises an anti-PSMA biding domain that comprises a heavy chain variable domain of the present disclosure, a light chain variable domain of the present disclosure, and a leader sequence having at least 75% sequence identity to SEQ ID NO: 48 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-PSMA binding domain of the present disclosure comprises an anti-PSMA biding domain that comprises a CSF2RA leader sequence according to SEQ ID NO: 137 (MLLLVTSLLLCEL-PHPAFLLIP; SEQ ID NO: 137). In embodiments a leader sequence may be encoded by nucleic acid sequence at least 75% sequence identity to atgcttctcctggtgacaagccttctgctctgt-gaattgccacacccagcattcctcctgattcct (SEQ ID NO: 256) (e.g., at least 75%, at least 80%, at least 90%, at least 95%, or 100% identity; e.g., 85-90%, 85-95%, 85-100%, 90-95%, 90-100%, or 95-100%). In certain embodiments, an anti-PSMA binding domain of the present disclosure comprises an anti-PSMA biding domain that comprises a heavy chain variable domain of the present disclosure, a light chain variable domain of the present disclosure, a linker of the present disclosure, and a leader sequence of the present disclosure.

A binding agent of the present disclosure that is based on an exemplary antibody provided herein, such as for example Abs 1-5, may be provided in any fragment or format, comprising a heavy chain variable domain according to the indicated exemplary antibody and a light chain variable domain according to the indicated exemplary antibody.

TABLE 4

Exemplary Antibody Sequences 1 (Ab1)

| SEQ ID NO: | Description | Sequence |
|---|---|---|
| 1 | Heavy Chain Variable Domain | EVQLVESGGGLVQPGGSMRLSCAASGFTFSDYYMAWVRQAP GKGLEWIANINYDGSNTYYADSLKGRFTISRDNSKNTLYLQM NSLRAEDTAVYYCARNWDGYYGYFDVWGQGTTVTSS |
| 2 | VH (DNA) | Gaggtgcaacttgtggagagcggaggaggtttagtgcaacccggaggcagcatgagactgag ctgcgccgccagcggcttcacattctccgactactacatggcttgggtccgacaagctcccggaa aaggactggagtggatcgccaacatcaactacgacggctccaacacctactacgccgactcttta aagggtcgtttcacaatctctcgtgacaacagcaagaacactttatatttacaaatgaactctttaagg gccgaggataccgccgtgtactactgcgctcgtaactgggacggctactacggctacttcgacgt gtggggccaaggaaccaccgtgaccgtgagcagc |
| 3 | CDRH1 IMGT (Prot) | GFTFSDYY |
| 4 | CDRH1 Kabat (Prot) | DYYMA |
| 5 | CDRH1 Chothia (Prot) | GFTFSD |
| 6 | CDRH2 IMGT (Prot) | INYDGSNT |
| 7 | CDRH2 Kabat (Prot) | NINYDGSNTYYADSLKG |

TABLE 4-continued

Exemplary Antibody Sequences 1 (Ab1)

| SEQ ID NO: | Description | Sequence |
|---|---|---|
| 8 | CDRH2 Chothia (Prot) | NINYDGSNTYYADSLKG |
| 9 | CDRH3 IMGT (Prot) | ARNWDGYYGYFDV |
| 10 | CDRH3 Kabat (Prot) | NWDGYYGYFDV |
| 11 | CDRH3 Chothia (Prot) | NWDGYYGYFDV |
| 12 | Light Chain Variable Domain | DIQLTQSPSSLSASVGDRVTITCRASSSVSHIYWYQQKPGKAP KPWIYRTSNLASGVPSRFSGSGSGTDYTLTISSLQPEDFATYYC QQYHTYPPTFGQGTKLEIK |
| 13 | VL (DNA) | Gatatccagctgacccagtccccttcctctctgtctgcgtctgttggcgatcgtgtcaccatcacttg tcgtgccagcagcagcgtgagccacatttattggtaccaacaaaagcccggcaaagcccctaag cctttggatctacagaacctccaatctggccagcggcgtgcccagcagattcagcggaagcggat ccggcaccgactacactttaaccatcagctctttacagcccgaggacttcgccacatactactgcc agcagtaccacacctatccccccacattcggccaaggaacaaagctggagattaag |
| 14 | CDRL1 IMGT (Prot) | SSVSH |
| 15 | CDRL1 Kabat (Prot) | RASSSVSHIY |
| 16 | CDRL1 Chothia (Prot) | RASSSVSHIY |
| 17 | CDRL2 IMGT (Prot) | RTS |
| 18 | CDRL2 Kabat (Prot) | RTSNLAS |
| 19 | CDRL2 Chothia (Prot) | RTSNLAS |
| 20 | CDRL3 IMGT (Prot) | QQYHTYPPT |
| 21 | CDRL3 Kabat (Prot) | QQYHTYPPT |
| 22 | CDRL3 Chothia (Prot) | QQYHTYPPT |
| 23 | ScFv | DIQLTQSPSSLSASVGDRVTITCRASSSVSHIYWYQQKPGKAP KPWIYRTSNLASGVPSRFSGSGSGTDYTLTISSLQPEDFATYYC QQYHTYPPTFGQGTKLEIKGSTSGSGKPGSGEGSTKGEVQLVE SGGGLVQPGGSMRLSCAASGFTFSDYYMAWVRQAPGKGLE WIANINYDGSNTYYADSLKGRFTISRDNSKNTLYLQMNSLRA EDTAVYYCARNWDGYYGYFDVWGQGTTVTVSS |
| 24 | ScFv | Gatatccagctgacccagtccccttcctctctgtctgcgtctgttggcgatcgtgtcaccatcacttg tcgtgccagcagcagcgtgagccacatttattggtaccaacaaaagcccggcaaagcccctaag cctttggatctacagaacctccaatctggccagcggcgtgcccagcagattcagcggaagcggat ccggcaccgactacactttaaccatcagctctttacagcccgaggacttcgccacatactactgcc agcagtaccacacctatccccccacattcggccaaggaacaaagctggagattaagggctccac ctccggaagcggcaaaccggtagcggcgagggctccacaaagggcgaggtgcaacttgtgg agagcggaggaggtttagtgcaacccggaggcagcatgagactgagctgcgccgccagcggc ttcacattctccgactactacatggcttgggtccgacaagctcccggaaaaggactggagtggatc gccaacatcaactacgacggctccaacacctactacgccgactcttttaaagggtcgtttcacaatct ctcgtgacaacagcaagaacactttatatttacaaatgaactctttaagggccgaggataccgccgt gtactactgcgctcgtaactgggacggctactacggctacttcgacgtgtggggccaaggaacca ccgtgaccgtgagcagc |

TABLE 5

Exemplary Antibody Sequences 2 (Ab2)

| SEQ ID NO: | Description | Sequence |
|---|---|---|
| 25 | Heavy Chain Variable Domain | QVQLVQSGAEVKKPGASVKLSCKASGYTFTTYWMHWVRQA PGQGLEWIGMIHPNSGSTNYAQKFQGRATLTVDTSTSTAYME LSSLRSEDTAVYYCARDPYDYGEDFDVWGQGTTVTVSS |
| 26 | VH (DNA) | Caagtgcagctggtgcagtccggcgccgaggtgaagaagcccggtgcttccgtgaagctgtctt gcaaagccagcggctacaccttcaccacctattggatgcactgggtccgacaagctcccggtcaa ggtctggagtggattggcatgatccaccccaactccggctccaccaactacgcccagaagttcca aggtcgtgccactttaacagtggataccagcaccagcaccgcctacatggagctgagtagtttga ggagcgaggacaccgccgtgtactattgcgctcgtgacccctacgactacggcgaggacttcga cgtgtggggccaaggaacaacagtgaccgtgagcagc |
| 27 | CDRH1 IMGT (Prot) | GYTFTTYW |
| 28 | CDRH1 Kabat (Prot) | TYWMH |
| 29 | CDRH1 Chothia (Prot) | GYTFTT |
| 30 | CDRH2 IMGT (Prot) | IHPNSGST |
| 31 | CDRH2 Kabat (Prot) | MIHPNSGSTNYAQKFQG |
| 32 | CDRH2 Chothia (Prot) | MIHPNSGSTNYAQKFQG |
| 33 | CDRH3 IMGT (Prot) | ARDPYDYGEDFDV |
| 34 | CDRH3 Kabat (Prot) | DPYDYGEDFDV |
| 35 | CDRH3 Chothia (Prot) | DPYDYGEDFDV |
| 36 | Light Chain Variable Domain | DIQMTQSPSSLSASVGDRVTVTCRASQNVNTNVAWYQQKPG KAPKVLIYSASYRNSGVPSRFSGSGSGTDFTLTISSVQPEDFAT YYCQQYNSYPFTFGQGTKLEIK |
| 37 | VL (DNA) | Gacatccagatgacccagagcccccagctctttaagtgccagcgtgggcgacagagtgacagtg acttgtcgtgccagccagaacgtgaataccaacgtggcttggtaccagcagaagcccggcaaag cccctaaggtgctgatctattccgcgtcttatcgtaactccggcgtgccttcgcgttttctgggtctg gtagcggcaccgacttcactttaacaatcagcagcgttcagcccgaagacttcgccacctactact gccagcaagtacaacagctatcccttactttcggtcaagggaccaagctcgagatcaaa |
| 38 | CDRL1 IMGT (Prot) | QNVNTN |
| 39 | CDRL1 Kabat (Prot) | RASQNVNTNVA |
| 40 | CDRL1 Chothia (Prot) | RASQNVNTNVA |
| 41 | CDRL2 IMGT (Prot) | MIHPNSGSTNYAQKFQG |
| 42 | CDRL2 Kabat (Prot) | SASYRNS |
| 43 | CDRL2 Chothia (Prot) | SASYRNS |
| 44 | CDRL3 IMGT (Prot) | DPYDYGEDFDV |

TABLE 5-continued

Exemplary Antibody Sequences 2 (Ab2)

| SEQ ID NO: | Description | Sequence |
|---|---|---|
| 45 | CDRL3 Kabat (Prot) | QQYNSYPFT |
| 46 | CDRL3 Chothia (Prot) | QQYNSYPFT |
| 47 | ScFv | DIQMTQSPSSLSASVGDRVTVTCRASQNVNTNVAWYQQKPG KAPKVLIYSASYRNSGVPSRFSGSGSGTDFTLTISSVQPEDFAT YYCQQYNSYPFTFGQGTKLEIKGSTSGSGKPGSGEGSTKGQV QLVQSGAEVKKPGASVKLSCKASGYTFTTYWMHWVRQAPG QGLEWIGMIHPNSGSTNYAQKFQGRATLTVDTSTSTAYMELS SLRSEDTAVYYCARDPYDYGEDFDVWGQGTTVTVSS |
| 48 | ScFv | Gacatccagatgacccagagccccagctctttaagtgccagcgtgggcgacagagtgacagtg acttgtcgtgccagccagaacgtgaataccaacgtggcttggtaccagcagaagcccggcaaag cccctaaggtgctgatctattccgcgtcttatcgtaactccggcgtgccttcgcgtttttctgggtctg gtagcggcaccgacttcactttaacaatcagcagcgttcagcccgaagacttcgccacctactact gccagcagtacaacagctatccctttactttcggtcaaggaccaagtcgagatcaaaggctcca ccagcggtagcggcaaacccggttccggcgagggctctaccaaggccaagtgcagctggtgc agtccggcgccgaggtgaagaagcccggtgcttccgtgaagctgtcttgcaaagccagcggcta caccttcaccacctattggatgcactgggtccgacaagctcccggtcaaggtctggagtggattgg catgatccaccccaactccggctccaccaactacgcccagaagttccaaggtcgtgccactttaac agtggataccagcaccagcaccgcctacatggagctgagtagtttgaggagcgaggacaccgc cgtgtactattgcgctcgtgaccccacgactacggcgaggacttcgacgtgtggggccaaggaa caacagtgaccgtgagcagc |

TABLE 6

Exemplary Antibody Sequences 3 (Ab3)

| SEQ ID NO: | Description | Sequence |
|---|---|---|
| 49 | Heavy Chain Variable Domain | EVQLVESGGGLVQPGGSMRLSCAASGFTFSDYYMAWVRQAP GKGLEWVANINYDGTSTYYADSLKGRFTISRDSSKNTLYLQM NSLRAEDTAVYYCARALDGYYGYLDVWGQGTTVTVSS |
| 50 | VH (DNA) | Gaggtgcagctggtggagtccggaggagggtttagtccaacccggtggcagcatgaggctgtctt gtgctgcctccggcttcactttttctgattactacatggcttgggtccgacaagctcccggaaaaggt ttagagtggggtggctaacatcaactacgacggcaccagcacctactatgccgacagcctcaagg gcagattcaccatctctcgtgattcgtctaaaaacactttatatttacaaatgaactctttaagagccga agataccgccgtgtactattgcgctcgtgcccttgacggctactacggatatttagacgtgtggggt caaggaacaaccgtgaccgtgtccagc |
| 51 | CDRH1 IMGT (Prot) | GFTFSDYY |
| 52 | CDRH1 Kabat (Prot) | DYYMA |
| 53 | CDRH1 Chothia (Prot) | GFTFSD |
| 54 | CDRH2 IMGT (Prot) | INYDGTST |
| 55 | CDRH2 Kabat (Prot) | NINYDGTSTYYADSLKG |
| 56 | CDRH2 Chothia (Prot) | NINYDGTSTYYADSLKG |
| 57 | CDRH3 IMGT (Prot) | ARALDGYYGYLDV |
| 58 | CDRH3 Kabat (Prot) | ALDGYYGYLDV |

TABLE 6-continued

Exemplary Antibody Sequences 3 (Ab3)

| SEQ ID NO: | Description | Sequence |
|---|---|---|
| 59 | CDRH3 Chothia (Prot) | ALDGYYGYLDV |
| 60 | Light Chain Variable Domain | DIQLTQSPSSLSASVGDRVTLTCRASQSISNNLHWYQQKPGKA PKLLIKYVSQSISGIPSRFSGSGLGTDFTLTISSVQPEDFATYYC QQSNSWPYTFGQGTKLEIK |
| 61 | VL (DNA) | Gacatccagctgacccagagccctagctctttaagcgctagcgtgggcgatagggtgactctga cttgtcgtgcgtcccaaagcattagcaacaatttacactggtaccagcagaagcccggaaaagcc cccaagctgctgatcaaatatgtgagccagagcatctccggcatcccctctcgttttctggtagcg gactgggcaccgactttactttaaccatcagcagcgtccagcccgaggacttcgccacatactact gccagcagagcaacagctggcccctatactttcggccaaggaacaaagctggagatcaag |
| 62 | CDRL1 IMGT (Prot) | QSISNN |
| 63 | CDRL1 Kabat (Prot) | RASQSISNNLH |
| 64 | CDRL1 Chothia (Prot) | RASQSISNNLH |
| 65 | CDRL2 IMGT (Prot) | YVS |
| 66 | CDRL2 Kabat (Prot) | YVSQSIS |
| 67 | CDRL2 Chothia (Prot) | YVSQSIS |
| 68 | CDRL3 IMGT (Prot) | QQSNSWPYT |
| 69 | CDRL3 Kabat (Prot) | QQSNSWPYT |
| 70 | CDRL3 Chothia (Prot) | QQSNSWPYT |
| 71 | ScFv | EVQLVESGGGLVQPGGSMRLSCAASGFTFSDYYMAWVRQAP GKGLEWVANINYDGTSTYYADSLKGRFTISRDSSKNTLYLQM NSLRAEDTAVYYCARALDGYYGYLDVWGQGTTVTVSSGSTS GSGKPGSGEGSTKGDIQLTQSPSSLSASVGDRVTLTCRASQSIS NNLHWYQQKPGKAPKLLIKYVSQSISGIPSRFSGSGLGTDFTL TISSVQPEDFATYYCQQSNSWPYTFGQGTKLEIK |
| 72 | ScFv | gaggtgcagctggtggagtccggaggaggtttagtccaacccggtggcagcatgaggctgtctt gtgctgcctccggcttcacttttttctgattactacatggcttgggtccgacaagctcccggaaaaggt ttagagtgggtggctaacatcaactacgacggcaccagcacctactatgccgacagcctcaagg gcagattcaccatctctcgtgattcgtctaaaaacactttatatttacaaatgaactctttaagagccga agataccgccgtgtactattgcgctcgtgccctcgacggctactacggatatttagacgtgtgggt caaggaacaaccgtgaccgtgtccagcggatcccctccggaagcggcaaaccggtagcgg cgaaggcagcaccaaaggagacatccagctgacccagagccctagctctttaagcgctagcgtg ggcgatagggtgactctgacttgtcgtgcgtcccaaagcattagcaacaatttacactggtaccag cagaagcccggaaaagcccccaagctgctgatcaaatatgtgagccagagcatctccggcatcc cctctcgttttctggtagcggactgggcaccgactttactttaaccatcagcagcgtccagcccga ggacttcgccacatactactgccagcagagcaacagctggcccctatactttcggccaaggaacaa agctggagatcaag |

TABLE 7

| | Exemplary Antibody Sequences 4 (Ab4) | |
|---|---|---|
| SEQ ID NO: | Description | Sequence |
| 73 | Heavy Chain Variable Domain | EVQLVESGGGLVQPGGSLRLSCAASGFTFSDYYMAWVRQAP GKGLEWVANINYDGSSTFYADSLKGRFTISRDNSKNTLYLQM NSLRAEDTAVYYCGRQVGYYDPMDYWGQGTTVTVSS |
| 74 | VH (DNA) | Gaggtgcagttggtggagagcggaggaggactggtgcagcccggtggctctttaagactcagc tgtgccgccagcggatttacattctccgactactacatggcttgggtccgacaagcccccgaaaa ggtttagagtgggtggccaacatcaactacgacggctcctccacattctacgccgactcttaaag ggtcgtttcaccatctctcgtgacaacagcaaaaatactttatatttacaaatgaactctttaagggcc gaggacaccgccgtgtactactgcggtcgtcaagttggctattacgacccatggactactgggg ccaaggaactaccgtgaccgtgagcagc |
| 75 | CDRH1 IMGT (Prot) | GFTFSDYY |
| 76 | CDRH1 Kabat (Prot) | DYYMA |
| 77 | CDRH1 Chothia (Prot) | GFTFSD |
| 78 | CDRH2 IMGT (Prot) | INYDGSST |
| 79 | CDRH2 Kabat (Prot) | NINYDGSSTFYADSLKG |
| 80 | CDRH2 Chothia (Prot) | NINYDGSSTFYADSLKG |
| 81 | CDRH3 IMGT (Prot) | GRQVGYYDPMDY |
| 82 | CDRH3 Kabat (Prot) | QVGYYDPMDY |
| 83 | CDRH3 Chothia (Prot) | QVGYYDPMDY |
| 84 | Light Chain Variable Domain | DIQLTQSPSSLSASVGDRVTITCRASSSVSHMYWYQQKPGKAP KPWIYRTSNLASGVPSRFSGSGSGTDYTLTISSMQPEDFATYY CQQYHSYPLTFGQGTKLEIK |
| 85 | VL (DNA) | Gacatccagctgacccagtcccccagctctttatccgctagcgtgggcgatagggtgaccatcac ttgtcgtgcgtcttcgtctgtgtctcatatgtactggtaccagcagaagcccggcaaggcccccaag ccttggatctatcgtacatccaatcttgcaagcggcgtcccttctcgttttctggttccgggtctggta ccgactacacttaaccatcagcagcatgcagcccgaggacttcgccacctactactgccagcag tatcactcctatcctttaactttttggccaaggaacaaagttggagatcaag |
| 86 | CDRL1 IMGT (Prot) | SSVSH |
| 87 | CDRL1 Kabat (Prot) | RASSSVSHMY |
| 88 | CDRL1 Chothia (Prot) | RASSSVSHMY |
| 89 | CDRL2 IMGT (Prot) | RTS |
| 90 | CDRL2 Kabat (Prot) | RTSNLAS |
| 91 | CDRL2 Chothia (Prot) | RTSNLAS |
| 92 | CDRL3 IMGT (Prot) | QQYHSYPLT |

TABLE 7-continued

Exemplary Antibody Sequences 4 (Ab4)

| SEQ ID NO: | Description | Sequence |
|---|---|---|
| 93 | CDRL3 Kabat (Prot) | QQYHSYPLT |
| 94 | CDRL3 Chothia (Prot) | QQYHSYPLT |
| 95 | ScFv | DIQLTQSPSSLSASVGDRVTITCRASSSVSHMYWYQQKPGKAP KPWIYRTSNLASGVPSRFSGSGSGTDYTLTISSMQPEDFATYY CQQYHSYPLTFGQGTKLEIKGSTSGSGKPGSGEGSTKGEVQL VESGGGLVQPGGSLRLSCAASGFTFSDYYMAWVRQAPGKGL EWVANINYDGSSTFYADSLKGRFTISRDNSKNTLYLQMNSLR AEDTAVYYCGRQVGYYDPMDYWGQGTTVTVSS |
| 96 | ScFv | Gacatccagctgacccagtcccccagctctttatccgctagcgtgggcgatagggtgaccatcac ttgtcgtgcgtcttcgtctgtgtctcatatgtactggtaccagcagaagcccggcaaggcccccaag ccttggatctatcgtacatccaatcttgcaagcggcgtcccttctcgttttctggttccgggtctggta ccgactacactttaaccatcagcagcatgcagcccgaggacttcgccacctactactgccagcag tatcactcctatcctttaacttttggccaaggaacaaagttggagatcaagggcagcacctccggta gcggaaagcccggtagcggcgagggcagcaccaagggagaggtgcagttggtggagagcgg aggaggactggtgcagcccgtggcctcttaagactcagctgtgccgccagcggatttacattctc cgactactacatggcttgggtccgacaagcccccggaaaaggtttagagtgggtggccaacatca actacgacggctcctccacattctacgccgactctttaaagggtcgtttcaccatctctcgtgacaac agcaaaaatactttatatttacaaatgaactctttaagggccgaggacaccgccgtgtactactgcg gtcgtcaagttggctattacgacccatggactactggggccaaggaactaccgtgaccgtgagc agc |

TABLE 8

Exemplary Antibody Sequences 5 (Ab5)

| SEQ ID NO: | Description | Sequence |
|---|---|---|
| 97 | Heavy Chain Variable Domain | EVQLVQSGAEVKKPGASVKISCKTSGYTFTEYTIHWVKQASG KGLEWIGNINPNNGGTTYNQKFEDRATLTVDKSTSTAYMELS SLRSEDTAVYYCAAGWNFDYWGQGTTVTVSS |
| 98 | VH (DNA) | Gaagttcaacttgtgcaaagcggggcagaagtgaaaaaacccggggcgagcgttaaaatatctt gtaaaacaagtggctacaccttcacggagtacaccatccactgggttaaacaagcttctggaaag ggacttgaatggatcgggaacataaacccaacaatgggggcactacttataatcaaaagtttgag gatcgggctaccctcacagtggataagtccacctccacagcttatatggaattgagtagccttagg agcgaggatacagccgtttattattgtgcggcgggctggaacttgactattggggcaagggac gacggtgacggtgtcctcc |
| 99 | CDRH1 IMGT (Prot) | GYTFTEYT |
| 100 | CDRH1 Kabat (Prot) | EYTIH |
| 101 | CDRH1 Chothia (Prot) | GYTFTE |
| 102 | CDRH2 IMGT (Prot) | INPNNGGT |
| 103 | CDRH2 Kabat (Prot) | NINPNNGGTTYNQKFED |
| 104 | CDRH2 Chothia (Prot) | NINPNNGGTTYNQKFED |
| 105 | CDRH3 IMGT (Prot) | AAGWNFDY |
| 106 | CDRH3 Kabat (Prot) | GWNFDY |

TABLE 8-continued

Exemplary Antibody Sequences 5 (Ab5)

| SEQ ID NO: | Description | Sequence |
|---|---|---|
| 107 | CDRH3 Chothia (Prot) | GWNFDY |
| 108 | Light Chain Variable Domain | DIVMTQSPSSLSASVGDRVTITCKASQDVGTAVDWYQQKPGK APKLLIYWASTRHTGVPDRFTGSGSGTDFTLTISSLQPEDFAD YFCQQYNSYPLTFGGGTKLEIK |
| 109 | VL (DNA) | Gacattgtgatgactcagtctccttcttctctttccgcttccgttggggaccgcgtcactataacttgta aagcgtcccaagatgtcggcaccgccgttgactggtaccagcaaaaacccgggaaagcgccga aactgctcatctactgggcttcaacccgccacacgggtgtcccggaccggtttacggggagcggt agtggaaccgatttcactctgaccattcctcccttcaaccggaagatttcgctgactactttgtcaa caatataattcatatcccctcactttcggagggggcacgaagttggaaataaag |
| 110 | CDRL1 IMGT (Prot) | QDVGTA |
| 111 | CDRL1 Kabat (Prot) | KASQDVGTAVD |
| 112 | CDRL1 Chothia (Prot) | KASQDVGTAVD |
| 113 | CDRL2 IMGT (Prot) | WAS |
| 114 | CDRL2 Kabat (Prot) | WASTRHT |
| 115 | CDRL2 Chothia (Prot) | WASTRHT |
| 116 | CDRL3 IMGT (Prot) | QQYNSYPLTF |
| 117 | CDRL3 Kabat (Prot) | QQYNSYPLT |
| 118 | CDRL3 Chothia (Prot) | QQYNSYPLT |
| 119 | ScFv | DIVMTQSPSSLSASVGDRVTITCKASQDVGTAVDWYQQKPGK APKLLIYWASTRHTGVPDRFTGSGSGTDFTLTISSLQPEDFAD YFCQQYNSYPLTFGGGTKLEIKGSTSGSGKPGSGEGSTKGEVQ LVQSGAEVKKPGASVKISCKTSGYTFTEYTIHWVKQASGKGL EWIGNINPNNGGTTYNQKFEDRATLTVDKSTSTAYMELSSLR SEDTAVYYCAAGWNFDYWGQGTTVTVSS |
| 120 | ScFv | Gacattgtgatgactcagtctccttcttctctttccgcttccgttggggaccgcgtcactataacttgta aagcgtcccaagatgtcggcaccgccgttgactggtaccagcaaaaacccgggaaagcgccga aactgctcatctactgggcttcaacccgccacacgggtgtcccggaccggtttacggggagcggt agtggaaccgatttcactctgaccattcctcccttcaaccggaagatttcgctgactactttgtcaa caatataattcatatcccctcactttcggagggggcacgaagttggaaataaagggtagcacctct ggtagcggcaagcctggctctggcgagggtagtaccaaaggagaagttcaacttgtgcaaagcg gggcagaagtgaaaaaacccggggcgagcgttaaaatatcttgtaaaacaagtggctacaccttc acggagtacaccatccactgggttaaacaagcttctggaaagggacttgaatggatcgggaacat aaacccaacaatgggggcactacttataatcaaaagtttgaggatcgggctaccctcacagtgg ataagtccacctccacagcttatatggaattgagtagccttaggagcgaggatacagccgtttattat tgtgcggcgggctggaactttgactattggggcaagggacgacggtgacggtgtcctcc |

Chimeric antigen receptors (CARs) are engineered receptors that may direct or redirect T cells or NK cells (e.g., patient or donor T or NK cells) to target a selected antigen. A CAR may be engineered to recognize an antigen and, when bound to that antigen, activate the immune cell to attack and destroy the cell bearing that antigen. When these antigens exist on tumor cells, an immune cell that expresses the CAR may target and kill the tumor cell. CARs generally comprise an extracellular binding motif that mediates antigen binding (e.g., an anti-PSMA binding domain), a transmembrane domain that spans, or is understood to span, the cell membrane when the CAR is present at a cell surface or cell membrane, and an intracellular (or cytoplasmic) signaling domain.

According to at least one non-limiting view, there have been at least three "generations" of CAR compositions. In a first generation of CARs, a binding motif (e.g., a single chain fragment variable, binding motif) is linked or connected to a signaling domain (e.g., CD3ζ) via a transmembrane domain, optionally comprising a hinge domain and one or more spacers. In a second generation of CARs, a costimulatory domain (CM1, such as CD28, 4-1BB, or OX-40) is introduced with the signaling domain (e.g., CD3ζ). In a third generation of CARs, a second costimulatory domain (CM2) is comprised.

TCRs are heterodimers composed of an α-chain and a β-chain. TCR signaling requires recruitment of signaling proteins that generate an immune synapse. In addition, TCR localization at the plasma membrane depends on CD3 complex, which is expressed in T cells. Engineered single chain TCRs may be generated, e.g., using transmembrane and signaling domains of CAR constructs, methods and constructs for which are known (e.g., sTCR and TCR-CAR molecules, e.g., fusion of a TCRβ chain with CD28 TM and CD28 and CD3ζ signaling modules). An anti-PSMA binding system of the present disclosure may comprise one or more antigen binding motifs that bind PSMA. In some embodiments, an antigen binding system further comprises a costimulatory domain, and/or an extracellular domain (e.g., a "hinge" or "spacer" region), and/or a transmembrane domain, and/or an intracellular (signaling) domain, and/or a CD3-zeta or CD3-epsilon activation domain. In some embodiments, an anti-PSMA binding system of the present disclosure comprises at least a binding motif that binds human PSMA, a costimulatory domain, an extracellular domain, a transmembrane domain, and a CD3-zeta or CD3-epsilon activating domain.

In some embodiments, an anti-PSMA CAR of the present disclosure may comprise an antigen binding system that comprises one or more, or all, of a leader peptide (P), an anti-PSMA binding domain (B), a costimulatory protein's extracellular domain (E), a transmembrane domain (T), a costimulatory domain (C), a second costimulatory domain (C'), and an activation domain (A). In some instances, an anti-PSMA CAR is configured according to the following: B E T A. In some instances, an anti-PSMA CAR is configured according to the following: P B E T A. In some instances, an anti-PSMA CAR is configured according to the following: B E T C A. In some instances, an anti-PSMA CAR is configured according to the following: P B E T C A. In some instances, an anti-PSMA CAR is configured according to the following: B E T C C' A. In some instances, an anti-PSMA CAR is configured according to the following: P B E T C C' A. In some embodiments, the an anti-PSMA CAR comprises a VH and a VL, optionally wherein the CAR is configured according to the following: P-VH-VL-E-T-C-A or P-VL-VH-E-T-C-A. In some embodiments, the VH and the VL are connected by a linker (L), optionally wherein the CAR is configured according to the following, from N-terminus to C-terminus: P-VH-L-VL-E-T-C-A or P-VH-L-VL-E-T-C-A.

One or more antigen binding motifs determine the target(s) of an antigen binding system. A binding motif of an antigen binding system may comprise any an anti-PSMA binding domain, e.g., an antibody provided by the present disclosure, e.g., a binding motif of the present disclosure. Binding domain are used in chimeric antigen receptors at least in part because they may be engineered to be expressed as part of a single chain along with the other CAR components. See, for example, U.S. Pat. Nos. 7,741,465, and 6,319,494 as well as Eshhar et al., Cancer Immunol Immunotherapy (1997) 45: 131-136, Krause et al., J. Exp. Med., Volume 188, No. 4, 1998 (619-626); Finney et al., Journal of Immunology, 1998, 161: 2791-2797, each of which is incorporated herein by reference with respect to binding domains in CARs. A binding domain or scFv, is a single chain antigen binding fragment comprising a heavy chain variable domain and a light chain variable domain, which heavy chain variable domain and light chain variable domain are linked or connected together. See, for example, U.S. Pat. Nos. 7,741,465, and 6,319,494 as well as Eshhar et al., Cancer Immunol Immunotherapy (1997) 45: 131-136, each of which is incorporated herein by reference with respect to binding motif domains. When derived from a parent antibody, a binding motif may retain some of, retain all of, or essentially retain the parent antibody's binding of a target antigen. In some embodiments, a CAR contemplated herein comprises antigen-specific binding domain that may be a scFv (a murine, human or humanized scFv) that binds an antigen expressed on a cancer cell. In a certain embodiment, the scFv binds PSMA.

In certain embodiments, the CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers $(G_{1-5}S_{1-5})n$ (SEQ ID NO: 257), where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, *Rev. Computational Chem.* 11173-142 (1992)). Other linkers contemplated herein include Whitlow linkers (see Whitlow, *Protein Eng.* 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker. In another embodiment, any of the constructs described herein comprise a "GSG" linker. In an example a glycine-serine linker comprises or consists of the amino acid sequence GS (SEQ ID NO: 121), which may be encoded by the nucleic acid sequence according to ggatcc (SEQ ID NO: 122) or gggtcc (SEQ ID NO: 123). In an example a glycine-serine linker comprises or consists of the amino acid sequence GGGSGGGS (SEQ ID NO: 124), which may be encoded by the nucleic acid sequence according to ggcggtggaagcggaggaggttcc (SEQ ID NO: 125). In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 126 (GST-SGSGKPGSGEGSTKG (SEQ ID NO: 126). In an embodiment, a linker is encoded by a nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid sequence according to ggctccacctccggaagcggcaaacccggtagcggcgagggctccacaaagggc (SEQ ID NO: 127)

In embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

In some embodiments, an Antigen binding system of the present disclosure may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof.

A hinge may be derived from a natural source or from a synthetic source. Hinge domains suitable for use in the CARs described herein include the hinge region derived from the extracellular regions of type 1 membrane proteins such as CD8a, CD4, CD28 and CD7, which may be wild-type hinge regions from these molecules or may be altered, for example a truncated CD28 hinge domain. A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8a, CD8p, CD 11a (ITGAL), CD 11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge. In embodiments, the hinge domain comprises a CD8a hinge region. In embodiments the CARs described herein comprise a hinge domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 129 (TTTPAPRPPTPAPTIASQPLSLRPEACRPAAGGAVHTRGLDFACD (SEQ ID NO: 129)). In embodiments, hinge domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to accacgacgccagcgccgcgaccaccaacaccggcgcccaccatcgcgtcgcaacccctgtccctgcgccccgaggcgtgccggcc agcggcggggggcgcagtgcacacgagggggctggacttcgcctgtgat (SEQ ID NO: 130).

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort (PSORT.org) and Prosite (prosite.expasy.org) are exemplary of such programs.

The type of transmembrane domain comprised in an antigen binding system described herein is not limited to any type. In some embodiments, a transmembrane domain is selected that is naturally associated with a binding motif and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRTAM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet. In embodiments the CARs described herein comprise a TM domain from CD8α having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 131 (IYIWAPLAGTCGVLLLSLVITLYC (SEQ ID NO: 131)). In embodiments, TM domain from CD8a is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to atctacatctgggcgcccttggccgggacttgtggggtccttctcctgtcactggttat-caccctttattgc (SEQ ID NO: 132).

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%/a, 85-95%, 85-100%, 90-95%, 90-100%, or 95-100%) identical to a nucleotide sequence known. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a polypeptide sequence known. Optionally, short spacers may form linkages between any or some of the extracellular, transmembrane, and intracellular domains of the CAR.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100

(SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

Illustrative examples of ITAM containing primary signaling domains that are useful in the present disclosure include those derived from TCRζ, FcRγ, FcRβ, DAP12, CD3γ, CD3δ, CD3ε, CD3ζ, CD22, CD79a, CD79b, and CD66d. In some embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain. In one embodiment, the CARs have a CD3ζ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 133. LRVKFSRSADAPAYQQGQNQLYNELNL-GRREEYDVLDKRRGRDPEMGGKPRRKNPQE GLY-NELQKDKMAEAYSEIGMKGERRRGKGHDGLYQGL-STATKDTYDALHMQALPPR (SEQ ID NO: 133). In embodiments, a CD3ζ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according (SEQ ID NO: 134)
ttgagagtgaagttcagcaggagcgcagacgcccccgcctatcagcaaggc cagaaccagctctataacgagctcaatttagggcgaagagaggagtacgat gttttggacaagaggcgtggccgggaccccgaaatgggggaaagccgaga aggaagaaccctcaggaaggcttgtacaatgaattgcagaaggataagatg gcggaggcatacagtgagattgggatgaaaggcgagcgccggaggggcaag gggcacgatggcctttatcagggtctcagtacagccaccaaggacacctac gacgccttcacatgcaagccctgcccctcgc.

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. In some embodiments, costimulatory molecules may include CD27, CD28, CD137 (4-IBB), OX40 (CD134), CD30, CD40, PD-I, ICOS (CD278), CTLA4, LFA-1, CD2, CD7, LIGHT, TRIM, LCK3, SLAM, DAPIO, LAG3, HVEM, and NKD2C, and CD83. In embodiments, the CARs described herein comprise a 4-IBB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 135. KRGRKKLLY-IFKQPFMRPVQTTQEEDGCSCRFPEEEEGGCE (SEQ ID NO: 135). In embodiments, a 4-IBB costimulatory domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to, which may be encoded by the nucleic acid sequence according to (SEQ ID NO: 136)
aaacggggcagaaagaaactcctgtatatattcaaacaaccatttatgaga ccagtacaaactactcaagaggaagatggctgtagctgccgatttccagaa gaagaagaaggaggatgtgaa.

The engineered CARs described herein may also comprise an N-terminal signal peptide or tag at the N-terminus of the scFv or antigen binding domain. In one embodiment, a heterologous signal peptide may be used. The antigen binding domain or scFV may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly any known tag sequence known in the art may also be used. In one embodiment a signal sequence is a CSF2RA signal sequence. In embodiments, the CARs described herein comprise a CSF2RA signal sequence having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 137;

(SEQ ID NO: 137)
MLLLVTSLLLCELPHPAFLLIP

SEQ ID
(SEQ ID NO: 138)
MEWTWVFLFLLSVTAGVHS, (SEQ ID NO: 139)
MALPVTALLLPLALLLHAARP.

Components of a CAR may be exchanged or "swapped" using routine techniques of biotechnology for equivalent components. To provide just a few non-limiting and partial examples, a CAR of the present disclosure may comprise a binding motif as provided herein in combination with a hinge provided herein and a costimulatory domain provided herein. In certain examples, a CAR of the present disclosure may comprise a leader sequence as provided herein together with a binding motif as provided herein in combination with a hinge provided herein and s costimulatory domain provided herein.

The present disclosure comprises conjugates in which an antibody of the present disclosure is associated with a therapeutic agent or a detectable moiety. In various embodiments, the therapeutic agent is an anti-cancer agent as provided herein. In certain embodiments, provided conjugate comprises one or more detectable moieties, i.e., is "labeled" with one or more such moieties. In some such embodiments, a conjugate of the present disclosure is useful in diagnostic or imaging applications, e.g., diagnosing or imaging cancer. Any of a wide variety of detectable moieties may be used in labeled antibody conjugates described herein. Suitable detectable moieties comprise, without limitation: various ligands, radionuclides; fluorescent dyes; chemiluminescent agents (such as, for example, acridinium esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; digoxigenin; haptens; and proteins for which antisera or monoclonal antibodies are available.

The present disclosure comprises nucleic acids encoding anti-PSMA binding domains provided herein. The present disclosure comprises nucleic acids encoding antibodies of the provided herein, comprising, without limitation, nucleic acids encoding anti-PSMA binding domains. The present disclosure comprises nucleic acids encoding antigen binding systems provided herein, comprising without limitation nucleic acids encoding anti-PSMA chimeric antigen receptors. The nucleic acid sequence of SEQ ID NO: 2 comprises and provides exemplary nucleic acid sequences corresponding to and encoding each of SEQ ID NOs: 1 and 3-11. The nucleic acid sequence of SEQ ID NO: 13 comprises and provides exemplary nucleic acid sequences corresponding to and encoding each of SEQ ID NOs: 12 and 14-22. The nucleic acid sequence of SEQ ID NO: 24 comprises and provides exemplary nucleic acid sequence corresponding to and encoding SEQ ID NOs: 23.

The nucleic acid sequence of SEQ ID NO: 26 comprises and provides exemplary nucleic acid sequences corresponding to and encoding each of SEQ ID NOs: 25 and 27-35. The nucleic acid sequence of SEQ ID NO: 37 comprises and provides exemplary nucleic acid sequences corresponding to and encoding each of SEQ ID NOs: 36 and 38-46. The nucleic acid sequence of SEQ ID NO: 48 comprises and provides an exemplary nucleic acid sequence corresponding to and encoding SEQ ID NOs: 47.

The nucleic acid sequence of SEQ ID NO: 50 comprises and provides exemplary nucleic acid sequences corresponding to and encoding each of SEQ ID NOs: 49 and 51-59. The nucleic acid sequence of SEQ ID NO: 61 comprises and provides exemplary nucleic acid sequences corresponding to and encoding each of SEQ ID NOs: 60 and 62-70. The nucleic acid sequence of SEQ ID NO: 72 comprises and provides an exemplary nucleic acid sequence corresponding to and encoding SEQ ID NOs: 71.

The nucleic acid sequence of SEQ ID NO: 74 comprises and provides exemplary nucleic acid sequences corresponding to and encoding each of SEQ ID NOs: 73 and 75-83. The nucleic acid sequence of SEQ ID NO: 85 comprises and provides exemplary nucleic acid sequences corresponding to and encoding each of SEQ ID NOs: 84 and 86-94. The nucleic acid sequence of SEQ ID NO: 76 comprises and provides an exemplary nucleic acid sequence corresponding to and encoding SEQ ID NOs: 95.

The nucleic acid sequence of SEQ ID NO: 98 comprises and provides exemplary nucleic acid sequences corresponding to and encoding each of SEQ ID NOs: 97 and 99-101. The nucleic acid sequence of SEQ ID NO: 109 comprises and provides exemplary nucleic acid sequences corresponding to and encoding each of SEQ ID NOs: 108 and 110-118. The nucleic acid sequence of SEQ ID NO: 108 comprises and provides an exemplary nucleic acid sequence corresponding to and encoding SEQ ID NOs: 107.

In one embodiment described herein, an anti-PSMA CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 140. DIQLTQSPSSLSASVGDRVTIT-CRASSSVSHIYWYQQKPGKAPKPWIYRTSN-LASGVPSR FSGSGSGTDYTLTISSLQPEDFA-TYYCQQYHTYPPTFGQGTKLEIKGSTSGSGKPGSGEG STKGEVQLVESGGGLVQPGGSMRLSCAASGFTFSDY-YMAWVRQAPGKGLEWIANINY DGSNTYYAD-SLKGRFTISRDNSKNTLYLQMNSLRAEDTAVYYCAR-NWDGYYGYFDV WGQGTTVTVSSGSTTTPAPRPPT-PAPTIASQPLSLRPEACRPAAGGAVHTRGLDFACDIY IWAPLAGTCGVLLLSLVITLYCKRGRKKLLYIFKQPF-MRPVQTTQEEDGCSCRFPEEEEG GCELRVKFSRS-ADAPAYQQGQNQLYNELNLGRREEYDVLDKRR-GRDPEMGGKPRRKN PQEGLYNELQKDKMAEAYSEI-GMKGERRRGKGHDGLYQGLSTATKDTYDALHMQAL PPR (SEQ ID NO: 140). In embodiments an anti-PSMA CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 141)
```
gatatccagctgacccagtcccttcctctctgtctgcgtctgttggcgat
cgtgtcaccatcacttgtcgtgccagcagcagcgtgagccacatttattgg
taccaacaaaagcccggcaaagcccctaagccttggatctacagaacctcc
aatctggccagcggcgtgcccagcagattcagcggaagcggatccggcacc
gactacactttaaccatcagctctttacagcccgaggacttcgccacatac
tactgccagcagtaccacacctatcccccacattcggccaaggaacaaag
ctggagattaagggctccacctccggaagcggcaaacccggtagcggcgag
ggctccacaaagggcgaggtgcaacttgtggagagcggaggaggtttagtg
caacccggaggcagcatgagactgagctgcgccgccagcggcttcacattc
tccgactactacatggcttgggtccgacaagctcccggaaaaggactggag
tggatcgccaacatcaactacgacggctccaacacctactacgccgactct
ttaaagggtcgtttcacaatctctcgtgacaacagcaagaacactttatat
ttacaaatgaactctttaagggccgaggataccgccgtgtactactgcgct
cgtaactgggacggctactacggctacttcgacgtgtggggccaaggaacc
accgtgaccgtgagcagcgggtccaccacgacgccagcgccgcgaccacca
acaccggcgccaccatcgcgtcgcaaccctgtccctgcgccccgaggcg
tgccggccagcggcgggggcgcagtgcacacgaggggctggacttcgcc
tgtgatatctacatctgggcgccttggccgggacttgtggggtccttctc
ctgtcactggttatcacccttttattgcaaacggggcagaaagaaactcctg
tatatattcaaacaaccatttatgagaccagtacaaactactcaagaggaa
gatggctgtagctgccgatttccagaagaagaagaaggaggatgtgaattg
agagtgaagttcagcaggagcgcagacgccccgcctatcagcaaggccag
aaccagctctataacgagctcaatttagggcgaagagaggagtacgatgtt
ttggacaagaggcgtggccgggaccccgaaatggggggaaagccgagaagg
aagaaccctcaggaaggcttgtacaatgaattgcagaaggataagatggcg
gaggcatacagtgagattgggatgaaaggcgagcgccggaggggcaagggg
cacgatggcctttatcagggtctcagtacagccaccaaggacacctacgac
gcccttcacatgcaagccctgccccctcgc.
```

In one embodiment described herein, an anti-PSMA CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 142. DIQMTQSPSSLSASVGDRVTVT-CRASQNVNTNVAWYQQKPGKAPKVLIYSASYRN-SGV PSRFSGSGSGTDFTLTISSVQPEDFATYYCQQYN-SYPFTFGQGTKLEIKGSTSGSGKPGSG EGSTKGQVQ-LVQSGAEVKKPGASVKLSCKASGYTFTTYW-MHWVRQAPGQGLEWIGM IHPNSGSTNYAQKFQG-RATLTVDTSTSTAYMELSSLRSEDTAVYYCARD-PYDYGEDFD VWGQGTTVTVSSGSTTTPAPRPPTPAP-TIASQPLSLRPEACRPAAGGAVHTRGLDFACDI YIWAPLAGTCGVLLLSLVITLYCKRGRKKLLY-IFKQPFMRPVQTTQEEDGCSCRFPEEEE GGCELR-VKFSRSADAPAYQQGQNQLYNELNLGRREEY-DVLDKRRGRDPEMGGKPRRK NPQEGLYNELQKDK-MAEAYSEIGMKGERRRGKGHDGLYQGLSTATKDTY-DALHMQA LPPR (SEQ ID NO: 142). In embodiments an anti-PSMA CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 143)
```
gacatccagatgacccagagccccagctctttaagtgccagcgtgggcgac
agagtgacagtgacttgtcgtgccagccagaacgtgaataccaacgtggct
tggtaccagcagaagcccggcaaagcccctaaggtgctgatctattccgcg
tcttatcgtaactccggcgtgccttcgcgttttctgggtctggtagcggc
accgacttcacttaacaatcagcagcgttcagcccgaagacttcgccacc
tactactgccagcagtacaacagctatccctttactttcggtcaagggacc
aagctcgagatcaaaggctccaccagcggtagcggcaaacccggttccggc
gagggctctaccaagggccaagtgcagctggtgcagtccggcgccgaggtg
aagaagcccggtgcttccgtgaagctgtcttgcaaagccagcggctacacc
ttcaccacctattggatgcactgggtccgacaagctcccggtcaaggtctg
gagtggattggcatgatccaccccaactccggctccaccaactacgcccag
aagttccaaggtcgtgccactttaacagtggataccagcaccagcaccgcc
tacatggagctgagtagtttgaggagcgaggacaccgccgtgtactattgc
gctcgtgaccctacgactacggcgaggacttcgacgtgtggggccaagga
acaacagtgaccgtgagcagcgggtccaccacgacgccagcgccgcgacca
ccaacaccggcgccaccatcgcgtcgcaaccctgtccctgcgccccgag
gcgtgccggccagcggcgggggcgcagtgcacacgaggggctggacttc
gcctgtgatatctacatctgggcgccttggccgggacttgtggggtccttt
ctcctgtcactggttatcacccttttattgcaaacggggcagaaagaaactc
ctgtatatattcaaacaaccatttatgagaccagtacaaactactcaagag
gaagatggctgtagctgccgatttccagaagaagaagaaggaggatgtgaa
ttgagagtgaagttcagcaggagcgcagacgccccgcctatcagcaaggc
cagaaccagctctataacgagctcaatttagggcgaagagaggagtacgat
gttttggacaagaggcgtggccgggaccccgaaatggggggaaagccgaga
aggaagaaccctcaggaaggcttgtacaatgaattgcagaaggataagatg
gcggaggcatacagtgagattgggatgaaaggcgagcgccggaggggcaag
gggcacgatggcctttatcagggtctcagtacagccaccaaggacacctac
gacgcccttcacatgcaagccctgccccctcgc.
```

In one embodiment described herein, an anti-PSMA CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 144. EVQLVESGGGLVQPGGSMRLS-CAASGFTFSDYYMAWVRQAPGKGLEWVANINY-DGTS TYYADSLKGRFTISRDSSKNTLYLQMNSLRAE-DTAVYYCARALDGYYGYLDVWGQGT TVTVSSG-STSGSGKPGSGEGSTKGDIQLTQSPSSLSASVGDRV- TLTCRASQSISNNLHWY QQKPGKAPKLLIKYVSQ-SISGIPSRFSGSGLGTDFTLTISSVQPEDFATYYCQQSN-SWPYT FGQGTKLEIKGSTTTPAPRPPTPAPTIA-SQPLSLRPEACRPAAGGAVHTRGLDFACDIYIW APLAGTCGVLLLSLVITLYCKRGRKKLLYIFKQPF-MRPVQTTQEEDGCSCRFPEEEEGGC ELRVKFSRS-ADAPAYQQGQNQLYNELNLGRREEYDVLDKRR-GRDPEMGGKPRRKNPQ EGLYNELQKDKMAEAYSEI-GMKGERRRGKGHDGLYQGLSTATKDTYDALHMQALPP R (SEQ ID NO: 144). In embodiments an anti-PSMA CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 145)
gaggtgcagctggtggagtccggaggaggtttagtccaacccggtggcagc atgaggctgtcttgtgctgcctccggcttcacttttctgattactacatg gcttgggtccgacaagctcccggaaaaggtttagagtgggtggctaacatc aactacgacggcaccagcacctactatgccgacagcctcaagggcagattc accatctctcgtgattcgtctaaaaacactttatatttacaaatgaactct ttaagagccgaagataccgccgtgtactattgcgctcgtgccctcgacggc tactacggatatttagacgtgtggggtcaaggaacaaccgtgaccgtgtcc agcggatccacctccggaagcggcaaacccggtagcggcgaaggcagcacc aaaggagacatccagctgacccagagccctagctctttaagcgctagcgtg ggcgatagggtgactctgacttgtcgtgcgtcccaaagcattagcaacaat ttacactggtaccagcagaagcccggaaaagcccccaagctgctgatcaaa tatgtgagccagagcatctccggcatcccctctcgtttttctggtagcgga ctgggcaccgactttactttaaccatcagcagcgtccagcccgaggacttc gccacatactactgccagcagagcaacagctggccctatactttcggccaa ggaacaaagctggagatcaaggggtccaccacgacgccagcgccgcgacca ccaacaccggcgcccaccatcgcgtcgcaacccctgtccctgcgccccgag gcgtgccggccagcggcgggggcgcagtgcacacgaggggctggacttc gcctgtgatatctacatctgggcgccttggccgggacttgtggggtcctt ctcctgtcactggttatcaccctttattgcaaacggggcagaaagaaactc ctgtatatattcaaacaaccatttatgagaccagtacaaactactcaagag gaagatggctgtagctgccgatttccagaagaagaagaaggaggatgtgaa ttgagagtgaagttcagcaggagcgcagacgcccccgcctatcagcaaggc cagaaccagctctataacgagctcaatttagggcgaagagaggagtacgat gttttggacaagaggcgtggccgggaccccgaaatggggggaaagccgaga aggaagaaccctcaggaaggcttgtacaatgaattgcagaaggataagatg gcggaggcatacagtgagattgggatgaaaggcgagcgccgggagggcaag gggcacgatggcctttatcagggtctcagtacagccaccaaggacacctac gacgcccttcacatgcaagccctgccccctcgc.

In one embodiment described herein, an anti-PSMA CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 146. DIVMTQSPSSLSASVGDRVTITCK-ASQDVGTAVDWYQQKPGKAPKLLIYWASTRHTGV PDRFTGSGSGTDFTLTISSLQPEDFADYFCQQYNSY-PLTFGGGTKLEIKGSTSGSGKPGSG EGSTK-GEVQLVQSGAEVKKPGASVKISCKTSGYTFT-EYTIHWVKQASGKGLEWIGNINP NNGGTTYNQKFE-DRATLTVDKSTSTAYMELSSLRSEDTAVYYCAAG-WNFDYWGQGTT VTVSSGSTTTPAPRPPTPAPTIA-SQPLSLRPEACRPAAGGAVHTRGLDFACDIYIWAPL-AG TCGVLLLSLVITLYCKRGRKKLLYIFKQPFMR-PVQTTQEEDGCSCRFPEEEEGGCELRVK FSRSADA-PAYQQGQNQLYNELNLGRREEYDVLDKRRGRDP-EMGGKPRRKNPQEGLYN ELQKDKMAEAYSEI-GMKGERRRGKGHDGLYQGLSTATKDTYDALHMQ-ALPPR (SEQ ID NO: 146). In embodiments an anti-PSMA CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 147)
gacattgtgatgactcagtctccttcttctctttccgcttccgttggggac cgcgtcactataacttgtaaagcgtcccaagatgtcggcaccgccgttgac tggtaccagcaaaaacccgggaaagcgccgaaactgctcatctactgggct tcaacccgccacacgggtgtcccggaccggtttacggggagcggtagtgga accgatttcactctgaccattcctcccttcaaccggaagatttcgctgac tactttgtcaacaatataattcatatcccctcactttcggagggggcacg aagttggaaataaagggtagcacctctggtagcggcaagcctggctctggc gagggtagtaccaaaggagaagttcaacttgtgcaaagcggggcagaagtg aaaaaacccggggcgagcgttaaaatatcttgtaaaacaagtggctacacc ttcacggagtacaccatccactgggttaaacaagcttctggaaagggactt gaatggatcgggaacataaacccaacaatgggggcactacttataatcaa aagtttgaggatcgggctaccctcacagtggataagtccacctccacagct tatatggaattgagtagccttaggagcgaggatacagccgtttattattgt gcggcgggctggaactttgactattggggcaagggacgacggtgacggtg tcctccgggtccaccacgacgccagcgccgcgaccaccaacaccggcgccc accatcgcgtcgcaacccctgtccctgcgccccgaggcgtgccggccagcg gcgggggcgcagtgcacacgaggggctggacttcgcctgtgatatctac atctgggcgcccttggccgggacttgtggggtccttctcctgtcactggtt atcaccctttattgcaaacggggcagaaagaaactcctgtatatattcaaa caaccatttatgagaccagtacaaactactcaagaggaagatggctgtagc tgccgatttccagaagaagaagaaggaggatgtgaattgagagtgaagttc agcaggagcgcagacgcccccgcctatcagcaaggccagaaccagctctat aacgagctcaatttagggcgaagagaggagtacgatgttttggacaagagg cgtggccgggaccccgaaatggggggaaagccgagaaggaagaacccctcag gaaggcttgtacaatgaattgcagaaggataagatggcggaggcatacagt -continued gagattgggatgaaaggcgagcgccggaggggcaaggggcacgatggcctt tatcagggtctcagtacagccaccaaggacacctacgacgcccttcacatg caagccctgcccctcgc.

In one embodiment described herein, an anti-PSMA CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 148. DIQLTQSPSSLSASVGDRVTITCRASSSVS-HMYWYQQKPGKAPKPWIYRTSNLASGVPS RFSGS-GSGTDYTLTISSMQPEDFATYYCQQYHSYPLTFGQ-GTKLEIKGSTSGSGKPGSGE GSTKGEVQLVESGG-GLVQPGGSLRLSCAASGFTFSDYYMAWVRQAPGK-GLEWVANIN YDGSSTFYADSLKGRFTISRDNSKNT-LYLQMNSLRAEDTAVYYCGRQVGYYDPMDYW GQGTTVTVSSGSTTTPAPRPPTPAPTIASQPLSLRPE-ACRPAAGGAVHTRGLDFACDIYI WAPLAGTCG-VLLLSLVITLYCKRGRKKLLYIFKQPFMRPVQT-TQEEDGCSCRFPEEEEG GCELRVKFSRSADAPA-YQQGQNQLYNELNLGRREEYDVLDKRRGRDPEMG-GKPRRKN PQEGLYNELQKDKMAEAYSEIGMKGER-RRGKGHDGLYQGLSTATKDTYDALHMQAL PPR (SEQ ID NO: 148). In embodiments an anti-PSMA CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 149)
gacatccagctgacccagtcccccagctctttatccgctagcgtgggcgat agggtgaccatcacttgtcgtgcgtcttcgtctgtgtctcatatgtactgg taccagcagaagcccggcaaggcccccaagccttggatctatcgtacatcc aatcttgcaagcggcgtcccttctcgtttttctggttccgggtctggtacc gactacacttaaccatcagcagcatgcagcccgaggacttcgccacctac tactgccagcagtatcactcctatcctttaacttttggccaaggaacaaag ttggagatcaagggcagcacctccggtagcggaaagcccggtagcggcgag ggcagcaccaagggagaggtgcagttggtggagagcggaggaggactggtg cagcccggtggctctttaagactcagctgtgccgccagcggatttacattc tccgactactacatggcttgggtccgacaagcccccggaaaaggtttagag tgggtggccaacatcaactacgacggctcctccacattctacgccgactct ttaaagggtcgtttcaccatctctcgtgacaacagcaaaaatactttatat ttacaaatgaactctttaagggccgaggacaccgccgtgtactactgcggt cgtcaagttggctattacgacccatggactactggggccaaggaactacc gtgaccgtgagcagcgggtccaccacgacgccagcgccgcgaccaccaaca ccggcgcccaccatcgcgtcgcaaccctgtccctgcgccccgaggcgtgc cggccagcggcggggggcgcagtgcacacgaggggggctggacttcgcctgt gatatctacatctgggcgcccttggccgggacttgtggggtccttctcctg tcactggttatcacccttttattgcaaacggggcagaaagaaactcctgtat atattcaaacaaccatttatgagaccagtacaaactactcaagaggaagat ggctgtagctgccgatttccagaagaagaagaaggaggatgtgaattgaga gtgaagttcagcaggagcgcagacgcccccgcctatcagcaaggccagaac cagctctataacgagctcaatttagggcgaagagaggagtacgatgttttg gacaagaggcgtggccgggaccccgaaatgggggaaagccgagaaggaag aaccctcaggaaggcttgtacaatgaattgcagaaggataagatggcggag gcatacagtgagattgggatgaaaggcgagcgccggaggggcaaggggcac gatggcctttatcagggtctcagtacagccaccaaggacacctacgacgcc cttcacatgcaagccctgcccctcgc.

Notch receptors are single pass transmembrane proteins that mediate cell-cell contact signaling and play a central role in development and other aspects of cell-to-cell communication between two contacting cells, in which one contacting cell has the Notch receptor, and the other contacting cell is a cell that exhibits a ligand on its surface which binds to the corresponding Notch receptor. The engagement of native Notch and Delta, it's native ligand, leads to two-step proteolysis of the Notch receptor that ultimately causes the release of the intracellular portion of the receptor from the membrane into the cytoplasm, where it moves to the nucleus. There the released domain alters cell behavior by functioning as a transcriptional regulator. Notch receptors are involved in and are required for a variety of cellular functions during development and are critical for the function of numerous cell-types across species.

Synthetic Notch receptors (synNotch receptors) disclosed herein can display one or more different binding moieties on the cell surface, for example, scFVs, nanobodies, single chain T-cell receptors, to name a few, that recognize a prostate specific cancer antigen (PSCA) causing the release of the intracellular, transcriptional regulatory portion of the receptor from the membrane into the cytoplasm resulting in transcriptional regulation. Engineered cells bearing synNotch receptors that encounter their specific target antigen (PSCA) will then be cleaved such that their cytosolic or intercellular fragment is free to translocate into the cell nucleus to regulate the transcription of any open reading frame (ORF) under the control of a synthetic promoter, for example a GAL4 promoter. As disclosed herein the ORF expressed is an anti-PSMA chimeric antigen T-cell receptor (CAR-T) that targets a separate, distinct target antigen (PSMA) for target cell killing, only after the priming target antigen (prostate specific cancer antigen (PSCA) in the synNotch receptors disclosed herein) detected by the synNotch receptor has been detected. This enables highly-specific combinatorial antigen pattern recognition to allow greater discrimination between diseased or cancerous cells and healthy cells. This could greatly enable the application of engineered CAR-T cells to safely target tumors with less side-effects on healthy tissue.

SynNotch receptor polypeptides of the present disclosure comprise: a) an extracellular anti-PSCA binding domain; b) a Notch receptor core polypeptide, where the Notch receptor polypeptide has a length of from 50 amino acids to 1000 amino acids, and comprises one or more ligand-inducible (PSCA binding) proteolytic cleavage sites; and c) an intracellular domain. Binding of the anti-PSCA binding domain to PSCA, for example on the surface of a prostate cancer cell, induces cleavage of the Notch receptor core polypeptide at the one or more ligand-inducible proteolytic cleavage sites, thereby releasing the intracellular domain. Release of the intracellular domain induces the expression of an anti-PSMA CAR in a cell that produces the anti-PSCA synNotch receptor polypeptide. The extracellular domain comprises an amino acid sequence that is heterologous to the Notch core receptor polypeptide. The intracellular domain comprises an amino acid sequence that is heterologous to the Notch core receptor polypeptide.

A synNotch receptor polypeptide of the present disclosure comprises an extracellular domain that includes an antigen binding domain that specifically binds prostate specific cancer antigen (PSCA), i.e. an anti-PSCA binding domain. In embodiments the anti-PSCA binding may comprise antigen-binding sequences as found in an antibody described herein. In some instances, an anti-PSCA binding domain comprises an antigen binding fragment described herein, such as an scFv. Unless otherwise indicated, it is to be appreciated the references to PSCA in the present disclosure relate to human PSCA. In various embodiments, an anti-PSCA binding motif comprises at least one heavy chain CDR (HCDR) provided herein, e.g., at least one HCDR disclosed in Table 9. In various embodiments, an anti-PSCA binding domain comprises two HCDRs provided herein, e.g., at least two HCDRs disclosed in Table 9. In various embodiments, an anti-PSCA binding domain comprises three HCDRs provided herein, e.g., three HCDRs disclosed in Table 9. In various embodiments, an anti-PSCA binding domain comprises at least one light chain CDR (LCDR) provided herein, e.g., at least one LCDR disclosed in Table 9. In various embodiments, an anti-PSCA binding domain comprises two LCDRs provided herein, e.g., at least two LCDRs disclosed in Table 9. In various embodiments, an anti-PSCA binding domain comprises three LCDRs provided herein, e.g., three LCDRs disclosed in Table 9.

In various embodiments, an anti-PSCA binding domain comprises at least one HCDR provided herein, e.g., at least one HCDR disclosed in Table 9, and at least one LCDR provided herein, e.g., at least one LCDR disclosed in Table 9. In various embodiments, an anti-PSCA binding domain comprises one HCDR provided herein, e.g., at least one HCDR disclosed in Table 9, and one LCDR provided herein, e.g., derived from the same Table of Table 9 as the HCDR(s). In various embodiments, an anti-PSCA binding domain comprises two HCDRs provided herein, e.g., at least two HCDRs disclosed in Table 9, and two LCDRs provided herein, e.g., at least two LCDRs disclosed in Table 9. In various embodiments, an anti-PSCA binding domain comprises two HCDRs provided herein, e.g., at least two HCDRs disclosed in Table 9, and two LCDRs provided herein, e.g., derived from the same Table of Table 9 as the HCDR(s). In various embodiments, an anti-PSCA binding domain comprises three HCDRs provided herein, e.g., three HCDRs disclosed in Table 9, and three LCDRs provided herein, e.g., three LCDRs disclosed in Table 9. In various embodiments, an anti-PSCA binding domain comprises three HCDRs provided herein, e.g., three HCDRs disclosed in Table 9, and three LCDRs derived from the same Table of Table 9 as the HCDR(s).

In various embodiments, an anti-PSCA binding domain comprises at least one heavy chain framework region (heavy chain FR) of a heavy chain variable domain disclosed herein, e.g., at least one heavy chain FR of a heavy chain variable domain disclosed in Table 9. In various embodiments, an anti-PSCA binding domain comprises two heavy chain FRs of a heavy chain variable domain disclosed herein, e.g., at least two heavy chain FRs of a heavy chain variable domain disclosed in Table 9. In various embodiments, an anti-PSCA binding domain comprises three heavy chain FRs of a heavy chain variable domain disclosed herein, e.g., three heavy chain FRs of a heavy chain variable domain disclosed in Table 9.

In various embodiments, an anti-PSCA binding domain comprises at least one light chain FR of a light chain variable domain disclosed herein, e.g., at least one light chain FR of a light chain variable domain disclosed in Table 9. In various embodiments, an anti-PSCA binding domain comprises two light chain FRs of a light chain variable domain disclosed herein, e.g., at least two light chain FRs of a light chain variable domain disclosed in Table 9. In various embodiments, an anti-PSCA binding domain comprises three light chain FRs of a light chain variable domain disclosed herein, e.g., three light chain FRs of a light chain variable domain disclosed in Table 9.

In various embodiments, an anti-PSCA binding domain comprises at least one heavy chain FR of a heavy chain variable domain disclosed herein, e.g., at least one heavy chain FR of a heavy chain variable domain disclosed in Table 9, and at least one light chain FR of a light chain variable domain disclosed herein, e.g., at least one light chain FR of a light chain variable domain disclosed in Table 9. In various embodiments, an anti-PSCA binding domain comprises one heavy chain FR of a heavy chain variable domain disclosed herein, e.g., at least one heavy chain FR of a heavy chain variable domain disclosed in Table 9, and one light chain FR of a light chain variable domain disclosed herein, e.g., derived from the same Table of Table 9 as the heavy chain FR(s). In various embodiments, an anti-PSCA binding domain comprises two heavy chain FRs of a heavy chain variable domain disclosed herein, e.g., at least two heavy chain FRs of a heavy chain variable domain disclosed in Table 9, and two light chain FRs of a light chain variable domain disclosed herein, e.g., at least two light chain FRs of a light chain variable domain disclosed in Table 9. In various embodiments, an anti-PSCA binding domain comprises two heavy chain FRs of a heavy chain variable domain disclosed herein, e.g., at least two heavy chain FRs of a heavy chain variable domain disclosed in Table 9, and two light chain FRs of a light chain variable domain disclosed herein, e.g., derived from the same Table of Table 9 as the heavy chain FR(s). In various embodiments, an anti-PSCA binding domain comprises three heavy chain FRs of a heavy chain variable domain disclosed herein, e.g., three heavy chain FRs of a heavy chain variable domain disclosed in Table 9, and three light chain FRs of a light chain variable domain disclosed herein, e.g., three light chain FRs of a light chain variable domain disclosed in Table 9. In various embodiments, an anti-PSCA binding domain comprises three heavy chain FRs of a heavy chain variable domain disclosed herein, e.g., three light chain FRs of a light chain variable domain disclosed in Table 9, and three light chain FRs derived from the same Table of Table 9 as the heavy chain FR(s).

Exemplary antibody sequences provided in Table 9 are suitable for use in any antibody format, comprising, e.g., a tetrameric antibody, a monospecific antibody, a bispecific antibody, an antigen binding fragment, or a binding motif. Heavy chain variable domains and light chain variable domains and portions thereof provided in Table 9 may be comprised in a binding motif.

In various embodiments, an anti-PSCA binding domain comprises one, two, or three FRs that together or each individually have at least 75% identity (e.g., at least 75%, at least 80%, at least 90%, at least 95%, or 100%, e.g., 85-90%, 85-95%, 85-100%, 90-95%, 90-100%, or 95-100%) to corresponding FR(s) of a heavy chain variable domain of a heavy chain variable domain disclosed in in Table 9. In various embodiments, an anti-PSCA binding domain comprises one, two, or three FRs that together or each individually have at least 75% identity (e.g., at least 75%, at least 80%, at least 90%, at least 95%, or 100%) to corresponding FR(s) of a light chain variable domain of a light chain variable domain disclosed in Table 9.

In various embodiments, an anti-PSCA binding domain comprises at least one heavy chain variable domain having at least 75% sequence identity to a heavy chain variable domain disclosed in Table 9 (e.g., at least 75%, at least 80%, at least 90%, at least 95%, or 100% identity; e.g., 85-90%, 85-95%, 85-100%, 90-95%, 90-100%, or 95-100%).

In various embodiments, an anti-PSCA binding domain comprises at least one light chain variable domain having at least 75% sequence identity to a light chain variable domain disclosed in Table 9 (e.g., at least 75%, at least 80%, at least 90%, at least 95%, or 100% identity; e.g., 85-90%, 85-95%, 85-100%, 90-95%, 90-100%, or 95-100%).

In various embodiments, an anti-PSCA binding domain comprises at least one heavy chain variable domain having at least 75% sequence identity to a heavy chain variable domain disclosed in Table 9 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in Table 9 (e.g., at least 75%, at least 80%, at least 90%, at least 95%, or 100% identity; e.g., 85-90%, 85-95%, 85-100%, 90-95%, 90-100%, or 95-100%).

Table 9 represents the heavy chain variable domain and light chain variable domain sequences of an exemplary antibody, comprising (i) the heavy chain variable domain of the exemplary antibody; (ii) a DNA sequence encoding the heavy chain variable domain (iii) three heavy chain variable domain CDRs of the heavy chain variable domain, according to IMGT, Kabat, and Chothia numbering; (iv) the light chain variable domain of the exemplary antibody; (v) a DNA sequence encoding the light chain variable domain; and (vi) three light chain variable domain CDRs of the light chain variable domain, according to IMGT, Kabat, and Chothia numbering. Information provided in each table provides framework amino acid sequences, as well as nucleotide sequences encoding each CDR amino acid sequence and nucleotide sequences encoding corresponding FR amino acid sequence.

In various embodiments an anti-PSCA binding domain may comprise a heavy chain variable domain (e.g., having at least 75% sequence identity to a heavy chain variable domain in Table 9, e.g., at least 80%, 85%, 90%, 95%, or 100% identity; e.g., 85-90%, 85-95%, 85-100%, 90-95%, 90-100%, or 95-100%), a light chain variable domain (e.g., having at least 75% sequence identity to a light chain variable domain in Table 9, e.g., at least 80%, 85%, 90%, 95%, or 100% identity; e.g., 85-90%, 85-95%, 85-100%, 90-95%, 90-100%, or 95-100%), and a linker (e.g., a linker according to SEQ ID NO: 126). In various embodiments a binding motif may comprise a leader sequence, a heavy chain variable domain (e.g., having at least 75% sequence identity to a heavy chain variable domain of any one of Table 9, e.g., at least 80%, 85%, 90%, 95%, or 100% identity; e.g., 85-90%, 85-95%, 85-100%, 90-95%, 90-100%, or 95-100%), a light chain variable domain (e.g., having at least 75% sequence identity to a light chain variable domain of any one of Table 9, e.g., at least 80%, 85%, 90%, 95%, or 100% identity; e.g., 85-90%, 85-95%, 85-100%, 90-95%, 90-100%, or 95-100%), and a linker. The linker joining the two variable domains will be apparent from the sequence in view of the present disclosure. For the avoidance of doubt, a heavy chain variable domain and a light chain variable domain may be present in any orientation, e.g., an orientation in which the heavy chain variable domain is C terminal of the light chain variable domain or in which the heavy chain variable domain is N terminal of the light chain variable domain. In various embodiments an anti-PSCA binding domain may comprise a linker according to SEQ ID NO: 126.

In certain embodiments, an anti-PSCA binding domain comprises a binding domain that comprises a heavy chain variable domain of the present disclosure, a light chain variable domain of the present disclosure, and a linker having at least 75% sequence identity to SEQ ID NO: 126 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-PSCA binding domain comprises a binding motif that comprises a linker according to SEQ ID NO: 126. In certain embodiments, an anti-PSCA binding domain comprises a binding motif that comprises a heavy chain variable domain of the present disclosure, a light chain variable domain of the present disclosure, and a leader sequence having at least 75% sequence identity to SEQ ID NO: 137, SEQ ID NO: 138, or SEQ ID NO: 139 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-PSCA binding domain comprises a binding motif that comprises a CSF2RA leader sequence according to SEQ ID NO: 137.

In certain embodiments, an anti-PSCA binding domain comprises a binding motif that comprises a heavy chain variable domain of the present disclosure, a light chain variable domain of the present disclosure, a linker of the present disclosure, and a leader sequence of the present disclosure.

A binding agent that is based on an exemplary antibody provided herein, such as for example Ab6, may be provided in any fragment or format, comprising a heavy chain variable domain according to the indicated exemplary antibody and a light chain variable domain according to the indicated exemplary antibody.

TABLE 9

Exemplary Antibody Sequences 6 (Ab6)

| SEQ ID NO: | Description | Sequence |
|---|---|---|
| 150 | Heavy Chain Variable Domain | QVQLQQWGAGLLKPSETLSLTCAVYGGSFSGNYWSWIRQPP GKGLEWIGEINHSGSTNYNPSLKSRVTISVDTSKNQFSLKLSS VTAADTAVYYCARGGSYNYFDYWGQGTLVTVSS |

TABLE 9-continued

Exemplary Antibody Sequences 6 (Ab6)

| SEQ ID NO: | Description | Sequence |
|---|---|---|
| 151 | VH (DNA) | Caagttcagctgcagcagtggggagctggtttactgaagcctagcgagacactgtctttaacatg cgccgtgtacggcggaagcttcagcggcaactattggagctggatcagacagcctcccggtaa gggttagagtggatcggcgagatcaaccactccggctccaccaactataaccctcttaaagtc tcgtgtgaccatctccgtggacaccagcaagaaccagttctctttaaagctgagctccgtgacag ccgccgacaccgctgtgtattactgtgctcgtggcggcagctacaactacttcgactactgggc caaggtacccctcgtgaccgtgtccagc |
| 152 | CDRH1 IMGT (Prot) | GGSFSGNY |
| 153 | CDRH1 Kabat (Prot) | GNYWS |
| 154 | CDRH1 Chothia (Prot) | GGSFSG |
| 155 | CDRH2 IMGT (Prot) | INHSGST |
| 156 | CDRH2 Kabat (Prot) | EINHSGSTNYNPSLKS |
| 157 | CDRH2 Chothia (Prot) | EINHSGSTNYNPSLKS |
| 158 | CDRH3 IMGT (Prot) | ARGGSYNYFDY |
| 159 | CDRH3 Kabat (Prot) | GGSYNYFDY |
| 160 | CDRH3 Chothia (Prot) | GGSYNYFDY |
| 161 | Light Chain Variable Domain | DIVMTQSPLSLPVTPGEPASISCRSSQSLLHSNGYNYLVWYLQ KPGQSPQLLIYLGSIRASGVPDRFSGSGSGTDFTLKISRVEAED VGVYYCMQPLQTPITFGQGTRLEIK |
| 162 | VL (DNA) | Gacatcgtgatgacacagagccctctgtctttacccgttaccccggtgaacccgctagcatcag ctgcagaagctcccagtctcttactccacagcaacggctacaactatttagtgtggtatttacagaaa cccggccagagccccagctgctgatttatctgggctccattcgtgctagcggcgtgcccgatag atttttccggcagcggaagcggcaccgacttcactttaaagatctctcgtgtggaggccgaggac gtgggcgtctactactgtatgcagcctctgcagaccccattaccttcggccaaggtactcgtctg gaaatcaag |
| 163 | CDRL1 IMGT (Prot) | QSLLHSNGYNY |
| 164 | CDRL1 Kabat (Prot) | RSSQSLLHSNGYNYLV |
| 165 | CDRL1 Chothia (Prot) | RSSQSLLHSNGYNYLV |
| 166 | CDRL2 IMGT (Prot) | LGS |
| 167 | CDRL2 Kabat (Prot) | LGSIRAS |
| 168 | CDRL2 Chothia (Prot) | LGSIRAS |
| 169 | CDRL3 IMGT (Prot) | MQPLQTPITF |
| 170 | CDRL3 Kabat (Prot) | MQPLQTPIT |

TABLE 9-continued

Exemplary Antibody Sequences 6 (Ab6)

| SEQ ID NO: | Description | Sequence |
|---|---|---|
| 171 | CDRL3 Chothia (Prot) | MQPLQTPIT |
| 172 | ScFv | DIVMTQSPLSLPVTPGEPASISCRSSQSLLHSNGYNYLVWYLQ KPGQSPQLLIYLGSIRASGVPDRFSGSGSGTDFTLKISRVEAED VGVYYCMQPLQTPITFGQGTRLEIKGSTSGSGKPGSGEGSTK GQVQLQQWGAGLLKPSETLSLTCAVYGGSFSGNYWSWIRQP PGKGLEWIGEINHSGSTNYNPSLKSRVTISVDTSKNQFSLKLS SVTAADTAVYYCARGGSYNYFDYWGQGTLVTVSS |
| 173 | ScFv | gacatcgtgatgacacagagccctctgtctttacccgttaccccggtgaacccgctagcatcag ctgcagaagctcccagtctttactccacagcaacggctacaactatttagtgtggtatttacagaaa cccggccagagcccccagctgctgatttatctgggctccattcgtgctagcggcgtgcccgatag attttccggcagcggaagcggcaccgacttcactttaaagatctctcgtgtggaggccgaggac gtgggcgtctactactgtatgcagcctctgcagacccccattaccttcggccaaggtactcgtctg gaaatcaagggcagcaccagcggcagcggaaaacccggaagcggcgagggaagcaccaa aggccaagttcagctgcagcagtggggagctggtttactgaagcctagcgagacactgtctttaa catcgcgcgtgtacggcggaagcttcagcggcaactattggagctggatcagacagcctcccg gtaagggtttagagtggatcggcgagatcaaccactccggctccaccaactataaccoctctttaa agtctcgtgtgaccatctccgtggacaccagcaagaaccagttctctttaaagctgagctccgtga cagccgccgacaccgctgtgtattactgtgctcgtggcggcagctacaactacttcgactactgg ggccaaggtaccctcgtgaccgtgtccagc |

As noted above, a synNotch receptor polypeptide comprises a Notch core receptor polypeptide having a length of from 50 amino acids to 1000 amino acids and comprising one or more ligand-inducible proteolytic cleavage sites. In embodiments, the Notch core receptor polypeptide present in a synNotch receptor polypeptide of the present disclosure has a length of from 50 amino acids to 1000 amino acids, e.g., from 50 amino acids to 75 amino acids, from 75 amino acids to 100 amino acids, from 100 amino acids to 150 amino acids, from 150 amino acids to 200 amino acids, from 200 amino acids to 250 amino acids, from 250 a to 300 amino acids, from 300 amino acids to 350 amino acids, from 350 amino acids to 400 amino acids, from 400 amino acids to 450 amino acids, from 450 amino acids to 500 amino acids, from 500 amino acids to 550 amino acids, from 550 amino acids to 600 amino acids, from 600 amino acids to 650 amino acids, from 650 amino acids to 700 amino acids, from 700 amino acids to 750 amino acids, from 750 amino acids to 800 amino acids, from 800 amino acids to 850 amino acids, from 850 amino acids to 900 amino acids, from 900 amino acids to 950 amino acids, or from 950 amino acids to 1000 amino acids. In some embodiments, the Notch core receptor polypeptide present in a synNotch receptor polypeptide of the present disclosure has a length of from 300 amino acids to 400 amino acids. In some embodiments, the Notch core receptor polypeptide present in a synNotch receptor polypeptide of the present disclosure has a length of from 300 amino acids to 350 amino acids. In some embodiments, the Notch core receptor polypeptide present in a synNotch receptor polypeptide of the present disclosure has a length of from 300 amino acids to 325 amino acids. In some embodiments, the Notch core receptor polypeptide present in a synNotch receptor polypeptide of the present disclosure has a length of from 350 amino acids to 400 amino acids. In some embodiments, the Notch core receptor polypeptide present in a synNotch receptor polypeptide of the present disclosure has a length of from 750 amino acids to 850 amino acids. In some embodiments, the Notch core receptor polypeptide present in a synNotch receptor polypeptide of the present disclosure has a length of from 50 amino acids to 75 amino acids. In some embodiments, the Notch core receptor polypeptide present in a synNotch receptor polypeptide of the present disclosure has a length of from 310 amino acids to 320 amino acids, e.g., 310 amino acids, 311 amino acids, 312 amino acids, 313 amino acids, 314 amino acids, 315 amino acids, 316 amino acids, 317 amino acids, 318 amino acids, 319 amino acids, or 320 amino acids. In some embodiments, the Notch core receptor polypeptide present in a synNotch receptor polypeptide of the present disclosure has a length of 315 amino acids. In some embodiments, the Notch core receptor polypeptide present in a synNotch receptor polypeptide of the present disclosure has a length of from 360 amino acids to 370 amino acids, e.g., 360 amino acids, 361 amino acids, 362 amino acids, 363 amino acids 364 amino acids, 365 amino acids, 366 amino acids, 367 amino acids, 368 amino acids, 369 amino acids, or 370 amino acids. In some embodiments, the Notch core receptor polypeptide present in a synNotch receptor polypeptide of the present disclosure has a length of 367 amino acids.

In some embodiments, the Notch core receptor polypeptide present in a synNotch receptor polypeptide of the present disclosure comprises an amino acid sequence having at least 75%, at least 80%, at least 85%, at least 90°/%, at least 95%, at least 98%, at least 99%, or 100%, amino acid sequence identity to the following amino acid sequence: IPYKIEAVKSEPVEPPLPSQLHLMYVAAAAFVLL-FFVGCGVLLSRKRRRQHGQL (SEQ ID NO: 174); where the Notch core receptor polypeptide comprises an S2 proteolytic cleavage site and an S3 proteolytic cleavage site; where the Notch receptor polypeptide has a length of from 50 amino acids (aa) to 65 aa, e.g., 50, 51, 52, 53, 54, 55, 56, 57, 58, 59, 60, 61, 62, 63, 64, or 65 aa.

In some embodiments, the Notch core receptor polypeptide present in a synNotch receptor polypeptide of the present disclosure comprises an amino acid sequence having at least 75%, at least 80%, at least 85%, at least 90%, at least 95%, at least 98%, at least 99%, or 100%, amino acid sequence identity to the following amino acid sequence: IPYKIEAVKSEPVEPPLPSQLHLMYVAAAAFVLL-FFVGCGVLLSRKRRRQLCIQKL (SEQ ID NO:175); where the TM domain is underlined; where the Notch core receptor polypeptide comprises an S2 proteolytic cleavage site and an S3 proteolytic cleavage site; where the Notch receptor polypeptide has a length of from 50 amino acids (aa) to 65 aa, e.g., 50, 51, 52, 53, 54, 55, 56, 57, 58, 59, 60, 61, 62, 63, 64, or 65 aa.

In some embodiments, the Notch core receptor polypeptide present in a synNotch receptor polypeptide of the present disclosure comprises, in order from N-terminus to C-terminus: i) a LNR-A segment; ii) a LNR-B segment; iii) a LNR-C segment; iv) an HD-N segment, v) an HD-C segment; and vi) a TM domain. A LNR-A segment, LNR-B segment, and LNR-C segment can collectively be referred to as an "LNR segment."

An LNR segment can comprise an amino acid sequence having at least 75%, at least 80%, at least 85%, at least 90%, at least 95%, at least 98%, at least 99%, or 100%, amino acid sequence identity to the following amino acid sequence: PPQIEEACELPECQVDAGNKVCNLQCNNHACGWD-GGDCSLNFNDPWKNCTQSLQCW KYFSDGHCDSQC-NSAGCLFDGFDCQLTEGQCNPLYDQYCKDHFSD-GHCDQGCNSAEC EWDGLDC (SEQ ID NO:176); and can have a length of from 118 to 122 amino acids (e.g., 118, 119, 120, 121, or 122 amino acids).

An HD segment (HD-N plus HD-C) can comprise an amino acid sequence having at least 75%, at least 80%, at least 85%, at least 90%, at least 95%, at least 98%, at least 99%, or 100%, amino acid sequence identity to the following amino acid sequence: AAGTLVLVVLLPPD-QLRNNSFHFLRELSHVLHTNVVFKRDAQGQQMIFP-YYGHEEELR KHPIKRSTVGWATSSLLPGTSGGRQR-RELDPMDIRGSIVYLEIDNRQCVQSSSQCFQSAT DVAAFLGALASLGSLNIPYKIEAVKSEPVEPPLP (SEQ ID NO:177), and can have a length of 150, 151, 152, 153, or 154 amino acids.

A transmembrane segment can comprise an amino acid sequence having at least 75%, at least 80%, at least 85%, at least 90%, at least 95%, at least 98%, at least 99%, or 100%, amino acid sequence identity to the following amino acid sequence: HLMYVAAAAFVLLFFVGCGVLLS (SEQ ID NO:178); and can have a length of 21, 22, 23, 24, or 25 amino acids.

In some embodiments, a Notch receptor polypeptide comprises an amino acid sequence having at least 75%, at least 80%, at least 85%, at least 90%, at least 95%, at least 98%, at least 99%, or 100%, amino acid sequence identity to the following amino acid sequence: PPQIEE-ACELPECQVDAGNKVCNLQCNNHACGWDGGD-CSLNFNDPWKNCTQSLQCW KYFSDGHCDSQCN-SAGCLFDGFDCQLTEGQCNPLYDQYCKDHFSDGH-CDQGCNSAEC EWDGLDCAEHVPERLAAGTLVLV-VLLPPDQLRNNSFHFLRELSHVLHTNVVFKRDAQG QQMIFPYYGHEEELRKHPIKRSTVGWATSSLLPGTSG-GRQRRELDPMDIRGSIVYLEIDN RQCVQSSSQCF-QSATDVAAFLGALASLGSLNIPYKIEAVKSEPVEPPLP-SQLHLMYVAA AFVLLFFVGCGVLLS (SEQ ID NO: 179), and has a length of from 300 amino acids to 310 amino acids (e.g., 300, 301, 302, 303, 304, 305, 306, 307, 308, 309, or 310 amino acids).

In some embodiments, a Notch core receptor polypeptide comprises an amino acid sequence having at least 75%, at least 80%, at least 85%, at least 90%, at least 95%, at least 98%, at least 99%, or 100%, amino acid sequence identity to the following amino acid sequence: PCVGSNPCYNQGTCEPTSENPFYRCLCPAKFNGLL-CHILDYSFTGGAGRDIPPPQI EEACELPECQVDAG-NKVCNLQCNNHACGWDGGDCSLNFNDPWKNCT-QSLQCWKYFS DGHCDSQCNSAGCLFDGFDCQL-TEGQCNPLYDQYCKDHFSDGHCDQGCNSAECEWDG LDCAEHVPERLAAGTLVLVVLLPPDQLRNNSFHFL-RELSHVLHTNVVFKRDAQGQQMI FPYYGHEEEL-RKHPIKRSTVGWATSSLLPGTSGGRQRRELDPM-DIRGSIVYLEIDNRQCV QSSSQCFQSATDVAAFL-GALASLGSLNIPYKIEAVKSEPVEPPLPSQLHLMY-VAAAAFVL LFFVGCGVLLS (SEQ ID NO:180); and has a length of from 350 amino acids to 370 amino acids (e.g., 350 351, 352, 353, 354, 355, 356, 357, 358, 359, 360, 361, 362, 363, 364, 365, 366, 367, 368, 369, or 370 amino acids).

In some embodiments, the Notch core receptor polypeptide present in a synNotch receptor polypeptide of the present disclosure comprises, in order from N-terminus to C-terminus: i) a single EGF repeat; ii) an LNR segment; iii) an HD-N segment, iv) an HD-C segment; and v) a TM domain.

An EGF repeat can comprise an amino acid sequence having at least 75%, at least 80%, at least 85%, at least 90%, at least 95%, at least 98%, at least 99%, or 100%, amino acid sequence identity to the following sequence: PCVG-SNPCYNQGTCEPTSENPFYRCLCPAKFNGLLCH (SEQ ID NO: 181); and can have a length of 35 amino acids to 40 amino acids (e.g., 35, 36, 37, 38, 39, or 40 amino acids.

An LNR segment can comprise an amino acid sequence having at least 75%, at least 80%, at least 85%, at least 90%, at least 95%, at least 98%, at least 99%, or 1000%, amino acid sequence identity to the following amino acid sequence: PPQIEEACELPECQVDAGNKVCNLQCNNHACGWD-GGDCSLNFNDPWKNCTQSLQCW KYFSDGHCDS-QCNSAGCLFDGFDCQLTEGQCNPLYDQYCKDH-FSDGHCDQGCNSAEC EWDGLDC (SEQ ID NO:182); and can have a length of from 118 to 122 amino acids (e.g., 118, 119, 120, 121, or 122 amino acids).

An HD segment (HD-N plus HD-C) can comprise an amino acid sequence having at least 75%, at least 80%, at least 85%, at least 90%, at least 95%, at least 98%, at least 99%, or 100%, amino acid sequence identity to the following amino acid sequence: AAGTLVLVVLL-PPDQLRNNSFHFLRELSHVLHTNVVFKRDAQGQQM-IFPYYGHEEELR KHPIKRSTVGWATSSLLPGTSG-GRQRRELDPMDIRGSIVYLEIDNRQCVQSSSQ-CFQSAT DVAAFLGALASLGSLNIPYKIEAVKSEPVEP-PLP (SEQ ID NO: 183); and can have a length of 150, 151, 152, 153, or 154 amino acids.

A transmembrane segment can comprise an amino acid sequence having at least 75%, at least 80%, at least 85%, at least 90° %, at least 95%, at least 98%, at least 99%, or 100%, amino acid sequence identity to the following amino acid sequence: HLMYVAAAAFVLLFFVGCGVLLS (SEQ ID NO:184); and can have a length of 21, 22, 23, 24, or 25 amino acids.

In some embodiments, a Notch core receptor polypeptide comprises a synthetic linker. For example, In some embodiments, a Notch core receptor polypeptide comprises, in order from N-terminus to C-terminus: i) a synthetic linker; ii) an EGF repeat; iii) an LNR segment; iv) an HD-N segment, v) an HD-C segment; and vi) a TM domain.

A synthetic linker can have a length of from about 10 amino acids (aa) to about 200 aa, e.g., from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A synthetic linker can have a length of from 10 aa to 30 aa, e.g., 10, 11, 12, 13, 14, 15, 16, 17, 18, 19, 20, 21, 22, 23, 24, 25, 26, 27, 28, 29, or 30 aa. A synthetic linker can have a length of from 30 aa to 50 aa, e.g., from 30 aa to 35 aa, from 35 aa to 40 aa, from 40 aa to 45 aa, or from 45 aa to 50 aa.

In some instances, a synthetic linker, as described herein, may include an extracellular protein structural domain or a portion thereof. Extracellular protein structural domains suitable for use as a synthetic linker include but are not limited to e.g., Ig-like extracellular structural domains, Fc extracellular structural domains, fibronectin extracellular structural domains and the like. In some instances, a synthetic linker may include a plurality of extracellular protein structural domains where the plurality may include a plurality of the same domain or a plurality of different domains.

In some embodiments, the Notch core receptor polypeptide present in a synNotch receptor polypeptide of the present disclosure comprises, in order from N-terminus to C-terminus: i) from two to eleven EGF repeats; ii) an LNR segment; iii) an HD-N segment, iv) an HD-C segment; and v) a TM domain.

In some embodiments, the Notch core receptor polypeptide present in a synNotch receptor polypeptide of the present disclosure comprises, in order from N-terminus to C-terminus: i) two EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) three EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) four EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) five EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) six EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) seven EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) eight EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) nine EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) ten EGF repeats; ii) an LNR segment; iii) an HD-N segment, iv) an HD-C segment; and v) a TM domain. In some embodiments, the Notch core receptor polypeptide present in a synNotch receptor polypeptide of the present disclosure comprises, in order from N-terminus to C-terminus: i) eleven EGF repeats; ii) an LNR segment; iii) an HD-N segment, iv) an HD-C segment; and v) a TM domain.

An EGF repeat can comprise an amino acid sequence having at least 75%, at least 80%, at least 85%, at least 900, at least 95%, at least 98%, at least 99%, or 100%, amino acid sequence identity to DINECVLSPCRHGASCQNTHG-GYRCHCQAGYSGRNCE; SEQ ID NO:185 and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to DIDDCRPNPCHNGGSCTDGIN-TAFCDCLPGFRGTFC; SEQ ID NO: 186 and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to DINECASDPCRNGANCTDCVD-SYTCTCPAGFSGIHCE; (SEQ ID NO: 187 and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99/o, or 100%, amino acid sequence identity to TESSCFNGGTCVDGINSFT-CLCPPGFTGSYCQ; SEQ ID NO: 188 and can have a length of from 30 amino acids (aa) to 35 aa (e.g., 30, 31, 32, 33, 34, or 35 aa).

An EGF repeat can comprise an amino acid sequence having at least 75%, at least 80%, at least 85%, at least 90%, at least 95%, at least 98%, at least 99%, or 100%, amino acid sequence identity to DVNECDSQPCLHGGTCQ-DGCGSYRCTCPQGYTGPNCQ; SEQ ID NO: 189 and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to DSSPCKNGGKCWQTH-TQYRCECPSGWT; SEQ ID NO: 190 and can have a length of from 25 amino acids (aa) to 30 aa, e.g., 25, 26, 27, 28, 29, or 30 aa.

An EGF repeat can comprise an amino acid sequence having at least 75%, at least 80%, at least 85%, at least 90%, at least 95%, at least 98%, at least 99%, or 100%, amino acid sequence identity to LVDECSPSPCQNGATCTDYLGGY-SCKCVAGYHGVNC; SEQ ID NO: 191 and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to IDECLSHPCQNGGTCLDLPN-TYKCSCPRGTQGVHCE; SEQ ID NO: 192 and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to CFNNGTCVDQVGGY- SCTCPPGFVGERCE; SEQ ID NO: 193 and can have a length of from 25 amino acids (aa) to 30 aa, e.g., 25, 26, 27, 28, 29, or 30 aa.

An EGF repeat can comprise an amino acid sequence having at least 75%, at least 80%, at least 85%, at least 90%, at least 95%, at least 98%, at least 99%, or 100%, amino acid sequence identity to DVNECLSNPC-DARGTQNCVQRVNDFHCECRAGHTGRRCE; (SEQ ID NO: 194) and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to PCVGSNPCYNQGTCEPTSENPFYR-CLCPAKFNGLLCH (SEQ ID NO: 195); and can have a length of 35 amino acids to 40 amino acids (e.g., 35, 36, 37, 38, 39, or 40 amino acids.

An LNR segment can comprise an amino acid sequence having at least 75%, at least 80%, at least 85%, at least 90%, at least 95%, at least 98%, at least 99%, or 1000/%, amino acid sequence identity to the following amino acid sequence: PPQIEEACELPECQVDAGNKVCNLQCNNHACGWD-GGDCSLNFNDPWKNCTQSLQCW KYFSDGHCDS-QCNSAGCLFDGFDCQLTEGQCNPLYDQYCKD-HFSDGHCDQGCNSAEC EWDGLDC (SEQ ID NO: 196); and can have a length of from 118 to 122 amino acids (e.g., 118, 119, 120, 121, or 122 amino acids).

An HD segment (HD-N plus HD-C) can comprise an amino acid sequence having at least 75%, at least 80%, at least 85%, at least 90%, at least 95%, at least 98%, at least 99%, or 100%, amino acid sequence identity to the following amino acid sequence: AAGTLVLVVLLPPDQL-RNNSFHFLRELSHVLHTNVVFKRDAQGQQMIFP-YYGHEEELR KHPIKRSTVGWATSSLLPGTSGGRQR-RELDPMDIRGSIVYLEIDNRQCVQSSSQCFQSAT DVAAFLGALASLGSLNIPYKIEAVKSEPVEPPLP (SEQ ID NO: 197); and can have a length of 150, 151, 152, 153, or 154 amino acids.

A transmembrane segment can comprise an amino acid sequence having at least 75%, at least 80%, at least 85%, at least 90%, at least 95%, at least 98%, at least 99%, or 100%, amino acid sequence identity to the following amino acid sequence: HLMYVAAAAFVLLFFVGCGVLLS (SEQ ID NO: 198; and can have a length of 21, 22, 23, 24, or 25 amino acids.

In some embodiments, a Notch core receptor polypeptide comprises a synthetic linker. For example, In some embodiments, a Notch core receptor polypeptide comprises, in order from N-terminus to C-terminus: i) two to eleven EGF repeats; ii) a synthetic linker; iii) an LNR segment; iv) an HD-N segment, v) an HD-C segment; and vi) a TM domain.

A synthetic linker can have a length of from about 10 amino acids (aa) to about 200 aa, e.g., from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A synthetic linker can have a length of from 10 aa to 30 aa, e.g., 10, 11, 12, 13, 14, 15, 16, 17, 18, 19, 20, 21, 22, 23, 24, 25, 26, 27, 28, 29, or 30 aa. A synthetic linker can have a length of from 30 aa to 50 aa, e.g., from 30 aa to 35 aa, from 35 aa to 40 aa, from 40 aa to 45 aa, or from 45 aa to 50 aa.

Notch receptor polypeptide comprising an HD-C segment and a TM domain

In some embodiments, a synNotch receptor polypeptide comprises, in order from N-terminus to C-terminus: i) an HD-C segment; and ii) a TM domain, where the synNotch receptor polypeptide does not include an LNR segment. In some embodiments, the LNR segment is replaced with a heterologous polypeptide.

A transmembrane segment can comprise an amino acid sequence having at least 75%, at least 80%, at least 85%, at least 90%, at least 95%, at least 98%, at least 99%, or 100%, amino acid sequence identity to the following amino acid sequence:

HLMYVAAAAFVLLFFVGCGVLLS (SEQ ID NO: 199); and can have a length of 21, 22, 23, 24, or 25 amino acids.

As discussed above, a synNotch receptor polypeptide of the present disclosure comprises: a) an extracellular anti-PSCA binding domain; b) a Notch core receptor polypeptide having a length of from 50 amino acids to 1000 amino acids, and comprising one or more ligand-inducible proteolytic cleavage sites; and c) an intracellular domain, where binding of the of extracellular anti-PSCA binding domain to PSCA induces cleavage of the Notch receptor polypeptide at the one or more ligand-inducible proteolytic cleavage sites, thereby releasing the intracellular domain.

In some embodiments, the synNotch receptor polypeptide includes only one ligand-inducible proteolytic cleavage site. In some embodiments, the synNotch receptor polypeptide includes two ligand-inducible proteolytic cleavage sites. In some embodiments, the synNotch receptor polypeptide includes three ligand-inducible proteolytic cleavage sites. For simplicity, ligand-inducible cleavage sites will be referred to herein as "SI," "S2," and "S3" ligand-inducible proteolytic cleavage sites.

In some embodiments, the synNotch receptor polypeptide includes an SI ligand-inducible proteolytic cleavage site. An SI ligand-inducible proteolytic cleavage site can be located between the HD-N segment and the HD-C segment. In some embodiments, the SI ligand-inducible proteolytic cleavage site is a furin-like protease cleavage site. A furin-like protease cleavage site can have the canonical sequence Arg-X-(Arg/Lys)-Arg, where X is any amino acid; the protease cleaves immediately C-terminal to the canonical sequence. In some embodiments, an amino acid sequence comprising an SI ligand-inducible proteolytic cleavage site can have the amino acid sequence GRRRRELDPM (SEQ ID NO: 200), where cleavage occurs between the "RE" sequence. As another example, an amino acid sequence comprising an SI ligand-inducible proteolytic cleavage site can have the amino acid sequence RQRRELDPM (SEQ ID NO: 201), where cleavage occurs between the "RE" sequence.

In some embodiments, the synNotch receptor polypeptide includes an S2 ligand-inducible proteolytic cleavage site. An S2 ligand-inducible proteolytic cleavage site can be located within the HD-C segment. In some embodiments, the S2 ligand-inducible proteolytic cleavage site is an ADAM-17-type protease cleavage site. An ADAM-17-type protease cleavage site can comprise an Ala-Val dipeptide sequence, where the enzyme cleaves between the Ala and the Val. In some embodiments, amino acid sequence comprising an S2 ligand-inducible proteolytic cleavage site can have the amino acid sequence KIEAVKSE (SEQ ID NO:128), where cleavage occurs between the "AV" sequence. As another example, an amino acid sequence comprising an S2 ligand-inducible proteolytic cleavage site can have the amino acid sequence KIEAVQSE (SEQ ID NO: 202), where cleavage occurs between the "AV" sequence.

In some embodiments, the synNotch receptor polypeptide includes an S3 ligand-inducible proteolytic cleavage site. An S3 ligand-inducible proteolytic cleavage site can be located within the TM domain. In some embodiments, the S3 ligand-inducible proteolytic cleavage site is a gamma-secretase (γ-secretase) cleavage site. A γ-secretase cleavage site can comprise a Gly-Val dipeptide sequence, where the enzyme cleaves between the Gly and the Val. In some embodiments, an S3 ligand-inducible proteolytic cleavage site has the amino acid sequence VGCGVLLS (SEQ ID NO: 203), where cleavage occurs between the "GV" sequence. In some embodiments, an S3 ligand-inducible proteolytic cleavage site comprises the amino acid sequence GCGVLLS (SEQ ID NO. 204).

In some embodiments, the synNotch receptor polypeptide lacks an SI ligand-inducible proteolytic cleavage site. In some embodiments, the synNotch receptor polypeptide lacks an S2 ligand-inducible proteolytic cleavage site. In some embodiments, the synNotch receptor polypeptide lacks an S3 ligand-inducible proteolytic cleavage site. In some embodiments, the synNotch receptor polypeptide lacks both an SI ligand-inducible proteolytic cleavage site and an S2 ligand-inducible proteolytic cleavage site. In some embodiments, the synNotch receptor polypeptide includes an S3 ligand-inducible proteolytic cleavage site; and lacks both an SI ligand-inducible proteolytic cleavage site and an S2 ligand-inducible proteolytic cleavage site.

In some embodiments, the synNotch receptor polypeptide comprises a Notch core that comprises an amino acid sequence having at least 75%, at least 80%, at least 85%, at least 90%, at least 95%, at least 98%, at least 99%, or 100%, amino acid sequence identity to the following amino acid sequence: ILDYSFTGGAGRDIPPPQIEEACELPECQ-VDAGNKVCNLQCNNHACGWDGGDCSLNFN DPW-KNCTQSLQCWKYFSDGHCDSQCNSAGCLFDGF-DCQLTEGQCNPLYDQYCKDHFS DGHCDQGCNSAE-CEWDGLDCAEHVPERLAAGTLVLVVLLPPDQ-LRNNSFHFLRELSHV LHTNVVFKRDAQGQQ-MIFPYYGHEEELRKHPIKRSTVGWATSSLLPGTSG-GRQRRELDP MDIRGSIVYLEIDNRQCVQSSSQC-FQSATDVAAFLGALASLGSLNIPYKIEAVKSEPVEPP LPSQLHLMYVAAAAFVLLFFVGCGVLLSRKRRRQH-GQLWFPEGFKVSEASKKKRREPL GEDSVGLKPLKN-ASDGALMDDNQNEWGDEDLETKKFRFEEPVV (SEQ ID NO: 205). In embodiments a notch core is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to:

```
                                    (SEQ ID NO: 206)
atcctggactacagcttcacaggtggcgctgggcgcgacattccccacc gcagattgaggaggcctgtgagctgcctgagtgccaggtggatgcaggca ataaggtctgcaacctgcagtgtaataatcacgcatgtggctgggatggt ggcgactgctccctcaacttcaatgaccctggaagaactgcacgcagtc tctacagtgctggaagtattttagcgacggccactgtgacagccagtgca actcggccggctgcctctttgatggcttcgactgccagctcaccgaggga cagtgcaacccctgtatgaccagtactgcaaggaccacttcagtgatgg ccactgcgaccagggctgtaacagtgccgaatgtgagtgggatggcctag actgtgctgagcatgtacccgagcggctggcagccggcaccctggtgctg gtggtgctgcttccacccgaccagctacggaacaactccttccactttct gcgggagctcagccacgtgctgcacaccaacgtggtcttcaagcgtgatg
``` cgcaaggccagcagatgatcttcccgtactatggccacgaggaagagctg cgcaagcacccaatcaagcgctctacagtgggttgggccacctcttcact gcttcctggtacaagtggtgggcgccagcgcagggagctggacccccatgg acatccgtggctccattgtctacctggagatcgacaaccggcaatgtgtg cagtcatcctcgcagtgcttccagagtgccaccgatgtggctgccttcct aggtgctcttgcgtcacttggcagcctcaatattccttacaagattgagg ccgtgaagagtgagccggtggagcctccgctgccctcgcagctgcacctc atgtacgtggcagcagccgccttcgtgctcctgttctttgtgggctgtgg ggtgctgctgtcccgcaagcgccggcgg.

In some embodiments, the chimeric Notch receptor polypeptide contains all or a portion of human Notch1, Notch2, Notch3, or Notch4. In some embodiments, the chimeric Notch receptor polypeptide contains all or a portion of SEQ ID NO: 244 SEQ II) NO: 245, SEQ ID NO: 246, SEQ ID NO: 247, or SEQ ID NO: 248. In some embodiments, a "portion" of Notch comprises the three NLR domains, the transmembrane domain, and a short cytosolic fragment including the native Nuclear Localization Sequence (NLS) of Notch.

Human neurogenic locus notch homolog protein 1 pre-protein NP_060087.3:

```
                                    (SEQ ID NO: 244)
MPPLLAPLLCLALLPALAARGPRCSQPGETCLNGGKCEAANGTEACVCGG

AFVGPRCQDPNPCLSTPCKNAGTCHVVDRRGVADYACSCALGFSGPLCLT

PLDNACLTNPCRNGGTCDLLTLTEYKCRCPPGWSGKSCQQADPCASNPCA

NGGQCLPFEASYTCHCPPSFHGPTCRQDVNECGQKPGLCRHGGTCHNEVG

SYRCVCRATHTGPNCERPYVPCSPSPCQNGGTCRPTGDVTHECACLPGFT

GQNCEENIDDCPGNNCKNGGACVDGVNTYNCRCPPEWTGQYCTEDVDECQ

LMPNACQNGGTCHNTHGGYNCVCVNGWTGEDCSENIDDCASAACFHGATC

HDRVASFYCECPHGRTGLLCHLNDACISNPCNEGSNCDTNPVNGKATCTC

PSGYTGPACSQDVDECSLGANPCEHAGKCINTLGSFECQCLQGYTGPRCE

IDVNECVSNPCQNDATCLDQTGEFQCTCMPGYEGVHCEVNTDECASSPCL

HNGRCLDKINEFQCECPTGFTGHLCQYDVDECASTPCKNGAKCLDGPNTY

TCVCTEGYTGTHCEVDIDECDPDPCHYGSCKDGVATFTCLCRPGYTGHHC

ETNINECSSQPCRHGGTCQDRDNAYLCFCLKGTTGPNCEINLDDQASSPC

DSGTCLDKIDGYECACEPGYTGSMCNINIDECAGNPCHNGGTCEDGINGF

TCRCPEGHDPTCLSEVNECNSNPCVHGACRDSLNGYKCDCDPGWSGTNCD

INNNECESNPCVNGGTCKDMTSGYVCTCREGFSGPNCQTNINECASNPCL

NQGTCIDDVAGYKCNCLLPYTGATCEVVLAPCAPSPCRNGGECRQSEDYE

SFSCVCPTGWQGQTCEVDINECVLSPCRHGASCQNTHGGYRCHCQAGYSG

RNCETDIDDCRPNPCHNGGSCTDGINTAFCDCLPGFRGTFCEEDINECAS

DPCRNGANCTDCVDSYTCTCPAGFSGIHCENNTPDCTESSCFNGGTCVDG

INSFTCLCPPGFTGSYCQHDVNECDSQPCLHGGTCQDGCGSYRCTCPQGY
```

-continued

```
TGPNCQNLVHWCDSSPCKNGGKCWQTHTQYRCECPSGWTGLYCDVPSVSC
EVAAQRQGVDVARLCQHGGLCVDAGNTHHCRCQAGYTGSYCEDLVDECSP
SPCQNGATCTDYLGGYSCKCVAGYHGVNCSEEIDECLSHPCQNGGTCLDL
PNTYKCSCPRGTQGVHCEINVDDCNPPVDPVSRSPKCFNNGTCVDQVGGY
SCTCPPGFVGERCEGDVNECLSNPCDARGTQNCVQRVNDFHCECRAGHTG
RRCESVINGCKGKPCKNGGTCAVASNTARGFTCKCPAGFEGATCENDART
CGSLRCLNGGTCISGPRSPTCLCLGPFTGPECQFPASSPCLGGNPCYNQG
TCEPTSESPFYRCLCPAKFNGLLCHILDYSFGGGAGRDIPPPLIEEACEL
PECQEDAGNKVCSLQCNNHACGWDGGDCSLNFNDPWKNCTQSLQCWKYFS
DGHCDSQCNSAGCLFDGFDCQRAEGQCNPLYDQYCKDHFSDGHCDQGCNS
AECEWDGLDCAEHVPERLAAGTLVVVVLMPPEQLRNSSFHFLRELSRVLH
TNVVFKRDAHGQQMIFPYYGREEELRKHPIKRAAEGWAAPDALLGQVKAS
LLPGGSEGGRRRRELDPMDVRGSIVYLEIDNRQCVQASSQCFQSATDVAA
FLGALASLGSLNIPYKIEAVQSETVEPPPPAQLHFMYVAAAAFVLLFFVG
CGVLLSRKRRRQHGQLWFPEGFKVSEASKKKRREPLGEDSVGLKPLKNAS
DGALMDDNQNEWGDEDLETKKFRFEEPVVLPDLDDQTDHRQWTQQHLDAA
DLRMSAMAPTPPQGEVDADCMDVNVRGPDGFTPLMIASCSGGGLETGNSE
EEEDAPAVISDFIYQGASLHNQTDRTGETALHLAARYSRSDAAKRLLEAS
ADANIQDNMGRTPLHAAVSADAQGVFQILIRNRATDLDARMHDGTTPLIL
AARLAVEGMLEDLINSHADVNAVDDLGKSALHWAAAVNNVDAAVVLLKNG
ANKDMQNNREETPLFLAAREGSYETAKVLLDHFANRDITDHMDRLPRDIA
QERMHHDIVRLLDEYNLVRSPQLHGAPLGGTPTLSPPLCSPNGYLGSLKP
QGVGKKVRKPSSKGLACGSKEAKDIKARRKKSQDGKGCLLDSSGMLSPVD
SLESPHGYLSDVASPPLLPSPFQQSPSVPLNHLPGMPDTHLGTGHLNVAA
KPEMAALGGGGRLAFETGPPRLSHLPVASGTSTVLGSSSGGALNFTVGGS
TSLNGQCEWLSRLQSGMVPNQYNPLRGSVAPGPLSTQAPSLQHGMVGPLH
SSLAASALSQMMSYQGLPSTRLATQPHLVQTQQVQPQNLQMQQQNLQPAN
IQQQQSIQPPPPPPQPHLGVSSAASGHLGRSFLSGEPSQADVQPLGPSSL
AVHTILPQESPALPTSLPSSLVPPVTAAQFLTPPSQHSYSSPVDNTPSHQ
LQVPEHPFLTPSPESPDQWSSSSPHSNVSDWSEGVSSPPTSMQSQIARIP
EAFK.
```

Human neurogenic locus notch homolog protein 2 isoform 1 preprotein NP_077719.2:

(SEQ ID NO: 245)
```
SMPALRPALLWALLALWLCCAAPAHALQCRDGYEPCVNEGMCVTYHNGTG
YCKCPEGFLEYCQHRDPCEKNRCQNGGTCVAQAMLGKATCRCASGFTGED
CQYSTSHPCFVSRPCLNGGTCHMLSRDTVECTCQVGFTGKECQWTDACLS
HPCANGSTCTTVANQFSCKCLTGFTGQKCETDVNECDIPGHCQHGGTCLN
LPGSYQCQCPQGFTGQYCDSLYVPCAPSPCVNGGTCRQTGDFTFECNCLP
GFEGSTCERNIDDCPNHRCQNGGVCVDGVNTYNCRCPPQWTGQFCTEDVD
ECLLQPNACQNGGTCANRNGGYGCVCVNGWSGDDCSENIDDCAFASCTPG
STCIDRVASFSCMCPEGKAGLLCHLDDACISNPCHKGALCDTNPLNGQYT
CTCPQGYKGADCTEDVDECAMANSNPCEHAGKCVNTDGAFHCECLKGYAG
PRCEMDINECHSDPCQNDATCLDKTGGFTCLCMPGFKGVHCELEINECQS
NPCVNNGQCVDKVNRFQCLCPPGFTGPVCQIDIDDCSSTPCLNGAKCIDH
PNGVECQCATGFTGVLCEENIDNCDPDPCHHGQCQDGIDSYTCICNPGYM
GATCSDQIDECYSSPCLNDGRCIDLVNGYQCNCQPGTSGVNCEINFDDCA
SNPCIHGTCMDGINRYSCVCSPGFTGQRCNIDIDECASNPCRKGATCING
VNGFRCTCPEGPHHPSCYSQVNECLSNPCIHGNCTGGLSGYKCLCDAGWV
GINCEVDKNECLSNPQONGGTCDNLVNGYRCTCKKGFKGYNCQVNIDECA
SNPCLNQGTCFDDISGYTCHCVLPYTGKNCQTVLAPCSPNPCENAAVCKE
SPNFESYTCLCAPGWQGQRCTIDIDECISKPCMNHGLCHNTQGSYMCECP
PGFSGMDCEEDIDDCLANPCQNGGSCMDGVNTFSCLCLPGFTGDKCQTDM
NECLSEPCKNGGTCSDYVNSYTCKCQAGFDGVHCENNINECTESSCFNGG
TCVDGINSFSCLCPVGFTGSFCLHEINECSSHPCLNEGTCVDGLGTYRCS
CPLGYTGKNCQTLVNLCSRSPCKNKGTCVQKKAESQCLCPSGWAGAYCDV
PNVSCDIAASRRGVLVEHLCQHSGVCINAGNTHYCQCFLGYTGSYCEEQL
DECASNPCQHGATCSDFTGGYRCECVPGYOGVNCEYEVDECQNQPCQNGG
TCIDLVNHFKCSCPPGTRGLLCEENIDDCARGPHCLNGGQCMDRTGGYSC
RCLPGFAGERCEGDINECLSNPCSSEGSLDCIQLTNDYLCVCRSAFTGRH
CETFVDVCPQMPCLNGGTCAVASNMPDGFTCRCPPGFSGARCQSSCGQVK
CRKGEQCVHTASGPRCFCPSPRDCESGCASSPCQHGGSCHPQRQPPYYSC
QCAPPFSGSRCELYTAPPSTPPATCLSQYCADKARDGVCDEACNSHACQW
DGGDCSLIMENPWANCSSPLPCWDYINNQCDELCNTVECLFDNFECQGNS
KTCKYDKYCADHFKDNHGDQGCNSEECGWDGLDCAADQPENLAEGTLVIV
VLMPPEQLLQDARSFLRALGTLLHTNLRIKRDSQGELMVYPYYGEKSAAM
KKQRMTRRSLPGEQEQEVAGSKVFLEIDNRQCVQDSDHCFKNTDAAAALL
ASHAIQGTLSYPLVSVVSESLTPERTQLLYLLAVAVVIILFILLGVIMAK
RKRKHGSLWLPEGFTLRRDASNHKRREPVGQDAVGLKNLSVQVSEANLTG
TGTSEHWVDDEGPQPKKVKAEDEALLSEEDDPIDRRPWTQQHLEAADIRR
TPSLALTPPQAEQEVDVLDVNVRGPDGCTPLMLASLRGGSSDLSDEDEDA
EDSSANIITDLVYQGASLQAQTDRTGEMALHLAARYSRADAAKRLLDAGA
DANAQDNMGRCPLHAAVAADAQGVFQILIRNRVTDLDARMNDGTTPLILA
ARLAVEGMVAELINCQADVNAVDDHGKSALHWAAAVNNVEATLLLLKNGA
NRDMQDNKEETPLFLAAREGSYEAAKILLDHFANRDITDHMDRLPRDVAR
DRMHHDIVRLLDEYNVTPSPPGTVLTSALSPVTCGPNRSFLSLKHTPMGK
KSRRPSAKSTMPTSLPNLAKEAKDAKGSRRKKSLSEKVQLSESSVTLSPV
DSLESPHTYVSDTTSSPMITSPGILQASPNPMLATAAPPAPVHAQHALSF
SNLHEMQPLAHGASTVLPSVSQLLSHHHTVSPGSGSAGSLSRLHPVPVPA
DWMNRMEVNETQYNEMFGMVLAPAEGTHPGIAPQSRPPEGKHITTPREPL
PPTVTFQLIPKGSIAQPAGAPQPQSTCPPAVAGPLPTMYQIPEMARLPSV
```

AFPTAMMPQQDGQVAQTILPAYHPFPASVGKYPTPPSQHSYASSNAAERT
PSHSGHLOGEHPYLTPSPESPDQWSSSSPHSASDWSDVTTSPTPGGAGGG
QRGPGTHMSEPPHNNMQVYA.

Human neurogenic locus notch homolog protein 2 isoform 2 precursor NP_001186930.1:

(SEQ ID NO: 246)
MPALRPALLWALLALWLCCAAPAHALQCRDGYEPCVNEGMCVTYHNGTGY
CKCPEGFLGEYCQHRDPCEKNRCQNGGTCVAQAMLGKATCRCASGFTGED
CQYSTSHPCFVSRPCLNGGTCHMLSRDTYECTCQVGFTGKECQWIDACLS
HPCANGSTCTTVANQFSCKCLTGFTGQKCETDVNECDIPGHCQHGGTCLN
LPGSYQCQCPQGFTGQYCDSLYVPCAPSPCVNGGTCRQTGDFTFECNCLP
GFEGSTCERNIDDCPNHRCQNGGVCVDGVNTYNCRCPPQWTGQFCTEDVD
ECLLQPNACQNGGTCANRNGGYGCVCVNGWSGDDCSENIDDCAFASCTPG
STCIDRVASFSCMCPEGKAGLLCHLDDACISNPCHKGALCDTNPLNGQYT
CTCPQGYKGADCTEDVDECAMANSNPCEHAGKCVNTDGAFHCECLKGYAG
PRCEMDINECHSDPCQNDATCLDKTGGFTCLCMPGFKGVHCELEINECQS
NPCVNNGQCVDKVNRFQCLCPPGFTGPVCQIDIDDCSSTPCLNGAKCIDH
PNGYECQCATGFTGVLCEENIDNCDPDPCHHGQCQDGIDSYTCICNPGYM
GATCSDQIDECYSSPCLNDGRCIDLVNGYQCNCQPGTSGVNCEINFDDAS
NPCIHGTCMDGINRYSVVCSPGFTGQRCNIDIDECASNPCRKGATCINGV
NGFRCTCPEGPHHPSCYSQVNECLSNPCIHGNCTGGLSGYKCLCDAGWVG
INCEVDKNECLSNPCQNGGTCDNLVNGYRCTCKKGFKGYNCQVNIDECAS
NPCLNQGTCFDDISGYTCHCVLPYTGKNCQTVLAPCSPNPCENAAVCKES
PNFESYTCLCAPGWQGQRCTIDIDECISKPCMNHGLCHNTQGSYMCECPP
GFSGMDCEEDIDDCLANPCQNGGSCMDGVNTFSCLCLPGFTGDKCQTDMN
ECLSEPCKNGGTCSDYVNSYTCKCQAGFDGVHCENNINECTESSCFNGGT
CVDGINSFSCLCPVGFTGSFCLHEINECSSHPCLNEGTCVDGLGTYRCSC
PLGYTGKNCQTLVNLCSRSPCKNKGTVQKKAESQCLCPSGWAGAYCDVPN
VSCDIAASRRGVLVEHLCQHSGVCINAGNTHYCQCPLGYTGSYCEEQLDE
CASNPCQHGATCSDFTGGYRCECVPGYQGVNCEYEVDECQNPCQNGGTC
IDLVNHFKCSCPPGTRGMKSSLSIFHPGHCLKL.

Human neurogenic locus notch homolog protein 3 precursor NP 000426.2;

(SEQ ID NO: 247)
MGPGARGRRRRRPMSPPPPPPPVRALPLLLLLAGPGAAAPPCLDGSPCA
NGGRCTQLPSREAACLCPPGWVGERCQLEDPCHSGPCAGRGVCQSSVVAG
TARFSCRCPRGFRGPDCSLPDPCLSSPCAHGARCSVGPDGRFLCSCPPGY
QGRSCRSDVDECRVGEPCRHGGTCLNTPGSFRCQCPAGYTGPLCENPAVP
CAPSPCRNGGTCRQSGDLTYDCACLPGFEQNCEVNVDDCPGHRCLNGGTC
VDGVNTYNCQCPPEWTGQFCTEDVDECQLQPNACHNGGTCFNTLGGHSCV
CVNGWTGESCSQNIDDCATAVCFHGATCHDRVASFYCACPMGKTGLLCHL

DDACVSNPCHEDATCDTNPVNGRATCTCPPGFTGGACDQDVDECSTGANP
CEHLGRCVNTQGSFLCQCGRGYTGPRCETDVNECLSGPCRNQATCLDRTG
QFTCTCMAGFTGTYCEVDIDECQSSPCVNGGVCKDRVNGFSCTCPSGFSG
STCQLDVDECASTPCRNGAKCVDQPDGYECRCAEGFEGTLCDRNVDDCSP
DPCHHGRCVDGIASFSCACAPGYTGTRCESQVDECRSQPCRHGGKCLDLV
DKYLCRCPSGTTGVNCEVNIDDCASNPCTFGVCRDGINRYDCVCQPGFTG
PLCNVEINECASSPCGEGGSCVDGENGFRCLCPPGSLPPLCLPPSHPCAH
EPCSHGTCYDAPGGFRCVCEPGWSGPRCSQSLARDACESQPCRAGGTCSS
DGMGFHCTCPPGVQQRQCELLSPCIPNPCEHGGRCESAPGQLPVCSCPQG
WQGPRCQQDVDECAGPAPCGPHGTCTNLAGSFSCTCHGGYTGPSCDQDIN
DCDPNPCLNGGSCQDGVGSFSCSCLPGFAGPRCARDVDECLSNPCGPGTC
TDHVASFTCTCPPGYGGFHCEODLPDCSPSSCFNGGTCVDGVNSFSCLCR
PGYTGAHCQHEADPCLSRPCLHGGVCSAAHPGFRCTCLESFTGPQCQTLV
DWCSRQPCOQGGRCVQTGAYCLCPPGWSGRLCDIRSLPCREAAAQTGVRL
EQLCQAGGQCVDEDSSHYCVCPEGRTGSHCEQEVDPCLAQPCQHGGTCRG
YMGGYMCECLPGYNGDNCEDDVDECASQPCQHGGSCIDLVARYLCSCPPG
TLGVLCEINEDDCGPGPPLDSGPRCLHNGTCVDLVGGFRCTCPPGYTGLR
CEADINECRSGACHAAHTRDCLQDPGGGFRCLCHAGFSGPRCQTVLSPCE
SQPCQHGGQCRPSPGPGGGLTFTCHCAQPFWGPRCERVARSCRELQCPVG
VPCQQTPRGPRCACPPGLSGPSCRSFPGSPPGASNASCAAAPCLHGGSCR
PAPLAPFFRCACAQGWTGPRCEAPAAAPEVSEEPRCPRAACQAKRGDQRC
DRECNSPGCGWDGGDCSLSVGDPWRQCEALQCWRLFNNSRCDPACSSPAC
LYDNFDCHAGGRERTCNPVYEKYCADHFADGRCDQGCNTEECGWDGLDCA
SEVPALLARGVLVLTVLLPPEELLRSSADFLQRLSAILRTSLRFRLDAHG
QAMVFPYHRPSPGSEPRARRELAPEVTGSVVMLEIDNRLCLQSPENDHCF
PDAQSAADYLGALSAVERLDFPYPLRDVRGEPLEPPEPSVPLLPLLVAGA
VLLLVILVLGVMVARRKREHSTLWFPEGFSLHKDVASGHKGRREPVGQDA
LGMKNMAKGESLMGEVATDWMDTECPEAKRLKVEEPGMGAEEEAVDCRQWT
QHHLVAADIRVAPAMALTPPQGDADADGMDVNVRGPDGFTPLMLASFCGG
ALEPMPTEEDEADDTSASIISDLTCQGAQLGARTDRTGETALHLAARYAR
ADAAKRLLDAGADTNAQDHSGRTPLHTAVTADAQGVFQILIRNRSTDLDA
RMADGSTALILAARLAVEGMVEELIASHADVNAVDELGKSALHWAAAVNN
VEATLALLKNGANKDMQDSKEETPLFLAAREGSYEAAKLLLDHFANREIT
DHLDRLPRDVAQERLHQDIVRLLDQPSGPRSPPGPHGLGPLLCPPGAFLP
GLKAAQSGSKKSRRPPGKAGLGPQGPRGRGKKLTIACPGPLADSSVTLSP
VDSLDSPRPFGGPPASPGGFPLEGPYAAATATAVSLAQLGGPGRAGLGRQ
PPGGCVLSLGLLNPVAVPLDWARLPPPAPPGPSFLLPLAPGPQLLNPGTP
VSPQERPPPYLAVPGHGEEYPAAGAHSSPPKARFLRVPSEHPYLTPSPES
PEHWASPSPPSLSDWSESTPSPATATGAMATTTGALPAQPLPLSVPSSLA
QAQTQLGPQPEVTPKRQVLA.

Human neurogenic locus notch homolog protein 4 pre-protein NP_004548.3:

(SEQ ID NO: 248)
MQPPSLLLLLLLLLLLCVSVVRPRGLLCGSFPEPCANGGTCLSLSLGQGT
CQCAPGFLGETCQFPDPCQNAQLCQNGGSCQALLPAPLGLPSSPSPLTPS
FLCTCLPGFTGERCQAKLEDPCPPSFCSKRGRCHIQASGRPQCSCMPGWT
GEQCQLRDFCSANPCVNGGVCLATYPQIQCHCPPGFEGHACERDVNECFQ
DPGPCPKGTSCHNTLGSFQCLCPVGQEGPRCELRAGPCPPRGCSNGGTCQ
LMPEKDSTFHLCLCPPGFTGPDCEVNPDNCVSHQCQNGGTCQDGLDTYTC
LCPETWTGWDCSEDVDECETQGPPHCRNGGTCQNSAGSFHCVCVSGWGGT
SCEENLDDCIAATCAPGSTCIDRVGSFSCLCPPGRTGLLCHLEDMCLSQP
CHGDAQCSTNPLTGSTLCLCQPGYSGPTCHQDLDECLMAQQGPSPCEHGG
SCLNTPGSFNCLCPPGYTGSRCEADHNECLSQPCHPGSTCLDLLATFHCL
CPPGLEGQLCEVETNECASAPCLNHADCHDLLNGFQCTCLPGFSGTRCEE
DIDECRSSPCANGGQCQDQPGAFHCKCLPGFEGPRCQTEVDECLSDPCPV
GASCLDLPGAFFCLCPSGFTGQLCEVPLCAPNLCQPKQTCKDQKDKANCL
CPDGSPGCAPPEDNCTCHHGHCQRSSCVCDVGWTGPECEAELGGCISAPC
AHGGTCYPQPSGYNCTCPTGYTGPTCSEEMTACHSGPCLNGGSCNPSPGG
YYCTCPPSHTGPQCQTSTDYCVSAPCFNGGTCVNRPGTFSCLCAMGFQGP
RCEGKLRPSCADSPCRNRATCQDSPQGPRCLCPTGYTGGSCQTLMDLCAQ
KPCPRNSHCLQTGPSFHCLCLQGWTGPLCNLPLSSCQKAALSQGIDVSSL
CHNGGLCVDSGPSYFCHCPPGFQGSLCQDHVNPCESRPCQNGATCMAQPS
GYLCQCAPGYDGONCSKELDACQSQPCHNHGTCTPKPGGFHCACPPGFVG
LRCEGDVDECLDQPCHPTGTAACHSLANAFYCQCLPGHTGQWCEVEIDPC
HSQPCFHGGTCEATAGSPLGFTCHCPKGFEGPTCSHRAPSCGFHHCHHGG
LCLPSPKPGFPPRCACLSGYGGPDCLTPPAPKGCGPPSPCLYNGSCSETT
GLGGPGFRCSCPHSSPGPRCQKPGAKGCEGRSGDGACDAGOSGPGGNWDG
GDCSLGVPDPWKGCPSHSRCWLLFRDGQCHPQCDSEECLFDGTDCETPPA
CTPAYDQYCHDHFHNGHCEKGCNTAECGWDGGDCRPEDGDPEWGPSLALL
VVLSPPALDQQLFALARVLSLTLRVGLWVRKDRDGRDMVYPYPGARAEEK
LGGIRDPTYQERAAPQTQPLGKETDSLSAGFVVVMGVDLSRCGPDHPASR
CPWDPGLLLRFLAAMAAVGALEPLLPGPLLAVHPHAGTAPPANQLPWPVL
CSPVAGVILLALGALLVLQLIRRRRREHGALWLPPGFTRRPRTQSAPHRR
RPPLGEDSTGLKALKPKAEVDEDGVVMCSGPEEGEEVGQAEETGPPSTCQ
LWSLSGGCGALPQAAMLIPPQESEMEAPDLDTRGPDGVTPLMSAVCCGEV
QSGTFQGAWLGCPEPWEPLLDGGACPQAHTVGTGETPLHLAARFSRPTAA
RRLLEAGANPNQPDRAGRTPLHAAVAADAREVCQLLLRSRQTAVDARTED
GTTPLMLAARLAVEDLVEELIAAQADVGARDKWGKTALHWAAAVNNARAA
RSLLQAGADKDAQDNREQTPLFLAAREGAVEVAQLLLGLGAARELRDQAG
LAPADVAHQRNHWDLLTLLEGAGPPEARHKATPGREAGPFPRARTVSVSV
PPHGGGALPRCRTLSAGAGPRGGGACLQARTWSVDLAARGGGAYSHCRSL

-continued
SGVGAGGGPTPRGRRFSAGMRGPRPNPAIMRGRYGVAAGRGGRVSTDDWP
CDWVALGACGSASNIPIPPPCLTPSPERGSPQLDCGPPALQHMPINQGGE
GKK.

In some embodiments, the Notch core of the chimeric Notch receptor polypeptide contains a portion of SEQ ID NO 244 SEQ ID NO 245, SEQ ID NO: 246, SEQ ID NO: 247, or SEQ ID NO: 248. In some embodiments, the chimeric Notch receptor polypeptide contains 50 to 1000 amino acids of SEQ ID NO: 244 SEQ ID NO. 245, SEQ ID NO: 246, SEQ ID NO: 247, or SEQ ID NO: 248. In some embodiments, the chimeric Notch receptor polypeptide contains 50 to 900 amino acids, 100 to 800 amino acids, 200 to 700 amino acids, 300 to 600 amino acids, 400 to 500 amino acids of SEQ ID NO: 244 SEQ II) NO 245, SEQ ID NO: 246, SEQ ID NO: 247, or SEQ ID NO: 248. In some embodiments, the amino acid sequence of Notch, as described herein, is at least 80% identical to a corresponding amino acid sequence in SEQ II) NO: 244 SEQ ID NO. 245, SEQ ID NO: 246, SEQ ID NO: 247, or SEQ ID NO: 248. In some embodiments, the amino acid sequence of Notch is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO. 244 SEQ ID NO. 245, SEQ ID NO: 246, SEQ ID NO: 247, or SEQ ID NO. 248 In some embodiments, the amino acid sequence of Notch, as described herein, can vary from the amino acid sequence of SEQ ID NO: 244 SEQ ID NO: 245, SEQ ID NO: 246, SEQ ID NO: 247, or SEQ ID NO: 248 by 1 to 50 amino acids, e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amino acids. Human Notch1 core regulatory domain (human Notch1 core regulatory region, hN1c) ile1427 after the last EGF repeat on NECD of human Notch1 (NP_060087) was used as the N-terminus of hN1c. The last Arg1762 of the 5 consecutive basic amino acids (RKRRR (SEQ ID NO: 249)) at the C-terminus of the transmembrane domain serves as the C-terminus of hN1C. The sequences of hN1c and mN1c were highly similar.

(SEQ ID NO: 250)
ILDYSFGGGAGRDIPPPLIEEACELPECQEDAGNKVCSLQCNNHACGWDGG
DCSLNFNDPWKNCTQSLQCWKVFSDGHCDSQCNSAGCLFDGFDCQRAEGQC
NPLYDQYCKDHFSDGHCDQGCNSAECEWDGLDCAEHVPERLAAGTLVVVVL
MPPEQLRNSSFHFLRELSRVLHTNVVFKRDAHGQQMIFPYYGREEELRKHP
IKRAAEGWAAPDALLGQVKASLLPGGSEGGRRRRELDPMDVRGSIVYLEID
NRQCVQASSQCFQSATDVAAFLGALASLGSLNIPYKIEAVQSETVEPPPPA
QLHFMYVAAAAFVLLFFVGCGVLLSRKRRRNRR 250) with hN1c at positions 1-294, 295-336 is TMD. Human Notch2 core regulatory domain (human Notch2 core regulatory region, hN2c): leu1413 after the last EGF repeat on NECD of human Notch2(NP_077719) was used as the N-terminus of hN2c. The last Arg1704 of the 4 consecutive basic amino acids (KRKR (SEQ ID NO: 258)) at the C-terminus of the transmembrane domain serves as the C-terminus of hN2C. LYTAPPSTPPATCLSQYCAD-KARDGVCDEACNSHACQWDGGDCSLTMENP-WANCSSP LPCWDYTINNQCDELCNTVECLFDN-FECQGNSKTCKYDKYCADHFKDNHCDQGCNSEE CGWDGLDCAADQPENLAEGTLVIVVLMPPEQLLQ-
DARSFLRALGTLLHTNLRIKRDSQ GELMVYPYY-
GEKSAAMKKQRMTRRSLPGEQEQEVAGSKVFLEI-
DNRQCVQDSDHCFK NTDAAAALLASHAIQGTLSY-
PLVSVVSESLTPERTQLLYLLAVAVVIILFIILLGVI-
MAKR KR (SEQ ID NO: 251). Human Notch3 core regulatory domain (human Notch3 core regulatory region, hN3 c): pro1375 after the last EGF repeat on NECD of human Notch3 (NP-000426) was used as the N-terminus of hN3 c. The last Arg1669 of the 4 consecutive basic amino acids (RRKR SEQ ID NO: 259)) at the C-terminus of the transmembrane domain served as the C-terminus of hN3C.
PAAAPEVSEEPRCPRAACQAKRGDQRCDRECNS-
PGCGWDGCDCSLSVGDPWRQCEAL QCWRLFNN-
SRCDPACSSPACLYDNFDCHAGGRERTCNPVYEKY-
CADIHFADGRCDQGC NTEECGWDGLDCASEVPAL-
LARGVLVLTVLLPPEELLRSSADFLQRLSAILRTSLRFRLD
AHGQAMVFPYHRPSPGSEPRARRELAPEVIGSVVM-
LEIDNRLCLQSPENDHCFPDAQSA ADYLGALSAVER-
LDFPYPLRDVRGEPLEPPEPSVPLLPLLVAGAVLLL-
VILVLGVMVAR RKR (SEQ ID NO: 252). Human Notch4 core regulatory domain (human Notch4 core regulatory region, hN3 c) pro1162 after the last EGF repeat on NECD of human Notch4 (NP-004548) was used as the N-terminus of hN4 c. The last Arg1476 of the 5 consecutive basic amino acids (RRRRRRR (SEQ ID NO 253)) at the C-terminus of the transmembrane domain serves as the C-terminus of hN4C.

(SEQ ID NO: 254)
PHSSPGPRCQKPGAKGCEGRSGDGACDAGCSGPGGNWDGGDCSLGVPDPWK

GCPSHSRCWLLFRDGQCHPQCDSEECLFDGYDCETPPACTPAYDQYCHDHF

HNGHCEKGCNTAECGWDGGDCRPEDGDPEWGPSLALLVVLSPPALDQQLFA

LARVLSLTLRVGLWVRKDRDGRDMVYPYPGARAEEKLGGTRDPTYQERAAP

QTQPLGKETDSLSAGFVVVMGVDLSRCGPDHPASRCPWDPGLLLRFLAAMA

AVGALEPLLPGPLLAVHPHAGTAPPANQLPWPVLCSPVAGVILLALGALLV

LQLIRRRRR.

As noted above, a synNotch receptor polypeptide of the present disclosure comprises an intracellular domain that is released following binding of the anti-PSCA binding domain to PSCA, where binding of the synNotch receptor polypeptide to PSCA induces cleavage of an above-mentioned proteolytic cleavage site. The intracellular domain comprises an amino acid sequence that is heterologous to the synNotch receptor polypeptide. In other words, the intracellular domain comprises an amino acid sequence that is not naturally present in a synNotch receptor polypeptide.

The intracellular domain, when released from the synNotch receptor polypeptide, provides an effector function, where the effector functions change in transcription of a target gene, which in this disclosure is the expression of an anti-PSMA CAR. In some embodiments, the intracellular domain, when released from the synNotch receptor polypeptide, provides for an increase in transcription of an anti-PSMA CAR.

In some cases, a transcription factor may be an artificial transcription factor (ATF) including but not limited to e.g., Zinc-finger-based artificial transcription factors (including e.g., those described in Sera T. Adv Drug Deliv Rev. 2009 61(7-8):513-26; Collins et al. Curr Opin Biotechnol. 2003 14(4):371-8; Onori et al. BMC Mol Biol. 2013 14:3 the disclosures of which are incorporated herein by reference in their entirety). In some embodiments, the intracellular domain is a transcriptional activator.

In some cases, the transcriptional activator is GAL4-VP16. In some cases, the transcriptional activator is GAL4-VP64. In some cases, the transcriptional activator is Tbx21. In some cases the transcriptional activator is an engineered protein, such as a zinc finger or TALE based DNA binding domain fused to an effector domain such as VP64 (transcriptional activation) or KRAB (transcriptional repression). A variety of other transcriptional transactivators are known in the art is suitable for use.

In some cases, the intracellular domain comprises an amino acid sequence having at least 75%, at least 80%, at least 85%, at least 90%, at least 95%, at least 98%, at least 99%, or 100%, amino acid sequence identity to the following GAL4-VP64 sequence:

(SEQ ID NO: 207)
MKLLSSIEQACDICRLKKLKCSKEKPKCAKCLKNNWECRYSPKTKRSPLTR

AHLTEVESRLERLEQLFLLIFPREDLDMILKMDSLQDIKALLTGLFVQDNV

NKDAVTDRLASVETDMPLTLRQHRISATSSSEESSNKGQRQLTVS

In some cases, the intracellular domain comprises an amino acid sequence having at least 75%, at least 80%, at least 85%, at least 90%, at least 95%, at least 98%, at least 99%, or 100%, amino acid sequence identity to the following GAL4-VP64 sequence: MKLLSSIEQACDI-CRLKKLKCSKEKPKCAKCLKNNWECRYSPKTKR-SPLTRAHLTEVES RLERLEQLFLLIFPREDLDMIL-KMDSLQDIKALLTGLFVQDNVNKDAVTDRLAS-VETDM PLTLRQHRISATSSSEESSNKGQRQLTVS-AAAGGSGGSGGSDALDDFDLDMLGSDALDD FDLDMLGSDALDDFDLDMLGSDALDDFDLDMLGS (SEQ ID NO: 208); and has a length of from 208 to 214 amino acids (e.g., 208, 209, 210, 211, 212, 213, or 214 amino acids).

In some cases, the intracellular domain comprises an amino acid sequence having at least 75%, at least 80%, at least 85%, at least 90%, at least 95%, at least 98%, at least 99%, or 100%, amino acid sequence identity to the following GAL4-VP64 sequence: MKLLSSIEQACDI-CRLKKLKCSKEKPKCAKCLKNNWECRYSPKTKR-SPLTRAHLTEVES RLERLEQLFLLIFPREDLDMIL-KMDSLQDIKALLTGLFVQDNVNKDAVTDRLAS-VETDM PLTLRQHRISATSSSEESSNKGQRQLTVSG-GGSGGGSDALDDFDLDMLGSDALDDFDLD MLGS-DALDDFDLDMLGSDALDDFDLDML (SEQ ID NO: 209), and has a length of from 208 to 214 amino acids (e.g., 203, 203, 204, 205, 206, 207, or 208 amino acids).

The present disclosure comprises nucleic acids encoding antigen binding systems provided herein, comprising without limitation nucleic acids encoding anti-PSCA synNotch antigen receptors. The nucleic acid sequence of SEQ ID NO: 151 comprises and provides exemplary nucleic acid sequences corresponding to and encoding each of SEQ ID NOs: 150 and 152-160. The nucleic acid sequence of SEQ ID NO: 162 comprises and provides exemplary nucleic acid sequences corresponding to and encoding each of SEQ ID NOs: 161 and 163-191. The nucleic acid sequence of SEQ ID NO: 173 comprises and provides exemplary nucleic acid sequence corresponding to and encoding SEQ ID NOs: 172.

In an embodiment an anti-PSCA synNotch receptor peptide comprises or consist of an amino acid sequence having at least 75%, at least 80%, at least 85%, at least 90%, at least 95%, at least 98%, at least 99%, or 100%, amino acid sequence identity to DIVMTQSPLSLPVTPGEPASIS-CRSSQSLLHSNGYNYLVWYLQKPGQSPQLLIYLG-SIRAS GVPDRFSGSGSGTDFTLKISRVEAE-DVGVYYCMQPLQTPITFGQGTRLEIKGSTSGSGKP GSGEGSTKGQVQLQQWGAGLLKPSETLSLTCA-VYGGSFSGNYWSWIRQPPGKGLEWIG EINHSG-STNYNPSLKSRVTISVDTSKNQFSLKLSSVTAAD-TAVYYCARGGSYNYFDYWG QGTLVTVSSILDYSFT-GGAGRDIPPPQIEEACELPECQVDAGNKVCNLQCNN-HACGWDG GDCSLNFNDPWKNCTQSLQCWKYFS-DGHCDSQCNSAGCLFDGFDCQLTEGQCNPLYD QYCKDHFSDGHCDQGCNSAECEWDGLDCAEHV-PERLAAGTLVLVVLLPPDQLRNNSF HFLRELSHV-LHTNVVFKRDAQGQQMIFPYYGHEEELRKH-PIKRSTVGWATSSLLPGTSG GRQRRELDPMDIRG-SIVYLEIDNRQCVQSSSQCFQSATDVAAFL-GALASLGSLNIPYKIE AVKSEPVEPPLPSQLHLMY-VAAAAFVLLFFVGCGVLLSRKRRRQHGQLWFP-EGFKVSE ASKKKRREPLGEDSVGLKPLKNASD-GALMDDNQNEWGDEDLETKKFRFEEPVVGSMK LLSSIEQACDICRLKKLKCSKEKPKCAKCLKNNWE-CRYSPKTKRSPLTRAHLTEVESRLE RLEQLFLLIF-PREDLDMILKMDSLQDIKALLTGLFVQDNVNK-DAVTDRLASVETDMPLT LRQHRISATSSSEESSNK-GQRQLTVSGGGSGGGSDALDDFDLDMLGSDAL-DDFDLDML GSDALDDFDLDMLGSDALDDFDLDML (SEQ ID NO: 210). In embodiments an anti-PSCA synNotch receptor is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 221)
gacatcgtgatgacacagagccctctgtctttacccgttaccccggtgaa cccgctagcatcagctgcagaagctcccagtcttactccacagcaacggc tacaactatttagtgtggtatttacagaaacccggccagagcccccagctg ctgatttatctgggctccattcgtgctagcggcgtgcccgatagattttcc ggcagcggaagcggcaccgacttcactttaaagatctctcgtgtggaggcc gaggacgtgggcgtctactactgtatgcagcctctgcagaccccccattacc ttcggccaaggtactcgtctggaaatcaagggcagcaccagcggcagcgga aaacccggaagcggcgagggaagcaccaaaggccaagttcagctgcagcag tggggagctggtttactgaagcctagcgagacactgtctttaacatgcgcc gtgtacggcggaagcttcagcggcaactattggagctggatcagacagcct cccggtaagggtttagagtggatcggcgagatcaaccactccggctccacc aactataacccctcttaaagtctcgtgtgaccatctccgtggacaccagc aagaaccagttctcttaaagctgagctccgtgacagccgccgacaccgct gtgtattactgtgctcgtggcggcagctacaactacttcgactactgggc caaggtaccctcgtgaccgtgtccagcatcctggactacagcttcacaggt ggcgctgggcgcgacattcccccaccgcagattgaggaggcctgtgagctg cctgagtgccaggtggatgcaggcaataaggtctgcaacctgcagtgtaat aatcacgcatgtggctgggatggtggcgactgctccctcaacttcaatgac ccctggaagaactgcacgcagtctctacagtgctggaagtattttagcgac ggccactgtgacagccagtgcaactcggccggctgcctctttgatggcttc -continued gactgccagctcaccgagggacagtgcaaccccctgtatgaccagtactgc aaggaccacttcagtgatggccactgcgaccagggctgtaacagtgccgaa tgtgagtgggatggcctagactgtgctgagcatgtacccgagcggctggca gccggcaccctggtgctggtggtgctgcttccacccgaccagctacggaac aactccttccactttctgcgggagctcagccacgtgctgcacaccaacgtg gtcttcaagcgtgatgcgcaaggccagcagatgatcttcccgtactatggc cacgaggaagagctgcgcaagcacccaatcaagcgctctacagtgggttgg gccacctcttcactgcttcctggtacaagtggtgggcgccagcgcagggag ctggacccatggacatccgtggctccattgtctacctggagatcgacaac cggcaatgtgtgcagtcatcctcgcagtgcttccagagtgccaccgatgtg gctgccttcctaggtgctcttgcgtcacttggcagcctcaatattccttac aagattgaggccgtgaagagtgagccggtggagcctccgctgccctcgcag ctgcacctcatgtacgtggcagcagccgccttcgtgctcctgttctttgtg ggctgtggggtgctgctgtcccgcaagcgccggcggcagcacggtcaactt tggttcccagaaggcttcaaggtctccgaagcctccaagaaaaagcgaagg gaaccactcggggaagacagtgtagggttgaaacctttgaagaacgccagc gatggagccttgatggatgataaccaaaatgaatggggtgatgaagacctg gaaaccaaaaagtttcgctttgaggaacctgtggtaggatccatgaaactc cttagcagcatcgaacaggcttgcgacatctgcaggttgaaaaaactcaag tgctcaaaagaaaagcctaagtgcgcaaagtgccttaaaaacaattgggaa tgtcgctatagccccaagacaaagcggagccctctcacgagagcacacctg actgaggtagaatctcgcttggagaggctggaacagcttttcctgcttatc tttccacgcgaggatctcgatatgatcctcaaaatggactccctccaggac atcaaagctctgctgactggactgtttgtacaggataatgtgaacaaggac gctgtgacagacagattggcaagcgtggagaccgatatgcccctgaccctt agacagcaccggatcagtgccacctcttctagcgaggaaagttcaaataaa ggacagcgccagctgacggtgagtggcggtggaagcggaggaggttccgac gctcttgatgatttcgatctcgacatgctgggatcagacgctctcgacgac ttcgatttggacatgcttggatccgacgctctcgatgatttcgacctcgac atgctcggatccgatgctctggatgactttgatcttgatatgctg As disclosed herein the intracellular domain is a polypeptide that, when released upon binding of the anti-PSCA binding domain to PSCA, induces production, in a cell that expresses the synNotch polypeptide, of an anti-PSMA CAR.

As the intracellular domain of a synNotch receptor polypeptide of the present disclosure, when released upon binding of the first member of the specific binding pair to a second member of the specific binding pair, may induce the expression of various polypeptides as described herein, in some instances, induced expression of two or more polypeptides may generate a logic gated circuit. Such logic gated circuits may include but are not limited to e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates).

In some embodiments an anti-PSCA synNotch receptor comprises a Myc tag, such as having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the amino acid sequence set forth as SEQ ID NO. 75 (EQKLISEEDL: SEQ ID NO: 222). In an embodiment, a Myc tag is encoded by the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to gagcagaagct-gattagcgaggaggattta (SEQ ID NO: 223).

Both engineered T cell receptors (TCR) and chimeric antigen receptor (CAR) therapies harness the specificity and immunotherapeutic effect of T cells for the treatment of a wide variety of malignancies. Some studies suggest that these therapies may be susceptible to the suppressive factors in the TME that result from T cell suppression by TGF-β (Bendle et al., J Immunol, 191:3232-3239 (2013) and Vong et al., Blood, 130:1791 (2017)). The present disclosure contemplates the use of the DN TGF-β Receptors described herein in combination with either TCR or CAR therapies as a way to maintain, or in some cases, restore TCR and/or CAR expansion in the presence of TGF-β suppression.

Chimeric antigen receptor (CAR) T cell therapy provides another therapeutic approach against tumor progression. Clinically, investigators have demonstrated that CAR expansion and persistence is correlated with therapeutic efficacy. Without being bound by any theory, it is believed that TGF-β repressed T cell populations found in the TME may be limiting CAR T cell expansion and persistence in patients who do not respond to CAR therapy. The resulting inhibitory cytokines in the TME are believed to limit CAR cell function and expansion. Thus, TGF-β could limit the efficacy of therapeutic engineered T cells.

Combining any CAR constructs or TCRs as described herein with a DN TGF-β receptors may restore, maintain or enhance the therapeutic effect of CAR T therapy challenged by TGF-β suppression. Thus, in one embodiment described herein, the DN TGF-β receptors, for example DN TGF-βRI or RII, are co-expressed in a T cell or an NK cell with an anti-PSMA CAR, either a constitutively or conditionally expressed as described herein. In some embodiment, the DN TGF-β receptors, for example DN TGF-βRI or RII, are co-expressed in a T cell or NK cell with an anti-PSMA CAR, such as described herein. In some embodiments the DN TGF-β receptors, for example DN TGF-βRI or RII, are co-expressed in a T cell or NK cell with an anti-PSMA CAR and an anti-PSCA synNotch receptor, such as described herein. DN TGF-β receptors are described in International Patent Publication No. PCT/US2020/070157, which is hereby incorporated herein by reference in its entirety.

Dominant negative TGF-β Receptors are designed to inhibit the immunosuppressive effects of TGF-β in the TME. These constructs may also stimulate cytokine signaling to enhance T cell or NK function in the TME. The constructs described herein may be used alone or in combination with each other, and/or in combination with other immunotherapies, in order to inhibit TGF-β induced immunosuppression.

The engineered TGF-β receptors may comprise an N-terminal signal peptide at the N-terminus, for example at the N-terminus of the extracellular ligand binding domain of DN TGF-βRI. In one embodiment, a heterologous signal peptide may be used. The extracellular domain of a DN TGF-βRI may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as a DN TGF-βRI is generally expressed at the cell surface as a mature protein lacking the signal peptide, whereas the precursor form of the polypeptide includes the signal peptide. Any suitable signal sequence may be used. In one embodiment described herein, the DN TGF-βRI comprises the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 224 or a portion thereof.

```
                                           (SEQ ID NO: 224)
            MEAAVAAPRPRLLLLVLAAAAAAAAALLPGATA.
```

A signal peptide or leader may facilitate the glycosylation of DN TGF-βRI. The signal sequence or leader is a peptide sequence generally present at either the N-terminus or C-terminus of newly synthesized proteins that directs their entry into the secretory pathway. In the present disclosure, the signal peptide is joined to the N-terminus of the extracellular antigen-binding domain of the DN TGF-βRI as a fusion protein. In one embodiment, the DN TGF-βRI comprises an extracellular ligand binding domain having at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRI and a signal peptide at the N-terminus of the extracellular domain TGF-βRI, having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 225.

```
                                           (SEQ ID NO: 225)
MEAAVAAPRPRLLLLVLAAAAAAAAALLPGATALQCFCHLCTKDNFTCVTD

GLCFVSVTETTDKVIHNSMCIAEIDLIPRDRPFVCAPSSKTGSVTTTYCCN

QDHCNKIELPTTVKSSPGLGPVEL.
```

The engineered DN TGF-βRII constructs may also comprise an N-terminal signal peptide at the N-terminus of the extracellular ligand binding domain of TGF-βRII. In one embodiment, a heterologous signal peptide may be used. The extracellular domain of a DN TGF-βRII may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as a DN TGF-βRII is generally found at the cell surface as a mature protein lacking the signal peptide, whereas the precursor form of the polypeptide includes the signal peptide. Any suitable signal sequence may be used. In one embodiment described herein, the DN TGF-βRII constructs described herein comprise a signal sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 226 or a portion thereof. MGRGLLRGLWPLHIVLWTRIAS (SEQ ID NO: 226). In another embodiment, the signal sequence is derived from Colony Stimulating Factor 2 Receptor Alpha subunit (CSF2Rα) comprising the amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 137 or a portion thereof. MLLLVTSLLLCELPHPAFLLIP (SEQ ID NO: 137). The signal sequences described herein may also be optionally used with any suitable protein tag, including but not limited to: V5-tag, myc-tag, HA-tag, Spot-tag, NE-tag. In one embodiment described herein, the signal sequence and tag comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 227. MLLLVTSLLLCELPHPAFLLIPEQKLISEEDL (SEQ ID NO: 227).

It is understood that use of this signal peptide is exemplary. Any suitable signal peptide, as are well known in the art, may be applied to the DN TGF-βRI or RII to provide cell surface expression in an immune cell. Useful signal peptides may be derived from cell surface proteins naturally expressed in the T cell NK cell or precursor cell thereof, including any of the signal peptides of the polypeptides disclosed herein. Thus, any suitable signal peptide may be utilized to direct the DN TGF-βRI RII to be expressed at the cell surface of a T cell or NK cell.

In embodiments, a DN TGF-βRI comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 228.

(SEQ ID NO: 228)
MEAAVAAPRPRLLLLVLAAAAAAAAALLPGATALQCFCHLCTKDNFTCVTD

GLCFVSVTETTDKVIHNSMCIAEIDLIPRDRPFVCAPSSKTGSVTTTYCCN

QDHCNKIELPTTVKSSPGLGPVELAAVIAGPVCFVCISLMLMVYIRVNRQ.

In one embodiment a DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 229:

(SEQ ID NO: 229)
MGRGLLRGLWPLHIVLWTRIASTIPPHVQKSVNNDMIVTDNNGAVKFPQLC

KFCDVRFSTCDNQKSCMSNCSITSICEKPQEVCVAVWRKNDENITLETVCH

DPKLPYHDFILEDAASPKCIMKEKKKPGETFFMCSCSSDECNDNIIFSEEY

NTSNPDLLLVIFQVTGISLLPPLGVAISVIIIFYCYRVNRQ.

In an embodiment a DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 230.

(SEQ ID NO: 230)
TIPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPD.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the wild-type TGF-βRII as shown in the amino acid sequence of SEQ ID NO: 231.

(SEQ ID NO: 231)
TIPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPDLLLVIFQVTGISLLPP

LGVAISVIIIFYCY.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 232.

(SEQ ID NO: 232)
TIPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPDSGPILLTISILSFFSV

ALLVIL.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) as shown in the amino acid sequence of SEQ ID NO: 233.

(SEQ ID NO: 233)
TIPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPDSGPILLTCPTISILSF

FSVALLVIL.

T In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 234.

(SEQ ID NO: 234)
ACVLWKKRIKPIVWPSLPDHKKTLEHLCKKPRKNLNVSFNPESFLDCQIHR

VDDIQARDEVEGFLQDTFPQQLEESEKQRLGGDVQSPNCPSEDVVITPESF

In one embodiment described herein, the DN TGF-βRII comprises an amino acid sequence at least 75% sequence identity to (such as, at least 75%, at least 80%, at least 90%, at least 95%, or 100% identity e.g., 85-90%, 85-95%, 85-100%, 90-95%, 90-100%, or 95-100%) the amino acid sequence of SEQ ID NO: 235.

(SEQ ID NO: 235)
TIPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIMK
EKKKPGETFFMCSCSSDECNDNIIFSEEYNTSNPDSGPILLTISILSFFSV
ALLVILACVLWKKRIKPIVWPSLPDHKKTLEHLCKKPRKNLNVSFNPESFL
DCQIHRVDDIQARDEVEGFLQDTFPQQLEESEKQRLGGDVQSPNCPSEDVV
ITPESFGRDSSLTCLAGNVSACDAPILSSSRSLDCRESGKNGPHVYQDLLL
SLGTTNSTLPPPFSLQSGILTLNPVAQGQPILTSLGSNQEEAYVTMSSFYQ
NQ.

In one embodiment described herein, the DN TGF-βRII comprises an amino acid sequence at least 75% sequence identity to (such as, at least 75%, at least 80%, at least 90%, at least 95%, or 100% identity; e.g., 85-90%, 85-95%, 85-100%, 90-95%, 90-100%, or 95-100%) to the amino acid sequence of SEQ ID NO: 236.

(SEQ ID NO: 236)
TIPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIMK
EKKKPGETFFMCSCSSDECNDNIIFSEEYNTSNPDSGPILLTCPTISILSF
FSVALLVILACVLWKKRIKPIVWPSLPDHKKTLEHLCKKPRKNLNVSFNPE
SFLDCQIHRVDDIQARDEVEGFLQDTFPQQLEESEKQRLGGDVQSPNCPSE
DVVITPESFGRDSSLTCLAGNVSACDAPILSSSRSLDCRESGKNGPHVYQD
LLLSLGTTNSTLPPPFSLQSGILTLNPVAQGQPILTSLGSNQEEAYVTMSS
FYQNQ.

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence of SEQ ID NO: 237.

(SEQ ID NO: 237)
MLLLVTSLLLCELPHPAFLLIPTIPPHVQKSVNNDMIVTDNNGAVKFPQLC
KFCDVRFSTCDNQKSCMSNCSITSICEKPQEVCVAVWRKNDENITLETVCH
DPKLPYHDFILEDAASPKCIMKEKKKPGETFFMCSCSSDECNDNIIFSEEY
NTSNPD.

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 238.

(SEQ ID NO: 238)
MLLLVTSLLLCELPHPAFLLIPEQKLISEEDLTIPPHVQKSVNNDMIVTDN
NGAVKFPQLCKFCDVRFSTCDNQKSCMSNCSITSICEKPQEVCVAVWRKND
ENITLETVCHDPKLPYHDFILEDAASPKCIMKEKKKPGETFFMCSCSSDEC
NDNIIFSEEYNTSNPD.

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 239.

(SEQ ID NO: 239)
MLLLVTSLLLCELPHPAFLLIPTIPPHVQKSVNNDMIVTDNNGAVKFPQLC
KFCDVRFSTCDNQKSCMSNCSITSICEKPQEVCVAVWRKNDENITLETVCH
DPKLPYHDFILEDAASPKCIMKEKKKPGETFFMCSCSSDECNDNIIFSEEY
NTSNPDSGPILLTISILSFFSVALLVILACVLWKKRIKPIVWPSLPDHKKT
LEHLCKKPRKNLNVSFNPESFLDCQIHRVDDIQARDEVEGFLQDTFPQQLE
ESEKQRLGGDVQSPNCPSEDVVITPESFGRDSSLTCLAGNVSACDAPILSS
SRSLDCRESGKNGPHVYQDLLLSLGTTNSTLPPPFSLQSGILTLNPVAQGQ
PILTSLGSNQEEAYVTMSSFYQNQ.

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 240.

(SEQ ID NO: 240)
MLLLVTSLLLCELPHPAFLLIPEQKLISEEDLTIPPHVQKSVNNDMIVTDN
NGAVKFPQLCKFCDVRFSTCDNQKSCMSNCSITSICEKPQEVCVAVWRKND
ENITLETVCHDPKLPYHDFILEDAASPKCIMKEKKKPGETFFMCSCSSDEC
NDNIIFSEEYNTSNPDSGPILLTISILSFFSVALLVILACVLWKKRIKPIV
WPSLPDHKKTLEHLCKKPRKNLNVSFNPESFLDCQIHRVDDIQARDEVEGF
LQDTFPQQLEESEKQRLGGDVQSPNCPSEDVVITPESFGRDSSLTCLAGNV
SACDAPILSSSRSLDCRESGKNGPHVYQDLLLSLGTTNSTLPPPFSLQSGI
LTLNPVAQGQPILTSLGSNQEEAYVTMSSFYQNQ.

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 241.

(SEQ ID NO: 241)
MLLLVTSLLLCELPHPAFLLIPTIPPHVQKSVNNDMIVTDNNGAVKFPQLC
KFCDVRFSTCDNQKSCMSNCSITSICEKPQEVCVAVWRKNDENITLETVCH
DPKLPYHDFILEDAASPKCIMKEKKKPGETFFMCSCSSDECNDNIIFSEEY

```
NTSNPDSGPILLTISILSFFSVALLVILACVLWKKRIKPIVWPSLPDHKKT

LEHLCKKPRKNLNVSFNPESFLDCQIHRVDDIQARDEVEGFLQDTFPQQLE

ESEKQRLGGDVQSPNCPSEDVVITPESFGRDSSLTCLAGNVSACDAPILSS

SRSLDCRESGKNGPHVYQDLLLSLGTTNSTLPPPFSLQSGILTLNPVAQGQ

PILTSLGSNQEEAYVTMSSFYQNQ.
```

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 242.

```
                                         (SEQ ID NO: 242)
MLLLVTSLLLCELPHPAFLLIPEQKLISEEDLTIPPHVQKSVNNDMIVTDN

NGAVKFPQLCKFCDVRFSTCDNQKSCMSNCSITSICEKPQEVCVAVWRKND

ENITLETVCHDPKLPYHDFILEDAASPKCIMKEKKKPGETFFMCSCSSDEC

NDNIIFSEEYNTSNPDSGPILLTCPTISILSFFSVALLVILACVLWKKRIK

PIVWPSLPDHKKTLEHLCKKPRKNLNVSFNPESFLDCQIHRVDDIQARDEV

EGFLQDTFPQQLEESEKQRLGGDVQSPNCPSEDVVITPESFGRDSSLTCLA

GNVSACDAPILSSSRSLDCRESGKNGPHVYQDLLLSLGTTNSTLPPPFSLQ

SGILTLNPVAQGQPILTSLGSNQEEAYVTMSSFYQNQ.
```

In an embodiment an engineered DN TGF-βRII comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID: 243.

```
                                         (SEQ ID NO: 243)
MLLLVTSLLLCELPHPAFLLIPTIPPHVQKSVNNDMIVTDNNGAVKFPQLC

KFCDVRFSTCDNQKSCMSNCSITSICEKPQEVCVAVWRKNDENITLETVCH

DPKLPYHDFILEDAASPKCIMKEKKKPGETFFMCSCSSDECNDNIIFSEEY

NTSNPDSGPILLTCPTISILSFFSVALLVILACVLWKKRIKPIVWPSLPDH

KKTLEHLCKKPRKNLNVSFNPESFLDCQIHRVDDIQARDEVEGFLQDTFPQ

QLEESEKQRLGGDVQSPNCPSEDVVITPESFGRDSSLTCLAGNVSACDAPI

LSSSRSLDCRESGKNGPHVYQDLLLSLGTTNSTLPPPFSLQSGILTLNPVA

QGQPILTSLGSNQEEAYVTMSSFYQNQ.
```

The present disclosure contemplates, the expression of polynucleotides encoding the anti-PSMA binding domains disclosed herein and the anti-PSMA CARs disclosed herein, co-expression of polynucleotides comprising the engineered DN TGF-β Receptors with constitutively expressed anti-PSMA CARs, conditionally expressed anti-PSMA CARs and anti-PSCA synNotch receptor described herein, fragments thereof, cells and compositions comprising the same, and vectors that express polypeptides. "Polypeptide," "polypeptide fragment," "peptide" and "protein" are, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in some embodiments, it may be desirable to improve the binding affinity and/or other biological properties of the engineered DN TGF-β Receptors, engineered anti-PSMA CARs and engineered anti-PSCA synNotch Receptors by introducing one or more substitutions, deletions, additions and/or insertions. Preferably, polypeptides of the disclosure include polypeptides having at least about 50%, 60%, 65%, 70%, 75%, 85%, 90%, 95%, 98%, or 99% amino acid identity thereto. Polypeptides of the disclosure include variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. Polypeptides include "polypeptide fragments." Polypeptide fragments refer to a polypeptide, which may be monomeric or multi-meric that has an amino-terminal deletion, a carboxyl-terminal deletion, and/or an internal deletion or substitution of a naturally-occurring or recombinantly-produced polypeptide. In certain embodiments, a polypeptide fragment may comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873, 192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants may be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Where expression of two or more polypeptides is desired, the polynucleotide sequences encoding them may be separated by an IRES sequence as discussed elsewhere herein. In another embodiment, two or more polypeptides may be expressed as a fusion protein that comprises one or more self-cleaving polypeptide sequences. In other embodiments, they are expressed from different promotors and can be in two or more (such as three) vectors. In some embodiments, an anti-PSMA CARs encoded in the same vector as an engineered DN TGF-β Receptor and is operably linked to the same promoter as the engineered DN TGF-β Receptor where the sequences are separated by an IRES sequence. In some embodiments, an anti-PSMA CARs encoded in the same vector as an engineered DN TGF-β Receptor is operably linked to a different promoter than the promotor the engineered DN TGF-β Receptor. In some embodiments, an anti-PSMA CARs encoded in the same vector as an engineered DN TGF-β Receptor is operably linked to a conditionally active promoter and the engineered DN TGF-β Receptor is operably linked to a constitutively active promotor. In some embodiments, an anti-PSCA synNotch receptor is encoded in a different vector than either an anti-PSMA CARs or an engineered DN TGF-β Receptor, which could be on the same or different vectors. In some embodiments, a nucleic acid encoding an anti-PSCA synNotch receptor is operably connected to a constitutively active promoter. In some embodiments, a nucleic acid encoding an anti-PSMA CAR is operably connected to a constitutively active promoter. In some embodiments, a nucleic acid encoding an anti-PSMA CAR is operably connected to a conditionally active promoter, for example active upon binding of the transcriptional activator domain of an anti-PSCA synNotch receptor. In some embodiments, a nucleic acid encoding an DN TGF-β Receptor is operably connected to a constitutively active promoter. In embodiments the transcriptional activator domain of an anti-PSCA synNotch receptor comprises GAL4-VP64 and the conditionally active promoter comprises one or more GAL4 binding sites, such as 1, 2, 3, 4, 5, 6, or 7 GAL4 binding sites. In an embodiment a GAL4 binding site has the nucleic acid sequence according to.

Polypeptides of the present disclosure include fusion polypeptides. In some embodiments, fusion polypeptides and polynucleotides encoding fusion polypeptides are provided. Fusion polypeptides and fusion proteins refer to a polypeptide having at least two, three, four, five, six, seven, eight, nine, or ten or more polypeptide segments. Fusion polypeptides are typically linked C-terminus to N-terminus, although they may also be linked C-terminus to C-terminus, N-terminus to N-terminus, or N-terminus to C-terminus. The polypeptides of the fusion protein may be in any order or a specified order. Fusion polypeptides or fusion proteins may also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other common techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site may be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J Gener. Viral.* 78, 699-722; Scymczak et al. (2004) *Nature Biotech.* 5, 589-594). Exemplary protease cleavage sites include, but are not limited to the cleavage sites of potyvirus Nia proteases (e.g., tobacco etch virus protease), potyvirus HC proteases, potyvirus P1 (P35) proteases, byovirus Nia proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites may be used. In other embodiments, self-cleaving peptides may include those polypeptide sequences obtained from potyvirus and cardiovirus 2A peptides, FMDV (foot-and-mouth disease virus), equine rhinitis A virus, Thosea asigna virus and porcine teschovirus. In other embodiments, the self-cleaving polypeptide site comprises a 2A or 2A-like site, sequence or domain (Donnelly et al., 2001. *J Gen. Viral.* 82:1027-1041).

Generally, it is understood that any appropriate viral vector or vectors may be used for transduction of the engineered constructs described herein. In one embodiment described herein, a cell (e.g., T cell or NK cell) is transduced with a retroviral vector, e.g., a lentiviral vector, encoding an engineered DN TGF-β Receptor construct and an engineered anti-PSMA CARs and/or engineered anti-PSCA synNotch receptors as described herein. The transduced T cells elicits a stable, long-term, and persistent response.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in some embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis encephalitis virus (CAEV); equine infectious anemia virus (EIAV); feline immunodeficiency virus (FIV); bovine immune deficiency virus (BIV); and simian immunodeficiency virus (SIV).

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-retroviral viral sequences. In one embodiment, a hybrid vector refers to a vector or transfer plasmid comprising retroviral e.g., lentiviral, sequences for reverse transcription, replication, integration and/or packaging.

In some embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the disclosure and are present in DNA form in the DNA plasmids of the disclosure. In one embodiment described herein, the expression vector is a lentivirus expression vector.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R, and U5. The U3 region contains the enhancer and promoter elements. The U5 region is the sequence between the primer binding site and the R region and contains the polyadenylation sequence. The R (repeat) region is flanked by the U3 and U5 regions. The LTR is composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. J of Virology, Vol. 69, No. 4; pp. 2101-2109. Several retroviral vectors use the minimal packaging signal (also referred to as the psi ['P'] sequence) needed for encapsidation of the viral genome. Thus, as used herein, the terms "packaging sequence," "packaging signal," "psi" and the symbol "'P," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the disclosure, the 3'LTR is modified such that the U5 region is replaced, for example, with an ideal poly(A) sequence. It should be noted that modifications to the LTRs such as modifications to the 3'LTR, the 5'LTR, or both 3' and 5'LTRs, are also contemplated herein.

An additional safety enhancement is provided by replacing the U3 region of the 5'LTR with a heterologous promoter to drive transcription of the viral genome during production of viral particles. Examples of heterologous promoters which may be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter may be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a includes the central polypurine tract and central termination sequences (cPPT and CTS) of a retrovirus, e.g., HIV-I or HIV-2. Suitable FLAP elements are described in U.S. Pat. No. 6,682,907 and in Zennou, et al., 2000, Cell, 101: 173. During HIV-I reverse transcription, central initiation of the plus-strand DNA at the central polypurine tract (cPPT) and central termination at the central termination sequence (CTS) lead to the formation of a three-stranded DNA structure: the HIV-I central DNA flap. While not wishing to be bound by any theory, the DNA flap may act as a cis-active determinant of lentiviral genome nuclear import and/or may increase the titer of the virus.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J Virol. 65: 1053; and Cullen et al., 1991. Cell 58: 423), and the hepatitis B virus post-transcriptional regulatory element (HPRE). Generally, the RNA export element is placed within the 3' UTR of a gene, and may be inserted as one or multiple copies.

In other embodiments, expression of heterologous sequences in viral vectors is increased by incorporating post-transcriptional regulatory elements, efficient polyadenylation sites, and optionally, transcription termination signals into the vectors. A variety of posttranscriptional regulatory elements may increase expression of a heterologous nucleic acid at the protein, e.g., woodchuck hepatitis virus post-transcriptional regulatory element (WPRE; Zufferey et al., 1999, J Virol., 73:2886); the post-transcriptional regulatory element present in hepatitis B virus (HPRE) (Huang et al., Mol. Cell. Biol., 5:3864); and the like (Liu et al., 1995, Genes Dev., 9:1766).

In some embodiments, vectors may include regulatory oligonucleotides having transcriptional or translational regulatory activity. Such an oligonucleotide can be used in a variety of gene expression configurations for regulating control of expression. A transcriptional regulatory oligonucleotide, can increase (enhance) or decrease (silence) the level of expression of a recombinant expression construct. Regulatory oligonucleotides may selectively regulate expression in a context specific manner, including, for example, for conferring tissue specific, developmental stage specific, or the like expression of the polynucleotide, including constitutive or inducible expression. A regulatory oligonucleotide of the disclosure also can be a component of an expression vector or of a recombinant nucleic acid molecule comprising the regulatory oligonucleotide operatively linked to an expressible polynucleotide. A regulatory element can be of various lengths from a few nucleotides to several hundred nucleotides.

Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences may promote mRNA stability by addition of a poly A tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of poly A signals that may be used in a vector of the disclosure, includes an ideal poly A sequence (e.g., AATAAA, ATTAAA, AGTAAA), a bovine growth hormone poly A sequence (BGHpA), a rabbit β-globin poly A sequence (rβgpA), or another suitable heterologous or endogenous poly A sequence known in the art.

Also described herein are "codon-optimized" nucleic acids. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells) by replacing at least one, more than one, or a significant number, of codons of the native sequence with codons that are more frequently or most frequently used in the genes of that species. Codon optimization does not alter the amino acid sequence of the encoded protein.

The codon-optimized nucleotide sequences presented in the instant disclosure can present improved properties related to expression efficacy. In some embodiments, the DNA sequence to be transcribed may be optimized to facilitate more efficient transcription and/or translation. In some embodiments, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding.

The vectors may have one or more LTRs, wherein any LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), and may optionally comprise a WPRE or HPRE. The skilled artisan would appreciate that many other different embodiments may be fashioned from the existing embodiments of the disclosure.

A "host cell" includes cells transfected, infected, or transduced in vivo, ex vivo, or in vitro with a recombinant vector or a polynucleotide of the disclosure. Host cells may include packaging cells, producer cells, and cells infected with viral vectors. In some embodiments, host cells infected with viral vector of the disclosure are administered to a subject in need of therapy. In certain embodiments, the term "target cell" is used interchangeably with host cell and refers to transfected, infected, or transduced cells of a desired cell type. In some embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present disclosure may be introduced into a packaging cell line, via transfection, transduction or infection, to generate a producer cell or cell line. The packaging vectors of the present disclosure may be introduced into human cells or cell lines by common methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene may be linked physically to genes encoding by the packaging vector, e.g., by IRES or self-cleaving viral peptides.

Viral envelope proteins (env) determine the range of host cells which may ultimately be infected and transformed by recombinant retroviruses generated from the cell lines. In the case of lentiviruses, such as HIV-1, HIV-2, SIV, FIV and EIV, the env proteins include gp41 and gp120. In some embodiments, the viral env proteins expressed by packaging cells of the disclosure are encoded on a separate vector from the viral gag and pol genes, as has been previously described.

Illustrative examples of retroviral-derived env genes which may be employed in the embodiments described herein include, but are not limited to: MLV envelopes, 10A1 envelope, BAEV, FeLV-B, RDI 14, SSAV, Ebola, Sendai, FPV (Fowl plague virus), and influenza virus envelopes. Similarly, genes encoding envelopes from RNA viruses (e.g., RNA virus families of Picomaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BL V, EBV, CAEV, SNV, ChTL V, STLV, MPMV SMRV, RAV, FuSV, MH2, AEV, AMV, CTIO, and EIAV.

In other embodiments, envelope proteins for pseudotyping a virus of present disclosure include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Barr virus (EBV), human herpesviruses (HHV), human herpesvirus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-Co V), West Nile virus, or any encephalitis causing virus.

The terms "pseudotype" or "pseudotyping" as used herein, refer to a virus whose viral envelope proteins have been substituted with those of another virus possessing other characteristics. For example, HIV may be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line may be employed to prepare packaging cells of the disclosure. Generally, the cells are mammalian cells. In another embodiment, the cells used to produce the packaging cell line are human cells. Suitable cell lines which may be used to produce the packaging cell line include, for example, CHO cells, BHK cells, MDCK cells, C3H 10T1/2 cells, FLY cells, Psi-2 cells, BOSC 23 cells, P A317 cells, WEHI cells, COS cells, BSC 1 cells, BSC 40 cells, BMT 10 cells, VERO cells, W138 cells, MRC5 cells, A549 cells, HTI080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) Nucl. Acids Res. 23:628-633, and N. R. Landau et al. (1992) J Virol. 66:5110-5113. Infectious virus particles may be collected from the packaging cells using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell or NK cell, is "transduced" if it comprises a gene or other polynucleotide sequence delivered to the cell by infection using a viral or retroviral vector. In some embodiments, a transduced cell comprises one or more genes or other polynucleotide sequences delivered by a retroviral or lentiviral vector in its cellular genome.

In some embodiments, host cells expressing one ore more of the constructs of the disclosure (anti-PSMA CAR, anti-PSCA synNotch receptor, and/or). The host cells may be transduced with one or more viral vectors comprising nucleic acid sequences encoding one or more polypeptides expressing a DN TGF-β receptor construct of the disclosure and an engineered TCR and/or a CAR. The host cells may be administered to a subject to treat and/or prevent T cell malignancies. Other methods relating to the use of viral vectors in gene therapy, which may be utilized according to certain embodiments of the present disclosure, may be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al., (1999) Liver 19:265-74; Oka, K. et al., (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J Hepatol. 23:746-58; Brody, S. L. and Crystal, R. G. (1994) Ann. NY Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al., (2000) Nature 408:483-8.

The compositions described herein may comprise one or more polynucleotides, polypeptides, vectors comprising same, and T cell compositions, as contemplated herein. One embodiment described herein is a composition comprising a modified T cell that co-expresses one or more engineered DN TGF-β Receptors described herein with an engineered TCR and/or CAR. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the present disclosure may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In one embodiment described herein, compositions of the present disclosure comprise an amount of modified T cells contemplated herein. It may generally be stated that a pharmaceutical composition comprising the T cells contemplated herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of cells will depend upon the ultimate use for which the composition is intended as will the type of cells included therein. T cells modified to express an engineered TCR or CAR may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised or immunosuppressed. In some, compositions comprising the modified T cells contemplated herein are used in the treatment of cancers. The modified T cells described herein may be administered either alone, or as a pharmaceutical composition in combination with carriers, diluents, excipients, and/or with other components such as IL-2, IL-7, and/or IL-15 or other cytokines or cell populations. In some embodiments, pharmaceutical compositions contemplated herein comprise an amount of genetically modified T cells, in combination with one or more pharmaceutically or physiologically acceptable carriers, diluents or excipients.

Pharmaceutical compositions comprising modified T cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for parenteral administration, e.g., intravascular (intravenous or intra-arterial), intraperitoneal or intramuscular administration.

The liquid pharmaceutical compositions, whether they be solutions, suspensions or other like form, may include one or more of the following: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Sterile injectable pharmaceutical composition are also included.

In some embodiments, compositions contemplated herein comprise an effective amount of an expanded modified T cell composition, alone or in combination with one or more therapeutic agents. Thus, the T cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics and anti-viral agents. Such therapeutic agents may be accepted in the art as a treatment for a disease state as described herein, such as a cancer. In one embodiment the compositions contemplated herein may also be administered with inhibitors of TGF-β, for example the small molecule inhibitor LY55299. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells contemplated herein may be administered in conjunction with any number of chemotherapeutic agents. Illustrative examples of chemotherapeutic agents include but are not limited to alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RPS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In some embodiments, NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol or propoxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary disease-modifying anti-rheumatic drugs (DMARDs) include azathioprine, cyclophosphamide, cyclosporine, methotrexate, penicillamine, leflunomide, sulfasalazine, hydroxychloroquine, Gold (oral (auranofin) and intramuscular) and minocycline.

In other embodiments, the therapeutic antibodies suitable for combination with the CAR modified T cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In some embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, 1L-2, 1L-3, 1L-4, 1L-5, 1L-6, IL-7, IL-8, IL-9, IL-10, IL-11, IL-12; IL-15, a tumor necrosis factor such as TNF-α or TNF-β; and other polypeptide factors including LIF and kit ligand (KL). As used herein, the term cytokine includes proteins from natural sources or from recombinant cell culture, and biologically active equivalents of the native sequence cytokines.

The present disclosure contemplates, in part, genetically modified T cell redirected to a target cell, e.g., a tumor or cancer cell, and that comprises the engineered DN TGF-β Receptors described herein and an engineered TCR or CAR having a binding domain that binds to target antigens on the cells, including the CAR-DN TGF-β Receptor constructs described herein. Cancer cells may also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In one embodiment, the target cell expresses an antigen, e.g., target antigen. In one embodiment, the target cell is a pancreatic parenchymal cell, pancreatic duct cell, hepatic cell, cardiac muscle cell, skeletal muscle cell, osteoblast, skeletal myoblast, neuron, vascular endothelial cell, pigment cell, smooth muscle cell, glial cell, fat cell, bone cell, chondrocyte, pancreatic islet cell, CNS cell, PNS cell, liver cell, adipose cell, hepatic cell, renal cell, lung cell, skin cell, ovary cell, follicular cell, epithelial cell, immune cell, or an endothelial cell.

In certain embodiments, the target cell is part of a pancreatic tissue, neural tissue, cardiac tissue, bone marrow, muscle tissue, bone tissue, skin tissue, liver tissue, hair follicles, vascular tissue, adipose tissue, lung tissue, and kidney tissue.

In a one embodiment, the target cell is a tumor cell. In another embodiment, the target cell is a cancer cell, such as a cell in a patient with cancer. Exemplary cells that may be killed with the disclosed methods include cells of prostate tumors. In one embodiment, the target cell is a malignant cell of the prostate.

The modified T cells and NK cells contemplated herein provide improved adoptive immunotherapy for use in the treatment of various conditions including, without limitation, cancer, infectious disease, autoimmune disease, inflammatory disease, and immunodeficiency. In some embodiments, the specificity of a primary T cell is redirected to tumor or cancer cells by genetically modifying the primary T cell engineered to co-express a TCR or CAR contemplated herein with an engineered DN TGF-β Receptor. For example, with the CAR-DN TGF-β Receptor constructs described herein, the antigen binding domain of the scFv of the CAR directs the T cell to the cells expressing the tumor antigen, and the TGF-β Receptor constructs described herein protect the population of such T cells by inhibiting the suppressive effect of TGF-β.

In one embodiment of the present disclosure includes a type of cellular therapy where T cells are modified to co-express an engineered DN TGF-β Receptor with an engineered TCR or CAR, including the CAR-DN TGF-β Receptor constructs described herein, that target cancer cells expressing a target antigen, and the modified T cell is infused to a recipient in need thereof. The infused cell is thus able to kill tumor cells in the recipient with minimal impact from TGF-β suppression.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli*; *Enterobacter*; *Erwinia*; *Klebsiella*; *Proteus*; *Salmonella*, e.g., *Salmonella typhimurium*; *Serratia*, e.g., *Serratia marcescans*, and *Shigella*; Bacilli such as *B. subtilis* and *B. licheniformis*; *Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof. Unlike antibody therapies or stand-alone TCR or CAR modified T cells, T cells (or any cells as described above) modified to co-express the engineered DN TGF-β Receptors described herein with an engineered TCR or CAR are able to not only replicate in vivo, and thus contribute to long-term persistence that may lead to sustained cancer therapy, but have the added advantage of avoiding the suppressive impact of TGF-β. Thus, in one embodiment described herein is a method of inhibiting the activity of TGF-β comprising administering to a subject in need thereof a therapeutically effective amount of the modified T cell co-expressing the DN TGF-β Receptors described herein and a TCR or CAR as described herein.

In another embodiment, T cells co-expressing the DN TGF-β Receptors with an engineered TCR or CAR as described herein may undergo T cell expansion such that a population of therapeutic T cells may remain or persist for an extended period. Thus, another embodiment described herein is a method of expanding a population of T cells comprising administering to a subject in need thereof a therapeutically effective amount of the T cells described herein.

In one embodiment described herein, the population of T cells remains between at between about 50% to about 100% after 7 days, at between about 60% to about 90% after 7 days, or at between about 70% to about 80% after 7 days. In another embodiment described herein, the population of T cells remains at about 50% after 7 days, at about 60% after 7 days, at about 70% after 7 days, at about 80% after 7 days, at about 90% after 7 days or at about 100% after 7 days.

In another embodiment described herein, administration of the modified T cells described herein results in an expansion of transduced T cells in the presence of TGF-β1 by about 10% to about 100%, about 20% to about 90%, or about 30% to about 80%. In another embodiment described herein, administration of the modified T cells described herein results in an expansion of transduced T cells in the presence of TGF-β1 by about 1%, about 5%, about 10%, about 20%, about 30%, about 40%, about 50%, 50%, about 55%, about 60%, about 65%, about 70%, about 75%, about 80%, about 85%, about 90%, about 95%, or about 100%.

In one embodiment described herein, administration of a modified T cell from a codon-optimized sequence as described herein results in an increase in expression efficiency by about 50%, about 55%, about 60%, about 65%, about 70%, about 75%, about 80%, about 85%, about 90%, about 95%, or about 100%. In another embodiment described herein, administration of a modified T cell from a codon-optimized sequence as described herein results in an increase in transduction efficiency by about 50%, about 55%, about 60%, about 65%, about 70%, about 75%, about 80%, about 85%, about 90%, about 95%, or about 100%.

Without being bound by any theory, it is believed that despite the promising use of CAR T cell therapy, constitutive tonic signaling in the absence of tumor antigen can result in reduced efficacy, poor CAR T cell survival and toxicity (Ajina et al., Mol Cancer Ther., 17(9):1795-1815(2018)). Thus, a CAR T cell therapy with reduced tonic signaling results superior performance. In one embodiment described herein, administration of a modified T cell from a codon-optimized sequence as described herein in the absence of tumor antigen results in a reduction of cytokine release by about 10%, about 20%, about 30%, about 40%, about 50%, 50%, about 55%, about 60%, about 65%, about 70%, about 75%, about 80%, about 85%, about 90%, about 95%, or about 100%. In one embodiment described herein, administration of a modified T cell from a codon-optimized sequence in the absence of tumor antigen results in a reduction of cytokine release by about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In another embodiment, administration of the modified T cell from a codon-optimized sequence as described herein results in a reduction in tumor volume of between about 50% to about 10% to about 100%, about 20% to about 90%, or about 30% to about 80%. In another embodiment the reduction in tumor volume is about 10%, about 20%, about 30%, about 40%, about 50%, 50%, about 55%, about 60%, about 65%, about 70%, about 75%, about 80%, about 85%, about 90%, about 95%, or about 100%.

Another embodiment described herein is a method of treating a cancer in a subject in need thereof comprising administering an effective amount, e.g., therapeutically effective amount of a composition comprising T cells co-expressing the DN TGF-β Receptors and a TCR or CAR as described herein. The quantity and frequency of administration will be determined by such factors as the condition of the patient, and the type and severity of the patient's disease, although appropriate dosages may be determined by clinical trials.

Another embodiment described herein is a method of treating a hepatic cancer in a subject in need thereof comprising administering an effective amount, e.g., therapeutically effective amount of a composition comprising T cells co-expressing the DN TGF-β Receptors and a TCR or CAR as described herein, including the CAR-DN TGF-β Receptor constructs described herein. The quantity and frequency of administration will be determined by such factors as the condition of the patient, and the type and severity of the patient's disease, although appropriate dosages may be determined by clinical trials.

In other embodiments, compositions comprising T cell genetically modified with a vector comprising a promoter operably linked to a polynucleotide encoding a DN TGF-β Receptor and a polynucleotide encoding a TCR or CAR, including the CAR-DN TGF-β Receptor constructs described herein, are used in the treatment of solid tumors or cancers including, without limitation, liver cancer, pancreatic cancer, lung cancer, breast cancer, bladder cancer, brain cancer, bone cancer, thyroid cancer, kidney cancer, skin cancer or virus induced cancers.

In some embodiments, compositions comprising T cell genetically modified with a vector comprising a promoter operably linked to a polynucleotide encoding a DN TGF-β Receptor and a polynucleotide encoding a CAR and/or a synNotch molecule, including the CAR-DN TGF-β Receptor constructs described herein, comprises an antigen-specific binding domain that binds an epitope of PSCA or PSMA are used in the treatment of various cancers.

In other embodiments, methods comprising administering a therapeutically effective amount of modified T cells contemplated herein or a composition comprising the same, to a patient in need thereof, alone or in combination with one or more therapeutic agents, are provided. In certain embodiments, the cells of the disclosure are used in the treatment of patients at risk for developing a cancer. Thus, the present disclosure provides methods for the treatment or prevention of a cancer comprising administering to a subject in need thereof, a therapeutically effective amount of the modified T cells of the disclosure.

One of ordinary skill in the art would recognize that multiple administrations of the compositions of the disclosure may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present disclosure, and reinfuse the patient with these activated and expanded T cells. This process may be carried out multiple times every few weeks. In certain embodiments, T cells may be activated from blood draws of from 10 cc to 400 cc. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In some embodiments, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of proinflammatory cytokines that may induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

In embodiments described herein is a method of treating a subject diagnosed with a cancer, comprising removing T cells from the subject, genetically modifying said T cells with a vector comprising a nucleic acid encoding an engineered DN TGF-β Receptor and an anti-PSMA CAR as contemplated herein, including the anti-PSMA CAR-DN TGF-β Receptor constructs described herein, thereby producing a population of modified T cells, and administering the population of modified T cells to the same subject. In embodiments described herein is a method of treating a subject diagnosed with a cancer, comprising removing T cells from the subject, genetically modifying said T cells with a vector comprising a nucleic acid encoding an engineered DN TGF-β Receptor and an anti-PSMA CAR as contemplated herein, including the anti-PSMA CAR-DN TGF-β Receptor constructs described herein, thereby producing a population of modified T cells, and administering the population of modified T cells to the same subject nucleic acid construct encoding an anti-PSCA synNotch molecule.

In certain embodiments, the present disclosure also provides methods for stimulating an effector cell mediated immune modulator response to a target cell population in a subject comprising the steps of administering to the subject an immune effector cell population expressing a nucleic acid construct encoding an engineered DN TGF-β Receptor and an anti-PSMA CAR molecule, including the CAR-DN TGF-β Receptor constructs described herein. In some example the immune effector cell population further express a nucleic acid construct encoding an anti-PSCA synNotch molecule.

The methods for administering the cell compositions described herein includes any method which is effective to result in reintroduction of ex vivo genetically modified immune effector cells that either directly express an engineered CAR in the subject or on reintroduction of the genetically modified progenitors of immune effector cells that on introduction into a subject differentiate into mature immune effector cells that express the engineered CAR, engineered DN TGF-β Receptor and an anti-PSMA CAR molecule, including the CAR-DN TGF-β Receptor constructs described herein. In some example the immune effector cell population further express a nucleic acid construct encoding an anti-PSCA synNotch molecule. One method comprises transducing peripheral blood T cells ex vivo with a nucleic acid construct in accordance with the present disclosure and returning the transduced cells into the subject.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those skilled in the art will readily recognize a variety of noncritical parameters that could be changed or modified to yield essentially similar results.

EXAMPLES

Example 1

CD3+ cells obtained from ALLCells® (Alameda, California) were isolated from peripheral blood mononuclear cells obtained from healthy donors and frozen down in CryoStor® cell cryopreservation media (Sigma Aldrich®). Pan CD3+ T cells were isolated from leukopaks containing peripheral blood mononuclear cells (PBMCs) by negative selection using a commercially available kit from STEMCELL Technologies™ (Vancouver, Canada) according to manufacturer's directions and then frozen in liquid nitrogen. Chimeric antigen receptor (CAR) T cells were generated from frozen human Pan CD3+ T cells. Before lentivirus transduction, the CD3+ pan T cells were thawed, and activated ex vivo using anti-CD3/CD28 Dynabeads®. (ThermoFisher Scientific) and 100 IU/ml exogenous interleukin-2 (IL-2) according to manufacturer recommendations. The activated cells were rested overnight. One day after anti-CD3/CD28 bead activation, T cells were plated and transduced with a lentiviral vector (with anti-PSMA CAR). Canonical CARs (CARs without synNotch receptor transcriptional activation) were transduced with a multiplicity of infection (MOI) of 6-9. Synthetic notch (synNotch) constructs were dually transduced with a synNotch lentivirus vector MOI of 6-9 and a CAR payload lentivirus vector MOI of 6-9. T cells were de-beaded 3 days after transduction and evaluated for expression and cytotoxicity assays between days 8 and 11 following transduction.

Canonicals CAR vectors included an EF1a promoter to drive constitutive expression of the anti-PSMA CAR. synNotch vectors included an EF1a promoter to drive constitutive expression of an anti-PSCA synNotch receptor. The CAR payload vectors (for synNotch receptor activated conditional expression) included 5× gal4 binding sites-minimal CMV promoter to drive conditional expression of the anti-PSMA CAR. synNotch constructs were transduced with synNotch and CAR payload vectors simultaneously as described above.

The anti-PSMA CARs used in the following examples included a CSF2RA signal sequence, an anti-PSMA scFv, CD8α hinge domain, an CD8a transmembrane domain, a 4-1BB co-stimulatory domain, and a CD3zeta signaling domain. The synNotch receptor included an anti-PSCA scFv, a murine Notch core, a gal4 DNA binding domain, and a vp64 transactivation domain. A myc tag was included to simulate ligand induced activation of the synNotch receptors.

Human prostate cell line 22RV1 and human leukemia cell line K562 were obtained from the American Type Culture Collection (ATCC). Cells were cultured at 37° C., 5% $CO_2$, in either Roswell Park Memorial Institute (RPMI; 22RV1) or Iscove's Modified Dulbecco's Medium (IMDM; K562), supplemented with 1% penicillin/streptomycin and 10% fetal bovine serum (FBS). 22RV1 and K562 cells were engineered to knockout (KO) or overexpress PSCA and PSMA as described in Table 10.

TABLE 10

| Cell Line | PSCA | PSMA |
|---|---|---|
| 22RV1 | − | + |
| 22RV1-PSMA KO | − | − |
| 22RV1-PSMA KO-PSCA | + | − |
| 22RV1-PSCA | + | + |
| K562 | − | − |
| K562-PSCA | + | − |
| K562-PSMA | − | + |
| K562-PSCA-PSMA | + | + |

Example 2

Seven days after transduction, T cells transduced as described in example 1 were harvested to determine transduction efficiencies. $1.5 \times 10^5$ T cells were plated in 96 well plates in duplicate. For canonical CAR T cells, T cells were cultured overnight in hTCM (human T cell media), that included of x-vivo 15 (Lonza (Basel, Switzerland)), 5% human serum (Valley Biomedical (Winchester, Virginia)), and 1% Glutamax (Gibco). For synNotch T receptor expressing cells, the T cells were cultured in the presence and absence of myc beads overnight to stimulate the synNotch receptor and thereby induce CAR expression. After overnight culture, CAR expression was measured using recombinant PSMA (rPSMA) containing a 6× His tag (SEQ ID NO: 260). The cells were stained with an anti-His antibody and the stained cells were detected via flow cytometry. Only cells bound by the rPSMA (and anti-His) are detected to measure expression. Table 11 shows canonical CAR expression. Table 12 shows synNotch and CAR payload expression.

TABLE 11

| Donor ID | Construct | scFv | | % CAR+ |
|---|---|---|---|---|
| #1 | 104 | Ab4 | 91.5% | 90.0% |
| | 101 | Ab1 | 95.4% | 95.4% |
| | 103 | Ab3 | 90.0% | 91.0% |
| | 105 | Ab5 | 84.4% | 83.9% |
| | UTD | | 0.9% | 1.1% |
| #2 | 104 | Ab4 | 90.7% | 92.0% |
| | 101 | Ab1 | 95.6% | 96.3% |
| | 103 | Ab3 | 93.2% | 92.7% |
| | 105 | Ab5 | 88.4% | 88.1% |
| | UTD | | 0.9% | 1.0% |

TABLE 11-continued

| Donor ID | Construct | scFv | % CAR+ | |
|---|---|---|---|---|
| #3 | 104 | Ab4 | 91.0% | 92.1% |
| | 101 | Ab1 | 95.6% | 96.5% |
| | 103 | Ab3 | 88.4% | 87.9% |
| | 105 | Ab5 | 83.2% | 83.6% |
| | UTD | | 0.7% | 0.7% |

TABLE 12

| Donor ID | Construct | scFv | % synNotch | | % CAR+ (Unstimulated) | | % CAR+ (Stimulated) | |
|---|---|---|---|---|---|---|---|---|
| #1 | Ab6 SynNotch/201 | Ab1 | 61.9% | 61.6% | 3.7% | 3.7% | 41.5% | 41.9% |
| | Ab6 SynNotch/202 | Ab2 | 71.1% | 71.2% | 1.2% | 1.5% | 26.1% | 24.2% |
| | Ab6 SynNotch/203 | Ab3 | 64.7% | 65.0% | 3.2% | 3.2% | 50.5% | 50.3% |
| | Ab6 SynNotch/205 | Ab5 | 59.8% | 59.6% | 2.5% | 2.8% | 52.4% | 52.6% |
| | UTD | | 1.0% | 1.0% | 0.9% | 1.1% | 0.6% | 0.8% |
| #2 | Ab6 SynNotch/201 | Ab1 | 59.3% | 58.8% | 6.5% | 6.1% | 49.1% | 51.8% |
| | Ab6 SynNotch/202 | Ab2 | 67.5% | 67.4% | 1.4% | 1.6% | 24.5% | 24.6% |
| | Ab6 SynNotch/203 | Ab3 | 62.8% | 62.5% | 5.6% | 5.5% | 57.5% | 57.4% |
| | Ab6 SynNotch/205 | Ab5 | 58.7% | 56.8% | 4.8% | 4.2% | 58.7% | 60.5% |
| | UTD | | 0.8% | 0.9% | 0.9% | 1.0% | 0.9% | 1.3% |
| #3 | Ab6 SynNotch/201 | Ab1 | 66.7% | 66.5% | 6.2% | 6.2% | 44.0% | 43.3% |
| | Ab6 SynNotch/202 | Ab2 | 77.7% | 77.8% | 1.4% | 1.4% | 42.5% | 40.9% |
| | Ab6 SynNotch/203 | Ab3 | 70.0% | 70.4% | 4.6% | 4.6% | 52.3% | 51.5% |
| | Ab6 SynNotch/205 | Ab5 | 66.5% | 66.3% | 5.5% | 5.3% | 57.1% | 56.9% |
| | UTD | | 1.1% | 1.0% | 0.7% | 0.7% | 1.1% | 1.1% |

Example 3

Figure 2:
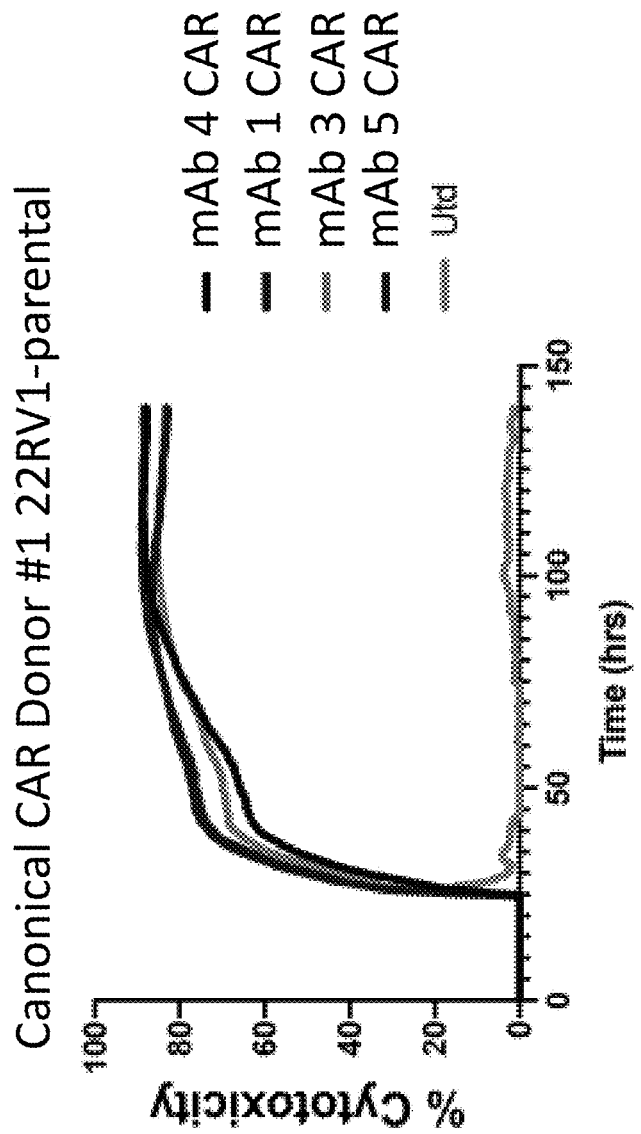
FIG. 2 is a graph of cytotoxicity vs time for the indicated canonical CARs.
Figure 3:
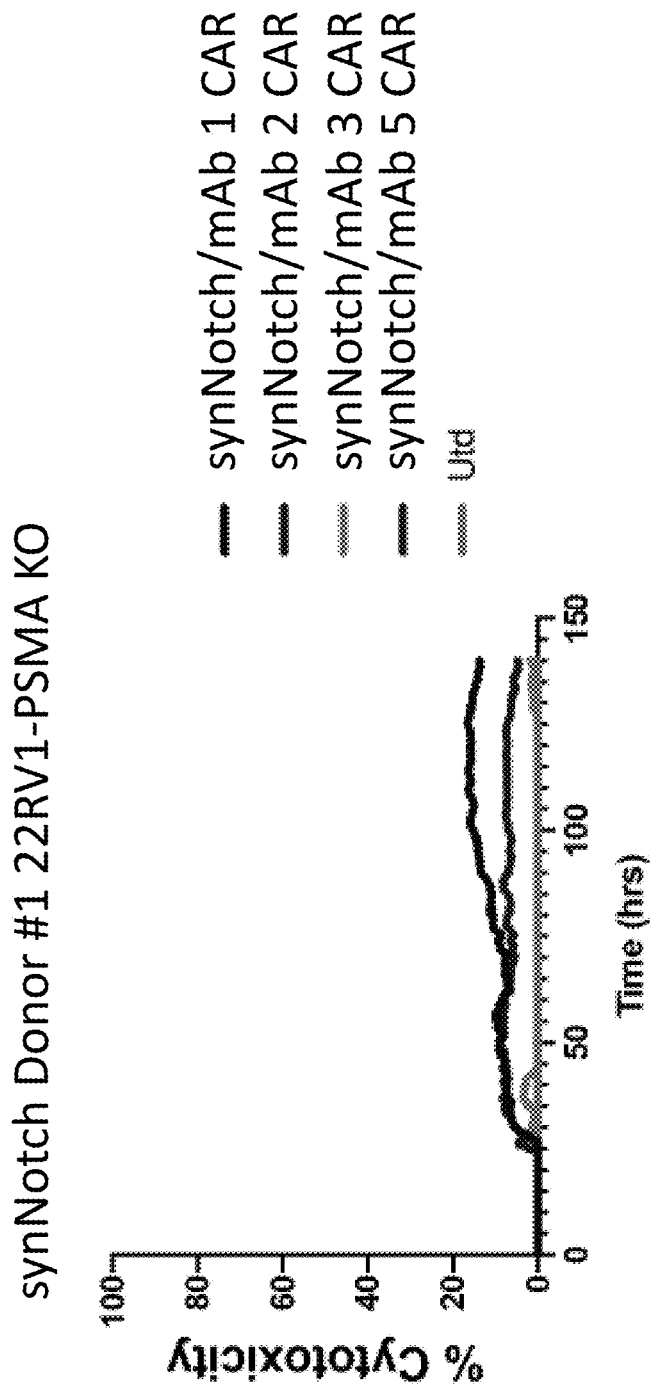
FIG. 3 is a graph of cytotoxicity vs time for the indicated canonical CARs.
Figure 4:
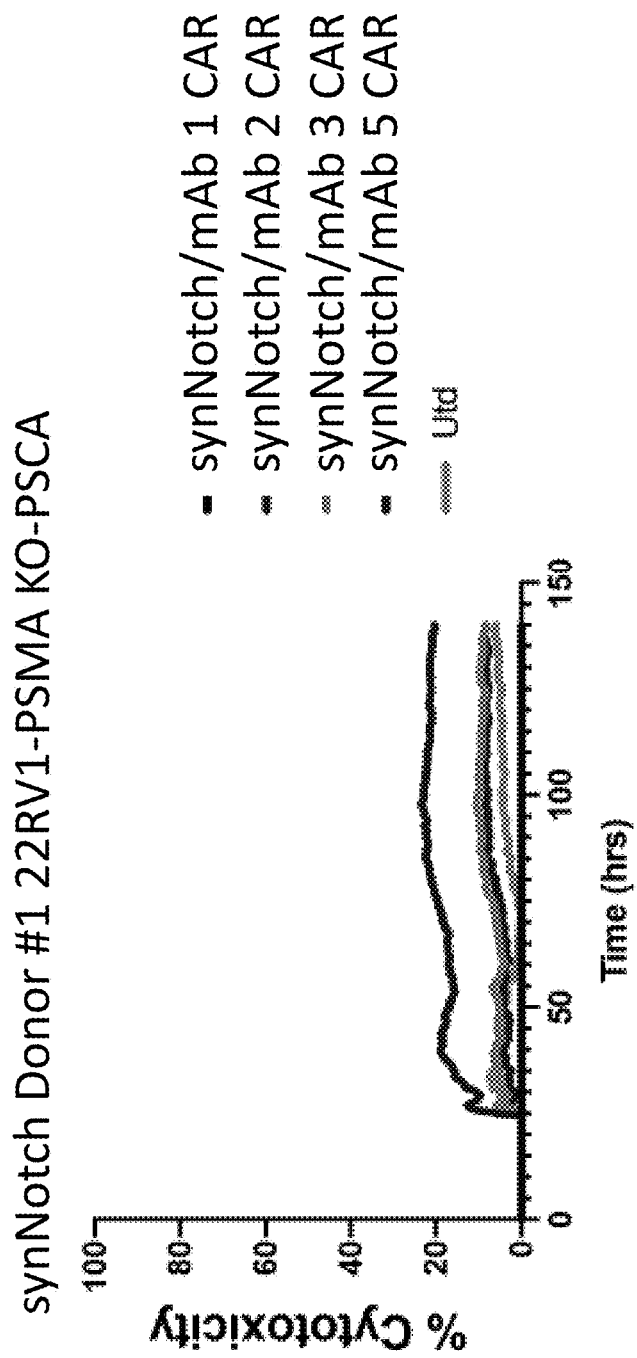
FIG. 4 is a graph of cytotoxicity vs time for the indicated synNotch activated CARs.
Figure 5:
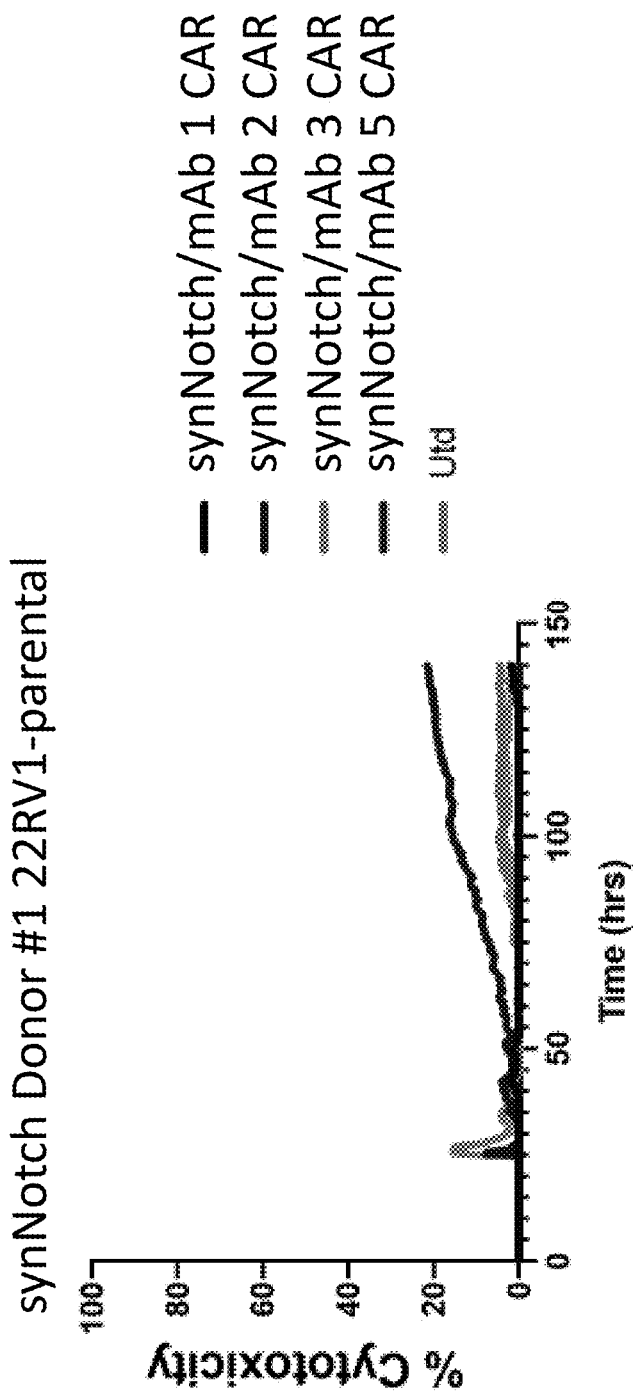
FIG. 5 is a graph of cytotoxicity vs time for the indicated synNotch activated CARs.
Figure 6:
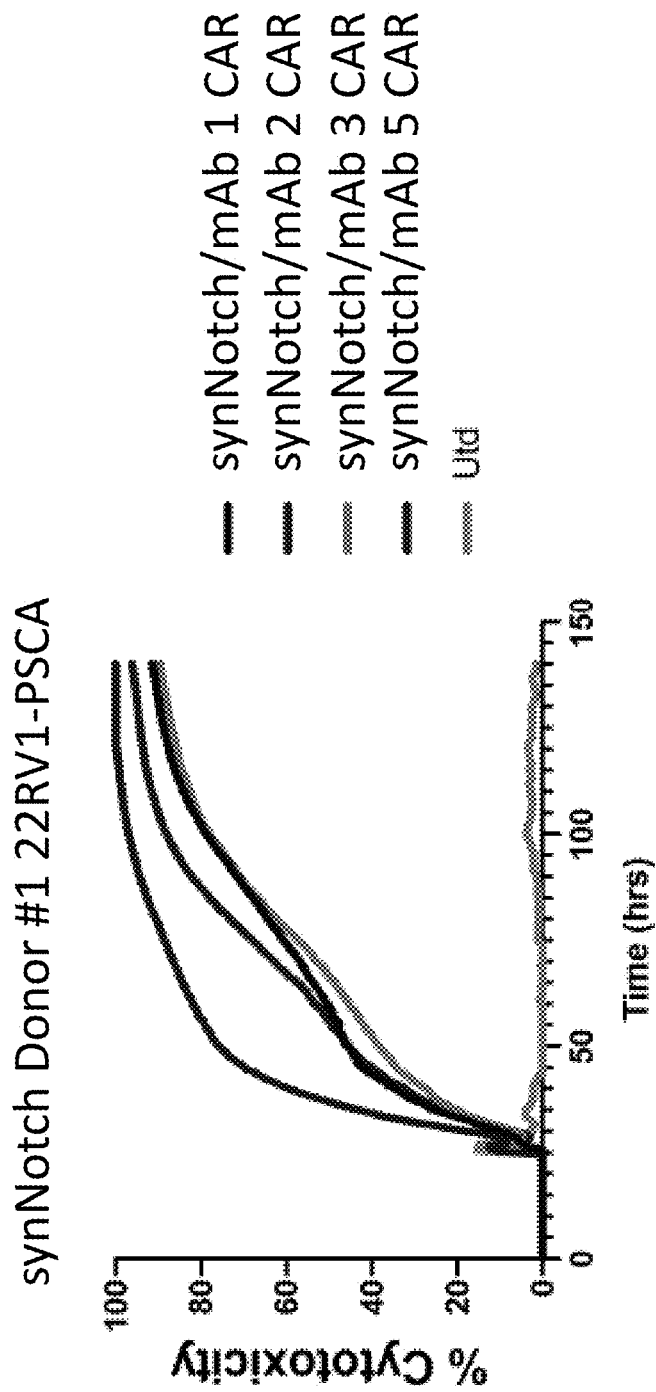
FIG. 6 is a graph of cytotoxicity vs time for the indicated synNotch activated CARs.

For T cell-dependent cytotoxicity assays, T cells cytotoxicity of T cells transduce as described in example 1 was measured in real time at an effector (T cell)-to-target cell (as described in Table 10) ratio (E:T) of 1:1. Target cells were plated on xCELLigence plates overnight with impedance measured every 15 min. Briefly, 50 µl of hTCM is added to the xCELLigence plate and a measurement is taken to create a baseline for the plate. Then $3\times10^4$ of each of the 4 different 22RV1 cell lines were plated on xCELLigence plates in 50 µl and impedance was measured every 15 min overnight (16-18 hrs). Lastly, $3\times10^4$ CAR+ effectors are added in 100 µl and impedance is measured every 15 min for an additional 72-96 hrs. The instrument takes each of the readings, called "Cell Index" and calculates a "% Cytotoxicity" based on how the Tumor cells alone have grown on the same plate. Target cells for canonical CAR T cells were 22RV1-PSMA knockout (KO) (FIG. 1) and 22RV1 (FIG. 2). Target cells for synNotch T cells were 22RV1-PSMA KO (FIG. 3), 22RV1-PSMA KO-PSCA (FIG. 4), 22RV1 (FIG. 5), and 22RV1-PSCA (FIG. 6).

Example 4

As described in Table 10 $5\times10^4$ target cells were co-cultured with $5\times10^4$ CAR+ T cells in a 96 well plate in hTCM media in a total volume of 200 µl for 72 hrs. Supernatants were then harvested and cytokine release (IFNγ and IL-2) was determined via Ella with IFNγ or IL-2 cartridges per manufactures recommendations (Protein Simple, San Jose CA).

TABLE 13

IFNγ release from canonical CARs co-cultured with 22RV1 cells.

| DONER #1: IFNγ | 4211 | 4212 | 4215 | 1550 | UTD |
|---|---|---|---|---|---|
| 22RV1-PSMA KO | 11.1 | 12.4 | 5.89 | 3.62 | 5.69 |
| | 7.31 | 20.5 | 6.06 | 118 | 6.48 |
| 22RV1 | 3919 | 2053 | 1132 | 899 | 6.28 |
| | 3678 | 1963 | 1364 | 820 | 5.65 |
| 22RV1-PSCA | 4699 | 2548 | 1673 | 1160 | 7.28 |
| | 3857 | 1973 | 1597 | 1103 | 6.6 |
| 22RV1-PSMA KO-PSCA | 9.08 | 11.7 | 4.51 | 1.01 | 5.39 |
| | 11.5 | 16 | 5.45 | 3.44 | 6.26 |

TABLE 14

IL-2 release from canonical CARs co-cultured with 22RV1 cells.

| DONER #1: IL-2 | 4211 | 4212 | 4215 | 1550 | UTD |
|---|---|---|---|---|---|
| 22RV1-PSMA KO | 3.99 | 0.455 | 2.22 | 0.529 | 2.62 |
| | 0.822 | 25.6 | 0 | 0.549 | 0.099 |
| 22RV1 | 12.6 | 7.18 | 6.53 | 6.18 | 2.06 |
| | 14.3 | 6.11 | 8.97 | 4.7 | 0.993 |
| 22RV1-PSCA | 13.8 | 7.14 | 8.69 | 7.98 | 10.2 |
| | 13.5 | 8.96 | 7.01 | 7.33 | 1.09 |
| 22RV1-PSMA KO-PSCA | 2.27 | 0.087 | 0.96 | 0.123 | 0.404 |
| | 1.95 | 0.35 | 0.567 | 0.621 | 0.576 |

TABLE 15

IFNγ release from canonical CARs co-cultured with K562 cells.

| DONER #1: IFNγ | 4211 | 4212 | 4215 | 1550 | UTD |
|---|---|---|---|---|---|
| K562 | 3.35 | 4.2 | 3.12 | 1.28 | 2.15 |
|  | 3.15 | 4.78 | 2.29 | 2.55 | 2.6 |
| K562-PSCA | 2.39 | 5.13 | 0.832 | 1.24 | 1.3 |
|  | 3.19 | 4.86 | 1.4 | 0.047 | 0.536 |
| K562-PSMA | 21043 | 13396 | 12236 | 13666 | 1.16 |
|  | 19426 | 18943 | 10892 | 15000 | 1.61 |
| K562-PSCA-PSMA | 22344 | 16388 | 15661 | 16464 | 5.85 |
|  | 28231 | 25309 | 16407 | 22367 | 3.19 |

TABLE 16

IL-2 release from canonical CARs co-cultured with K562 cells.

| DONER #1: IL-2 | 4211 | 4212 | 4215 | 1550 | UTD |
|---|---|---|---|---|---|
| K562 | 1.63 | 0.531 | 1.36 | 0.555 | 0.691 |
|  | 0 | 0.448 | 7.33 | 0.58 | 0.644 |
| K562-PSCA | 0.822 | 0.384 | 1.42 | 0 | 0.273 |
|  | 0 | 0 | 0 | 0.062 | 0 |
| K562-PSMA | 16661 | 17413 | 25446 | 21569 | 0 |
|  | 20680 | 21031 | 25759 | 23822 | 0 |
| K562-PSCA-PSMA | 23093 | 20216 | 29370 | 28190 | 0.063 |
|  | 24756 | 22018 | 33154 | 25095 | 0.028 |

TABLE 17

IFNγ release from synNotch T cells co-cultured with 22RV1 cells.

| DONER #1: IFNγ | 1912/4204 | 1912/4206 | 1912/4207 | 1912/4209 | UTD |
|---|---|---|---|---|---|
| 22RV1-PSMA KO | 1.74 | 6.31 | 2.89 | 2.47 | 5.69 |
|  | 2.97 | 6.13 | 2.61 | 3.16 | 6.48 |
| 22RV1 | 31.6 | 48.7 | 21.4 | 18.3 | 6.28 |
|  | 13.2 | 84.9 | 21.1 | 18.8 | 5.65 |
| 22RV1-PSCA | 13081 | 16970 | 11493 | 11273 | 7.28 |
|  | 14236 | 12507 | 11823 | 8820 | 6.6 |
| 22RV1-PSMA KO-PSCA | 11 | 37.8 | 7.31 | 5.11 | 5.39 |
|  | 11.4 | 30.5 | 6.57 | 4.78 | 6.26 |

TABLE 18

IL-2 release from synNotch T cells co-cultured with 22RV1 cells.

| DONER #1: IL-2 | 1912/4204 | 1912/4206 | 1912/4207 | 1912/4209 | UTD |
|---|---|---|---|---|---|
| 22RV1-PSMA KO | 5.08 | 0.638 | 3.53 | 0 | 2.62 |
|  | 1.86 | 1.51 | 1.11 | 0 | 0.099 |
| 22RV1 | 27.4 | 32.7 | 31.4 | 26.3 | 2.06 |
|  | 20 | 27.2 | 27.3 | 32.8 | 0.993 |
| 22RV1-PSCA | 2204 | 1022 | 937 | 715 | 10.2 |
|  | 2544 | 966 | 835 | 829 | 1.09 |
| 22RV1-PSMA KO-PSCA | 24.7 | 9.39 | 4.94 | 10.7 | 0.404 |
|  | 23.7 | 2.64 | 2.33 | 10.3 | 0.576 |

TABLE 19

IFNγ release from synNotch T cells co-cultured with K562 cells.

| DONER #1: IFNγ | 1912/4204 | 1912/4206 | 1912/4207 | 1912/4209 | UTD |
|---|---|---|---|---|---|
| K562 | 1.93 | 2.4 | 1.99 | 0.317 | 2.15 |
|  | 1.03 | 5.36 | 1.35 | 2.66 | 2.6 |
| K562-PSCA | 7.83 | 41.1 | 4.31 | 0 | 1.3 |
|  | 8.63 | 45.3 | 3.15 | 4.16 | 0.536 |
| K562-PSMA | 31.2 | 17.5 | 18.2 | 2.56 | 1.16 |
|  | 28.9 | 32.4 | 15.6 | 10 | 1.61 |
| K562-PSCA-PSMA | 39889 | 37494 | 38511 | 29710 | 5.85 |
|  | 40127 | 47355 | 42126 | 35489 | 3.19 |

TABLE 20

IL-2 release from synNotch T cells co-cultured with K562 cells.

| DONER #1: IL-2 | 1912/4204 | 1912/4206 | 1912/4207 | 1912/4209 | UTD |
|---|---|---|---|---|---|
| K562 | 1.59 | 1.54 | 2.16 | 0 | 0.691 |
|  | 1.16 | 0.655 | 0.355 | 0.615 | 0.644 |
| K562-PSCA | 3.22 | 0.819 | 3.02 | 2.37 | 0.273 |
|  | 5.65 | 0.187 | 0.45 | 2.23 | 0 |
| K562-PSMA | 9.42 | 8.49 | 9.77 | 2.5 | 0 |
|  | 5.22 | 5.99 | 7.43 | 4.26 | 0 |
| K562-PSCA-PSMA | 44348 | 85959 | 29228 | 37515 | 0.063 |
|  | 35870 | 55799 | 25689 | 25276 | 0.028 |

TABLE 21

IFNγ release from canonical CARs co-cultured with 22RV1 cells.

| DONER #2: IFNγ | 4211 | 4212 | 4215 | 1550 | UTD |
|---|---|---|---|---|---|
| 22RV1-PSMA KO | 16 | 15.3 | 5.81 | 2.19 | 0.787 |
|  | 14.5 | 19.5 | 4.77 | 2.21 | 4.4 |
| 22RV1 | 4537 | 4056 | 3063 | 1891 | 2.19 |
|  | 4417 | 3047 | 2301 | 1408 | 1.38 |

TABLE 21-continued

IFNγ release from canonical CARs co-cultured with 22RV1 cells.

| DONER #2: IFNγ | 4211 | 4212 | 4215 | 1550 | UTD |
|---|---|---|---|---|---|
| 22RV1-PSCA | 4928 | 4636 | 2657 | 2080 | 1.44 |
|  | 5795 | 3771 | 3106 | 1993 | 0.591 |
| 22RV1-PSMA KO-PSCA | 13.2 | 15.8 | 5.5 | 0.645 | 1.3 |
|  | 11.9 | 9.08 | 4.42 | 0.933 | 1.53 |

TABLE 22

IL-2 release from canonical CARs co-cultured with 22RV1 cells.

| DONER #2: IL-2 | 4211 | 4212 | 4215 | 1550 | UTD |
|---|---|---|---|---|---|
| 22RV1-PSMA KO | 3.07 | 1.79 | 2.32 | 0 | 0.655 |
|  | 0.192 | 0 | 1.78 | 3.1 | 1.6 |
| 22RV1 | 9.61 | 4.28 | 6.86 | 7.59 | 0.956 |
|  | 7.49 | 3.96 | 3.97 | 0.849 | 0.704 |
| 22RV1-PSCA | 8.1 | 3.93 | 6.32 | 5 | 0.486 |
|  | 8.81 | 3.15 | 3.92 | 4.08 | 0.501 |
| 22RV1-PSMA KO-PSCA | 0.143 | 1.4 | 2.57 | 0 | 0.481 |
|  | 0.427 | 0 | 1.55 | 0 | 0 |

TABLE 23

IFNγ release from Canonical CARs co-cultured with K562 cells.

| DONER #2: IFNγ | 4211 | 4212 | 4215 | 1550 | UTD |
|---|---|---|---|---|---|
| K562 | 11 | 10.2 | 3.68 | 4.93 | 1.06 |
|  | 11.1 | 7.76 | 5.76 | 4.7 | 2.95 |
| K562-PSCA | 12.8 | 11.4 | 7.68 | 4.95 | 2.74 |
|  | 11.3 | 8.26 | 3.69 | 2.04 | 2.33 |
| K562-PSMA | 29454 | 32708 | 29759 | 25791 | 2.63 |
|  | 27437 | 26993 | 29358 | 25893 | 1.85 |
| K562-PSCA-PSMA | 38792 | 37657 | 25578 | 36122 | 3.21 |
|  | 33466 | 28020 | 34273 | 33250 | 1.63 |

TABLE 24

IL-2 release from Canonical CARs co-cultured with K562 cells.

| DONER #2: IL-2 | 4211 | 4212 | 4215 | 1550 | UTD |
|---|---|---|---|---|---|
| K562 | 0 | 0.342 | 0.416 | 1.06 | 0.113 |
|  | 0 | 0 | 0.146 | 0 | 0 |
| K562-PSCA | 0.108 | 0 | 0.498 | 0.162 | 0 |
|  | 0.041 | 0 | 0 | 0.578 | 0 |
| K562-PSMA | 23311 | 17945 | 29384 | 32289 | 0.336 |
|  | 23012 | 18898 | 32330 | 35611 | 0 |
| K562-PSCA-PSMA | 30215 | 29211 | 40977 | 43314 | 0 |
|  | 26986 | 24065 | 43911 | 47153 | 0.016 |

TABLE 25

IFNγ release from synNotch T cells co-cultured with 22RV1 cells.

| DONER #2: IFNγ | 1912/4204 | 1912/4206 | 1912/4207 | 1912/4209 | UTD |
|---|---|---|---|---|---|
| 22RV1-PSMA KO | 1.56 | 13.6 | 2.94 | 2.22 | 0.787 |
|  | 2.75 | 16.2 | 3.96 | 1.62 | 4.4 |
| 22RV1 | 68.9 | 101 | 42.7 | 21.4 | 2.19 |
|  | 50.4 | 66.6 | 37.5 | 22.4 | 1.38 |
| 22RV1-PSCA | 16212 | 15199 | 12526 | 8831 | 1.44 |
|  | 15016 | 17913 | 13830 | 9328 | 0.591 |
| 22RV1-PSMA KO-PSCA | 27.4 | 84.1 | 16 | 4.5 | 1.3 |
|  | 24.6 | 117 | 14.7 | 6.81 | 1.53 |

TABLE 26

IL-2 release from synNotch T cells co-cultured with 22RV1 cells.

| DONER #2: IL-2 | 1912/4204 | 1912/4206 | 1912/4207 | 1912/4209 | UTD |
|---|---|---|---|---|---|
| 22RV1-PSMA KO | 0.368 | 0 | 1.92 | 0.506 | 0.655 |
|  | 0.121 | 0.748 | 0.134 | 0.709 | 1.6 |
| 22RV1 | 34.8 | 20 | 26.3 | 17 | 0.956 |
|  | 20.4 | 9.11 | 16.9 | 12 | 0.704 |
| 22RV1-PSCA | 1241 | 94.6 | 287 | 440 | 0.486 |
|  | 1307 | 115 | 258 | 556 | 0.501 |
| 22RV1-PSMA KO-PSCA | 24.6 | 3.84 | 2.11 | 3.46 | 0.481 |
|  | 12.3 | 2.01 | 3.11 | 3.57 | 0 |

TABLE 27

IFNγ release from synNotch T cells co-cultured with K562 cells.

| DONER #2: IFNγ | 1912/4204 | 1912/4206 | 1912/4207 | 1912/4209 | UTD |
|---|---|---|---|---|---|
| K562 | 1.93 | 11.9 | 3.58 | 2.4 | 1.06 |
|  | 0.916 | 11.7 | 2.52 | 1.71 | 2.95 |
| K562-PSCA | 13.8 | 230 | 10.2 | 11.8 | 2.74 |
|  | 7.68 | 213 | 8.92 | 9.95 | 2.33 |
| K562-PSMA | 37.7 | 63.4 | 92.1 | 11.6 | 2.63 |
|  | 48.4 | 38.7 | 43 | 12.7 | 1.85 |
| K562-PSCA-PSMA | 36941 | 49398 | 49600 | 40575 | 3.21 |
|  | 43708 | 43476 | 49110 | 36315 | 1.63 |

TABLE 28

IL-2 release from synNotch T cells co-cultured with K562 cells.

| DONER #2: IL-2 | 1912/4204 | 1912/4206 | 1912/4207 | 1912/4209 | UTD |
|---|---|---|---|---|---|
| K562 | 0 | 0 | 0.618 | 0 | 0.113 |
|  | 0 | 2.03 | 0 | 0.104 | 0 |
| K562-PSCA | 2.28 | 0.907 | 1.19 | 4.97 | 0 |
|  | 0 | 0.522 | 1.11 | 0 | 0 |
| K562-PSMA | 9.73 | 10.1 | 12.4 | 15.7 | 0.336 |
|  | 9.4 | 5.04 | 6.94 | 6.17 | 0 |
| K562-PSCA-PSMA | 56844 | 53309 | 41059 | 33992 | 0 |
|  | 56812 | 56739 | 28879 | 26926 | 0.016 |

TABLE 29

IFNγ release from Canonical CARs co-cultured with 22RV1 cells.

| DONER #3: IFNγ | 4211 | 4212 | 4215 | 1550 | UTD |
|---|---|---|---|---|---|
| 22RV1-PSMA KO | 15.7 | 31.8 | 2.89 | 0 | 2.91 |
|  | 14.9 | 23.1 | 3.11 | 0 | 3.52 |
| 22RV1 | 963 | 1087 | 333 | 266 | 8.43 |
|  | 1095 | 1233 | 406 | 248 | 3.77 |
| 22RV1-PSCA | 1453 | 1509 | 392 | 313 | 5.41 |
|  | 1352 | 1270 | 431 | 299 | 2.42 |
| 22RV1-PSMA KO-PSCA | 14.4 | 42.4 | 1.19 | 0 | 2.15 |
|  | 12.1 | 25.6 | 1.31 | 0 | 2.67 |

TABLE 30

IL-2 release Canonical CARs co-cultured with 22RV1 cells.

| DONER #3: IL-2 | 4211 | 4212 | 4215 | 1550 | UTD |
|---|---|---|---|---|---|
| 22RV1-PSMA KO | 1.93 | 3.46 | 0.137 | 0.13 | 0 |
|  | 0 | 3.64 | 0 | 1.35 | 1.16 |
| 22RV1 | 7.01 | 6.67 | 4.83 | 6.16 | 21.4 |
|  | 9.46 | 5.1 | 3.25 | 4.59 | 6.83 |

TABLE 30-continued

IL-2 release Canonical CARs co-cultured with 22RV1 cells.

| DONER #3: IL-2 | 4211 | 4212 | 4215 | 1550 | UTD |
|---|---|---|---|---|---|
| 22RV1-PSCA | 6.85 | 2.77 | 3.55 | 4.78 | 8.2 |
| | 9.16 | 2.82 | 2.74 | 4.36 | 1.88 |
| 22RV1-PSMA KO-PSCA | 0 | 0.907 | 2.11 | 0 | 0 |
| | 0.022 | 0.465 | 0.147 | 0 | 0.948 |

TABLE 31

IFNγ release from Canonical CARs co-cultured with K562 cells.

| DONER #3: IFNγ | 4211 | 4212 | 4215 | 1550 | UTD |
|---|---|---|---|---|---|
| K562 | 3.95 | 12.1 | 2.44 | 0.122 | 1.74 |
| | 7.59 | 10.9 | 2.57 | 1.56 | 2.7 |
| K562-PSCA | 5.17 | 20 | 1.64 | 2.16 | 1.14 |
| | 4.76 | 24.4 | 0 | 0.684 | 1.43 |
| K562-PSMA | 20686 | 23162 | 10258 | 13894 | 37.9 |
| | 24434 | 22309 | 14384 | 19840 | 33.7 |
| K562-PSCA-PSMA | 26446 | 18179 | 18075 | 17588 | 50.9 |
| | 21796 | 27232 | 15897 | 17508 | 52.4 |

TABLE 32

IL-2 release from synNotch T cells co-cultured with K562 cells.

| DONER #3: IL-2 | 4211 | 4212 | 4215 | 1550 | UTD |
|---|---|---|---|---|---|
| K562 | 4.15 | 5.44 | 5.44 | 5.65 | 8.79 |
| | 3.01 | 5.5 | 4.1 | 5.66 | 4.97 |
| K562-PSCA | 3.84 | 6.64 | 3.18 | 6.29 | 5.75 |
| | 3.84 | 4.89 | 2.78 | 4.32 | 4.46 |
| K562-PSMA | 16547 | 11304 | 17363 | 14695 | 16.7 |
| | 15454 | 12690 | 17380 | 16003 | 27.4 |
| K562-PSCA-PSMA | 22756 | 17217 | 29446 | 21885 | 29.9 |
| | 19618 | 16775 | 22623 | 21235 | 32.5 |

TABLE 33

IFNγ release from synNotch T cells co-cultured with 22RV1 cells.

| DONER #3: IFNγ | 1912/4204 | 1912/4206 | 1912/4207 | 1912/4209 | UTD |
|---|---|---|---|---|---|
| 22RV1-PSMA KO | 1.85 | 2.4 | 0.691 | 2.57 | 2.91 |
| | 1.97 | 1.52 | 2.05 | 0.436 | 3.52 |
| 22RV1 | 33.2 | 58.6 | 26.4 | 12.8 | 8.43 |
| | 16.6 | 47.4 | 24 | 10.9 | 3.77 |
| 22RV1-PSCA | 6124 | 9040 | 8200 | 5535 | 5.41 |
| | 6378 | 9062 | 6616 | 5078 | 2.42 |
| 22RV1-PSMA KO-PSCA | | 49.2 | 6.68 | 20.5 | 2.15 |
| | 38.3 | 36.8 | 11.3 | 15.6 | 2.67 |

TABLE 34

IL-2 release from synNotch T cells co-cultured with 22RV1 cells.

| DONER #3: IL-2 | 1912/4204 | 1912/4206 | 1912/4207 | 1912/4209 | UTD |
|---|---|---|---|---|---|
| 22RV1-PSMA KO | 1.39 | 0 | 1.4 | 1.25 | 0 |
| | 0.439 | 0 | 0 | 0.338 | 1.16 |
| 22RV1 | 44.1 | 43.8 | 45.3 | 10.4 | 21.4 |
| | 24.8 | 40 | 39.2 | 17.6 | 6.83 |
| 22RV1-PSCA | 1031 | 1179 | 503 | 225 | 8.2 |
| | 1120 | 1243 | 609 | 323 | 1.88 |
| 22RV1-PSMA KO-PSCA | 93 | 13.7 | 12.2 | 45.9 | 0 |
| | 71.4 | 10.1 | 12.1 | 40.3 | 0.948 |

TABLE 35

IFNγ release from synNotch T cells co-cultured with K562 cells.

| DONER #3: IFNγ | 1912/4204 | 1912/4206 | 1912/4207 | 1912/4209 | UTD |
|---|---|---|---|---|---|
| K562 | 1.64 | 3.65 | 1.73 | 0.13 | 1.74 |
| | 1.44 | 3.53 | 0.594 | 0.654 | 2.7 |
| K562-PSCA | 16.9 | 59.4 | 10.7 | 3.56 | 1.14 |
| | 38.1 | 75.6 | 7.93 | 10.6 | 1.43 |
| K562-PSMA | 18.5 | 14.7 | 20.3 | 3.97 | 37.9 |
| | 34.2 | 10.5 | 23.1 | 2.94 | 33.7 |
| K562-PSCA-PSMA | 33444 | 46610 | 38118 | 25258 | 50.9 |
| | 31062 | 37241 | 30922 | 25004 | 52.4 |

TABLE 36

IL-2 release from synNotch T cells co-cultured with K562 cells.

| DONER #3: IL-2 | 1912/4204 | 1912/4206 | 1912/4207 | 1912/4209 | UTD |
|---|---|---|---|---|---|
| K562 | 5.42 | 4.53 | 4.4 | 4.98 | 8.79 |
| | 4.72 | 4.39 | 5.03 | 4.97 | 4.97 |
| K562-PSCA | 18.1 | 8.88 | 13.9 | 9.25 | 5.75 |
| | 21.1 | 6.29 | 11.7 | 12.9 | 4.46 |
| K562-PSMA | 12.3 | 17.5 | 17.5 | 13.3 | 16.7 |
| | 14.7 | 16.1 | 13.1 | 8.45 | 27.4 |
| K562-PSCA-PSMA | 35691 | 57642 | 28190 | 33381 | 29.9 |
| | 33075 | 44658 | 22130 | 26937 | 32.5 |

Example 5

22RV1 or mitomycin C treated-K562 cells were co-cultured with Cell Trace Violet (CTV) labeled-T cells in a 96 well plate for 96 hrs. Following incubation, plates were analyzed via flow cytometry for dilution of CTV.

TABLE 37

% Divided canonical CAR T cells following K562 co-culture.

| Donor ID | Construct | scFv | K562 | K562-PSCA | K562-PSMA | K562-PSCA-PSMA | T cells only |
|---|---|---|---|---|---|---|---|
| #1 | 104 | Ab4 | 1.54 | 1.62 | 87.9 | 89.15 | 1.86 |
| | 101 | Ab1 | 2.73 | 3.41 | 93.85 | 94.5 | 4.26 |
| | 103 | Ab3 | 1.99 | 2.23 | 92.5 | 93.85 | 3.1 |
| | 105 | Ab5 | 4.34 | 5.12 | 88.95 | 87.1 | 6.19 |
| | UTD | | | | | | |
| #2 | 104 | Ab4 | 0.28 | 0.56 | 89.1 | 90.45 | 0.41 |
| | 101 | Ab1 | 0.58 | 0.47 | 91 | 93.3 | 0.54 |
| | 103 | Ab3 | 0.31 | 0.92 | 90.95 | 92.95 | 0.49 |
| | 105 | Ab5 | 0.17 | 1.3 | 92.65 | 93.55 | 0.15 |
| | UTD | | 5.83 | 3.01 | 7.35 | 5.91 | 8.31 |
| #3 | 104 | Ab4 | 0.5 | 0.77 | 93.4 | 94.8 | 2.21 |
| | 101 | Ab1 | 1.47 | 1.22 | 92.9 | 94 | 4.07 |
| | 103 | Ab3 | 0.96 | 1.36 | 95.6 | 96.6 | 3.11 |
| | 105 | Ab5 | 1.85 | 2.28 | 96.3 | 96.3 | 7.5 |
| | UTD | | 3.57 | 4.99 | 5.57 | 3.99 | 6.58 |

TABLE 38

% Divided canonical CAR T cells following 22RV1 co-culture.

| Donor ID | Construct | scFv | 22RV1-PSMA KO | 22RV1 | 22RV1-PSCA | 22RV1-PSMA KO-PSCA | T cells only |
|---|---|---|---|---|---|---|---|
| #1 | 104 | Ab4 | 0.89 | 89 | 89.3 | 0.67 | 1.86 |
| | 101 | Ab1 | 3.76 | 94.25 | 94.15 | 3.27 | 4.26 |
| | 103 | Ab3 | 1.03 | 87.7 | 89.75 | 0.88 | 3.1 |

TABLE 38-continued

% Divided canonical CAR T cells following 22RV1 co-culture.

| Donor ID | Construct | scFv | 22RV1-PSMA KO | 22RV1 | 22RV1-PSCA | 22RV1-PSMA KO-PSCA | T cells only |
|---|---|---|---|---|---|---|---|
| | 105 | Ab5 | 4.63 | 78.1 | 81.35 | 3.72 | 6.19 |
| | UTD | | | | | | |
| #2 | 104 | Ab4 | | 91.55 | 90.75 | 0.14 | 0.41 |
| | 101 | Ab1 | 0.61 | 91.6 | 92.3 | 0.73 | 0.54 |
| | 103 | Ab3 | 0.08 | 90.1 | 90.9 | 0.21 | 0.49 |
| | 105 | Ab5 | 0 | 90.7 | 91.55 | 0.05 | 0.15 |
| | UTD | | 2.98 | 3.08 | 2.95 | 2.33 | 8.31 |
| #3 | 104 | Ab4 | 0.16 | 87.9 | 90.3 | 0.2 | 2.21 |
| | 101 | Ab1 | 0.7 | 91 | 92.95 | 0.47 | 4.07 |
| | 103 | Ab3 | 0.41 | 93.75 | 94.65 | 0.33 | 3.11 |
| | 105 | Ab5 | 2.35 | 84.35 | 87.6 | 1.17 | 7.5 |
| | UTD | | 7.03 | 7.02 | 5.72 | 5.76 | 6.58 |

TABLE 39

% Divided synNotch T cells following K562 co-culture.

| Donor ID | Construct | scFv | K562 | K562-PSCA | K562-PSMA | K562-PSCA-PSMA | T cells only |
|---|---|---|---|---|---|---|---|
| #1 | Ab6 SynNotch/201 | Ab1 | 1.75 | 1.79 | 7.46 | 31.15 | 0.93 |
| | Ab6 SynNotch/202 | Ab2 | 25.8 | 33.35 | 35.8 | 68.65 | 31.25 |
| | Ab6 SynNotch/203 | Ab3 | 1.01 | 2.22 | 6.49 | 37.65 | 1.41 |
| | Ab6 SynNotch/205 | Ab5 | 7.14 | 6.3 | 11.26 | 43.05 | 8.09 |
| | UTD | | | | | | |
| #2 | Ab6 SynNotch/201 | Ab1 | 1.82 | 3.47 | 7.78 | 16.6 | 0.98 |
| | Ab6 SynNotch/202 | Ab2 | 29.6 | 31.4 | 40.55 | 59.5 | 35.9 |
| | Ab6 SynNotch/203 | Ab3 | 0.34 | 2.93 | 7.92 | 15.95 | |
| | Ab6 SynNotch/205 | Ab5 | 1.62 | 3.12 | 10.34 | 16.15 | 2.49 |
| | UTD | | 5.83 | 3.01 | 7.35 | 5.91 | 8.31 |
| #3 | Ab6 SynNotch/201 | Ab1 | 3.82 | 17.15 | 12.55 | 56.65 | 5.66 |
| | Ab6 SynNotch/202 | Ab2 | 6.32 | 26.6 | 17 | 61.35 | 7.45 |
| | Ab6 SynNotch/203 | Ab3 | 7.47 | 24.74 | 21.95 | 67.85 | 8.34 |
| | Ab6 SynNotch/205 | Ab5 | 7.67 | 35.9 | 18.45 | 75.65 | 12.3 |
| | UTD | | 3.57 | 4.99 | 5.57 | 3.99 | 6.58 |

TABLE 40

% Divided synNotch T cells following 22RV1 co-culture.

| Donor ID | Construct | scFv | 22RV1-PSMA KO | 22RV1 | 22RV1-PSCA | 22RV1-PSMA KO-PSCA | T cells only |
|---|---|---|---|---|---|---|---|
| #1 | Ab6 SynNotch/201 | Ab1 | 0.88 | 1.56 | 28.2 | 1.75 | 0.93 |
| | Ab6 SynNotch/202 | Ab2 | 29.45 | 31.45 | 77.75 | 23.9 | 31.25 |
| | Ab6 SynNotch/203 | Ab3 | 1.11 | 2.29 | 48.1 | 1.17 | 1.41 |
| | Ab6 SynNotch/205 | Ab5 | 2.68 | 3.25 | 52.1 | 2.52 | 8.09 |
| | UTD | | | | | | |
| #2 | Ab6 SynNotch/201 | Ab1 | | 0.69 | 15.85 | 0.52 | 0.98 |
| | Ab6 SynNotch/202 | Ab2 | | 18.65 | 47.95 | 16.55 | 35.9 |
| | Ab6 SynNotch/203 | Ab3 | | 0.42 | 16.8 | 0.59 | |
| | Ab6 SynNotch/205 | Ab5 | | 1.83 | 22.1 | 0.91 | 2.49 |
| | UTD | | 2.98 | 3.08 | 2.95 | 2.33 | 8.31 |
| #3 | Ab6 SynNotch/201 | Ab1 | 7.08 | 10.58 | 53.7 | 10.62 | 5.66 |
| | Ab6 SynNotch/202 | Ab2 | 9.39 | 13.55 | 62.25 | 18.5 | 7.45 |
| | Ab6 SynNotch/203 | Ab3 | 10.45 | 18.5 | 65.35 | 12.65 | 8.34 |
| | Ab6 SynNotch/205 | Ab5 | 11.6 | 14.75 | 75.95 | 14.6 | 12.3 |
| | UTD | | 7.03 | 7.02 | 5.72 | 5.76 | 6.58 |

Example 6

Female NSG mice were implanted with $5\times10^5$ K562-PSCA-PSMA subcutaneously in the dorsal flank in 50% Matrigel. On day 14, mice were dosed with either $2\times10^6$ or $5\times10^6$ CAR+ T cells. Tumors were measured via calipers.

TABLE 41

| Canonical CAR Days post tumor implantation | Vehicle | | | | | | | |
|---|---|---|---|---|---|---|---|---|
| 14 | 108 | 108 | 108 | 126 | 126 | 126 | 126 | 144 |
| 17 | 365 | 365 | 288 | 405 | 405 | 405 | 405 | 405 |
| 21 | 1183 | 864 | 787 | 847 | 1183 | 1080 | 1008 | 1268 |
| 24 | 1666 | 1470 | 1437 | 1437 | 1666 | 1764 | 1764 | 1862 |
| 27 | 2560 | 2025 | 2138 | 2432 | 2560 | 2890 | 2560 | 2890 |
| UT | | | | | | | | |
| 14 | 108 | 108 | 108 | 126 | 126 | 126 | 126 | 144 |
| 17 | 365 | 196 | 405 | 320 | 405 | 405 | 405 | 405 |
| 21 | 726 | 666 | 864 | 908 | 1183 | 936 | 1099 | 1183 |
| 24 | 1470 | 1183 | 1913 | 1296 | 1913 | 1568 | 1913 | 1666 |
| 27 | | 2025 | 2746 | 2250 | 2560 | | 2746 | 2304 |
| Ab1-17 canonical 2e6 | | | | | | | | |
| 14 | 108 | 108 | 108 | 126 | 126 | 126 | 126 | 144 |
| 17 | 288 | 172 | 172 | 288 | 256 | 288 | 256 | 288 |
| 21 | 726 | 550 | 500 | 1008 | 936 | 847 | 726 | 1099 |
| 24 | 1099 | 936 | 666 | 1268 | 1268 | 1080 | 936 | 1568 |
| 27 | | 1080 | 726 | 1352 | 1521 | 1437 | 1008 | 2025 |
| 30 | | 1008 | 550 | 1352 | 1521 | 1862 | 1268 | |
| 34 | | 726 | 365 | 1080 | 1437 | 1437 | 1268 | |
| 37 | | 550 | 256 | 600 | 1080 | 847 | 936 | |
| 41 | | 500 | 196 | 405 | 726 | 650 | 550 | |
| 44 | | 500 | 196 | 320 | | 405 | 405 | |
| 48 | | 405 | | | | 288 | 365 | |
| 51 | | 288 | | | | 172 | 288 | |
| 55 | | 196 | | | | 108 | 256 | |
| Ab1-17 canonical 5e6 | | | | | | | | |
| 14 | 108 | 108 | 108 | 126 | 126 | 126 | 126 | 144 |
| 17 | 405 | 172 | 256 | 365 | 256 | 320 | 320 | 405 |
| 21 | 936 | 550 | 666 | 864 | 936 | 787 | 847 | 1268 |
| 24 | 1268 | 864 | 936 | 1008 | 1268 | 1080 | 1080 | 1764 |
| 27 | 726 | 550 | 405 | | 1470 | 1080 | 1152 | 1960 |
| 30 | 320 | 365 | 172 | | 1470 | 550 | 1080 | 1666 |
| 34 | 126 | 108 | 63 | | 500 | 365 | 486 | 908 |
| 37 | 32 | 63 | 14 | | 288 | 256 | 486 | 600 |
| 41 | 4 | 14 | 1 | | 288 | 172 | 320 | |
| 44 | 1 | 4 | | | 288 | 172 | | |
| 48 | | 1 | | | | 63 | | |
| 51 | | 1 | | | | 32 | | |
| 55 | | 1 | | | | 32 | | |
| Ab4 canonical 2e6 | | | | | | | | |
| 14 | 108 | 108 | 108 | 126 | 126 | 126 | 126 | 144 |
| 17 | 256 | 256 | 196 | 320 | 320 | 288 | 365 | 500 |
| 21 | 864 | 726 | 600 | 1008 | 908 | 847 | 1008 | 1470 |
| 24 | 1183 | 936 | 726 | 1666 | 1152 | 1080 | 1268 | 1764 |
| 27 | 1568 | 1008 | 936 | | 1224 | 1764 | 2025 | 2432 |
| 30 | 1352 | 1008 | 1183 | | 1606 | | 1764 | |
| 34 | 1666 | 1080 | 1568 | | 1606 | | | |
| 37 | 1666 | 1080 | 1568 | | 1960 | | | |
| 41 | 2025 | 1080 | 1568 | | 2250 | | | |
| 44 | | 1080 | 2025 | | | | | |
| Ab4 canonical 5e6 | | | | | | | | |
| 14 | 108 | 108 | 108 | 126 | 126 | 126 | 126 | 144 |
| 17 | 196 | 288 | 196 | 405 | 320 | 288 | 405 | 320 |
| 21 | 787 | 936 | 666 | 1008 | 936 | 1099 | 1268 | 1008 |
| 24 | 1008 | 1268 | 726 | 1352 | 1268 | 1764 | 1666 | 1352 |
| 27 | 1152 | 1568 | 864 | 1268 | 1268 | 1862 | 2025 | 1764 |
| 30 | 1152 | 1568 | 936 | 1666 | 1268 | 2025 | | 1764 |
| 34 | 1008 | 1183 | 726 | 936 | | | | 1183 |
| 37 | 288 | 446 | 288 | 405 | | | | 550 |
| 41 | 63 | 320 | 172 | 365 | | | | 320 |
| 44 | 4 | 288 | 108 | 288 | | | | |
| 48 | 1 | 172 | | | | | | |
| 51 | | 63 | | | | | | |
| Ab3-21 canonical 2e6 | | | | | | | | |
| 14 | 108 | 108 | 108 | 108 | 126 | 126 | 126 | 144 |
| 17 | 196 | 196 | 196 | 288 | 365 | 288 | 288 | 288 |
| 21 | 666 | 666 | 864 | 1099 | 864 | 1008 | 936 | 847 |
| 24 | 787 | 726 | 1268 | 1568 | 1183 | 1268 | 1470 | 1268 |
| 27 | 1008 | | 1666 | 2304 | 2176 | 2025 | 1913 | 1666 |
| 30 | 1080 | | 2138 | | | | 2304 | 2025 |
| 34 | 1080 | | | | | | | |
| 37 | 1268 | | | | | | | |
| Ab3-21 canonical 5e6 | | | | | | | | |
| 14 | 108 | 108 | 108 | 108 | 126 | 126 | 126 | 144 |
| 17 | 256 | 256 | 256 | 365 | 256 | 320 | 365 | 320 |
| 21 | 666 | 936 | 864 | 1183 | 847 | 1008 | 1099 | 1080 |
| 24 | 1008 | 1183 | 1008 | 1372 | 1268 | 1352 | 1470 | 1666 |
| 27 | 1008 | 1183 | 1183 | 1372 | 1268 | 1437 | 1688 | |
| 30 | 1080 | 1183 | 1470 | 1372 | | 1666 | 2048 | |
| 34 | 1080 | 864 | 1800 | 1099 | | 1352 | | |
| 37 | 847 | 666 | 1800 | | | 1352 | | |
| 41 | 847 | 666 | | | | | | |
| 44 | | 365 | | | | | | |
| 48 | | 288 | | | | | | |
| 51 | | 172 | | | | | | |
| Ab5 canonical 2e6 | | | | | | | | |
| 14 | 108 | 108 | 108 | 108 | 126 | 126 | 126 | 144 |
| 17 | 172 | 172 | 256 | 196 | 405 | 365 | 256 | 288 |
| 21 | 500 | 726 | 726 | 600 | 936 | 1099 | 787 | 1008 |
| 24 | 864 | 1152 | 1183 | 1099 | 1470 | | 1183 | 1470 |
| 27 | 864 | 1352 | 1666 | 1372 | | | 1800 | 1666 |
| 30 | 936 | 1568 | 2025 | 1800 | | | | 2025 |
| 34 | 1008 | 1470 | | 2176 | | | | |
| 37 | 1008 | 1470 | | | | | | |
| 41 | 1268 | 1183 | | | | | | |
| 44 | 2025 | 1183 | | | | | | |
| 48 | | 1183 | | | | | | |
| 51 | | 1183 | | | | | | |
| Ab5 canonical 5e6 | | | | | | | | |
| 14 | 108 | 108 | 108 | 108 | 126 | 126 | 126 | 144 |
| 17 | 196 | 288 | 196 | 256 | 256 | 365 | 405 | 320 |
| 21 | 550 | 726 | 600 | 600 | 864 | 847 | 1008 | 700 |
| 24 | 726 | 936 | 600 | 787 | | 1268 | 1568 | 847 |
| 27 | 500 | 936 | 365 | 550 | | 1352 | | 847 |
| 30 | 365 | 726 | 365 | 365 | | | | 847 |
| 34 | 172 | 320 | 172 | 256 | | | | 288 |
| 37 | 63 | 288 | 63 | 172 | | | | 172 |
| 41 | 63 | 256 | 32 | 172 | | | | 48 |
| 44 | 32 | 108 | 14 | 108 | | | | 32 |
| 48 | 4 | 63 | 4 | 63 | | | | |
| 51 | 4 | 32 | 4 | 14 | | | | |
| 55 | 4 | 4 | 1 | 4 | | | | |

TABLE 41

| synNotch Days post tumor implantation | Vehicle | | | | | | | |
|---|---|---|---|---|---|---|---|---|
| 14 | 108 | 108 | 108 | 126 | 126 | 126 | 126 | 144 |
| 17 | 365 | 365 | 288 | 405 | 405 | 405 | 405 | 405 |
| 21 | 1183 | 864 | 787 | 847 | 1183 | 1080 | 1008 | 1268 |
| 24 | 1666 | 1470 | 1437 | 1437 | 1666 | 1764 | 1764 | 1862 |
| 27 | 2560 | 2025 | 2138 | 2432 | 2560 | 2890 | 2560 | 2890 |

TABLE 41-continued

| synNotch Days post tumor implantation | Vehicle | | | | | | | |
|---|---|---|---|---|---|---|---|---|
| | UT | | | | | | | |
| 14 | 108 | 108 | 108 | 126 | 126 | 126 | 126 | 144 |
| 17 | 365 | 196 | 405 | 320 | 405 | 405 | 405 | 405 |
| 21 | 726 | 666 | 864 | 908 | 1183 | 936 | 1099 | 1183 |
| 24 | 1470 | 1183 | 1913 | 1296 | 1913 | 1568 | 1913 | 1666 |
| 27 | | 2025 | 2746 | 2250 | 2560 | | 2746 | 2304 |
| | Ab1-17 synNotch 2e6 | | | | | | | |
| 14 | 108 | 108 | 108 | 126 | 126 | 126 | 126 | 144 |
| 17 | 172 | 288 | 245 | 256 | 320 | 405 | 256 | 446 |
| 21 | 666 | 726 | 700 | 787 | 650 | 1268 | 864 | 847 |
| 24 | 1008 | 1268 | 908 | 1183 | 847 | | 1183 | 1080 |
| 27 | 1080 | 2025 | 908 | 1268 | 1183 | | 1568 | |
| 30 | 1080 | | 908 | 1268 | 1470 | | 1568 | |
| 34 | 288 | | 908 | 1268 | 1470 | | 1268 | |
| 37 | 288 | | 600 | 1268 | 1268 | | 1268 | |
| 41 | 288 | | 600 | | 1268 | | 1268 | |
| 44 | 196 | | 320 | | 1352 | | 1470 | |
| 48 | 172 | | 126 | | 1437 | | 1688 | |
| 51 | | | 108 | | | | | |
| 55 | | | 108 | | | | | |
| | Ab1-17 synNotch 5e6 | | | | | | | |
| 14 | 108 | 108 | 108 | 126 | 126 | 126 | 126 | 144 |
| 17 | 256 | 256 | 196 | 365 | 256 | 446 | 365 | 405 |
| 21 | 726 | 936 | 600 | 936 | 666 | 1089 | 1089 | 864 |
| 24 | 936 | 936 | 787 | 1568 | 666 | 1368 | 1368 | 1183 |
| 27 | 1008 | 726 | 600 | 2025 | 666 | 1368 | 1368 | |
| 30 | 666 | 550 | 550 | | 405 | 1368 | 1080 | |
| 34 | 365 | 500 | 288 | | 172 | 567 | 550 | |
| 37 | 365 | 365 | 172 | | 108 | 416 | 256 | |
| 41 | 256 | 172 | 108 | | 32 | 245 | 196 | |
| 44 | 172 | 108 | 63 | | 32 | 144 | 172 | |
| 48 | 126 | 108 | 32 | | 32 | 88 | 108 | |
| 51 | 63 | 32 | 32 | | 32 | 88 | 32 | |
| 55 | 63 | 32 | 32 | | 32 | 88 | 32 | |
| | Ab2-7 synNotch 2e6 | | | | | | | |
| 14 | 108 | 108 | 108 | 126 | 126 | 126 | 126 | 144 |
| 17 | 256 | 288 | 196 | 320 | 365 | 365 | 405 | 320 |
| 21 | 666 | 787 | 666 | 936 | 864 | 1183 | 1080 | 1080 |
| 24 | 864 | 1080 | 726 | 1080 | 1268 | 1268 | 1352 | 1521 |
| 27 | 864 | | 864 | 1152 | 1352 | 1268 | 1521 | 1862 |
| 30 | 864 | | 864 | 1152 | 1666 | 1800 | 1521 | 2156 |
| 34 | 666 | | 726 | 847 | 1568 | 2176 | 1080 | |
| 37 | 288 | | 405 | 446 | 1268 | | 847 | |
| 41 | 172 | | 288 | 405 | 1268 | | 787 | |
| 44 | 172 | | 288 | 365 | 1268 | | 446 | |
| 48 | 108 | | 88 | 256 | 1268 | | 446 | |
| 51 | 108 | | 88 | 172 | 1268 | | 405 | |
| 55 | 108 | | 75 | 172 | 1268 | | | |
| | Ab2-7 synNotch 5e6 | | | | | | | |
| 14 | 108 | 108 | 108 | 126 | 126 | 126 | 126 | 144 |
| 17 | 172 | 172 | 256 | 245 | 365 | 288 | 320 | 288 |
| 21 | 600 | 550 | 936 | 800 | 1008 | 787 | 787 | 787 |
| 24 | 600 | 600 | 936 | 1029 | 1183 | 787 | 1008 | 847 |
| 27 | 365 | 365 | 726 | 968 | 1183 | 500 | 1008 | 527 |
| 30 | 256 | 256 | 365 | 650 | 550 | 365 | 650 | |
| 34 | 108 | 75 | 172 | 320 | 288 | 256 | 352 | |
| 37 | 63 | 32 | 63 | 221 | 172 | 172 | 320 | |
| 41 | 63 | 14 | 63 | | 108 | 108 | 221 | |
| 44 | 14 | 14 | 63 | | 108 | 108 | 221 | |
| 48 | 4 | 4 | 32 | | 63 | 63 | 126 | |
| 51 | | 4 | 32 | | 32 | 32 | 63 | |
| 55 | | 4 | 32 | | 32 | 32 | 32 | |
| | Ab3-21 synNotch 2e6 | | | | | | | |
| 14 | 108 | 108 | 108 | 108 | 126 | 126 | 126 | 144 |
| 17 | 288 | 365 | 256 | 196 | 365 | 256 | 405 | 320 |
| 21 | 936 | 936 | 666 | 600 | 1008 | 726 | 1268 | 1008 |
| 24 | 1470 | 1099 | 1099 | 936 | 1568 | 1268 | 1913 | |
| 27 | 1913 | 1372 | 1183 | 1183 | 2025 | 1666 | 2432 | |
| 30 | 2138 | 1800 | 1268 | | | | 2138 | |
| 34 | | 2025 | 2025 | | | | | |
| | Ab3-21 synNotch 5e6 | | | | | | | |
| 14 | 108 | 108 | 108 | 108 | 126 | 126 | 126 | 144 |
| 17 | 256 | 288 | 256 | 196 | 196 | 288 | 288 | 365 |
| 21 | 550 | 847 | 666 | 550 | 486 | 936 | 864 | 787 |
| 24 | 936 | 847 | 864 | 787 | 908 | | 1470 | 1080 |
| 27 | 1099 | 1008 | 726 | 1008 | 968 | | 1800 | 1960 |
| 30 | 1099 | 1268 | 726 | 1437 | 1029 | | 2025 | |
| 34 | 1688 | 1470 | 726 | | 1089 | | | |
| 37 | 1800 | | 726 | | 1440 | | | |
| 41 | 2176 | | 726 | | 2058 | | | |
| | Ab5 synNotch 2e6 | | | | | | | |
| 14 | 108 | 108 | 108 | 108 | 126 | 126 | 126 | 144 |
| 17 | 365 | 288 | 320 | 256 | 365 | 320 | 405 | 405 |
| 21 | 864 | 650 | 1183 | 550 | 936 | 726 | 787 | 1008 |
| 24 | 1372 | 1183 | 1913 | 1099 | 1568 | 1268 | 1183 | 1666 |
| 27 | 1800 | 1800 | 2890 | | 2304 | 2304 | 1568 | 2025 |
| 30 | 2025 | 2304 | | | | | 2025 | |
| | Ab5 synNotch 5e6 | | | | | | | |
| 14 | 108 | 108 | 108 | 108 | 126 | 126 | 126 | 144 |
| 17 | 288 | 196 | 221 | 288 | 365 | 196 | 365 | 288 |
| 21 | 726 | 500 | 650 | 936 | 1183 | 726 | 1099 | 1080 |
| 24 | 936 | 550 | 650 | 1183 | | 726 | 1372 | 1268 |
| 27 | 666 | 405 | 600 | 1183 | | 726 | 1470 | 1690 |
| 30 | 500 | 288 | 446 | 1372 | | 486 | | 1960 |
| 34 | 500 | 196 | 288 | 1470 | | 486 | | 2250 |
| 37 | 365 | 63 | 108 | 1470 | | 352 | | |
| 41 | | 32 | 75 | 1913 | | 352 | | |
| 44 | | 14 | 14 | 2025 | | 352 | | |
| 48 | | 14 | 14 | | | 352 | | |
| 51 | | 14 | 14 | | | 256 | | |
| 55 | | 14 | 14 | | | | | |

Example 7

Female NSG mice were implanted with $5\times10^5$ K562-PSCA-PSNMA subcutaneously in the dorsal flank in 50% Matrigel. On day 13, mice were dosed with either $2\times10^6$ or $5\times10^6$ CAR+ T cells. Tumors were measured via calipers.

| Day post inoculation | Vehicle | | | | | | | |
|---|---|---|---|---|---|---|---|---|
| 13 | 108 | 108 | 108 | 126 | 126 | 172 | 172 | 172 |
| 16 | 172 | 172 | 256 | 365 | 221 | 288 | 256 | 256 |
| 20 | 550 | 500 | 726 | 787 | 650 | 600 | 726 | 936 |
| 23 | 1008 | 787 | 1268 | 1352 | 968 | 1080 | 1568 | 1568 |
| 27 | 2138 | 2048 | 2304 | | 1606 | 2025 | 2304 | 2890 |
| 30 | | | | | 2058 | | | |
| | Nontransduced | | | | | | | |
| 13 | 108 | 108 | 126 | 126 | 126 | 144 | 172 | 172 |
| 16 | 172 | 288 | 256 | 256 | 196 | 320 | 256 | 288 |
| 20 | 500 | 726 | 666 | 726 | 787 | 1008 | 650 | 864 |
| 23 | 1099 | 1183 | 1268 | 1268 | 1183 | 1764 | 1152 | 1470 |
| 27 | 2048 | 2890 | 2457 | 2601 | 2432 | 2890 | 2432 | 2916 |
| | synNotch/mAb1 anti-PSMA CAR (2e6) | | | | | | | |
| 13 | 108 | 108 | 126 | 126 | 126 | 144 | 172 | 172 |
| 16 | 172 | 172 | 256 | 365 | 196 | 365 | 405 | 256 |
| 20 | 446 | 365 | 650 | 864 | 446 | 787 | 1099 | 550 |
| 23 | 486 | 405 | 1080 | 1372 | 700 | 1080 | 1688 | 864 |
| 27 | 650 | 288 | 1437 | 1470 | 527 | 1470 | 2176 | 1099 |
| 30 | 700 | 196 | 1666 | 1470 | 486 | 1800 | | 787 |
| 34 | 700 | 172 | 2025 | 1268 | 245 | 1568 | | 726 |
| 38 | 486 | 108 | | 936 | 196 | 1268 | | 500 |

| Day post inoculation | Vehicle | | | | | | |
|---|---|---|---|---|---|---|---|
| 41 | 196 | 108 | 787 | 126 | 787 | | 500 |
| 44 | 172 | 75 | 486 | 108 | 550 | | 500 |
| 48 | 172 | 75 | 550 | 32 | 550 | | 500 |
| synNotch/mAb1 anti-PSMA CAR+DNR (2e6) | | | | | | | |
| 13 | 108 | 108 | 126 | 126 | 126 | 144 | 172 | 172 |
| 16 | 256 | 108 | 256 | 320 | 365 | 196 | 365 | 256 |
| 20 | 446 | 256 | 550 | 666 | 600 | 666 | 864 | 726 |
| 23 | 666 | 320 | 726 | 666 | 787 | 936 | 1183 | 1099 |
| 27 | 726 | 352 | 787 | 726 | 650 | 1470 | 1470 | 1183 |
| 30 | 666 | 245 | 726 | 666 | 446 | 1470 | 1470 | 1080 |
| 34 | 446 | 126 | 550 | 365 | 320 | 1568 | 1470 | 1080 |
| 38 | 320 | 126 | 405 | 288 | 196 | 1372 | 787 | 787 |
| 41 | 144 | 108 | 256 | 256 | 172 | 936 | 666 | 600 |
| 44 | 144 | 108 | 288 | 256 | 126 | 864 | 550 | 550 |
| 48 | 75 | 32 | 196 | 75 | 63 | 666 | 550 | 446 |
| synNotch/mAb1 anti-PSMA CAR (5e6) | | | | | | | |
| 13 | 108 | 108 | 126 | 126 | 126 | 144 | 172 | 172 |
| 16 | 172 | 196 | 172 | 196 | 256 | 365 | 365 | 405 |
| 20 | 288 | 245 | 288 | 405 | 405 | 936 | 1099 | 936 |
| 23 | 288 | 352 | 288 | 405 | 405 | 1080 | 1470 | 1268 |
| 27 | 108 | 221 | 172 | 196 | 196 | 1152 | 1800 | 1183 |
| 30 | 63 | 172 | 144 | 172 | 126 | 787 | 1470 | 726 |
| 34 | 63 | 126 | 75 | 108 | 108 | 486 | 600 | 666 |
| 38 | 14 | 108 | 88 | 108 | 108 | 352 | 550 | 500 |

| Day post inoculation | Vehicle | | | | | | |
|---|---|---|---|---|---|---|---|
| 41 | 14 | 88 | 88 | 88 | 63 | 320 | 500 | 405 |
| 44 | 14 | 108 | 126 | 63 | 63 | 320 | 365 | 320 |
| 48 | 14 | 108 | 32 | 32 | 32 | 288 | 288 | 288 |
| synNotch/mAb1 anti-PSMA CAR+DNR (5e6) | | | | | | | |
| 13 | 108 | 108 | 126 | 126 | 126 | 126 | 172 | 172 |
| 16 | 172 | 172 | 256 | 288 | 256 | 256 | 288 | 405 |
| 20 | 256 | 446 | 550 | 726 | 500 | 666 | 666 | 1008 |
| 23 | 196 | 787 | 666 | 864 | 550 | 600 | 726 | 1568 |
| 27 | 126 | 787 | 550 | 787 | 405 | 500 | 864 | 1666 |
| 30 | 108 | 405 | 288 | 550 | 256 | 288 | 726 | 1470 |
| 34 | 75 | 320 | 256 | 446 | 126 | 196 | 405 | 550 |
| 38 | 32 | 221 | 196 | 320 | 75 | 172 | 256 | 365 |
| 41 | 18 | 221 | 196 | 288 | 63 | 172 | 196 | 196 |
| 44 | 14 | 221 | 196 | 288 | | 196 | 256 | 196 |
| 48 | 0 | 172 | 126 | 256 | | 75 | | 172 |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An antibody, or antigen binding fragment thereof comprising an anti-prostate-specific membrane antigen (PSMA) binding domain, wherein the anti-PSMA binding domain comprises sequences of three heavy chain complementarity determining regions (HCDRs) of any one of the heavy chain variable region (HCVR) selected from the group consisting of SEQ ID NOs: 1, 25, 49, and 73, and sequences of three light chain complementarity determining regions (LCDRs) of the light chain variable region (LCVR) selected from the group consisting of SEQ ID NOs: 12, 36, 60, and 84, wherein the antibody, or antigen binding fragment thereof comprises a first domain comprising three HCDRs and a second domain comprising three LCDRs, wherein:

the HCDRs and LCDRs comprise:
(i) an HCDR1 according to any of SEQ ID NOs: 3-5; an HCDR2 according to any of SEQ ID NOs: 6-7; an HCDR3 according to any one of SEQ ID NOs: 9-10; an LCDR1 according to any of SEQ ID NOs: 14-15; an LCDR2 according to any of SEQ ID NOS: 17-18; an LCDR3 according to SEQ ID NO: 20;
(ii) an HCDR1 according to any of SEQ ID NOs: 27-29; an HCDR2 according to any of SEQ ID NOs: 30-31; an HCDR3 according to any one of SEQ ID NOs: 33-34; an LCDR1 according to any of SEQ ID NOs: 38-39; an LCDR2 according to SEQ ID NO: 42; an LCDR3 according to SEQ ID NO: 45;
(iii) an HCDR1 according to any of SEQ ID NOs: 51-53; an HCDR2 according to any of SEQ ID NOs: 54-55; an HCDR3 according to any one of SEQ ID NOs: 57-58; an LCDR1 according to any of SEQ ID NOs: 62-63; an LCDR2 according to any of SEQ ID NOs: 65-66; an LCDR3 according to SEQ ID NO: 68; or
(iv) an HCDR1 according to any of SEQ ID NOs: 75-77; an HCDR2 according to any of SEQ ID NOs: 78-79; an HCDR3 according to any one of SEQ ID NOs: 81-82; an LCDR1 according to any of SEQ ID NOs: 86-87; an LCDR2 according to any of SEQ ID NOs: 89-90; an LCDR3 according to SEQ ID NO: 92.

2. A chimeric antigen receptor, comprising the antibody, or antigen binding fragment thereof of claim 1.

3. The chimeric antigen receptor of claim 2, further comprising a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD28, CD33, CD37, CD45, CD64, CD80, CD86, CD134, CD137, CD154, or a zeta chain of a T cell receptor, or any combination thereof.

4. A nucleic acid encoding the chimeric antigen receptor of claim 3.

5. A recombinant vector comprising the nucleic acid of claim 4.

6. The recombinant vector of claim 5, wherein the nucleic acid encoding the chimeric antigen receptor is operatively connected to a constitutively active promotor or a conditionally activated promoter.

7. The recombinant vector of claim 6, wherein the conditionally activated promoter comprises at least one transcriptional activator binding site.

8. The recombinant vector of claim 7, wherein the at least one transcriptional activator binding site comprises one or more GAL4 binding sites.

9. The recombinant vector of claim 5, wherein the recombinant vector further comprises a nucleic acid encoding a dominant negative TGFβ receptor (DN TGFβR), comprising:
an extracellular domain (ECD) from a TGF-β receptor
and a transmembrane domain (TMD), wherein the DN TGFβR lacks amino acid residues responsible for signaling and phosphorylation present in a wild-type TGF-β receptor.

10. A host cell transformed with the recombinant vector of claim 5.

11. The host cell of claim 10, where the host cell comprises a T cell or an NK cell.

12. A method of treating a disease with PSMA expression in a patient in need thereof, comprising administering the antibody, or antigen binding fragment of claim 1 to the patient.

13. The method of claim 12, where the disease is a prostate cancer.

14. A method of inducing an immune response or immunizing a subject against a prostate cancer, the method comprising administering the antibody, or antigen binding fragment of claim 1 to the subject.

15. A nucleic acid encoding the antibody, or antigen binding fragment thereof of claim 1.

16. A recombinant vector comprising the nucleic acid of claim 15.

17. The recombinant vector of claim 16, wherein the nucleic acid encoding the antibody, or antigen binding fragment thereof is operatively connected to a constitutively active promotor or a conditionally activated promoter.

18. The recombinant vector of claim 17, wherein the conditionally activated promoter comprises at least one transcriptional activator binding site.

19. The recombinant vector of claim 18, wherein the at least one transcriptional activator binding site comprises one or more GAL4 binding sites.

20. The recombinant vector of claim 16, wherein the recombinant vector further comprises a nucleic acid encoding a dominant negative TGFβ receptor (DN TGFβR), comprising:
an extracellular domain (ECD) from a TGF-β receptor
and a transmembrane domain (TMD), wherein the DN TGFβR lacks amino acid residues responsible for signaling and phosphorylation present in a wild-type TGF-β receptor.

21. A host cell transformed with the recombinant vector of claim 16.

* * * * *